United States Patent

Goulet et al.

[11] Patent Number: 5,565,560
[45] Date of Patent: Oct. 15, 1996

[54] O-ARYL,O-ALKYL,O-ALKENYL AND O-ALKYNYLMACROLIDES HAVING IMMUNOSUPPRESSIVE ACTIVITY

[75] Inventors: Mark Goulet, Westfield; Helen M. Organ, Fanwood; William H. Parsons, Edison; Peter J. Sinclair, Highland Park; Frederick Wong, Glen Ridge; Matthew J. Wyvratt, Mountainside, all of N.J.

[73] Assignee: Merck & Co., Inc., Rahway, N.J.

[21] Appl. No.: 132,072

[22] Filed: Oct. 4, 1993

Related U.S. Application Data

[63] Continuation-in-part of Ser. No. 875,036, May 1, 1992, Pat. No. 5,250,678, which is a continuation-in-part of Ser. No. 809,998, Dec. 18, 1991, abandoned, which is a continuation-in-part of Ser. No. 699,407, May 13, 1991, abandoned.

[51] Int. Cl.$^6$ .................. C07D 491/16; A61K 31/435
[52] U.S. Cl. .................................................. 540/456
[58] Field of Search ............................................ 540/456

[56] References Cited

U.S. PATENT DOCUMENTS 5,250,678  10/1993  Goulet et al. ............................ 540/456
5,349,061  9/1994  Sinclair et al. ......................... 540/456

*Primary Examiner*—Robert T. Bond
*Attorney, Agent, or Firm*—Mollie M. Yang; David L. Rose

[57] ABSTRACT

O-Aryl, O-alkyl, O-alkenyl and O-alkynyl-macrolides of the general structural Formula I:

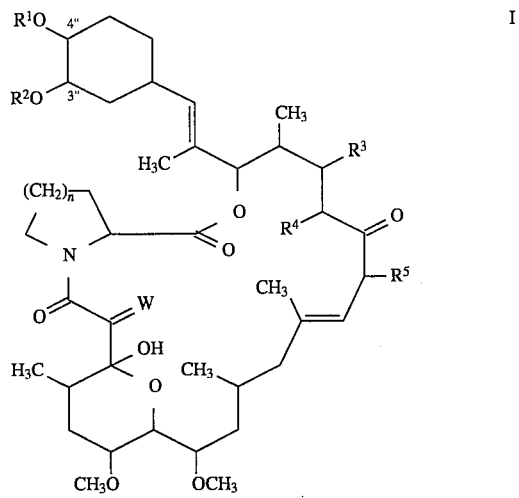

have been prepared from suitable precursors by alkylation and/or arylation at C-3" and/or C-4" of the cyclohexyl ring. These macrolide immunosuppressants are useful in a mammalian host for the treatment of autoimmune diseases, infectious diseases and/or the prevention of rejection of foreign organ transplants and/or related afflictions, diseases and illnesses.

2 Claims, No Drawings

O-ARYL,O-ALKYL,O-ALKENYL AND O-ALKYNYLMACROLIDES HAVING IMMUNOSUPPRESSIVE ACTIVITY

SUMMARY OF THE INVENTION

This application is a continuation-in-part of application Ser. No. 07/875,036, filed May 1, 1992, now issued as U.S. Pat. No. 5,250,678, issued Oct. 5, 1993, which in turn is a continuation-in-part of application Ser. No. 07/809,998, filed Dec. 18, 1991, now abandoned, which in turn is a continuation-in-pan of application Ser. No. 07/699,407, filed May 13, 1991, now abandoned.

The present invention is related to O-aryl, O-alkyl, O-alkenyl and O-alkynylmacrolides which are useful in a mammalian subject for the treatment of autoimmune diseases (such as juvenile-onset or recent-onset diabetes mellitus, multiple sclerosis, and rheumatoid arthritis, liver disease, posterior uveitis, allergic encephalomyelitis, and glomerulonephritis), immunodepression, infectious diseases and/or the prevention of rejection of foreign organ transplants, (e.g. bone marrow, kidney, liver, heart, skin, small-bowel, and pancreatic islet-cell transplants, including xeno transplants), the topical treatment of inflammatory and hyperproliferative skin diseases and cutaneous manifestations of immunologically-mediated illnesses (such as: psoriasis, atopical dermatitis, contact dermatitis and further eczematous dermatitises, seborrhoeic dermatitis, Lichen planus, Pemphigus, bullous Pemphigoid, Epidermolysis bullosa, urticaria, angioedemas, vasculitides, erythemas, cutaneous eosinophilias, Lupus erythematosus or Alopecia areata), male pattern alopecia, alopecia senilis, reversible obstructive airways disease, particularly asthma, intimation of mucosa and blood vessels, cytomegalovirus infection, multidrug resistance, idiopathic thromboytopenic purpura, Behcet's syndrome, conjunctivitis, Crohn's disease, Mooren's ulcer, uveitis, servere intraocular inflammation and/or hepatic injury associated with ischemia. The present compounds are further useful in combination with a 5α-reductase inhibitor, a cyclosporin, a potassium channel opener or a phospholipid in a mammalian host for the treatment of baldness, especially male pattern alopecia, female pattern alopecia, alopecia senilis, or alopecia areata. In addition, some of the compounds of this invention may have antagonistic properties and so have utility in the reversal of immunosuppressive activity and/or diminishing the toxicity of other immunosuppressive agents.

More particularly, this invention relates to compounds of the general structural Formula I:

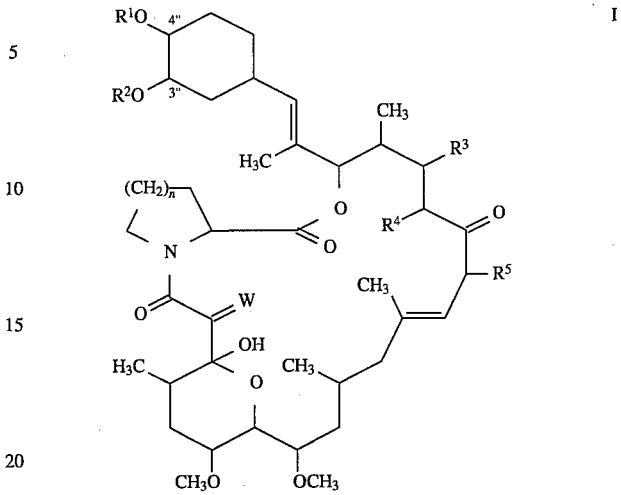

wherein $R^1$, $R^2$, $R^3$, $R^4$, $R^5$, W and n are hereinafter defined.

This invention also relates to pharmaceutical compositions containing the compounds, and to a method of use of the present compounds and other agents for the treatment and prevention of certain afflictions, diseases and illnesses.

BRIEF DESCRIPTION OF DISCLOSURES IN THE ART

Fujisawa United States, European and Japanese patents and applications (U.S. Pat. No. 4,894,366, issued Jan. 16, 1990, EPO Publication No. 0,184,162 and PBJ Disclosure 63-17884) and publications (J. Am. Chem. Soc., 1987, 109, 5031 and J. Antibiotics 1987, 40, 1249) disclose 17-allyl-1, 14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone (FR-900506) (FK-506) (L-679,934), 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone (FR-900520) and related compounds which are the starting materials for the preparation of the compounds described. The synthetic preparation of the aforementioned starting material (FR-900506) has been reported (J. Am. Chem. Soc., 1989, 111, 1157). A Sandoz U.S. patent (U.S. Pat. No. 5,011,844) and European patent application (EPO Publication No. 0,356,399) disclose stereoisomers of FR-900506 and derivatives at the 17-position. Fisons European and WIPO patent applications (EPO Publication No. 0,323,042 and PCT Publication No. WO89/05304) disclose various derivatives of FR-900506, FR-900520 and related compounds. A Sandoz European patent application (EPO Publication No. 0,437,680) discloses chloro, bromo, iodo and azido derivatives of FR-900506, FR-900520 and related compounds. A Merck European patent application (EPO Publication No. 0,428,365) discloses various amino derivatives of FR-900506, FR-900520 and related compounds. A Fujisawa UK patent application (UK Publication No. GB 2,245,891A) discloses various aryl(lower alkyl) and heteroaryl derivatives of FR-900506, FR-900520 and related compounds. Merck WIPO patent applications (PCT Publication Nos. WO 93/05058 & WO 93/05059) disclose various heteroaryl derivatives of FR-900506, FR-900520 and related compounds.

Fujisawa United States patents (U.S. Pat. No. 4,929,611, issued May 29, 1990 and U.S. Pat. No. 4,956,352, issued Sep. 11, 1990) disclose the use of FK-506-type compounds in treating resistance to transplantation. A Sandoz European patent application (EPO Publication No. 0,315,978) discloses the use of FR-900506 and related compounds in the topical treatment of inflammatory and hyperproliferative skin diseases and of cutaneous manifestations of immunologically-mediated illness. A Fisons World patent application (PCT Publication WO 90/14826) discloses the use of FR-900506 and related compounds in the treatment of reversible obstructive airways disease, particularly asthma. A Fujisawa European patent application (EPO Publication NO. 0,423,714) discloses the use of FK-506 and derivatives as hair revitalizing agents. Various studies have suggested the efficacy of FK-506 in the treatment of a number of ailments, including rheumatoid arthritis (C. Arita, et al., Clincial exp. Immunol., 1990, 82, 456–461; N. Inamura, et al., Clin. Immunol. Immunopathol. 1988, 46, 82–90), recent-onset diabetes (N. Murase, et al., Diabetes, 1990, 39, 1584–86; N. Murase, et al., Lancet, 1990, 336, 373–74), posterior uveitis (H. Kawashima, Invest. Ophthalmul. Vis. Sci., 1988, 29, 1265–71), hepatic injury associated with ischemia (M. Sakr, et al., Life Sci., 1990, 47, 687–91) allergic encephalomyelitis (K. Deguchi, et al., Brain Nerve, 1990, 42, 391–97), glomerulonephritis (J. McCauley, et al., Lancet, 1990, 335, 674), systemic lupus erythematosus (K. Takabayashi, et al., Clin. Immunol. Immunopathol,, 1989, 51, 110–117), multidrug resistance (M. Naito, et al., Cancer Chemother. Pharmacol., 1992, 29, 195–200), inflammation of mucosa and blood vessels (PCT Publication WO 91/17754), cytomegalovirus infection (UK Publication GB 2,247,620A), and idiopathic thrombocytopenic purpura and Basedow's disease (PCT Publication WO 91/19495).

BACKGROUND OF THE INVENTION

Immunoregulatory abnormalities have been shown to exist in a wide variety of "autoimmune" and chronic inflammatory diseases, including systemic lupus erythematosis, chronic rheumatoid arthritis, type 1 diabetes mellitus, type 2 adult onset diabetes, inflammatory bowel disease, biliary cirrhosis, uveitis, multiple sclerosis and other disorders such as Crohn's disease, ulcerative colitis, bullous pemphigoid, sarcoidosis, psoriasis, ichthyosis, and Graves ophthalmopathy. Although the underlying pathogenesis of each of these conditions may be quite different, they have in common the appearance of a variety of autoantibodies and self-reactive lymphocytes. Such self-reactivity may be due, in part, to a loss of the homeostatic controls under which the normal immune system operates.

Similarly, following a bone-marrow or an organ transplantation, the host lymphocytes recognize the foreign tissue antigens and begin to produce antibodies which lead to graft rejection.

One end result of an autoimmune or a rejection process is tissue destruction caused by inflammatory cells and the mediators they release. Antiinflammatory agents such as NSAID's and corticosteroids act principally by blocking the effect or secretion of these mediators but do nothing to modify the immunologic basis of the disease. On the other hand, cytotoxic agents such as cyclophosphamide, act in such a nonspecific fashion that both the normal and autoimmune responses are shut off. Indeed, patients treated with such nonspecific immunosuppressive agents are as likely to succumb from infection as they are from their autoimmune disease.

Cyclosporin A which was approved by the US FDA in 1983 is currently the leading drug used to prevent rejection of transplanted organs. The drug acts by inhibiting the body's immune system from mobilizing its vast arsenal of natural protecting agents to reject the transplant's foreign protein. Though cyclosporin A is effective in fighting transplant rejection, it is nephrotoxic and is known to cause several undesirable side effects including kidney failure, abnormal liver function and gastrointestinal discomfort.

Newer, safer drugs exhibiting less side effects are constantly being searched for in the field.

The 23-membered tricyclo-macrolide immunosuppressant, tacrolimus, FR-900506, FK-506,

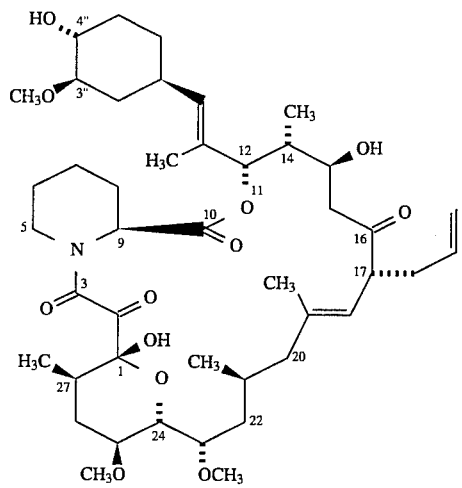

(17-allyl-1,14-dihydroxy-12-[2'-(4"-hydroxy-3"-methoxy-cyclohexyl)-1'-methylvinyl]-23,25-dimethyl-13,19,21,27-tetramethyl-11,28-dioxa-4-azatricyclo-[22.3.1.0$^{4,9}$]-octa-cos-18-ene-2,3,10,16-tetraone) and related compounds which were isolated and characterized by Tanaka, Kuroda, and co-workers at Fujisawa Pharmaceutical Co. in Japan, see J. Am. Chem. Soc., 1987, 109, 5031, and U.S. Pat. No. 4,894,366, issued Jan. 16, 1990) have been shown to possess exceptional immunosuppressive activity. Fujisawa United States patents (U.S. Pat. No. 4,929,611, issued May 29, 1990 and U.S. Pat. No. 4,956,352, issued Sep. 11, 1990) disclose the use of FK-506-type compounds in treating resistance to transplantation. In particular, the compound FR-900506 has been reported to be 100 times more effective than cyclosporin in the supression of in vitro immune systems (J. Antibiotics 1987, 40, 1256). In addition, these compounds are reputed to possess topical activity in the treatment of inflammatory and hyperproliferative skin diseases and cutaneous manifestations of immunologically-mediated illnesses (EPO Pub. No. 0,315,978).

The compound FK-506 and related compounds further have been suggested to be useful in the treatment of obstructive airways disease, particularly asthma (PCT Publication WO 90/14826), male pattern alopecia or alopecia senilis (EPO Publication No. 0,423,714), rheumatoid arthitis (C. Arita, et al., Clincial exp. Immunol., 1990, 82, 456–46 1; N. Inamura, et al., Clin. Immunol. Immunopathol. 1988, 46, 82–90), recent-onset diabetes (N. Murase, et al., *Diabetes*, 1990, 39, 1584–86; N. Murase, et al., *Lancet*, 1990, 336, 373–74), posterior uveitis (H. Kawashima, *Invest. Ophthalmol. Vis. Sci.*, 1988, 29, 1265–71), hepatic injury associated with ischemia (M. Sakr, et al., *Life Sci.*, 1990, 47, 687–91) allergic encephalomyelitis (K. Deguchi, et al., *Brain Nerve*, 1990, 42, 391–97), glomerulonephritis (J. McCauley, et al., *Lancet*, 1990, 335, 674), systemic lupus erythematosus (K. Takabayashi, et al., *Clin. Immunol. Immunopathol.*, 1989, 51, 110–117) multidrug resistance (M. Naito, et al., *Cancer Chemother. Pharmacol.*, 1992, 29, 195–200), inflammation of mucosa and blood vessels (PCT Publication WO 92/17754), cytomegalovirus infection (UK Publication GB 2,247,620A), and idiopathic thrombocytopenic purpura and Basedow's disease (PCT Publication WO 91/19495).

Baldness or alopecia, in addition to male pattern alopecia, female pattern alopecia, and alopecia senilis, includes alopecia areta, and further, diseases accompanied by basic skin lesions such as cicatrix or infectious tumors, or accompanied by systemic disorders, for examples, an internal secretion abnormality or nutritional disorder.

In regard to alopecia areata, it is considered that an autoimmune phenomenon participates therein, and therefore, the administration of a substance having an immunosuppressive action can have therapeutical effect on alopecia areata.

The causes of human pattern alopecia (also called "androgenic alopecia") and alopecia senilis are considered to be: an activation of male hormones at organs such as hair roots and the sebum gland; a lowering in the amount of blood reaching the hair follicles; a scalp abnormality caused by an excessive secretion of sebum, a formation or peroxides, or a propagation of bacteria; genetic; causes; and aging.

The compound minoxidil (6-amino-1,2-dihydro-1-hydroxy-2-imino-4-piperidinopyrimidine) was approved by the FDA for the treatment of male pattern baldness in August 1988. Minoxidil was also approved by the FDA for the treatment of female androgenetic alopecia on Aug. 13, 1991. The preparation of minoxidil is described in U.S. Pat. Nos. 3,382,247, 3,644,364 and 4,098,791. Upjohn United States Patents (U.S. Pat. Nos. 4,139,619 and 4,596,812) discloses the use of minoxidil in the topical treatment of human baldness. Similarly, an Upjohn United States Patent (U.S. Pat. No. 5,026,691) discloses the use of minoxidil and an antiinflammatory agent for the treatment of patterned male and female alopecia. Japanese patent Kokai 61-260010 states that topical minoxidil formulations containing other specified agents may be prepared. An Upjohn WIPO patent application (PCT Publication No. WO 92/09259) discloses a method and composition for promoting hair growth in mammals comprising the administration of a potassium channel opener and an androgen receptor blocker. A University of Miami WIPO patent application (PCT Publication No. WO 92/12703) discloser a method of stimulating hair growth comprising the topical application of a phospholipid.

Merck U.S. Pat. No. 4,760,071 discloses the 5α-reductase inhibitor 17β-(N-tert-butylcarbamoyl)-4-aza-5α-androst-1-en-3-one. Harris, et al., (*Proc. Natl. Acad. Sci. USA*, 89, 10787–10791 (Nov. 1992)) and Melin, et al. (*J. Steroid Biochem. Molec. Biol.*, 44(2), 121–131 (1993)) disclose the use of scalp-selective 5α-reductase inhibitors in the treatment of male pattern baldness, acne and hirsutism.

DETAILED DESCRIPTION OF THE INVENTION

A. Scope of the Invention

The novel compound of this invention has structural Formula I:

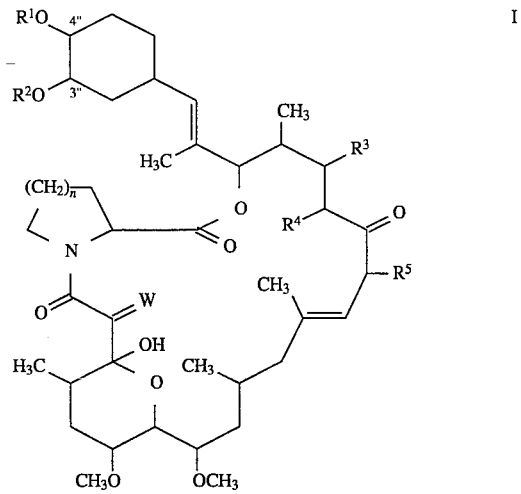

or a pharmaceutically acceptable salt thereof, wherein:
$R^1$ and $R^2$ are independently selected from:
(1) hydrogen;
(2) phenyl;
(3) substituted phenyl in which the substituents are X, Y and Z;
(4) 1- or 2-naphthyl;
(5) substituted 1- or 2-naphthyl in which the substituents are X, Y and Z;
(6) biphenyl;
(7) substituted biphenyl in which the substituents are X, Y and Z;
(8) $C_{1-10}$ alkyl;
(9) substituted $C_{1-10}$ alkyl in which one or more substituent(s) is(are) selected from:
(a) hydroxy,
(b) oxo,
(c) $C_{1-6}$alkoxy,
(d) phenyl-$C_{1-3}$alkoxy,
(e) substituted phenyl-$C_{1-3}$alkoxy, in which the substituents on phenyl are X, Y and Z,
(f) —OCO—$C_{1-6}$alkyl,
(g) —$NR^6R^7$, wherein $R^6$ and $R^7$ are independently selected from
(i) hydrogen,
(ii) $C_{1-10}$alkyl unsubstituted or substituted with one or more of the substituent(s) selected from:
(a') phenyl, which is unsubstituted or substituted with X, Y and Z,
(b') —OH,
(c') $C_{1-6}$alkoxy,
(d') —$CO_2H$,
(e') —$CO_2$—$C_{1-6}$alkyl,
(f') —$C_{3-7}$cycloalkyl, and
(g') —$OR^{11}$,
(iii) $C_{3-10}$alkenyl unsubstituted or substituted with or more of the substituent(s) selected from:
(a') phenyl, which is unsubstituted or substituted with X, Y and Z, (b') —OH,
(c') $C_{1-6}$alkoxy,
(d') —CO$_2$H,
(e') —CO$_2$—$C_{1-6}$alkyl,
(f') —$C_{3-7}$cycloalkyl, and
(g') —OR$^{11}$,
(iv) or where R$^6$ and R$^7$ and the N to which they are attached can form an unsubstituted or substituted 3–7-membered saturated heterocyclic ring which can include one or two additional heteroatoms independently selected from the group consisting of O, S(O)$_p$, NR$^{14}$, wherein R$^{14}$ is hydrogen or $C_{1-6}$ alkyl unsubstituted or substituted by phenyl, and p is 0, 1 or 2, the ring being selected from the group consisting of: aziridine, morpholine, thiomorpholine, thiomorpholine-oxide, thiomorpholine-dioxide, piperidine, pyrrolidine, and piperazine,
(h) —NR$^6$CO—$C_{1-6}$alkyl-R$^7$, wherein R$^6$ is defined above,
(i) —NR$^6$CO$_2$—$C_{1-6}$alkyl-R$^7$,
(j) —NR$^6$CONR$^6$R$^7$,
(k) —OCONR$^6$R$^7$,
(l) —COOR$^6$,
(m) —CHO,
(n) phenyl,
(o) substituted phenyl in which the substituents are X, Y and Z,
(p) phenyloxy,
(q) substituted phenyloxy in which the substituents are X, Y and Z,
(r) 1- or 2-naphthyl,
(s) substituted 1- or 2-naphthyl in which the substituents are X, Y and Z,
(t) biphenyl,
(u) substituted biphenyl in which the substituents are X, Y and Z;
(v) —OR$^{11}$, and
(w) —S(O)$_p$—$C_{1-6}$alkyl;
(10) $C_{3-10}$ alkenyl;
(11) substituted $C_{3-10}$ alkenyl in which one or more substituent(s) is(are) selected from:
(a) hydroxy,
(b) oxo,
(c) $C_{1-6}$alkoxy,
(d) phenyl-$C_{1-3}$alkoxy,
(e) substituted phenyl-$C_{1-3}$alkoxy, in which the substituents on phenyl are X, Y and Z,
(f) —OCO—$C_{1-6}$alkyl,
(g) —NR$^6$R$^7$, wherein R$^6$ and R$^7$ are as defined above,
(h) —NR$^6$CO—$C_{1-6}$alkyl, wherein R$^6$ is as defined above,
(i) —COOR$^6$, wherein R$^6$ is as defined above,
(j) —CHO,
(k) phenyl,
(l) substituted phenyl in which the substituents are X, Y and Z,
(m) 1- or 2-naphthyl,
(n) substituted 1- or 2-naphthyl in which the substituents are X, Y and Z,
(o) biphenyl,
(p) substituted biphenyl in which the substituents are X, Y and Z,
(q) —OR$^{11}$, and
(r) —S(O)$_p$—$C_{1-6}$alkyl;
(12) $C_{3-10}$alkynyl;
(13) substituted $C_{3-10}$alkynyl in which one or more substituent(s) is(are) selected from:
(a) hydroxy,
(b) oxo,
(c) $C_{1-6}$alkoxy,
(d) phenyl-$C_{1-3}$alkoxy,
(e) substituted phenyl-$C_{1-3}$alkoxy, in which the substituents on phenyl are X, Y and Z,
(f) —OCO—$C_{1-6}$alkyl,
(g) —NR$^6$R$^7$, wherein R$^6$ and R$^7$ are as defined above,
(h) —NR$^6$CO—$C_{1-6}$alkyl, wherein R$^6$ is as defined above,
(i) —COOR$^6$, wherein R$^6$ is as defined above,
(j) —CHO,
(k) phenyl,
(l) substituted phenyl in which the substituents are X, Y and Z,
(m) 1- or 2-naphthyl,
(n) substituted 1- or 2-naphthyl in which the substituents are X, Y and Z,
(o) biphenyl,
(p) substituted biphenyl in which the substituents are X, Y and Z, and
(q) —OR$^{11}$;
with the proviso that R$^1$ and R$^2$ are not simultaneously hydrogen, methyl or combinations thereof;
R$^3$ is hydrogen, hydroxy, —OR$^{11}$ or $C_{1-6}$ alkoxy;
R$^4$ is hydrogen, or R$^3$ and R$^4$ taken together form a double bond;
R$^5$ is methyl, ethyl, propyl or allyl;
R$^{11}$ is selected from:
(a) —PO(OH)O—M$^+$, wherein M$^+$ is a positively charged inorganic or organic counterion,
(b) —SO$_3$—M$^+$,
(c) —CO(CH$_2$)$_q$CO$_2$—M$^+$, wherein q is 1–3, and
(d) —CO—$C_{1-6}$alkyl-NR$^6$R$^7$, wherein R$^6$ and R$^7$ are as defined above and the alkyl is unsubstituted or substituted with one or more substituents selected from:
(i) hydroxy,
(ii) $C_{1-6}$alkoxy,
(iii) —NR$^{16}$R$^{17}$, wherein R$^{16}$ and R$^{17}$ are independently selected from:
(a') hydrogen, and
(b') $C_{1-6}$alkyl,
(iv) —COOR$^6$, wherein R$^6$ is as defined above,
(v) phenyl,
(vi) substituted phenyl in which the substituents are X, Y and Z,
(vii) —SH, and
(viii) —S—$C_{1-6}$alkyl;
W is O or (H, OH);
X, Y and Z independently are selected from:
(a) hydrogen,
(b) $C_{1-7}$ alkyl,
(c) $C_{2-6}$ alkenyl,
(d) halogen,
(e) —(CH$_2$)$_m$—NR$^6$R$^7$, wherein R$^6$ and R$^7$ are as defined above, and m is 0 to 2,
(f) —CN,
(g) —CHO,
(h) —CF$_3$,
(i) —SR$^8$, wherein R$^8$ is hydrogen, $C_{1-6}$alkyl, trifluoromethyl, or phenyl,
(j) —SOR$^8$, wherein R$^8$ is as defined above,
(k) —SO$_2$R$^8$, wherein R$^8$ is as defined above,
(l) —CONR$^6$R$^7$, wherein R$^6$ and R$^7$ are as defined above, (m) $R^9O(CH_2)_m$— wherein $R^9$ is hydrogen, $C_{1-3}$ alkyl, hydroxy-$C_{2-3}$alkyl, trifluoromethyl, phenyl or naphthyl and m is as defined above, (n) —$CH(OR^{12})(OR^{13})$, wherein $R^{12}$ and $R^{13}$ are $C_{1-3}$alkyl or taken together form an ethyl or propyl bridge, (o)

wherein $R^9$ and m are as defined above, and (p)

wherein $R^9$ and m are as defined above, and (q) —$OR^{11}$;

or any two of adjacent X, Y and Z can be joined to form a ring having 5, 6 or 7 ring atoms, said ring atoms comprising 1 or 2 oxygen atoms, the remaining ring atoms being carbon, selected from the group consisting of: dioxolanyl, dihydrofuranyl, dihydropyranyl, and dioxanyl; and n is 1 or 2.

The compounds of the present invention have asymmetric centers and this invention includes all of the optical isomers and mixtures thereof.

In addition compounds with carbon-carbon double bonds may occur in Z- and E-forms with all isomeric forms of the compounds being included in the present invention.

When any variable (e.g., alkyl, aryl, $R^6$, $R^7$, $R^8$, $R^9$, $R^{10}$, $R^{11}$, etc.) occurs more than one time in any variable or in Formula I, its definition on each occurrence is independent of its definition at every other occurrence.

As used herein, the term "alkyl" includes those alkyl groups of a designated number of carbon atoms of either a straight, branched, or cyclic configuration. Examples of "alkyl" include methyl, ethyl, propyl, isopropyl, butyl, sec- and tert-butyl, pentyl, hexyl, heptyl, cyclopropyl, cyclobutyl, cyclopentyl, cyclohexyl, cycloheptyl, norbornyl, and the like. "Alkoxy" represents an alkyl group of indicated number of carbon atoms attached through an oxygen bridge, such as methoxy, ethoxy, propoxy, butoxy and pentoxy.

"Alkanoyl" is intended to include those alkylcarbonyl groups of specified number of carbon atoms, which are exemplified by formyl, acetyl, propanoyl and butyryl; "alkanoyloxy" is intended to include those alkylcarbonyl groups of specified number of carbon atoms attached through an oxygen bridge, which are exemplified by formyloxy, acetoxy, propionoyloxy, and butyryloxy. "Alkenyl" is intended to include hydrocarbon chains of a specified number of carbon atoms of either a straight- or branched-configuration and at least one unsaturation, which may occur at any point along the chain, such as ethenyl, propenyl, butenyl, pentenyl, dimethyl pentenyl, and the like, and includes E and Z forms, where applicable; and "arylalkyl" represents aryl groups as herein defined which are attached through a straight or branched chain alkyl group of from one to six carbon atoms, such as, for example, benzyl, phenethyl, 3,3-diphenylpropyl, and the like. "Halogen", as used herein, means fluoro, chloro, bromo and iodo.

As will be understood by those skilled in the art, pharmaceutically acceptable salts include, but are not limited to salts with inorganic acids such as hydrochloride, sulfate, phosphate, diphosphate, hydrobromide, and nitrate or salts with an organic acid such as malate, maleate, fumarate, tartrate, succinate, citrate, acetate, lactate, methanesulfonate, p-toluenesulfonate or palmoate, salicylate and stearate. Similarly pharmaceutically acceptable cations include, but are not limited to sodium, potassium, calcium, aluminum, lithium and ammonium (especially ammonium salts with amines of the formula $HNR^6R^7$).

One embodiment of the present invention encompasses the compounds of Formula I wherein:

$R^1$ and $R^2$ are independently selected from:
(1) hydrogen;
(2) methyl;
(3) phenyl;
(4) substituted phenyl in which the substituents are X, Y and Z;
(5) 1- or 2-naphthyl;
(6) substituted 1- or 2-naphthyl in which the substituents are X, Y and Z;
(7) biphenyl; and
(8) substituted and biphenyl in which the substituents are X, Y and Z;
with the proviso that $R^1$ and $R^2$ are not simultaneously hydrogen, methyl or combinations thereof;

$R^3$ is hydrogen, hydroxy, or $C_{1-6}$ alkoxy;
$R^4$ is hydrogen, or $R^3$ and $R^4$ taken together form a double bond;
$R^5$ is methyl, ethyl, propyl or allyl;
$R^{11}$ is selected from:
(a) —$PO(OH)O—M^+$, wherein $M^+$ is a positively charged inorganic or organic counterion,
(b) —$SO_3—M^+$,
(c) —$CO(CH_2)_qCO_2—M^+$, wherein q is 1–3, and
(d) —$CO—C_{1-6}$alkyl-$NR^6R^7$, wherein $R^6$ and $R^7$ are as defined below and the alkyl is unsubstituted or substituted with one or more substituents selected from:
(i) hydroxy,
(ii) $C_{1-6}$alkoxy,
(iii) —$NR^{16}R^{17}$, wherein $R^{16}$ and $R^{17}$ are independently selected from:
(a') hydrogen, and
(b') $C_{1-6}$alkyl,
(iv) —$COOR^6$, wherein $R^6$ is as defined below,
(v) phenyl,
(vi) substituted phenyl in which the substituents are X, Y and Z,
(vii) —SH, and
(viii) —S—$C_{1-6}$alkyl;

W is O or (H, OH);

X, Y and Z are independently, selected from:
(a) hydrogen,
(b) $C_{1-7}$ alkyl,
(c) $C_{2-6}$ alkenyl,
(d) halogen,
(e) —$(CH_2)_m$—$NR^6R^7$, wherein $R^6$ and $R^7$ are, independently selected from
(i) hydrogen, or
(ii) $C_{1-6}$ alkyl unsubstituted or substituted with phenyl, and
m is 0 to 2,
(f) —CN, (g) —CHO,
(h) —CF$_3$,
(i) —SR$^8$, wherein R$^8$ is hydrogen, C$_{1-6}$alkyl, trifluoromethyl, or phenyl,
(j) —SOR$^8$, wherein R$^8$ is as defined above,
(k) —SO$_2$R$^8$, wherein R$^8$ is as defined above,
(l) —CONR$^6$R$^7$, wherein R$^6$ and R$^7$ are as defined above,
(m) R$^9$O(CH$_2$)$_m$— wherein R$^9$ is hydrogen, C$_{1-3}$ alkyl, hydroxy-C$_{2-3}$alkyl, trifluoromethyl, phenyl or naphthyl and m is as defined above,
(n) —CH(OR$^{12}$)(OR$^{13}$), wherein R$^{12}$ and R$^{13}$ are C$_{1-3}$ alkyl or taken together form an ethyl or propyl bridge,
(o)

wherein R$^9$ and m are as defined above, and
(p)

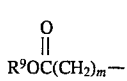

wherein R$^9$ and m are as defined above, and
(q) —OR$^{11}$;
or any two of adjacent X, Y and Z can be joined to form a ring having 5,6 or 7 ring atoms, said ring atoms comprising 1 or 2 oxygen atoms, the remaining ring atoms being carbon, selected from the group consisting of: dioxolanyl, dihydrofuranyl, dihydropyranyl, and dioxanyl; and
n is 1 or 2.
Another embodiment of the present invention encompasses the compounds of Formula I wherein:
R$^1$ and R$^2$ are independently selected from:
(1) hydrogen;
(2) C$_{1-10}$ alkyl;
(3) substituted C$_{1-10}$ alkyl in which one or more substituent(s) is(are) selected from:
(a) hydroxy,
(b) oxo,
(c) C$_{1-6}$-alkoxy,
(d) phenyl-C$_{1-3}$alkoxy,
(e) substituted phenyl-C$_{1-3}$alkoxy, in which the substituents on phenyl are X, Y and Z,
(f) —OCO—C$_{1-6}$alkyl,
(g) —NR$^6$R$^7$, wherein R$^6$ and R$^7$ are independently selected from
(i) hydrogen,
(ii) C$_{1-10}$alkyl unsubstituted or substituted with one or more of the substituent(s) selected from:
(a') phenyl, which is unsubstituted or substituted with X, Y and Z,
(b') —OH,
(c') C$_{1-6}$alkoxy,
(d') —CO$_2$H,
(e') —CO$_2$—C$_{1-6}$alkyl,
(f') —C$_{3-7}$cycloalkyl, and
(g') —OR$^{11}$,
(iii) C$_{3-10}$alkenyl unsubstituted or substituted with one or more of the substituent(s) selected from:
(a') phenyl, which is unsubstituted or substituted with X, Y and Z,
(b') —OH,
(c') C$_{1-6}$alkoxy,
(d') —CO$_2$H,
(e') —CO$_2$—C$_{1-6}$alkyl,
(f') —C$_{3-7}$cycloalkyl, and
(g') —OR$^{11}$,
(iv) or where R$^6$ and R$^7$ and the N to which they are attached can form an unsubstituted or substituted 3–7-membered saturated heterocyclic ring which can include one or two additional heteroatoms independently selected from the group consisting of O, S(O)$_p$, NR$^{14}$, wherein R$^{14}$ is hydrogen or C$_{1-6}$ alkyl unsubstituted or substituted by phenyl, and p is 0, 1 or 2, the ring being selected from the group consisting of: aziridine, morpholine, thiomorpholine, thiomorpholine-oxide, thiomorpholine-dioxide, piperidine, pyrrolidine, and piperazine,
(h) —NR$^6$CO—C$_{1-6}$alkyl-R$^7$, wherein R$^6$ is as defined above,
(i) —NR$^6$CO$_2$—C$_{1-6}$alkyl-R$^7$,
(j) —NR$^6$CONR$^6$R$^7$,
(k) —OCONR$^6$R$^7$,
(l) —COOR$^6$,
(m) —CHO,
(n) phenyl,
(o) substituted phenyl in which the substituents are X, Y and Z,
(p) phenyloxy,
(q) substituted phenyloxy in which the substituents are X, Y and Z,
(r) 1- or 2-naphthyl,
(s) substituted 1- or 2-naphthyl in which the substituents are X, Y and Z,
(t) biphenyl,
(u) substituted biphenyl in which the substituents are X, Y and Z;
(v) —OR11, and
(w) —S(O)$_p$—C$_{1-6}$alkyl;
(4) C$_{3-10}$ alkenyl;
(5) substituted C$_{3-10}$ alkenyl in which one or more substituent(s) is(are) selected from:
(a) hydroxy,
(b) oxo,
(c) C$_{1-6}$alkoxy,
(d) phenyl-C$_{1-3}$alkoxy,
(e) substituted phenyl-C$_{1-3}$alkoxy, in which the substituents on phenyl are X, Y and Z,
(f) —OCO—C$_{1-6}$alkyl,
(g) —NR$^6$R$^7$, wherein R$^6$ and R$^7$ are as defined above
(h) —NR$^6$CO—C$_{1-6}$alkyl, wherein R$^6$ is as defined above,
(i) —COOR$^6$, wherein R$^6$ is as defined above,
(j) —CHO,
(k) phenyl,
(l) substituted phenyl in which the substituents are X, Y and Z,
(m) 1- or 2-naphthyl,
(n) substituted 1- or 2-naphthyl in which the substituents are X, Y and Z,
(o) biphenyl,
(p) substituted biphenyl in which the substituents are X, Y and Z,
(q) —OR$^{11}$, and
(r) —S(O)$_p$—C$_{1-6}$alkyl;
(6) C$_{3-10}$alkynyl;
(7) substituted C$_{3-10}$alkynyl in which one or more substituent(s) is(are) selected from:

(a) hydroxy,
(b) oxo,
(c) $C_{1-6}$alkoxy,
(d) phenyl-$C_{1-3}$alkoxy,
(e) substituted phenyl-$C_{1-3}$alkoxy, in which the substituents on phenyl are X, Y and Z,
(f) —OCO—$C_{1-6}$alkyl,
(g) —$NR^6R^7$, wherein $R^6$ and $R^7$ are as defined above,
(h) —$NR^6$CO—$C_{1-6}$alkyl, wherein $R^6$ is as defined above,
(i) —$COOR^6$, wherein $R^6$ is as defined above,
(j) —CHO,
(k) phenyl,
(l) substituted phenyl in which the substituents are X, Y and Z,
(m) 1- or 2-naphthyl,
(n) substituted 1- or 2-naphthyl in which the substituents are X, Y and Z,
(o) biphenyl,
(p) substituted biphenyl in which the substituents are X, Y and Z, and
(q) —$OR^{11}$;
with the proviso that $R^1$ and $R^2$ are not simultaneously hydrogen, methyl or combinations thereof;
$R^3$ is hydrogen, hydroxy, —$OR^{11}$ or $C_{1-6}$ alkoxy;
$R^4$ is hydrogen, or $R^3$ and $R^4$ taken together form a double bond;
$R^5$ is methyl, ethyl, propyl or allyl;
$R^{11}$ is selected from:
  (a) —PO(OH)O—$M^+$, wherein $M^+$ is a positively charged inorganic or organic counterion,
  (b) —$SO_3$—$M^+$,
  (c) —CO$(CH_2)_q$$CO_2$—$M^+$, wherein q is 1–3, and
  (d) —CO—$C_{1-6}$alkyl-$NR^6R^7$, wherein $R^6$ and $R^7$ are as defined above and the alkyl is unsubstituted or substituted with one or more substituents selected from:
    (i) hydroxy,
    (ii) $C_{1-6}$alkoxy,
    (iii) —$NR^{16}R^{17}$, wherein $R^{16}$ and $R^{17}$ are independently selected from:
      (a') hydrogen, and
      (b') $C_{1-6}$alkyl,
    (iv) —$COOR^6$, wherein $R^6$ is as defined above,
    (v) phenyl,
    (vi) substituted phenyl in which the substituents are X, Y and Z,
    (vii) —SH, and
    (viii) —S—$C_{1-6}$alkyl;
W is O or (H, OH);
X, Y and Z independently are selected from:
  (a) hydrogen,
  (b) $C_{1-7}$ alkyl,
  (c) $C_{2-6}$ alkenyl,
  (d) halogen,
  (e) —$(CH_2)_m$—$NR^6R^7$, wherein $R^6$ and $R^7$ are as defined above, and m is 0 to 2,
  (f) —CN,
  (g) —CHO,
  (h) —$CF_3$,
  (i) —$SR^8$, wherein $R^8$ is hydrogen, $C_{1-6}$alkyl, trifluoromethyl, or phenyl,
  (j) —$SOR^8$, wherein $R^8$ is as defined above,
  (k) —$SO_2R^8$, wherein $R^8$ is as defined above,
  (l) —$CONR^6R^7$, wherein $R^6$ and $R^7$ are as defined above,
  (m) $R^9O(CH_2)_m$— wherein $R^9$ is hydrogen, $C_{1-3}$ alkyl, hydroxy-$C_{2-3}$alkyl, trifluoromethyl, phenyl or naphthyl and m is as defined above,
  (n) —$CH(OR^{12})(OR^{13})$, wherein $R^{12}$ and $R^{13}$ are $C_{1-3}$alkyl or taken together form an ethyl or propyl bridge,
  (o)

wherein $R^9$ and m are as defined above, and
  (p)

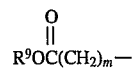

wherein $R^9$ and m are as defined above, and
  (q) —$OR^{11}$;
or any two of adjacent X, Y and Z can be joined to form a ring having 5, 6 or 7 ring atoms, said ring atoms comprising 1 or 2 oxygen atoms, the remaining ring atoms being carbon, selected from the group consisting of: dioxolanyl, dihydrofuranyl, dihydropyranyl, and dioxanyl; and
n is 1 or 2.

In the present invention it is preferred that in compounds of Formula I:
$R^1$ and $R^2$ are independently selected from:
  (1) hydrogen;
  (2) phenyl;
  (3) substituted phenyl in which the substituents are X, Y and Z;
  (4) 1- or 2-naphthyl;
  (5) substituted 1- or 2-naphthyl in which the substituents are X, Y and Z;
  (6) $C_{1-10}$ alkyl;
  (7) substituted $C_{1-10}$ alkyl in which one or more substituent(s) is(are) selected from
    (a) hydroxy,
    (b) oxo,
    (c) $C_{1-6}$-alkoxy,
    (d) phenyl-$C_{1-3}$alkoxy,
    (e) substituted phenyl-$C_{1-3}$alkoxy, in which the substituents on phenyl are X, Y and Z,
    (f) —OCO—$C_{1-6}$alkyl,
    (g) —$NR^6R^7$, wherein $R^6$ and $R^7$ are independently selected from
      (i) hydrogen,
      (ii) $C_{1-10}$alkyl unsubstituted or substituted with one or more of the substituent(s) selected from:
        (a') phenyl, which is unsubstituted or substituted with X, Y and Z,
        (b') —OH,
        (c') $C_{1-6}$alkoxy,
        (d') —$CO_2H$,
        (e') —$CO_2$—$C_{1-6}$alkyl,
        (f') —$C_{3-7}$cycloalkyl, and
        (g') —$OR^{11}$,
      (iii) $C_{3-10}$alkenyl unsubstituted or substituted with one or more of the substituent(s) selected from:
        (a') phenyl, which is unsubstituted or substituted with X, Y and Z,
        (b') —OH, (c') $C_{1-6}$alkoxy,
(d') —$CO_2H$,
(e') —$CO_2$—$C_{1-6}$alkyl,
(f') —$C_{3-7}$cycloalkyl, and
(g') —$OR^{11}$,
(iv) or where $R^6$ and $R^7$ and the N to which they are attached may form an unsubstituted or substituted 3–7-membered saturated heterocyclic ring which may include one or two additional heteroatoms independently selected from the group consisting of O, $S(O)_p$, $NR^{14}$, wherein $R^{14}$ is hydrogen or $C_{1-6}$ alkyl unsubstituted or substituted by phenyl, and p is 0, 1 or 2, the ring being selected from the group consisting of: aziridine, morpholine, thiomorpholine, thiomorpholine-oxide, thiomorpholine-dioxide, piperidine, pyrrolidine, and piperazine, (h) —$NR^6CO$—$C_{1-6}$alkyl-$R^7$, wherein $R^6$ is as defined above,
(i) —$NR^6CO_2$—$C_{1-6}$alkyl-$R^7$,
(j) —$NR^6CONR^6R^7$,
(k) —$OCONR^6R^7$,
(l) —$COOR^6$,
(m) —CHO,
(n) phenyl,
(o) substituted phenyl in which the substituents are X, Y and Z,
(p) phenyloxy,
(q) substituted phenyloxy in which the substituents are X, Y and Z,
(r) 1- or 2-naphthyl,
(s) substituted 1- or 2- and naphthyl in which the substituents are X, Y and Z, and
(t) —$OR^{11}$;

(8) $C_{3-10}$ alkenyl;
(9) substituted $C_{3-10}$ alkenyl in which one or more substituent(s) is(are) selected from:
(a) hydroxy,
(b) oxo,
(c) $C_{1-6}$ alkoxy,
(d) —$OCOC_{1-6}$ alkyl,
(e) $C_{2-8}$ alkenyl,
(f) phenyl,
(g) substituted phenyl in which the substituents are X, Y and Z,
(h) 1- or 2-naphthyl, and
(i) substituted 1- or 2-naphthyl in which the substituents are X, Y and Z,

(10) $C_{3-10}$ alkynyl;
(11) substituted $C_{3-10}$ alkynyl in which one or more substituent(s) is(are) selected from:
(a) hydroxy,
(b) oxo,
(c) $C_{1-6}$ alkoxy,
(d) —$OCOC_{1-6}$ alkyl,
(e) phenyl,
(f) substituted phenyl in which the substituents are X, Y and Z,
(g) 1- or 2-naphthyl, and
(h) substituted 1- or 2-naphthyl in which the substituents are X, Y and Z;

with the proviso that $R^1$ and $R^2$ are not simultaneously hydrogen, methyl or combinations thereof;
$R^3$ is hydrogen, or hydroxy;
$R^4$ is hydrogen;
$R^5$ is ethyl, propyl or allyl;
$R^{11}$ is selected from:
(a) —$PO(OH)O$—$M^+$, wherein $M^+$ is a positively charged inorganic or organic counterion,
(b) —$SO_3$—$M^+$,
(c) —$CO(CH_2)_qCO_2$—$M^+$, wherein q is 1–3, and
(d) —$CO$—$C_{1-6}$alkyl-$NR^6R^7$, wherein $R^6$ and $R^7$ are as defined above and the alkyl is unsubstituted or substituted with one or more substituents selected from:
(i) hydroxy,
(ii) $C_{1-6}$alkoxy,
(iii) —$NR^{16}R^{17}$, wherein $R^{16}$ and $R^{17}$ are independently selected from:
(a') hydrogen, and
(b') $C_{1-6}$alkyl,
(iv) —$COOR^6$, wherein $R^6$ is as defined above,
(v) phenyl,
(vi) substituted phenyl in which the substituents are X, Y and Z,
(vii) —SH, and
(viii) —S—$C_{1-6}$alkyl;

W is O or (H, OH);
X, Y and Z independently are selected from:
(a) hydrogen,
(b) $C_{1-7}$ alkyl,
(c) $C_{2-6}$ alkenyl,
(d) halogen,
(e) —CN,
(f) —CHO,
(g) —$CF_3$,
(h) —$SR^8$, wherein $R^8$ is hydrogen, $C_{1-6}$alkyl, trifluoromethyl, or phenyl,
(i) —$CONR^6R^7$, wherein $R^6$ and $R^7$ are as defined above,
(j) $R^9O(CH_2)_m$— wherein $R^9$ is hydrogen, $C_{1-3}$ alkyl, hydroxy-$C_{2-3}$alkyl, trifluoromethyl, phenyl or naphthyl and m is as defined above,
(k) —$CH(OR^{12})(OR^{13})$, wherein $R^{12}$ and $R^{13}$ are $C_{1-3}$alkyl or taken together form an ethyl or propyl bridge,
(l)

$$\underset{\|}{R^9CO(CH_2)_m-}^{O}$$

wherein $R^9$ and m are as defined above,
(m)

$$\underset{\|}{R^9OC(CH_2)_m-}^{O}$$

wherein $R^9$ and m are as defined above, and;
(n) —$OR^{11}$;

or any two of adjacent X, Y and Z may be joined to form a ring having 5, 6 or 7 ring atoms, said ring atoms comprising 1 or 2 oxygen atoms, the remaining ring atoms being carbon, selected from the group consisting of: dioxolanyl, dihydrofuranyl, dihydropyranyl, and dioxanyl; and
n is 2;
and pharmaceutically acceptable salts thereof.

Representative compounds of the present invention include the compounds of Formula V, VI, VII and VIII:

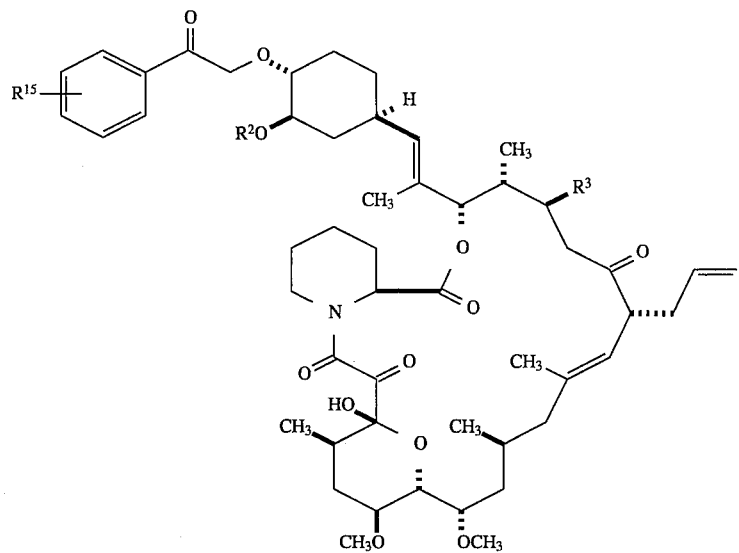
V
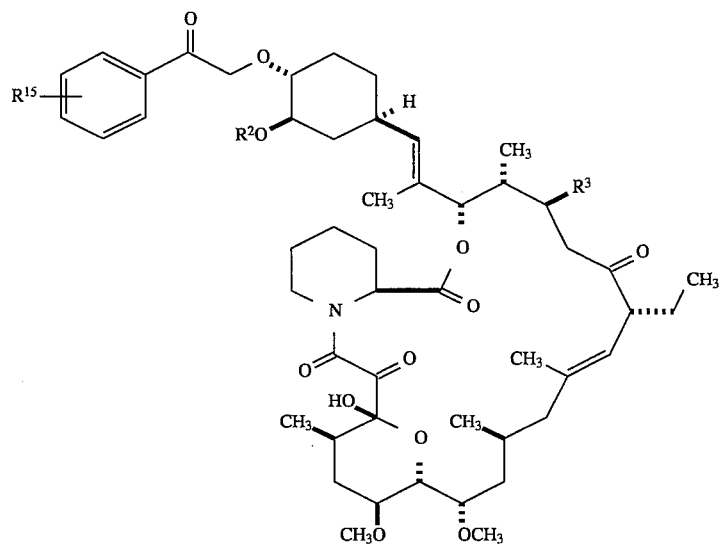
VI
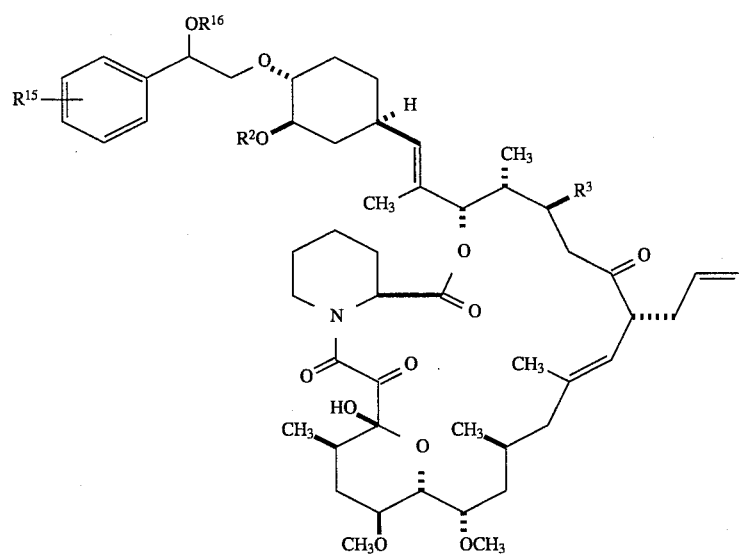
VII

VII

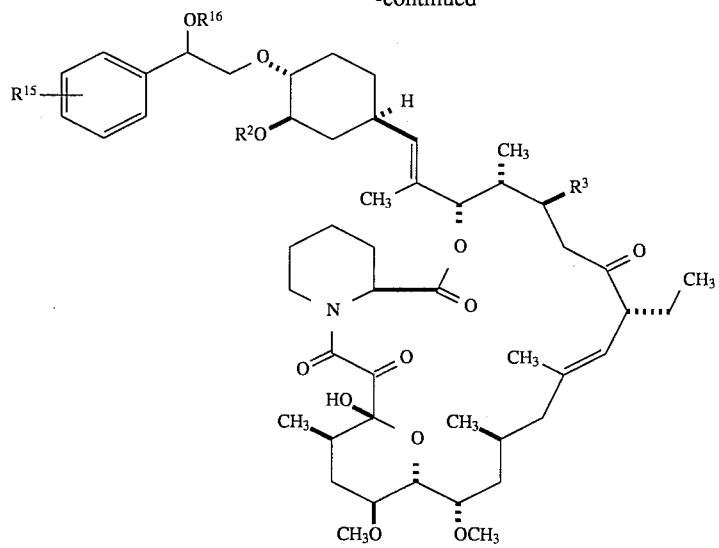

wherein $R^{16}$ is H, methyl, ethyl, allyl or benzyl, $R^3$ is OH or H and $R^{15}$ and $R^2$ are selected from the following groups of substituents:

| $R^{15}$ | $R^2$ |
|---|---|
| H | H |
| 2-F | H |
| 2-Cl | H |
| 2-Br | H |
| 2-CN | H |
| 2-CH$_3$ | H |
| 2-CF$_3$ | H |
| 2-CH$_3$CH$_2$ | H |
| 2-OH | H |
| 2-NO$_2$ | H |
| 2-NH$_2$ | H |
| 2-CF$_3$O | H |
| 2-CH$_3$O | H |
| 2-CH$_3$CH$_2$O | H |
| 2-CH$_3$S | H |
| 2-CH$_3$S(O) | H |
| 2-CH$_3$SO$_2$ | H |
| 3-F | H |
| 3-Cl | H |
| 3-Br | H |
| 3-CN | H |
| 3-CH$_3$ | H |
| 3-CF$_3$ | H |
| 3-CH$_3$CH$_2$ | H |
| 3-OH | H |
| 3-NO$_2$ | H |
| 3-NH$_2$ | H |
| 3-CF$_3$O | H |
| 3-CH$_3$O | H |
| 3-CH$_3$CH$_2$O | H |
| 3-CH$_3$S | H |
| 3-CH$_3$S(O) | H |
| 3-CH$_3$SO$_2$ | H |
| 4-F | H |
| 4-Cl | H |
| 4-Br | H |
| 4-CN | H |
| 4-CH$_3$ | H |
| 4-CF$_3$ | H |
| 4-CH$_3$CH$_2$ | H |
| 4-OH | H |
| 4-NO$_2$ | H |
| 4-NH$_2$ | H |
| 4-CF$_3$O | H |
| 4-CH$_3$O | H |
| 4-CH$_3$CH$_2$O | H |
| 4-CH$_3$S | H |

-continued

| $R^{15}$ | $R^2$ |
|---|---|
| 4-CH$_3$S(O) | H |
| 4-CH$_3$SO$_2$ | H |
| 3,5-di-F | H |
| 3,5-di-Cl | H |
| 3,5-di-Br | H |
| 3,5-di-CH$_3$ | H |
| 3,5-di-CH$_3$CH$_2$ | H |
| 3,5-di-CH$_3$O | H |
| 3,5-di-CH$_3$CH$_2$O | H |
| H | CH$_3$ |
| 2-F | CH$_3$ |
| 2-Cl | CH$_3$ |
| 2-Br | CH$_3$ |
| 2-CN | CH$_3$ |
| 2-CH$_3$ | CH$_3$ |
| 2-CF$_3$ | CH$_3$ |
| 2-CH$_3$CH$_2$ | CH$_3$ |
| 2-OH | CH$_3$ |
| 2-NO$_2$ | CH$_3$ |
| 2-NH$_2$ | CH$_3$ |
| 2-CF$_3$O | CH$_3$ |
| 2-CH$_3$O | CH$_3$ |
| 2-CH$_3$CH$_2$O | CH$_3$ |
| 2-CH$_3$S | CH$_3$ |
| 2-CH$_3$S(O) | CH$_3$ |
| 2-CH$_3$SO$_2$ | CH$_3$ |
| 3-F | CH$_3$ |
| 3-Cl | CH$_3$ |
| 3-Br | CH$_3$ |
| 3-CN | CH$_3$ |
| 3-CH$_3$ | CH$_3$ |
| 3-CF$_3$ | CH$_3$ |
| 3-CH$_3$CH$_2$ | CH$_3$ |
| 3-OH | CH$_3$ |
| 3-NO$_2$ | CH$_3$ |
| 3-NH$_2$ | CH$_3$ |
| 3-CF$_3$O | CH$_3$ |
| 3-CH$_3$O | CH$_3$ |
| 3-CH$_3$CH$_2$O | CH$_3$ |
| 3-CH$_3$S | CH$_3$ |
| 3-CH$_3$S(O) | CH$_3$ |
| 3-CH$_3$SO$_2$ | CH$_3$ |
| 4-F | CH$_3$ |
| 4-Cl | CH$_3$ |
| 4-Br | CH$_3$ |
| 4-CN | CH$_3$ |
| 4-CH$_3$ | CH$_3$ |
| 4-CF$_3$ | CH$_3$ |
| 4-CH$_3$CH$_2$ | CH$_3$ |
| 4-OH | CH$_3$ |

| R$^{15}$ | R$^2$ |
|---|---|
| 4-NO$_2$ | CH$_3$ |
| 4-NH$_2$ | CH$_3$ |
| 4-CF$_3$O | CH$_3$ |
| 4-CH$_3$O | CH$_3$ |
| 4-CH$_3$CH$_2$O | CH$_3$ |
| 4-CH$_3$S | CH$_3$ |
| 4-CH$_3$S(O) | CH$_3$ |
| 4-CH$_3$SO$_2$ | CH$_3$ |
| 3,5-di-F | CH$_3$ |
| 3,5-di-Cl | CH$_3$ |
| 3,5-di-Br | CH$_3$ |
| 3,5-di-CH$_3$ | CH$_3$ |
| 3,5-di-CH$_3$CH$_2$ | CH$_3$ |
| 3,5-di-CH$_3$O | CH$_3$ |
| 3,5-di-CH$_3$CH$_2$O | CH$_3$ |
| H | CH$_3$CH$_2$ |
| 2-F | CH$_3$CH$_2$ |
| 2-Cl | CH$_3$CH$_2$ |
| 2-Br | CH$_3$CH$_2$ |
| 2-CN | CH$_3$CH$_2$ |
| 2-CH$_3$ | CH$_3$CH$_2$ |
| 2-CF$_3$ | CH$_3$CH$_2$ |
| 2-CH$_3$CH$_2$ | CH$_3$CH$_2$ |
| 2-OH | CH$_3$CH$_2$ |
| 2-NO$_2$ | CH$_3$CH$_2$ |
| 2-NH$_2$ | CH$_3$CH$_2$ |
| 2-CF$_3$O | CH$_3$CH$_2$ |
| 2-CH$_3$O | CH$_3$CH$_2$ |
| 2-CH$_3$CH$_2$O | CH$_3$CH$_2$ |
| 2-CH$_3$S | CH$_3$CH$_2$ |
| 2-CH$_3$S(O) | CH$_3$CH$_2$ |
| 2-CH$_3$SO$_2$ | CH$_3$CH$_2$ |
| 3-F | CH$_3$CH$_2$ |
| 3-Cl | CH$_3$CH$_2$ |
| 3-Br | CH$_3$CH$_2$ |
| 3-CN | CH$_3$CH$_2$ |
| 3-CH$_3$ | CH$_3$CH$_2$ |
| 3-CF$_3$ | CH$_3$CH$_2$ |
| 3-CH$_3$CH$_2$ | CH$_3$CH$_2$ |
| 3-OH | CH$_3$CH$_2$ |
| 3-NO$_2$ | CH$_3$CH$_2$ |
| 3-NH$_2$ | CH$_3$CH$_2$ |
| 3-CF$_3$O | CH$_3$CH$_2$ |
| 3-CH$_3$O | CH$_3$CH$_2$ |
| 3-CH$_3$CH$_2$O | CH$_3$CH$_2$ |
| 3-CH$_3$S | CH$_3$CH$_2$ |
| 3-CH$_3$S(O) | CH$_3$CH$_2$ |
| 3-CH$_3$SO$_2$ | CH$_3$CH$_2$ |
| 4-F | CH$_3$CH$_2$ |
| 4-Cl | CH$_3$CH$_2$ |
| 4-Br | CH$_3$CH$_2$ |
| 4-CN | CH$_3$CH$_2$ |
| 4-CH$_3$ | CH$_3$CH$_2$ |
| 4-CF$_3$ | CH$_3$CH$_2$ |
| 4-CH$_3$CH$_2$ | CH$_3$CH$_2$ |
| 4-OH | CH$_3$CH$_2$ |
| 4-NO$_2$ | CH$_3$CH$_2$ |
| 4-NH$_2$ | CH$_3$CH$_2$ |
| 4-CF$_3$O | CH$_3$CH$_2$ |
| 4-CH$_3$O | CH$_3$CH$_2$ |
| 4-CH$_3$CH$_2$O | CH$_3$CH$_2$ |
| 4-CH$_3$S | CH$_3$CH$_2$ |
| 4-CH$_3$S(O) | CH$_3$CH$_2$ |
| 4-CH$_3$SO$_2$ | CH$_3$CH$_2$ |
| 3,5-di-F | CH$_3$CH$_2$ |
| 3,5-di-Cl | CH$_3$CH$_2$ |
| 3,5-di-Br | CH$_3$CH$_2$ |
| 3,5-di-CH$_3$ | CH$_3$CH$_2$ |
| 3,5-di-CH$_3$CH$_2$ | CH$_3$CH$_2$ |
| 3,5-di-CH$_3$O | CH$_3$CH$_2$ |
| 3,5-di-CH$_3$CH$_2$O | CH$_3$CH$_2$ |
| H | allyl |
| 2-F | allyl |
| 2-Cl | allyl |
| 2-Br | allyl |
| 2-CN | allyl |
| 2-CH$_3$ | allyl |
| 2-CF$_3$ | allyl |
| 2-CH$_3$CH$_2$ | allyl |
| 2-OH | allyl |
| 2-NO$_2$ | allyl |
| 2-NH$_2$ | allyl |
| 2-CF$_3$O | allyl |
| 2-CH$_3$O | allyl |
| 2-CH$_3$CH$_2$O | allyl |
| 2-CH$_3$S | allyl |
| 2-CH$_3$S(O) | allyl |
| 2-CH$_3$SO$_2$ | allyl |
| 3-F | allyl |
| 3-Cl | allyl |
| 3-Br | allyl |
| 3-CN | allyl |
| 3-CH$_3$ | allyl |
| 3-CF$_3$ | allyl |
| 3-CH$_3$CH$_2$ | allyl |
| 3-OH | allyl |
| 3-NO$_2$ | allyl |
| 3-NH$_2$ | allyl |
| 3-CF$_3$O | allyl |
| 3-CH$_3$O | allyl |
| 3-CH$_3$CH$_2$O | allyl |
| 3-CH$_3$S | allyl |
| 3-CH$_3$S(O) | allyl |
| 3-CH$_3$SO$_2$ | allyl |
| 4-F | allyl |
| 4-Cl | allyl |
| 4-Br | allyl |
| 4-CN | allyl |
| 4-CH$_3$ | allyl |
| 4-CF$_3$ | allyl |
| 4-CH$_3$CH$_2$ | allyl |
| 4-OH | allyl |
| 4-NO$_2$ | allyl |
| 4-NH$_2$ | allyl |
| 4-CF$_3$O | allyl |
| 4-CH$_3$O | allyl |
| 4-CH$_3$CH$_2$O | allyl |
| 4-CH$_3$S | allyl |
| 4-CH$_3$S(O) | allyl |
| 4-CH$_3$SO$_2$ | allyl |
| 3,5-di-F | allyl |
| 3,5-di-Cl | allyl |
| 3,5-di-Br | allyl |
| 3,5-di-CH$_3$ | allyl |
| 3,5-di-CH$_3$CH$_2$ | allyl |
| 3,5-di-CH$_3$O | allyl |
| 3,5-di-CH$_3$CH$_2$O | allyl |
| H | CH$_3$CH$_2$CH$_2$ |
| 2-F | CH$_3$CH$_2$CH$_2$ |
| 2-Cl | CH$_3$CH$_2$CH$_2$ |
| 2-Br | CH$_3$CH$_2$CH$_2$ |
| 2-CN | CH$_3$CH$_2$CH$_2$ |
| 2-CH$_3$ | CH$_3$CH$_2$CH$_2$ |
| 2-CF$_3$ | CH$_3$CH$_2$CH$_2$ |
| 2-CH$_3$CH$_2$ | CH$_3$CH$_2$CH$_2$ |
| 2-OH | CH$_3$CH$_2$CH$_2$ |
| 2-NO$_2$ | CH$_3$CH$_2$CH$_2$ |
| 2-NH$_2$ | CH$_3$CH$_2$CH$_2$ |
| 2-CF$_3$O | CH$_3$CH$_2$CH$_2$ |
| 2-CH$_3$O | CH$_3$CH$_2$CH$_2$ |
| 2-CH$_3$CH$_2$O | CH$_3$CH$_2$CH$_2$ |
| 2-CH$_3$S | CH$_3$CH$_2$CH$_2$ |
| 2-CH$_3$S(O) | CH$_3$CH$_2$CH$_2$ |
| 2-CH$_3$SO$_2$ | CH$_3$CH$_2$CH$_2$ |
| 3-F | CH$_3$CH$_2$CH$_2$ |
| 3-Cl | CH$_3$CH$_2$CH$_2$ |
| 3-Br | CH$_3$CH$_2$CH$_2$ |
| 3-CN | CH$_3$CH$_2$CH$_2$ |
| 3-CH$_3$ | CH$_3$CH$_2$CH$_2$ |
| 3-CF$_3$ | CH$_3$CH$_2$CH$_2$ |
| 3-CH$_3$CH$_2$ | CH$_3$CH$_2$CH$_2$ |
| 3-OH | CH$_3$CH$_2$CH$_2$ |
| 3-NO$_2$ | CH$_3$CH$_2$CH$_2$ |
| 3-NH$_2$ | CH$_3$CH$_2$CH$_2$ |
| 3-CH$_3$O | CH$_3$CH$_2$CH$_2$ |
| 3-CH$_3$CH$_2$O | CH$_3$CH$_2$CH$_2$ |

| R¹⁵ | R² |
|---|---|
| 3-CH₃S | CH₃CH₂CH₂ |
| 3-CH₃S(O) | CH₃CH₂CH₂ |
| 3-CH₃SO₂ | CH₃CH₂CH₂ |
| 4-F | CH₃CH₂CH₂ |
| 4-Cl | CH₃CH₂CH₂ |
| 4-Br | CH₃CH₂CH₂ |
| 4-CN | CH₃CH₂CH₂ |
| 4-CH₃ | CH₃CH₂CH₂ |
| 4-CF₃ | CH₃CH₂CH₂ |
| 4-CH₃CH₂ | CH₃CH₂CH₂ |
| 4-OH | CH₃CH₂CH₂ |
| 4-NO₂ | CH₃CH₂CH₂ |
| 4-NH₂ | CH₃CH₂CH₂ |
| 4-CF₃O | CH₃CH₂CH₂ |
| 4-CH₃O | CH₃CH₂CH₂ |
| 4-CH₃CH₂O | CH₃CH₂CH₂ |
| 4-CH₃S | CH₃CH₂CH₂ |
| 4-CH₃S(O) | CH₃CH₂CH₂ |
| 4-CH₃SO₂ | CH₃CH₂CH₂ |
| 3,5-di-F | CH₃CH₂CH₂ |
| 3,5-di-Cl | CH₃CH₂CH₂ |
| 3,5-di-Br | CH₃CH₂CH₂ |
| 3,5-di-CH₃ | CH₃CH₂CH₂ |
| 3,5-di-CH₃CH₂ | CH₃CH₂CH₂ |
| 3,5-di-CH₃O | CH₃CH₂CH₂ |
| 3,5-di-CH₃CH₂O | CH₃CH₂CH₂ |
| H | HOCH₂CH₂ |
| 2-F | HOCH₂CH₂ |
| 2-Cl | HOCH₂CH₂ |
| 2-Br | HOCH₂CH₂ |
| 2-CN | HOCH₂CH₂ |
| 2-CH₃ | HOCH₂CH₂ |
| 2-CF₃ | HOCH₂CH₂ |
| 2-CH₃CH₂ | HOCH₂CH₂ |
| 2-OH | HOCH₂CH₂ |
| 2-NO₂ | HOCH₂CH₂ |
| 2-NH₂ | HOCH₂CH₂ |
| 2-CF₃O | HOCH₂CH₂ |
| 2-CH₃O | HOCH₂CH₂ |
| 2-CH₃CH₂O | HOCH₂CH₂ |
| 2-CH₃S | HOCH₂CH₂ |
| 2-CH₃S(O) | HOCH₂CH₂ |
| 2-CH₃SO₂ | HOCH₂CH₂ |
| 3-F | HOCH₂CH₂ |
| 3-Cl | HOCH₂CH₂ |
| 3-Br | HOCH₂CH₂ |
| 3-CN | HOCH₂CH₂ |
| 3-CH₃ | HOCH₂CH₂ |
| 3-CF₃ | HOCH₂CH₂ |
| 3-CH₃CH₂ | HOCH₂CH₂ |
| 3-OH | HOCH₂CH₂ |
| 3-NO₂ | HOCH₂CH₂ |
| 3-NH₂ | HOCH₂CH₂ |
| 3-CF₃O | HOCH₂CH₂ |
| 3-CH₃O | HOCH₂CH₂ |
| 3-CH₃CH₂O | HOCH₂CH₂ |
| 3-CH₃S | HOCH₂CH₂ |
| 3-CH₃S(O) | HOCH₂CH₂ |
| 3-CH₃SO₂ | HOCH₂CH₂ |
| 4-F | HOCH₂CH₂ |
| 4-Cl | HOCH₂CH₂ |
| 4-Br | HOCH₂CH₂ |
| 4-CN | HOCH₂CH₂ |
| 4-CH₃ | HOCH₂CH₂ |
| 4-CF₃ | HOCH₂CH₂ |
| 4-CH₃CH₂ | HOCH₂CH₂ |
| 4-OH | HOCH₂CH₂ |
| 4-NO₂ | HOCH₂CH₂ |
| 4-NH₂ | HOCH₂CH₂ |
| 4-CF₃O | HOCH₂CH₂ |
| 4-CH₃O | HOCH₂CH₂ |
| 4-CH₃CH₂O | HOCH₂CH₂ |
| 4-CH₃S | HOCH₂CH₂ |
| 4-CH₃S(O) | HOCH₂CH₂ |
| 4-CH₃SO₂ | HOCH₂CH₂ |
| 3,5-di-F | HOCH₂CH₂ |
| 3,5-di-Cl | HOCH₂CH₂ |
| 3,5-di-Br | HOCH₂CH₂ |
| 3,5-di-CH₃ | HOCH₂CH₂ |
| 3,5-di-CH₃CH₂ | HOCH₂CH₂ |
| 3,5-di-CH₃O | HOCH₂CH₂ |
| 3,5-di-CH₃CH₂O | HOCH₂CH₂ |
| H | (CH₃)₂CH |
| 2-F | (CH₃)₂CH |
| 2-Cl | (CH₃)₂CH |
| 2-Br | (CH₃)₂CH |
| 2-CN | (CH₃)₂CH |
| 2-CH₃ | (CH₃)₂CH |
| 2-CF₃ | (CH₃)₂CH |
| 2-CH₃CH₂ | (CH₃)₂CH |
| 2-OH | (CH₃)₂CH |
| 2-NO₂ | (CH₃)₂CH |
| 2-NH₂ | (CH₃)₂CH |
| 2-CF₃O | (CH₃)₂CH |
| 2-CH₃O | (CH₃)₂CH |
| 2-CH₃CH₂O | (CH₃)₂CH |
| 2-CH₃S | (CH₃)₂CH |
| 2-CH₃S(O) | (CH₃)₂CH |
| 2-CH₃SO₂ | (CH₃)₂CH |
| 3-F | (CH₃)₂CH |
| 3-Cl | (CH₃)₂CH |
| 3-Br | (CH₃)₂CH |
| 3-CN | (CH₃)₂CH |
| 3-CH₃ | (CH₃)₂CH |
| 3-CF₃ | (CH₃)₂CH |
| 3-CH₃CH₂ | (CH₃)₂CH |
| 3-OH | (CH₃)₂CH |
| 3-NO₂ | (CH₃)₂CH |
| 3-NH₂ | (CH₃)₂CH |
| 3-CF₃O | (CH₃)₂CH |
| 3-CH₃O | (CH₃)₂CH |
| 3-CH₃CH₂O | (CH₃)₂CH |
| 3-CH₃S | (CH₃)₂CH |
| 3-CH₃S(O) | (CH₃)₂CH |
| 3-CH₃SO₂ | (CH₃)₂CH |
| 4-F | (CH₃)₂CH |
| 4-Cl | (CH₃)₂CH |
| 4-Br | (CH₃)₂CH |
| 4-CN | (CH₃)₂CH |
| 4-CH₃ | (CH₃)₂CH |
| 4-CF₃ | (CH₃)₂CH |
| 4-CH₃CH₂ | (CH₃)₂CH |
| 4-OH | (CH₃)₂CH |
| 4-NO₂ | (CH₃)₂CH |
| 4-NH₂ | (CH₃)₂CH |
| 4-CF₃O | (CH₃)₂CH |
| 4-CH₃O | (CH₃)₂CH |
| 4-CH₃CH₂O | (CH₃)₂CH |
| 4-CH₃S | (CH₃)₂CH |
| 4-CH₃S(O) | (CH₃)₂CH |
| 4-CH₃SO₂ | (CH₃)₂CH |
| 3,5-di-F | (CH₃)₂CH |
| 3,5-di-Cl | (CH₃)₂CH |
| 3,5-di-Br | (CH₃)₂CH |
| 3,5-di-CH₃ | (CH₃)₂CH |
| 3,5-di-CH₃CH₂ | (CH₃)₂CH |
| 3,5-di-CH₃O | (CH₃)₂CH |
| 3,5-di-CH₃CH₂O | (CH₃)₂CH |

Representative compounds of the present invention include the compounds of Formula IX and X:

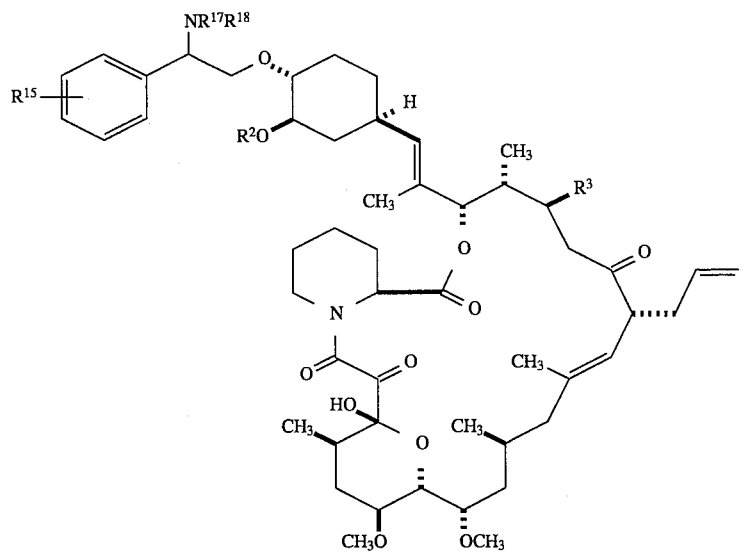

IX

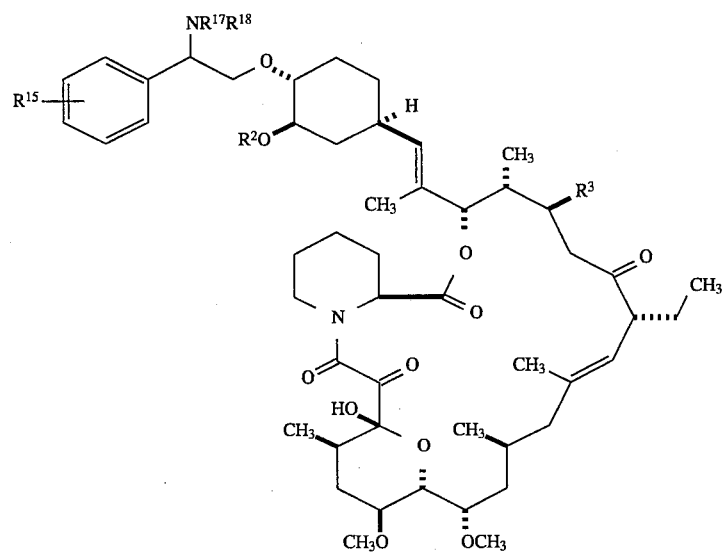

X wherein $R^{17}$ and $R^{18}$ are hydrogen, methyl or ethyl and $R^3$ is OH or H and $R^{15}$ and $R^2$ are selected from the following groups of substituents:

| $R^{15}$ | $R^2$ |
|---|---|
| H | H |
| 2-F | H |
| 2-Cl | H |
| 2-Br | H |
| 2-CN | H |
| 2-CH$_3$ | H |
| 2-CF$_3$ | H |
| 2-CH$_3$CH$_2$ | H |
| 2-OH | H |
| 2-NO$_2$ | H |
| 2-NH$_2$ | H |
| 2-CF$_3$O | H |
| 2-CH$_3$O | H |
| 2-CH$_3$CH$_2$O | H |
| 2-CH$_3$S | H |
| 2-CH$_3$S(O) | H |
| 2-CH$_3$SO$_2$ | H |
| 3-F | H |
| 3-Cl | H |
| 3-Br | H |
| 3-CN | H |

-continued

| $R^{15}$ | $R^2$ |
|---|---|
| 3-CH$_3$ | H |
| 3-CF$_3$ | H |
| 3-CH$_3$CH$_2$ | H |
| 3-OH | H |
| 3-NO$_2$ | H |
| 3-NH$_2$ | H |
| 3-CF$_3$O | H |
| 3-CH$_3$O | H |
| 3-CH$_3$CH$_2$O | H |
| 3-CH$_3$S | H |
| 3-CH$_3$S(O) | H |
| 3-CH$_3$SO$_2$ | H |
| 4-F | H |
| 4-Cl | H |
| 4-Br | H |
| 4-CN | H |
| 4-CH$_3$ | H |
| 4-CF$_3$ | H |
| 4-CH$_3$CH$_2$ | H |
| 4-OH | H |
| 4-NO$_2$ | H |
| 4-NH$_2$ | H |
| 4-CF$_3$O | H |
| 4-CH$_3$O | H |
| 4-CH$_3$CH$_2$O | H |

| R$^{15}$ | R$^2$ |
|---|---|
| 4-CH$_3$S | H |
| 4-CH$_3$S(O) | H |
| 4-CH$_3$SO$_2$ | H |
| 3,5-di-F | H |
| 3,5-di-Cl | H |
| 3,5-di-Br | H |
| 3,5-di-CH$_3$ | H |
| 3,5-di-CH$_3$CH$_2$ | H |
| 3,5-di-CH$_3$O | H |
| 3,5-di-CH$_3$CH$_2$O | H |
| H | CH$_3$ |
| 2-F | CH$_3$ |
| 2-Cl | CH$_3$ |
| 2-Br | CH$_3$ |
| 2-CN | CH$_3$ |
| 2-CH$_3$ | CH$_3$ |
| 2-CF$_3$ | CH$_3$ |
| 2-CH$_3$CH$_2$ | CH$_3$ |
| 2-OH | CH$_3$ |
| 2-NO$_2$ | CH$_3$ |
| 2-NH$_2$ | CH$_3$ |
| 2-CF$_3$O | CH$_3$ |
| 2-CH$_3$O | CH$_3$ |
| 2-CH$_3$CH$_2$O | CH$_3$ |
| 2-CH$_3$S | CH$_3$ |
| 2-CH$_3$S(O) | CH$_3$ |
| 2-CH$_3$SO$_2$ | CH$_3$ |
| 3-F | CH$_3$ |
| 3-Cl | CH$_3$ |
| 3-Br | CH$_3$ |
| 3-CN | CH$_3$ |
| 3-CH$_3$ | CH$_3$ |
| 3-CF$_3$ | CH$_3$ |
| 3-CH$_3$CH$_2$ | CH$_3$ |
| 3-OH | CH$_3$ |
| 3-NO$_2$ | CH$_3$ |
| 3-NH$_2$ | CH$_3$ |
| 3-CF$_3$O | CH$_3$ |
| 3-CH$_3$O | CH$_3$ |
| 3-CH$_3$CH$_2$O | CH$_3$ |
| 3-CH$_3$S | CH$_3$ |
| 3-CH$_3$S(O) | CH$_3$ |
| 3-CH$_3$SO$_2$ | CH$_3$ |
| 4-F | CH$_3$ |
| 4-Cl | CH$_3$ |
| 4-Br | CH$_3$ |
| 4-CN | CH$_3$ |
| 4-CH$_3$ | CH$_3$ |
| 4-CF$_3$ | CH$_3$ |
| 4-CH$_3$CH$_2$ | CH$_3$ |
| 4-OH | CH$_3$ |
| 4-NO$_2$ | CH$_3$ |
| 4-NH$_2$ | CH$_3$ |
| 4-CF$_3$O | CH$_3$ |
| 4-CH$_3$O | CH$_3$ |
| 4-CH$_3$CH$_2$O | CH$_3$ |
| 4-CH$_3$S | CH$_3$ |
| 4-CH$_3$S(O) | CH$_3$ |
| 4-CH$_3$SO$_2$ | CH$_3$ |
| 3,5-di-F | CH$_3$ |
| 3,5-di-Cl | CH$_3$ |
| 3,5-di-Br | CH$_3$ |
| 3,5-di-CH$_3$ | CH$_3$ |
| 3,5-di-CH$_3$CH$_2$ | CH$_3$ |
| 3,5-di-CH$_3$O | CH$_3$ |
| 3,5-di-CH$_3$CH$_2$O | CH$_3$ |
| H | CH$_3$CH$_2$ |
| 2-F | CH$_3$CH$_2$ |
| 2-Cl | CH$_3$CH$_2$ |
| 2-Br | CH$_3$CH$_2$ |
| 2-CN | CH$_3$CH$_2$ |
| 2-CH$_3$ | CH$_3$CH$_2$ |
| 2-CF$_3$ | CH$_3$CH$_2$ |
| 2-CH$_3$CH$_2$ | CH$_3$CH$_2$ |
| 2-OH | CH$_3$CH$_2$ |
| 2-NO$_2$ | CH$_3$CH$_2$ |
| 2-NH$_2$ | CH$_3$CH$_2$ |
| 2-CF$_3$O | CH$_3$CH$_2$ |
| 2-CH$_3$O | CH$_3$CH$_2$ |
| 2-CH$_3$CH$_2$O | CH$_3$CH$_2$ |
| 2-CH$_3$S | CH$_3$CH$_2$ |
| 2-CH$_3$S(O) | CH$_3$CH$_2$ |
| 2-CH$_3$SO$_2$ | CH$_3$CH$_2$ |
| 3-F | CH$_3$CH$_2$ |
| 3-Cl | CH$_3$CH$_2$ |
| 3-Br | CH$_3$CH$_2$ |
| 3-CN | CH$_3$CH$_2$ |
| 3-CH$_3$ | CH$_3$CH$_2$ |
| 3-CF$_3$ | CH$_3$CH$_2$ |
| 3-CH$_3$CH$_2$ | CH$_3$CH$_2$ |
| 3-OH | CH$_3$CH$_2$ |
| 3-NO$_2$ | CH$_3$CH$_2$ |
| 3-NH$_2$ | CH$_3$CH$_2$ |
| 3-CF$_3$O | CH$_3$CH$_2$ |
| 3-CH$_3$O | CH$_3$CH$_2$ |
| 3-CH$_3$CH$_2$O | CH$_3$CH$_2$ |
| 3-CH$_3$S | CH$_3$CH$_2$ |
| 3-CH$_3$S(O) | CH$_3$CH$_2$ |
| 3-CH$_3$SO$_2$ | CH$_3$CH$_2$ |
| 4-F | CH$_3$CH$_2$ |
| 4-Cl | CH$_3$CH$_2$ |
| 4-Br | CH$_3$CH$_2$ |
| 4-CN | CH$_3$CH$_2$ |
| 4-CH$_3$ | CH$_3$CH$_2$ |
| 4-CF$_3$ | CH$_3$CH$_2$ |
| 4-CH$_3$CH$_2$ | CH$_3$CH$_2$ |
| 4-OH | CH$_3$CH$_2$ |
| 4-NO$_2$ | CH$_3$CH$_2$ |
| 4-NH$_2$ | CH$_3$CH$_2$ |
| 4-CF$_3$O | CH$_3$CH$_2$ |
| 4-CH$_3$O | CH$_3$CH$_2$ |
| 4-CH$_3$CH$_2$O | CH$_3$CH$_2$ |
| 4-CH$_3$S | CH$_3$CH$_2$ |
| 4-CH$_3$S(O) | CH$_3$CH$_2$ |
| 4-CH$_3$SO$_2$ | CH$_3$CH$_2$ |
| 3,5-di-F | CH$_3$CH$_2$ |
| 3,5-di-Cl | CH$_3$CH$_2$ |
| 3,5-di-Br | CH$_3$CH$_2$ |
| 3,5-di-CH$_3$ | CH$_3$CH$_2$ |
| 3,5-di-CH$_3$CH$_2$ | CH$_3$CH$_2$ |
| 3,5-di-CH$_3$O | CH$_3$CH$_2$ |
| 3,5-di-CH$_3$CH$_2$O | CH$_3$CH$_2$ |
| H | allyl |
| 2-F | allyl |
| 2-Cl | allyl |
| 2-Br | allyl |
| 2-CN | allyl |
| 2-CH$_3$ | allyl |
| 2-CF$_3$ | allyl |
| 2-CH$_3$CH$_2$ | allyl |
| 2-OH | allyl |
| 2-NO$_2$ | allyl |
| 2-NH$_2$ | allyl |
| 2-CF$_3$O | allyl |
| 2-CH$_3$O | allyl |
| 2-CH$_3$CH$_2$O | allyl |
| 2-CH$_3$S | allyl |
| 2-CH$_3$S(O) | allyl |
| 2-CH$_3$SO$_2$ | allyl |
| 3-F | allyl |
| 3-Cl | allyl |
| 3-Br | allyl |
| 3-CN | allyl |
| 3-CH$_3$ | allyl |
| 3-CF$_3$ | allyl |
| 3-CH$_3$CH$_2$ | allyl |
| 3-OH | allyl |
| 3-NO$_2$ | allyl |
| 3-NH$_2$ | allyl |
| 3-CF$_3$O | allyl |
| 3-CH$_3$O | allyl |
| 3-CH$_3$CH$_2$O | allyl |
| 3-CH$_3$S | allyl |
| 3-CH$_3$S(O) | allyl |
| 3-CH$_3$SO$_2$ | allyl |
| 4-F | allyl |

-continued

| R$^{15}$ | R$^2$ |
|---|---|
| 4-Cl | allyl |
| 4-Br | allyl |
| 4-CN | allyl |
| 4-CH$_3$ | allyl |
| 4-CF$_3$ | allyl |
| 4-CH$_3$CH$_2$ | allyl |
| 4-OH | allyl |
| 4-NO$_2$ | allyl |
| 4-NH$_2$ | allyl |
| 4-CF$_3$O | allyl |
| 4-CH$_3$O | allyl |
| 4-CH$_3$CH$_2$O | allyl |
| 4-CH$_3$S | allyl |
| 4-CH$_3$S(O) | allyl |
| 4-CH$_3$SO$_2$ | allyl |
| 3,5-di-F | allyl |
| 3,5-di-Cl | allyl |
| 3,5-di-Br | allyl |
| 3,5-di-CH$_3$ | allyl |
| 3,5-di-CH$_3$CH$_2$ | allyl |
| 3,5-di-CH$_3$O | allyl |
| 3,5-di-CH$_3$CH$_2$O | allyl |
| H | CH$_3$CH$_2$CH$_2$ |
| 2-F | CH$_3$CH$_2$CH$_2$ |
| 2-Cl | CH$_3$CH$_2$CH$_2$ |
| 2-Br | CH$_3$CH$_2$CH$_2$ |
| 2-CN | CH$_3$CH$_2$CH$_2$ |
| 2-CH$_3$ | CH$_3$CH$_2$CH$_2$ |
| 2-CF$_3$ | CH$_3$CH$_2$CH$_2$ |
| 2-CH$_3$CH$_2$ | CH$_3$CH$_2$CH$_2$ |
| 2-OH | CH$_3$CH$_2$CH$_2$ |
| 2-NO$_2$ | CH$_3$CH$_2$CH$_2$ |
| 2-NH$_2$ | CH$_3$CH$_2$CH$_2$ |
| 2-CF$_3$O | CH$_3$CH$_2$CH$_2$ |
| 2-CH$_3$O | CH$_3$CH$_2$CH$_2$ |
| 2-CH$_3$CH$_2$O | CH$_3$CH$_2$CH$_2$ |
| 2-CH$_3$S | CH$_3$CH$_2$CH$_2$ |
| 2-CH$_3$S(O) | CH$_3$CH$_2$CH$_2$ |
| 2-CH$_3$SO$_2$ | CH$_3$CH$_2$CH$_2$ |
| 3-F | CH$_3$CH$_2$CH$_2$ |
| 3-Cl | CH$_3$CH$_2$CH$_2$ |
| 3-Br | CH$_3$CH$_2$CH$_2$ |
| 3-CN | CH$_3$CH$_2$CH$_2$ |
| 3-CH$_3$ | CH$_3$CH$_2$CH$_2$ |
| 3-CF$_3$ | CH$_3$CH$_2$CH$_2$ |
| 3-CH$_3$CH$_2$ | CH$_3$CH$_2$CH$_2$ |
| 3-OH | CH$_3$CH$_2$CH$_2$ |
| 3-NO$_2$ | CH$_3$CH$_2$CH$_2$ |
| 3-NH$_2$ | CH$_3$CH$_2$CH$_2$ |
| 3-CF$_3$O | CH$_3$CH$_2$CH$_2$ |
| 3-CH$_3$O | CH$_3$CH$_2$CH$_2$ |
| 3-CH$_3$CH$_2$O | CH$_3$CH$_2$CH$_2$ |
| 3-CH$_3$S | CH$_3$CH$_2$CH$_2$ |
| 3-CH$_3$S(O) | CH$_3$CH$_2$CH$_2$ |
| 3-CH$_3$SO$_2$ | CH$_3$CH$_2$CH$_2$ |
| 4-F | CH$_3$CH$_2$CH$_2$ |
| 4-Cl | CH$_3$CH$_2$CH$_2$ |
| 4-Br | CH$_3$CH$_2$CH$_2$ |
| 4-CN | CH$_3$CH$_2$CH$_2$ |
| 4-CH$_3$ | CH$_3$CH$_2$CH$_2$ |
| 4-CF$_3$ | CH$_3$CH$_2$CH$_2$ |
| 4-CH$_3$CH$_2$ | CH$_3$CH$_2$CH$_2$ |
| 4-OH | CH$_3$CH$_2$CH$_2$ |
| 4-NO$_2$ | CH$_3$CH$_2$CH$_2$ |
| 4-NH$_2$ | CH$_3$CH$_2$CH$_2$ |
| 4-CF$_3$O | CH$_3$CH$_2$CH$_2$ |
| 4-CH$_3$O | CH$_3$CH$_2$CH$_2$ |
| 4-CH$_3$CH$_2$O | CH$_3$CH$_2$CH$_2$ |
| 4-CH$_3$S | CH$_3$CH$_2$CH$_2$ |
| 4-CH$_3$S(O) | CH$_3$CH$_2$CH$_2$ |
| 4-CH$_3$SO$_2$ | CH$_3$CH$_2$CH$_2$ |
| 3,5-di-F | CH$_3$CH$_2$CH$_2$ |
| 3,5-di-Cl | CH$_3$CH$_2$CH$_2$ |
| 3,5-di-Br | CH$_3$CH$_2$CH$_2$ |
| 3,5-di-CH$_3$ | CH$_3$CH$_2$CH$_2$ |
| 3,5-di-CH$_3$CH$_2$ | CH$_3$CH$_2$CH$_2$ |
| 3,5-di-CH$_3$O | CH$_3$CH$_2$CH$_2$ |
| 3,5-di-CH$_3$CH$_2$O | CH$_3$CH$_2$CH$_2$ |

-continued

| R$^{15}$ | R$^2$ |
|---|---|
| H | HOCH$_2$CH$_2$ |
| 2-F | HOCH$_2$CH$_2$ |
| 2-Cl | HOCH$_2$CH$_2$ |
| 2-Br | HOCH$_2$CH$_2$ |
| 2-CN | HOCH$_2$CH$_2$ |
| 2-CH$_3$ | HOCH$_2$CH$_2$ |
| 2-CF$_3$ | HOCH$_2$CH$_2$ |
| 2-CH$_3$CH$_2$ | HOCH$_2$CH$_2$ |
| 2-OH | HOCH$_2$CH$_2$ |
| 2-NO$_2$ | HOCH$_2$CH$_2$ |
| 2-NH$_2$ | HOCH$_2$CH$_2$ |
| 2-CF$_3$O | HOCH$_2$CH$_2$ |
| 2-CH$_3$O | HOCH$_2$CH$_2$ |
| 2-CH$_3$CH$_2$O | HOCH$_2$CH$_2$ |
| 2-CH$_3$S | HOCH$_2$CH$_2$ |
| 2-CH$_3$S(O) | HOCH$_2$CH$_2$ |
| 2-CH$_3$SO$_2$ | HOCH$_2$CH$_2$ |
| 3-F | HOCH$_2$CH$_2$ |
| 3-Cl | HOCH$_2$CH$_2$ |
| 3-Br | HOCH$_2$CH$_2$ |
| 3-CN | HOCH$_2$CH$_2$ |
| 3-CH$_3$ | HOCH$_2$CH$_2$ |
| 3-CF$_3$ | HOCH$_2$CH$_2$ |
| 3-CH$_3$CH$_2$ | HOCH$_2$CH$_2$ |
| 3-OH | HOCH$_2$CH$_2$ |
| 3-NO$_2$ | HOCH$_2$CH$_2$ |
| 3-NH$_2$ | HOCH$_2$CH$_2$ |
| 3-CF$_3$O | HOCH$_2$CH$_2$ |
| 3-CH$_3$O | HOCH$_2$CH$_2$ |
| 3-CH$_3$CH$_2$O | HOCH$_2$CH$_2$ |
| 3-CH$_3$S | HOCH$_2$CH$_2$ |
| 3-CH$_3$S(O) | HOCH$_2$CH$_2$ |
| 3-CH$_3$SO$_2$ | HOCH$_2$CH$_2$ |
| 4-F | HOCH$_2$CH$_2$ |
| 4-Cl | HOCH$_2$CH$_2$ |
| 4-Br | HOCH$_2$CH$_2$ |
| 4-CN | HOCH$_2$CH$_2$ |
| 4-CH$_3$ | HOCH$_2$CH$_2$ |
| 4-CF$_3$ | HOCH$_2$CH$_2$ |
| 4-CH$_3$CH$_2$ | HOCH$_2$CH$_2$ |
| 4-OH | HOCH$_2$CH$_2$ |
| 4-NO$_2$ | HOCH$_2$CH$_2$ |
| 4-NH$_2$ | HOCH$_2$CH$_2$ |
| 4-CF$_3$O | HOCH$_2$CH$_2$ |
| 4-CH$_3$O | HOCH$_2$CH$_2$ |
| 4-CH$_3$CH$_2$O | HOCH$_2$CH$_2$ |
| 4-CH$_3$S | HOCH$_2$CH$_2$ |
| 4-CH$_3$S(O) | HOCH$_2$CH$_2$ |
| 4-CH$_3$SO$_2$ | HOCH$_2$CH$_2$ |
| 3,5-di-F | HOCH$_2$CH$_2$ |
| 3,5-di-Cl | HOCH$_2$CH$_2$ |
| 3,5-di-Br | HOCH$_2$CH$_2$ |
| 3,5-di-CH$_3$ | HOCH$_2$CH$_2$ |
| 3,5-di-CH$_3$CH$_2$ | HOCH$_2$CH$_2$ |
| 3,5-di-CH$_3$O | HOCH$_2$CH$_2$ |
| 3,5-di-CH$_3$CH$_2$O | HOCH$_2$CH$_2$ |
| H | (CH$_3$)$_2$CH |
| 2-F | (CH$_3$)$_2$CH |
| 2-Cl | (CH$_3$)$_2$CH |
| 2-Br | (CH$_3$)$_2$CH |
| 2-CN | (CH$_3$)$_2$CH |
| 2-CH$_3$ | (CH$_3$)$_2$CH |
| 2-CF$_3$ | (CH$_3$)$_2$CH |
| 2-CH$_3$CH$_2$ | (CH$_3$)$_2$CH |
| 2-OH | (CH$_3$)$_2$CH |
| 2-NO$_2$ | (CH$_3$)$_2$CH |
| 2-NH$_2$ | (CH$_3$)$_2$CH |
| 2-CF$_3$O | (CH$_3$)$_2$CH |
| 2-CH$_3$O | (CH$_3$)$_2$CH |
| 2-CH$_3$CH$_2$O | (CH$_3$)$_2$CH |
| 2-CH$_3$S | (CH$_3$)$_2$CH |
| 2-CH$_3$S(O) | (CH$_3$)$_2$CH |
| 2-CH$_3$SO$_2$ | (CH$_3$)$_2$CH |
| 3-F | (CH$_3$)$_2$CH |
| 3-Cl | (CH$_3$)$_2$CH |
| 3-Br | (CH$_3$)$_2$CH |
| 3-CN | (CH$_3$)$_2$CH |
| 3-CH$_3$ | (CH$_3$)$_2$CH |

31
-continued

| $R^{15}$ | $R^2$ |
|---|---|
| 3-CF$_3$ | (CH$_3$)$_2$CH |
| 3-CH$_3$CH$_2$ | (CH$_3$)$_2$CH |
| 3-OH | (CH$_3$)$_2$CH |
| 3-NO$_2$ | (CH$_3$)$_2$CH |
| 3-NH$_2$ | (CH$_3$)$_2$CH |
| 3-CF$_3$O | (CH$_3$)$_2$CH |
| 3-CH$_3$O | (CH$_3$)$_2$CH |
| 3-CH$_3$CH$_2$O | (CH$_3$)$_2$CH |
| 3-CH$_3$S | (CH$_3$)$_2$CH |
| 3-CH$_3$S(O) | (CH$_3$)$_2$CH |
| 3-CH$_3$SO$_2$ | (CH$_3$)$_2$CH |
| 4-F | (CH$_3$)$_2$CH |
| 4-Cl | (CH$_3$)$_2$CH |
| 4-Br | (CH$_3$)$_2$CH |
| 4-CN | (CH$_3$)$_2$CH |
| 4-CH$_3$ | (CH$_3$)$_2$CH |
| 4-CF$_3$ | (CH$_3$)$_2$CH |
| 4-CH$_3$CH$_2$ | (CH$_3$)$_2$CH |
| 4-OH | (CH$_3$)$_2$CH |
| 4-NO$_2$ | (CH$_3$)$_2$CH |
| 4-NH$_2$ | (CH$_3$)$_2$CH |
| 4-CF$_3$O | (CH$_3$)$_2$CH |
| 4-CH$_3$O | (CH$_3$)$_2$CH |
| 4-CH$_3$CH$_2$O | (CH$_3$)$_2$CH |
| 4-CH$_3$S | (CH$_3$)$_2$CH |
| 4-CH$_3$S(O) | (CH$_3$)$_2$CH |
| 4-CH$_3$SO$_2$ | (CH$_3$)$_2$CH |
| 3,5-di-F | (CH$_3$)$_2$CH |
| 3,5-di-Cl | (CH$_3$)$_2$CH |
| 3,5-di-Br | (CH$_3$)$_2$CH |
| 3,5-di-CH$_3$ | (CH$_3$)$_2$CH |
| 3,5-di-CH$_3$CH$_2$ | (CH$_3$)$_2$CH |
| 3,5-di-CH$_3$O | (CH$_3$)$_2$CH |
| 3,5-di-CH$_3$CH$_2$O | (CH$_3$)$_2$CH |

Representative compounds of the present invention include the compounds of Formula XI, XII, XIII or XIV:

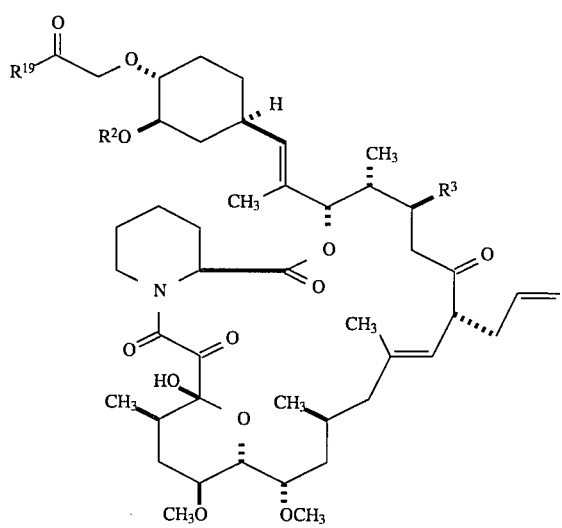

XI

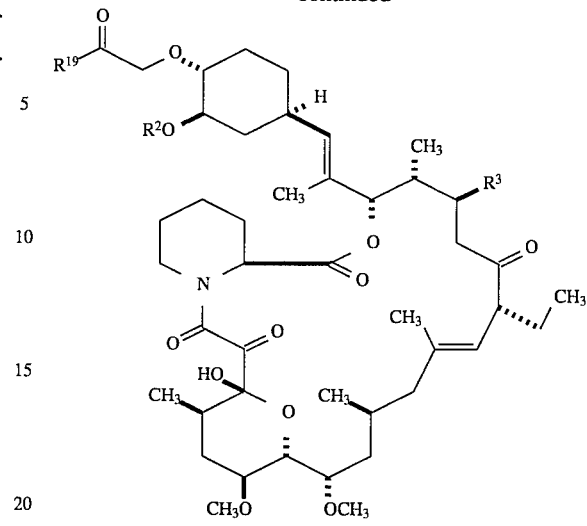

XII

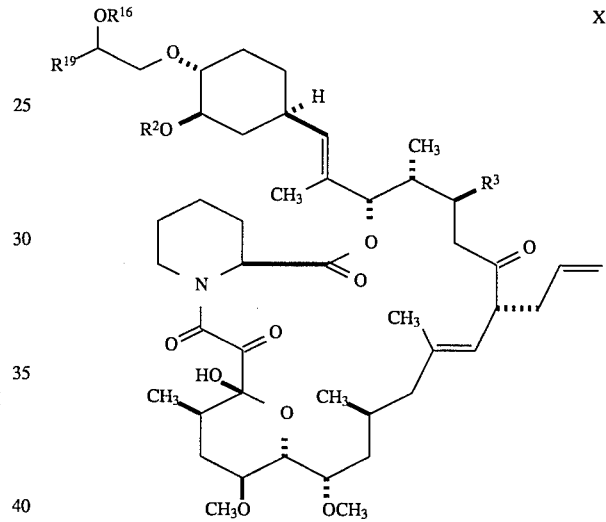

XIII

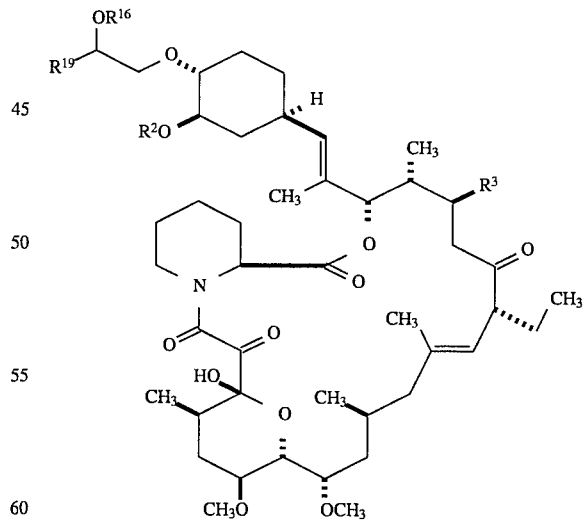

XIV wherein $R^{16}$ is H, methyl, ethyl, allyl or benzyl, $R^3$ is H or OH, $R^2$ is H, CH$_3$, CH$_3$CH$_2$, allyl, CH$_3$CH$_2$CH$_2$, HOCH$_2$CH$_2$CH$_2$, or (CH$_3$)$_2$CH and $R^{19}$ is selected from the following group of substituents:

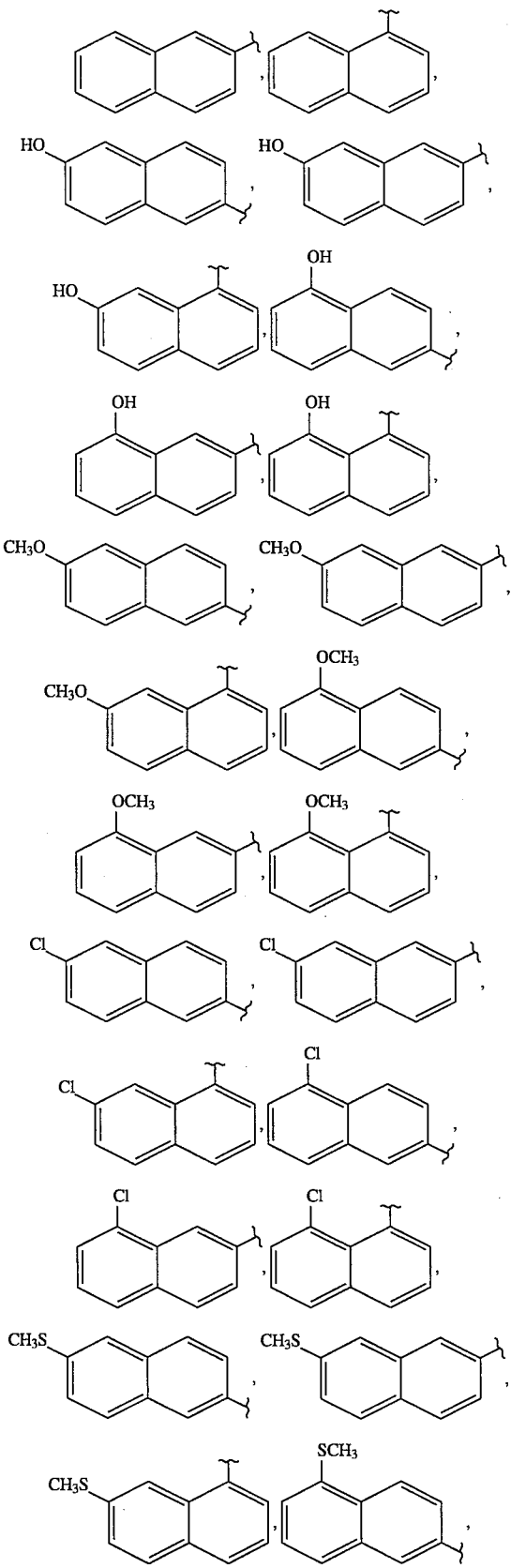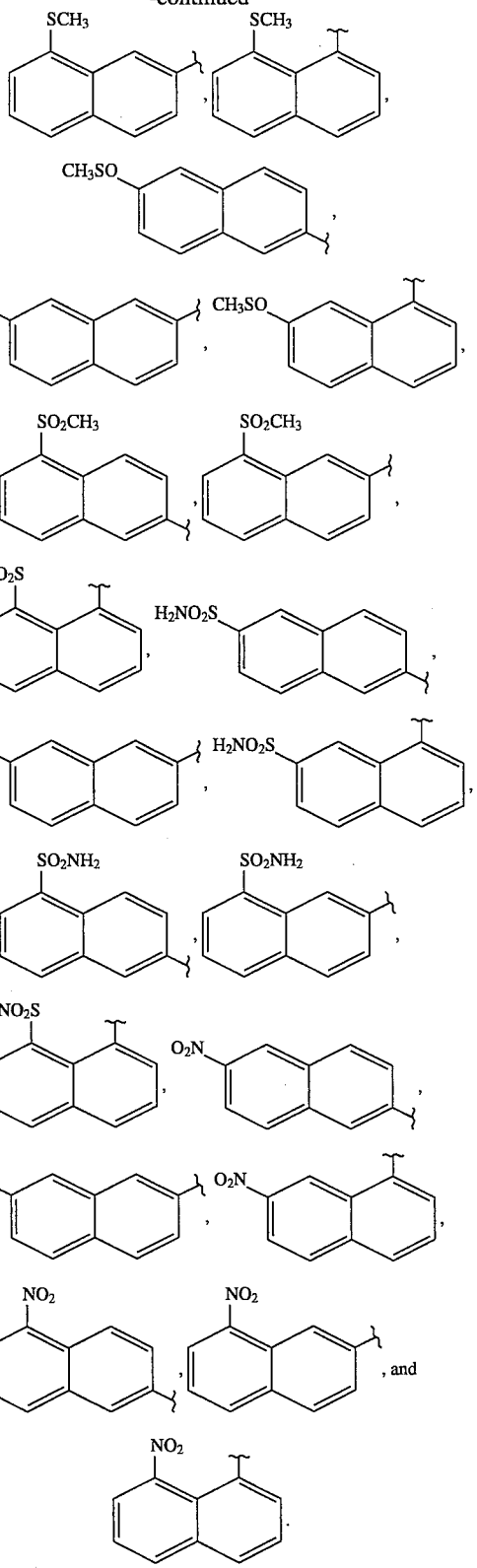
Representative compounds of the present invention include the compounds identified as follows:

17-Ethyl-1,14-dihydroxy-12-[2'-(4"-phenyloxy-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(3"-phenyloxy-4"-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"-phenyloxy-3"-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"-(4'''-fluorophenyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"-(4'''-chlorophenyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"-(4'''-methylphenyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(3"-(4'''-methylphenyloxy)-4"-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"-(4'''-methylphenyloxy)-3"-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"-(4'''-phenoxyphenyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"-(4'''-phenoxyphenyloxy)-3"-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(3"-(4'''-phenoxyphenyloxy)-4"-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"-(naphth-1-yloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(3"-(naphth-1-yloxy)-4"-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"-(naphth-1-yl-oxy)-3"-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"-(naphth-2-yloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"-(naphth-2-yloxy)-3"-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(3"-(napth-2-yloxy)-4"-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1-hydroxy-12-[2'-(4"-(naphth-2-yloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"-(6'''-methoxy-naphth-2-yloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(3"-(6'''-methoxy-naphth-2-yloxy)-4"-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"-(6'''-methoxy-naphth-2-yloxy)-3"-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(3"-(4'''-methoxyphenyloxy)-4"-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"-(4'''-methoxyphenyloxy)-3"-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(3"-(3'''-methoxyphenyloxy)-4"-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"-(3'''-methoxyphenyloxy)-3"-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(3"-(4'''-hydroxyphenyloxy)-4"-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"-(4'''-hydroxyphenyloxy)-3"-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"-(6'''-hydroxynaphth-2-yloxy)-3"-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(3"-(6'''-hydroxynaphth-2-yloxy)-4"-hydroxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"-(3''',4'''-dichlorophenyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"-(phenanthr-9-yl-oxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"-(3''',4'''-methylenedioxyphenyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Ethyl-1,14-dihydroxy-12-[2'-(4"-(2''',3'''-dihydrobenzofuran-5-yloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone;

17-Allyl-1,14-dihydroxy-12-[2'-(4"-(naphth-2-yloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16tetraone;

17-Ethyl-1,14-dihydroxy-12-[2'-(4"-(1''',4'''-benzodioxane-6 -yloxy)-3"-methoxycyclohexyl)-1'-methylvinyl]-23,25-dimethoxy-13,19,21,27-tetramethyl-11,28 -dioxa-4-azatricyclo[22.3.1.0$^{4,9}$]octacos-18-ene-2,3,10,16-tetraone;

17-Ethyl-1,2,14-trihydroxy-12-[2'-(4"-(naphth-2-yl-oxy)-3"-methoxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-3,10,16-trione;

17-Ethyl-1-hydroxy-12-[2'-(4"-(4'''-dimethylamino)-phenyloxy-3"-hydroxycyclohexyl)-1'-methylvinyl]-23,25-dimethoxy-13,19,21,27-tetramethyl-11,28-dioxa-4 -azatricyclo[22.3.1.0$^{4,9}$]-octacos-18-ene-2,3,10,16-tetraone;

17-Ethyl-1-hydroxy-12-[2'-(4"-hydroxy-3"-(4'''-dimethylamino)-phenyloxycyclohexyl)-1'-methylvinyl]-23,25-dimethoxy-13,19,21,27-tetramethyl-11,28-dioxa-4 -azatricyclo[22.3.1.0$^{4,9}$]-octacos-18-ene-2,3,10,16-tetraone;

17-Ethyl-1,14-dihydroxy-12-[2'-(4"-allyloxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4"-(2'''-butynyloxy)-3"-methoxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16tetraone;

17-Ethyl-1,14-dihydroxy-12-[2'-(4"-cinnamyloxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16tetraone;

17-Ethyl-1,14-dihydroxy-12-[2'-(3"-methoxy-4"-phenylpropyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16tetraone;

17-Ethyl-1,14-dihydroxy-12-[2'-(4"-allyloxy-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(3"-allyloxy-4"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(3"-hydroxy-4"-isopropyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16tetraone;

17-Ethyl-1,14-dihydroxy-12-[2'-(4"-hydroxy-3"-isopropyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16tetraone;

17-Ethyl-1,14-dihydroxy-12-[2'-(4"-sec-butenyloxy-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(3"-sec-butenyloxy-4"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4"-(trans-2'''-butenyloxy)-3"-hydroxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone;

17-Ethyl-1,14-dihydroxy-12-[2'-(3"-(trans-2'''-butenyloxy)-4"-hydroxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone;

17-Ethyl-1,14-dihydroxy-12-[2'-(3"-hydroxy-4"-(3'''-methyl-2 -butenyloxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone;

17-Ethyl-1,14-dihydroxy-12-[2'-(4"-hydroxy-3"-(3'''-methyl-2 -butenyloxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone;

17-Ethyl-1,14-dihydroxy-12-[2'-(3"-hydroxy-4"-(2'''-methylpropenyloxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone;

17-Ethyl-1,14-dihydroxy-12-[2'-(4"-hydroxy-3"-(2'''-methylpropenyloxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone;

17-Ethyl-1,14-dihydroxy-12-[2'-(4"-cinnamyloxy-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(3"-cinnamyloxy-4"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4"-sec-butenyloxy-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(3"-sec-butenyloxy-4"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4"-cinnamyloxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18 -ene-2,3,10,16-tetraone;

17-Ethyl-1-hydroxy-12-[2'-(3"-methoxy-4"-phenylpropyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4"-(4'''-methoxyphenyloxy)-3"-methoxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone;

17-Ethyl-1,14-dihydroxy-12-[2'-(4"-(3'''-methoxyphenyloxy)-3"-methoxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone;

17-Ethyl-1,14-dihydroxy-12-[2'-(4"-(6'''-hydroxy-naphth-2-yloxy)-3"-methoxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone;

17-Ethyl-1,14-dihydroxy-12-[2'-(4"-(4'''-hydroxyphenyloxy)-3"-methoxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone;

17-Ethyl-1,14-dihydroxy-12-[2'-(4"-(4'''-methylthiophenyloxy)-3"-methoxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone;

17-Ethyl-1,14-dihydroxy-12-[2'-(4"-(2'''-methylphenyloxy)-3"-methoxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone;

17-Ethyl-1,14-dihydroxy-12-[2'-(4"-(3'''-methylphenyloxy)-3"-methoxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone;

17-Ethyl-1,14-dihydroxy-12-[2'-(4"-(3''',4'''-dimethylphenyloxy)-3"-methoxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone;

17-Ethyl-1-hydroxy-12-[2'-(4''-allyloxy-3''-methoxycyclohexyl)-1'-methylvinyl]-23,25-dimethoxy-13,19,-21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4''-(2'''-butynyloxy)-3''-methoxycyclohexyl)-1'-methylvinyl]-23,25-dimethoxy-13,19,21,27-tetramethyl-1,28-dioxa-4-azatricyclo[22.3.1.0$^{4,9}$]octacos-18-ene-2,3,10,16-tetraone;

17-Ethyl-1-hydroxy-12-[2'-(4''-cinnamyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(3''-methoxy-4''-phenylpropyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4''-allyloxy-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(3''-allyloxy-4''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(3''-hydroxy-4''-isopropyloxycyclohexyl)-1'-methylvinyl]-23,25-dimethoxy 13,19,21,27-tetramethyl-11,28-dioxa-4-azatricyclo[22.3.1.0$^{4,9}$]-octacos-18-ene-2,3,10,16-tetraone;

17-Ethyl-1-hydroxy-12-[2'-(4''-hydroxy-3''-isopropyloxycyclohexyl)-1-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone;

17-Ethyl-1-hydroxy-12-[2'-(4''-(trans-2'''-butenyloxy)-3''-hydroxycyclohexyl)-1'-methylvinyl]23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(3''-(trans-2'''-butenyloxy)-4''-hydroxycyclohexyl)-1'-methylvinyl]23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(3''-hydroxy-4''-(3'''-methyl-2-butenyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4''-hydroxy-3''-(3'''-methyl-2-butenyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(3''-hydroxy-4''-(2'''-methylpropenyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4''-hydroxy-3''-(2'''-methylpropenyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(3''-cinnamyloxy-4''-hydroxycyclohexyl)-1'-methylvinyl]-23,25-dimethoxy-13,19,21,27-tetramethyl-11,28-dioxa-4-azatricyclo [22.3.1.0$^{4,9}$]octacos-18-ene-2,3,10,16-tetraone;

17-Ethyl-1,14-dihydroxy-12-[2'-(4''-sec-phenethyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(2'''-methylcinnamyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(4'''-methyl-2'''-4'''-hexadienyoxy)-3''-methoxycyclohexyl)-1'-methylvinyl]-23,25-dimethoxy-3,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(p-methoxycinnamyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(3''',4'''-methylenedioxycinnamyloxy)-3''-methoxycyclohexyl)-1'-methylvinyl]-23,25-dimethoxy-13,19,21,27-tetramethyl-11,28-dioxa-4-azatricyclo-22.3.1.0$^{4,9}$]octacos-18-ene-2,3,10,16-tetraone;

17-Ethyl-1,14-dihydroxy-12-[2'-(4''-(4''',4'''-dimethyl-2'''-trans-pentenyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(3'''-cyclohexyl-2'''-trans-propenyloxy)-3''-methoxycyclohexyl)-1'-methylvinyl]-23,25-dimethoxy-13,19,21,27-tetramethyl-11,28-dioxa-4-azatricyclo-22.3.1.0$^{4,9}$]octacos-18-ene-2,3,10,16-tetraone;

17-Ethyl-1,14-dihydroxy-12-[2'-(4''-p-fluorocinnamyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-p-chlorocinnamyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-p-bromocinnamyloxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(3''-methoxy-4''-p-fluorophenylpropyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(3'',4''-diallyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(3'',4''-dipropyloxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone;

17-Ethyl-1,14-dihydroxy-12-[2'-(4''-(2'''-benzylamino)ethoxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4''-(2'''-benzylamino)ethoxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(2'''-benzyloxyethoxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-benzyloxymethoxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4''-(napth-2-yloxy)-3''-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4"-(ethoxycarbomethoxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4"-(p-hydroxycinnamyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4"-(p-hydroxycinnamyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4"-(2'''-phenyl-2'''-oxo-ethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4"-(2'''-phenyl-2'''-oxo-ethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4"-(2'''-phenyl-2'''-oxo-ethyloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4"-(2'''-(3''''-methoxyphenyl)-2'''-oxo-ethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4"-(2'''-(3''''-methoxyphenyl)-2'''-oxo-ethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4"-(2'''-(3''''-methoxyphenyl)-2'''-oxo-ethyloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4"-(2'''-(4''''-methoxyphenyl)-2'''-oxo-ethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4"-(2'''-(4''''-methoxyphenyl)-2'''-oxo-ethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos18-ene-2,3,10,16-tetraone;

17-Ethyl-1,14-dihydroxy-12-[2'-(4"-(2'''-(4''''-methoxyphenyl)-2'''-oxo-ethyloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4"-(2'''-(3'''',5''''-dimethoxyphenyl)-2'''-oxo-ethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4"-(2'''-(3'''',5''''-dimethoxyphenyl)-2'''-oxo-ethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4"-(2'''-(3'''',5''''-dimethoxyphenyl)-2'''-oxo-ethyloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4"-(2'''-(3'''',5''''-difluorophenyl)-2'''-oxo-ethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4"-(2'''-(3'''',5''''-difluorophenyl)-2'''-oxo-ethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4"-(2'''-(3'''',5''''-difluorophenyl)-2'''-oxo-ethyloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4"-(2'''-(4''''-hydroxyphenyl)-2'''-oxo-ethyloxy)-3"-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-1-hydroxy-12-[2'-(4"-(2'''-(4''''-hydroxyphenyl)-2'''-oxo-ethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4"-(2'''-(4''''-hydroxyphenyl)-2'''-oxo-ethyloxy)-3"-hydroxycyclohexyl)-1'-methylvinyl]-23,25-dimethoxy-13,19,21,27-tetramethyl-11,28-dioxa-4-azatricyclo [22.3.1.0$^{4,9}$]octacos-18-ene-2,3,10,16-tetraone;

17-Ethyl-1,14-dihydroxy-12-[2'-(4"-(2'''-phenyl-2'''-hydroxyethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4"-(2'''-phenyl-2'''-hydroxyethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4"-(2'''-phenyl-2'''-hydroxyethyloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4"-(2'''-(3''''-methoxyphenyl)-2'''-hydroxyethyloxy)-3"-methoxycyclohexyl)-1'-methylvinyl]-23,25-dimethoxy-13,19,21,27-tetramethyl-11,28-dioxa-4-azatricyclo-22.3.1.0$^{4,9}$]octacos-18-ene-2,3,10,16-tetraone;

17-Ethyl-1-hydroxy-12-[2'-(4"-(2'''-(3''''-methoxyphenyl)-2'''-hydroxyethyloxy)-3"-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-1,14-dihydroxy-12-[2'-(4"-(2'''-(3''''-methoxyphenyl)-2'''-hydroxyethyloxy)-3"-hydroxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-1,14-dihydroxy-12-[2'-(4"-(2'''-(3'''',5''''-dimethoxyphenyl)-2'''-hydroxyethyloxy)-3"-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-1-hydroxy-12-[2'-(4"-(2'''-(3"",5""-dimethoxyphenyl)-2'''-hydroxyethyloxy)-3"-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18 -ene-2,3,10,16-tetraone;

17-Ethyl-1,14-dihydroxy-12-[2'-(4"-(2'''-(3"",5""-dimethoxyphenyl)-2'''-hydroxyethyloxy)-3"-hydroxycyclohexyl)-1'-methylvinyl]-23,25-dimethoxy-13,19,21,27-tetramethyl-11,28-dioxa-4-azatricyclo-[22.3.1.0$^{4,9}$]octacos-18 -ene-2,3,10,16-tetraone;

17-Ethyl-1,14-dihydroxy-12-[2'-(4"-(2'''-(3"",5""-difluorophenyl)-2'''-hydroxyethyloxy)-3"-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18 -ene-2,3,10,16-tetraone;

17-Ethyl-1-hydroxy-12-[2'-(4"-(2'''-(3"",5""-difluorophenyl-2'''-hydroxyethyloxy)-3"-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18 -ene-2,3,10,16-tetraone;

17-Ethyl-1,14-dihydroxy-12-[2'-(4"-(2'''-(3"",5""-difluorophenyl)-2'''-hydroxyethyloxy)-3"-hydroxycyclohexyl)-1'-methylvinyl]-23,25 -dimethoxy-13,19,21,27-tetramethyl-11,28-dioxa-4-azatricyclo-[22.3.1.0$^{4,9}$]octacos-18-ene-2,3,10,16 -tetraone;

17-Ethyl-1,14-dihydroxy-12-[2'-(4"-(2'''-(4""-hydroxyphenyl)-2'''-hydroxyethyloxy)-3"-methoxycyclohexyl)-1'-methylvinyl]-23,25-dimethoxy-13,19,21,27 -tetramethyl-11,28-dioxa-4-azatricyclo-[22.3.1.0$^{4,9}$]octacos-18-ene-2,3,10,16-tetraone;

17-Ethyl-1-hydroxy-12-[2'-(4"-(2'''-(4""-hydroxyphenyl)-2'''-hydroxyethyloxy)-3"-methoxycyclohexyl)-1'-methylvinyl]-23,25-dimethoxy-13,19,21,27 -tetramethyl-11,28-dioxa-4-azatricyclo-[22.3.1.0$^{4,9}$]octacos-18-ene-2,3,10,16-tetraone;

17-Ethyl-1,14-dihydroxy-12-[2'-(4"-(2'''-(4""-hydroxyphenyl)-2'''-hydroxyethyloxy)-3"-hydroxycyclohexyl)-1'-methylvinyl]-23,25-dimethoxy-13,19,21,27 -tetramethyl-11,28-dioxa-4-azatricyclo-[22.3.1.0$^{4,9}$]octacos-18-ene-2,3,10,16-tetraone;

17-Ethyl-1,14-dihydroxy-12-[2'-(4"-(m-fluorocinnamyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4"-(3''',5"'-difluorocinnamyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4"-(m-nitrocinnamyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4"-(3'''-phenyl-2'''-propynyloxy)-3"-methoxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone;

17-Ethyl-1,14-dihydroxy-12-[2'-(4"-(2'''-phenyl-2'''-propenyloxy)-3"-methoxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone;

17-Ethyl-1,14-dihydroxy-12-[2'-(4"-(p-hydroxycinnamyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4"-(p-hydroxyphenpropyloxy)-3"-methoxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone;

17-Ethyl-1,14-dihydroxy-12-[2'-(4"-(m-hydroxycinnamyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4"-(m-hydroxymethylbenzyloxy )-3"-methoxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone;

17-Ethyl-1,14-dihydroxy-12-[2'-(4"-(m-hydroxycinnamyloxy)-3"-hydroxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone;

17-Ethyl-1,14-dihydroxy-12-[2'-(4"-(3''',5'''-difluorocinnamyloxy)-3"-hydroxycyclohexyl)-1'-methylvinyl]-23, 25-dimethoxy-13,19,21,27-tetramethyl-11,28 -dioxa-4-azatricyclo[22.3.1.0$^{4,9}$]octacos-18-ene-2,3,10,16-tetraone;

17-Ethyl-1,14-dihydroxy-12-[2'-(4"-(p-carboxybenzyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4"-(m-carboxybenzyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4"-(m-carbomethoxybenzyloxy)-3"-methoxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone;

17-Ethyl-1,14-dihydroxy-12-[2'-(4"-(m-isopropylcarboxamidobenzyloxy)-3"-methoxycyclohexyl)-1'-methylvinyl]- 23,25-dimethoxy-13,19,21,27-tetramethyl-11,28 -dioxa-4-azatricyclo[22.3.1.0$^{4,9}$]octacos-18-ene-2,3,10, 16-tetraone;

17-Ethyl-1,14-dihydroxy-12-[2'-(4"-(m-butylcarboxamidobenzyloxy)-3"-methoxycyclohexyl)-1'-methylvinyl]-23, 25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4"-acetamidoxy-3"-methoxycyclohexyl)-1'-methylvinyl]-23,25-dimethoxy-13,19, 21,27-tetramethyl-11,28-dioxa-4-azatricyclo[22.3.1.0$^{4,9}$] octacos-18-ene-2,3,10,16-tetraone;

17-Ethyl-1,14-dihydroxy-12-[2'-(4"-carboxymethoxy-3"-methoxycyclohexyl)-1'-methylvinyl]-23,25-dimethoxy-13,19,21,27-tetramethyl-11,28-dioxa-4-azatricyclo[22-3.1.0$^{4,9}$]octacos-18-ene-2,3,10,16-tetraone;

17-Ethyl-1,14-dihydroxy-12-[2'-(4"-(N-phenylacetamidoxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4"-(N-benzylacetamidoxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4"-carboxymethoxy-3"-methoxycyclohexyl)-1'-methylvinyl]-23,25-dimethoxy-13,19, 21,27-tetramethyl-11,28-dioxa-4-azatricyclo[22.3.1.0$^{4,9}$] octacos-18-ene-2,3,10,16-tetraone;

17-Ethyl-1-hydroxy-12-[2'-(4"-(N-benzylamidoxymethoxy-3"methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4"-(N-methyltyrosine)amidoxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4"-(2'"-(m-methylphenyl)-2'"-oxo-ethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4"-(2'"-(p-methylphenyl)-2'"-oxo-ethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4"-(2'"-(m-methylphenyl)-2'"-hydroxyethyloxy)-3"-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-Ethyl-1,14-dihydroxy-12-[2'-(4"-(2'"-(m-ethylphenyl)-2'"-oxo-ethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4"-(2'"-phenylethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4"-(2'"-phenyl-2'"-acetoxyethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4"-(2'"-morpholinoethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4"-(naphth-2-ylmethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4"-(4'",5'"-methylenedioxybenzyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4"-(4'"-N,N,-dimethylaminophenyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4"-(3'"-fluorophenyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4"-(3'"-(2'"-dioxolanylphenyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4"-(3'"-formylphenyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4"-(3'"-carboxyphenyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4"-(3'",4'"-dimethoxyphenyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4"-(4'"-trifluoromethylphenyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1,14-dihydroxy-12-[2'-(4"-(3'",5'"-bis(trifluoromethyl)phenyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4"-(4'"-methylphenyloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4"-hydroxy-3"-(4'"-methylphenyloxy)cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4"-(4'"-hydroxyphenyloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4"-hydroxy-3"-(4'"-hydroxyphenyloxy)cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4"-(4'"-hydroxymethylphenyloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone and;

17-Ethyl-1-hydroxy-12-[2'-(4"-hydroxy-3"-(4'"-hydroxymethylphenyloxy)cyclohexyl)-1'-methylvinyl]-23,25-dimethoxy-13,19,21,27-tetramethyl-11,28-dioxa-4-azatricyclo[22.3.1.0$^{4,9}$]octacos-18-ene2,3,10,16-tetraone;

17-Ethyl-1-hydroxy-12-[2'-(4"-hydroxy-3"-(4'"-formylphenyloxy)cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4"-(4'"-N,N-dimethylaminophenyloxy)-3"-hydroxycyclohexyl)-1'-methyl-vinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4"-hydroxy-3"-(4'"-N,N-dimethylaminophenyloxy)cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4"-phenyloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4"-hydroxy-3"-phenyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4"-(4'"-methoxyphenyloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone and;

17-Ethyl-1-hydroxy-12-[2'-(4"-hydroxy-3"-(4'"-methoxyphenyloxy)cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-Ethyl-1-hydroxy-12-[2'-(4"-(3'"-methoxyphenyloxy)-3"-hydroxycyclohexyl)-1'-methylvinyl]-23,25-dimethoxy-13,19,21,27-tetramethyl-1,28-dioxa-4-azatricyclo[22.3.1.0$^{4,9}$]octacos-18-ene-2,3,10,16-tetraone;

17-Ethyl-1-hydroxy-12-[2'-(4"-hydroxy-3"-(3'''-methoxyphenyloxy)cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2'''-p-t-butylphenyl-2'''-oxoethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2'''-m-nitrophenyl-2'''-oxoethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2'''-m-isopropoxyphenyl-2'''-oxoethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2'''-m-bromophenyl-2'''-oxoethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2'''-m-fluorophenyl-2'''-oxoethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2'''-m-chloromethylphenyl)-2'''-oxoethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2'''-m-cyanophenyl-2'''-oxoethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2'''-m,m-difluorophenyl-2'''-oxoethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2'''-m,m-dimethylphenyl-2'''-oxoethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2'''-m-chlorophenyl-2'''-oxoethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2'''-m-triflouromethylphenyl)-2'''-oxoethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2'''-(2-naphthyl)-2'''-oxoethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2'''-m-fluorophenyl-2'''-hydroxyethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2'''-m-chloromethylphenyl-2'''-hydroxyethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2'''-m,m-dimethylphenyl-2'''-hydroxyethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2'''-m-chlorophenyl-2'''-hydroxyethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2'''-m-trifluoromethylphenyl-2'''-hydroxyethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2'''-(2-naphthyl)-2'''-hydroxyethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2'''-phenyl-2'''-benzyloxyethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2'''-phenyl-2'''-allyloxyethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2'''-phenyl-2'''-methoxyethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone;

17-ethyl-1,14-dihydroxy-12-[2'-(4"-(2'''-phenyl-2'''-aminoethyloxy)3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2'''-phenyl-2'''-oxoethyloxy)-3"-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2'''-phenyl-2'''-oxoethyloxy)-3"-propyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2'''-phenyl-2'''-oxoethyloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2'''-(m-fluorophenyl-2'''-oxoethyloxy)-3"-isopropoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2'''-(m-fluorophenyl-2'''-oxoethyloxy)-3"-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2'''-(m-fluorophenyl-2'''-oxoethyloxy)-3"-propyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2'''-(m-fluorophenyl-2'''-oxoethyloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2'''-(m-methylphenyl-2'''-oxoethyloxy)-3"-isopropoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2'''-(m-methylphenyl-2'''-oxoethyloxy)-3"-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2'''-(m-methylphenyl-2'''-oxoethyloxy)-3"-propyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2'''-(m-methylphenyl-2'''-oxoethyloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2'''-(m-methoxyphenyl-2'''-oxoethyloxy)-3"-isopropoxycyclohexyl)-1'-methylvinyl]-23,25dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2'''-(m-methoxyphenyl-2'''-oxoethyloxy)-3"-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2'''-(m-methoxyphenyl-2'''-oxoethyloxy)-3"-propyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2'''-(m-methoxyphenyl-2'''-oxoethyloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1-hydroxy-12-[2'-(4"-(2'''-phenyl-2'''-oxoethyloxy)-3"-isopropoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1-hydroxy-12-[2'-(4"-(2'''-phenyl-2'''-oxoethyloxy)-3"-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1-hydroxy-12-[2'-(4"-(2'''-phenyl-2'''-oxoethyloxy)-3"propyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1-hydroxy-12-[2'-(4"-(2'''-phenyl-2'''-oxoethyloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1-hydroxy-12-[2'-(4"-(2'''-(m-fluorophenyl-2'''-oxoethyloxy)-3"-isopropoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone;

17-ethyl-1-hydroxy-12-[2'-(4"-(2'''-(m-fluorophenyl-2'''-oxoethyloxy)-3"-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1-hydroxy-12-[2'-(4"-(2'''-(m-fluorophenyl-2'''-oxoethyloxy)-3"-propyloxycyclohexyl)-1'-methylvinyl]-23,25-dimethoxy-3,19,21,27-tetramethyl-11,28-dioxa-4-azatricyclo-[22.3.1.0$^{4,9}$]octacos-18-ene-2,3,10,16-tetraone;

17-ethyl-1-hydroxy-12-[2'-(4"-(2'''-(m-fluorophenyl-2'''-oxoethyloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1-hydroxy-12-[2'-(4"-(2'''-(m-methylphenyl-2'''-oxoethyloxy)-3"-isopropoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1-hydroxy-12-[2'-(4"-(2'''-(m-methylphenyl-2'''-oxoethyloxy)-3"-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1-hydroxy-12-[2'-(4"-(2'''-(m-methylphenyl-2'''-oxoethyloxy)-3"-propyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1-hydroxy-12-[2'-(4"-(2'''-(m-methylphenyl-2'''-oxoethyloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1-hydroxy-12-[2'-(4"-(2'''-(m-methoxyphenyl-2'''-oxoethyloxy)-3"-isopropoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1-hydroxy-12-[2'-(4"-(2'''-(m-methoxyphenyl-2'''-oxoethyloxy)-3"-allyloxycyclohexyl)-1'-methylvinyl]-23,25-dimethoxy13,19,21,27-tetramethyl-11,28-dioxa-4-azatricyclo[22.3.1.0$^{4,9}$]octacos-18-ene-2,3,10,16-tetraone;

17-ethyl-1-hydroxy-12-[2'-(4"-(2'''-(m-methoxyphenyl-2'''-oxoethyloxy)-3"-propyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1-hydroxy-12-[2'-(4"-(2'''-(m-methoxyphenyl-2'''-oxoethyloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1-hydroxy-12-[2'-(4"-(2'''-(3"",5""-dimethoxyphenyl-2'''-oxoethyloxy)-3"-isopropoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1-hydroxy-12-[2'-(4"-(2'''-(3"",5""-dimethoxyphenyl-2'''-oxoethyloxy)-3"-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1-hydroxy-12-[2'-(4"-(2"'-(3"",5""-dimethoxyphenyl-2"'-oxoethyloxy)-3"-propyloxycyclohexyl)-1'-methylvinyl]-23,25 -dimethoxy-13,19,21,27-tetramethyl-11, 28-dioxa-4-azatricyclo[22.3.1.0$^{4,9}$]octacos-18-ene-2,3, 10,16 -tetraone;

17-ethyl-1-hydroxy-12-[2'-(4"-(2"'-(3"",5""-dimethoxyphenyl-2"'-oxoethyloxy)-3"-hydroxycyclohexyl)-1'-methylvinyl]-23,25 -dimethoxy-13,19,21,27-tetramethyl-11, 28-dioxa-4-azatricyclo[22.3.1.0$^{4,9}$]octacos-18-ene-2,3, 10,16 -tetraone;

17-ethyl-1-hydroxy-12-[2'-(4"-(2"'-(3"",5""-dimethoxyphenyl-2"'-hydroxyethyloxy)-3"-isopropoxycyclohexyl)-1'-methylvinyl]-23,25 -dimethoxy-13,19,21,27-tetramethyl-11,28-dioxa-4-azatricyclo[22.3.1.0$^{4,9}$]octacos-18-ene-2, 3,10,16 -tetraone;

17-ethyl-1-hydroxy-12-[2'-(4"-(2"'-(3"",5""-dimethoxyphenyl-2"'-hydroxyethyloxy)-3"-allyloxycyclohexyl)-1'-methylvinyl]-23,25 -dimethoxy-13,19,21,27-tetramethyl-11, 28-dioxa-4-azatricyclo[22.3.1.0$^{4,9}$]octacos-18-ene-2,3, 10,16 -tetraone;

17-ethyl-1-hydroxy-12-[2'-(4"-(2"'-(3"",5""-dimethoxyphenyl-2"'-hydroxyethyloxy)-3"-propyloxycyclohexyl)-1'-methylvinyl]-23,25 -dimethoxy-13,19,21,27-tetramethyl-11,28-dioxa-4-azatricyclo[22.3.1.0$^{4,9}$]octacos-18-ene-2, 3,10,16 -tetraone;

17-ethyl-1-hydroxy-12-[2'-(4"-(2"'-(3"",5""-dimethoxyphenyl-2"'-hydroxyethyloxy)-3"-hydroxycyclohexyl)-1'-methylvinyl]-23,25 -dimethoxy-13,19,21,27-tetramethyl-11, 28-dioxa-4-azatricyclo[22.3.1.0$^{4,9}$]octacos-18-ene-2,3, 10,16 -tetraone;

17-ethyl-1,14-dihydroxy-12-[2'-(4"-(2"'-(3"",5""-dimethoxyphenyl-2"'-oxoethyloxy)-3"-isopropoxycyclohexyl)-1'-methylvinyl]-23,25 -dimethoxy-13,19,21,27-tetramethyl-11,28-dioxa-4-azatricyclo[22.3.1.0$^{4,9}$]octacos-18-ene-2, 3,10,16 -tetraone;

17-ethyl-1,14-dihydroxy-12-[2'-(4"-(2"'-(3"",5""-dimethoxyphenyl-2"'-oxoethyloxy)-3"-allyloxycyclohexyl)-1'-methylvinyl]-23,25 -dimethoxy-13,19,21,27-tetramethyl-11, 28-dioxa-4-azatricyclo[22.3.1.0$^{4,9}$]octacos-18-ene-2,3, 10,16 -tetraone;

17-ethyl-1,14-dihydroxy-12-[2'-(4"-(2"'-(3"",5""-dimethoxyphenyl-2"'-oxoethyloxy)-3"-propyloxycyclohexyl)-1'-methylvinyl]-23,25 -dimethoxy-13,19,21,27-tetramethyl-11,28-dioxa-4-azatricyclo[22.3.1.0$^{4,9}$]octacos-1 8-ene-2, 3,10,16 -tetraone;

17-ethyl-1,14-dihydroxy-12-[2'-(4"-(2"'-(3"",5""-dimethoxyphenyl-2"'-oxoethyloxy)-3"-hydroxycyclohexyl)-1'-methylvinyl]-23,25 -dimethoxy-13,19,21,27-tetramethyl-11, 28-dioxa-4-azatricyclo[22.3.1.0$^{4,9}$]octacos-18-ene-2,3, 10,16 -tetraone;

17-ethyl-1,14-dihydroxy-12-[2'-(4"-(2"'-(3"",5""-dimethoxyphenyl-2"'-hydroxyethyloxy)-3"-isopropoxycyclohexyl)-1'-methylvinyl]-23,25 -dimethoxy-13,19,21,27-tetramethyl-11,28-dioxa-4-azatricyclo[22.3.1.0$^{4,9}$]octacos-18-ene-2,3,10,16 -tetraone;

17-ethyl-1,14-dihydroxy-12-[2'-(4"-(2"'-(3"",5""-dimethoxyphenyl-2"'-hydroxyethyloxy)-3"-allyloxycyclohexyl)-1'-methylvinyl]-23,25 -dimethoxy-13,19,21,27-tetramethyl-11,28-dioxa-4-azatricyclo[22.3.1.0$^{4,9}$]octacos-1 8-ene-2,3,10,16 -tetraone;

17-ethyl-1,14-dihydroxy-12-[2'-(4"-(2"'-(3"",5""-dimethoxyphenyl-2"'-hydroxyethyloxy)-3"-propyloxycyclohexyl)-1'-methylvinyl]-23,25 -dimethoxy-13,19,21,27-tetramethyl-11,28-dioxa-4-azatricyclo[22.3.1.0$^{4,9}$]octacos-18-ene-2,3,10,16 -tetraone;

17-ethyl-1,14-dihydroxy-12-[2'-(4"-(2"'-(3"",5""-dimethoxyphenyl-2"'-hydroxyethyloxy)-3"-hydroxycyclohexyl)-1'-methylvinyl]-23,25 -dimethoxy-13,19,21,27-tetramethyl-11,28-dioxa-4-azatricyclo[22.3.1.0$^{4,9}$]octacos-18-ene-2,3,10,16 -tetraone;

17-ethyl-1-hydroxy-12-[2'-(4"-(2"'-(3"",5""-dimethylphenyl-2"'-oxoethyloxy)-3"-isopropoxycyclohexyl)-1'-methylvinyl]-23,25 -dimethoxy-13,19,21,27-tetramethyl-11, 28-dioxa-4-azatricyclo[22.3.1.0$^{4,9}$]octacos-18-ene-2,3, 10,16 -tetraone;

17-ethyl-1-hydroxy-12-[2'-(4"-(2"'-(3"",5""-dimethylphenyl-2"'-oxoethyloxy)-3"-allyloxycyclohexyl)-1'-methylvinyl]-23,25 -dimethoxy-13,19,21,27-tetramethyl-11, 28-dioxa-4-azatricyclo[22.3.1.0$^{4,9}$]octacos-18-ene-2,3, 10,16 -tetraone;

17-ethyl-1-hydroxy-12-[2'-(4"-(2"'-(3"",5""-dimethylphenyl-2"'-oxoethyloxy)-3"-propyloxycyclohexyl)-1'-methylvinyl]-23,25 -dimethoxy-13,19,21,27-tetramethyl-11, 28-dioxa-4-azatricyclo[22.3.1.0$^{4,9}$]octacos-1 8-ene-2,3, 10,16 -tetraone;

17-ethyl-1-hydroxy-12-[2'-(4"-(2"'-(3"",5""-dimethylphenyl-2"'-oxoethyloxy)-3"-hydroxycyclohexyl)-1'-methylvinyl]-23,25-dimethoxy-13,19,21,27 -tetramethyl-11, 28-dioxa-4-azatricyclo[22.3.1.0$^{4,9}$]octacos-18-ene-2,3, 10,16-tetraone;

17-ethyl-1-hydroxy-12-[2'-(4"-(2"'-(3"",5""-dimethylphenyl-2"'-hydroxyethyloxy)-3"-isopropoxycyclohexyl)-1'-methylvinyl]-23,25 -dimethoxy-13,19,21,27-tetramethyl-11,28-dioxa-4-azatricyclo[22.3.1.0$^{4,9}$]octacos-18-ene-2, 3,10,16 -tetraone;

17-ethyl-1-hydroxy-12-[2'-(4"-(2"'-(3"",5""-dimethylphenyl-2"'-hydroxyethyloxy)-3"-allyloxycyclohexyl)-1'-methylvinyl]-23,25 -dimethoxy-13,19,21,27-tetramethyl-11, 28-dioxa-4-azatricyclo[22.3.1.0$^{4,9}$]octacos-18-ene-2,3, 10,16 -tetraone;

17-ethyl-1-hydroxy-12-[2'-(4"-(2"'-(3"",5""-dimethylphenyl-2"'-hydroxyethyloxy)-3"-propyloxycyclohexyl)-1'-methylvinyl]-23,25 -dimethoxy-13,19,21,27-tetramethyl-11,28-dioxa-4-azatricyclo[22.3.1.0$^{4,9}$]octacos-18-ene-2, 3,10,16 -tetraone;

17-ethyl-1-hydroxy-12-[2'-(4"-(2"'-(3"",5""-dimethylphenyl-2"'-hydroxyethyloxy)-3"-hydroxycyclohexyl)-1'-methylvinyl]-23,25 -dimethoxy-13,19,21,27-tetramethyl-11, 28-dioxa-4-azatricyclo [22.3.1.0$^{4,9}$]octacos-18-ene-2,3, 10,16 -tetraone;

17-ethyl-1,14-dihydroxy-12-[2'-(4"-(2"'-(3"",5""-dimethylphenyl-2"'-oxoethyloxy)-3"-isopropoxycyclohexyl)-1'-methylvinyl]-23,25 -dimethoxy-13,19,21,27-tetramethyl-11,28-dioxa-4-azatricyclo[22.3.1.0$^{4,9}$]octacos-18-ene-2, 3,10,16 -tetraone;

17-ethyl-1,14-dihydroxy-12-[2'-(4"-(2"'-(3"",5""-dimethylphenyl-2"'-oxoethyloxy)-3"-allyloxycyclohexyl)-1'-methylvinyl]-23,25 -dimethoxy-13,19,21,27-tetramethyl-11, 28-dioxa-4-azatricyclo[22.3.1.0$^{4,9}$]octacos-18-ene-2, 3,10,16 -tetraone;

17-ethyl-1,14-dihydroxy-12-[2'-(4"-(2"'-(3"",5""-dimethylphenyl-2"'-oxoethyloxy)-3"-propyloxycyclohexyl)-1'-methylvinyl]-23,25 -dimethoxy-13,19,21,27-tetramethyl-11, 28-dioxa-4-azatricyclo[22.3.1.0$^{4,9}$]octacos-18-ene-2, 3,10,16 -tetraone;

17-ethyl-1,14-dihydroxy-12-[2'-(4"-(2"'-(3"",5""-dimethylphenyl-2"'-oxoethyloxy)-3"-hydroxycyclohexyl)-1'-methylvinyl]-23,25 -dimethoxy-13,19,21,27-tetramethyl-11,28-dioxa-4-azatricyclo[22.3.1.0$^{4,9}$]octacos-18-ene-2, 3,10,16 -tetraone;

17-ethyl-1,14-dihydroxy-12-[2'-(4"-(2"'-(3"",5""-dimethylphenyl-2"'-hydroxyethyloxy)-3"-isopropoxycyclohexyl)-1'-methylvinyl]-23,25 -dimethoxy-13,19,21,27-tetramethyl-11,28-dioxa-4-azatricyclo[22.3.1.0$^{4,9}$]octacos-18-ene-2,3,10,16 -tetraone;

17-ethyl-1,14-dihydroxy-12-[2'-(4"-(2"'-(3"",5""-dimethylphenyl-2"'-hydroxyethyloxy)-3"-allyloxycyclohexyl)-1'-methylvinyl]-23,25 -dimethoxy-13,19,21,27-tetramethyl-11,28-dioxa-4-azatricyclo[22.3.1.0$^{4,9}$]octacos-18-ene-2,3,10,16 -tetraone;

17-ethyl-1,14-dihydroxy-12-[2'-(4"-(2'''-(3'''',5''''-dimethylphenyl-2'''-hydroxyethyloxy)-3"-propyloxycyclohexyl)-1'-methylvinyl]-23,25 -dimethoxy-13,19,21,27-tetramethyl-11,28-dioxa-4-azatricyclo[22.3.1.0$^{4,9}$]octacos-18-ene-2,3,10,16 -tetraone;

17-ethyl-1,14-dihydroxy-12-[2'-(4"-(2'''-(3'''',5''''-dimethylphenyl-2'''-hydroxyethyloxy)-3"-hydroxycyclohexyl)-1'-methylvinyl]-23,25 -dimethoxy-13,19,21,27-tetramethyl-11,28-dioxa-4-azatricyclo[22.3.1.0$^{4,9}$]octacos-18-ene-2,3,10,16 -tetraone;

17-ethyl-1,14-dihydroxy-12-[2'-(4"-(2'''-phenyl-2'''-hydroxyethyloxy)-3"-isopropoxycyclohexyl)-1'-methylvinyl]-23,25-dimethoxy-13,19,21,27-tetramethyl-11,28 -dioxa-4-azatricyclo[22.3.1.0$^{4,9}$]octacos-18-ene-2,3,10,16-tetraone;

17-ethyl-1,14-dihydroxy-12-[2'-(4"-(2'''-phenyl-2'''-hydroxyethyloxy)-3"-allyloxycyclohexyl)-1'-methylvinyl]-23,25-dimethoxy-13,19,21,27-tetramethyl-11,28 -dioxa-4-azatricyclo[22.3.1.0$^{4,9}$]octacos-18-ene-2,3,10,16-tetraone;

17-ethyl-1,14-dihydroxy-12-[2'-(4"-(2'''-phenyl-2'''-hydroxyethyloxy)-3"-propyloxycyclohexyl)-1'-methylvinyl]-23,25-dimethoxy-13,19,21,27-tetramethyl-11,28 -dioxa-4-azatricyclo[22.3.1.0$^{4,9}$]octacos-18-ene-2,3,10,16-tetraone;

17-ethyl-1,14-dihydroxy-12-[2'-(4"-(2'''-phenyl-2'''-hydroxyethyloxy)-3"-hydroxycyclohexyl)-1'-methylvinyl]-23,25-dimethoxy-13,19,21,27-tetramethyl-11,28 -dioxa-4-azatricyclo[22.3.1.0$^{4,9}$]octacos-18-ene-2,3,10,16-tetraone;

17-ethyl-1,14-dihydroxy-12-[2'-(4"-(2'''-(m-fluorophenyl-2'''-hydroxyethyloxy)-3"-isopropoxycyclohexyl)-1'-methylvinyl]-23,25-dimethoxy-13,19,21,27-tetramethyl-11,28 -dioxa-4-azatricyclo[22.3.1.0$^{4,9}$]octacos-18-ene-2,3,10,16-tetraone;

17-ethyl-1,14-dihydroxy-12-[2'-(4"-(2'''-(m-fluorophenyl-2'''-hydroxyethyloxy)-3"-allyloxycyclohexyl)-1'-methylvinyl]-23,25-dimethoxy-13,19,21,27-tetramethyl-11, 28- dioxa-4-azatricyclo[22.3.1.0$^{4,9}$]octacos-18-ene-2,3, 10,16-tetraone;

17-ethyl-1,14-dihydroxy-12-[2'-(4"-(2'''-(m-fluorophenyl-2'''-hydroxyethyloxy)-3"-propyloxycyclohexyl)-1'-methylvinyl]-23,25-dimethoxy-13,19,21,27-tetramethyl-11, 28- dioxa-4-azatricyclo[22.3.1.0$^{4,9}$]octacos-18-ene-2,3, 10,16-tetraone;

17-ethyl-1,14-dihydroxy-12-[2'-(4"-(2'''-(m-fluorophenyl-2'''-hydroxyethyloxy)-3"-hydroxycyclohexyl)-1'-methylvinyl]-23,25-dimethoxy-13,19,21,27-tetramethyl-11, 28- dioxa-4-azatricyclo[22.3.1.0$^{4,9}$]octacos-18-ene-2,3, 10,16-tetraone;

17-ethyl-1,14-dihydroxy-12-[2'-(4"-(2'''-(m-methylphenyl-2'''-hydroxyethyloxy)-3"-isopropoxycyclohexyl)-1'-methylvinyl]-23,25-dimethoxy-13,19,21,27-tetramethyl-11,28 -dioxa-4-azatricyclo[22.3.1.0$^{4,9}$]octacos-18-ene-2, 3,10,16-tetraone;

17-ethyl-1,14-dihydroxy-12-[2'-(4"-(2'''-(m-methylphenyl-2'''-hydroxyethyloxy)-3"-allyloxycyclohexyl)-1'-methylvinyl]-23,25-dimethoxy-13,19,21,27-tetramethyl-11, 28- dioxa-4-azatricyclo[22.3.1.0$^{4,9}$]octacos-18-ene-2,3, 10,16-tetraone;

17-ethyl-1,14-dihydroxy-12-[2'-(4"-(2'''-(m-methylphenyl-2'''-hydroxyethyloxy)-3"-propyloxycyclohexyl)-1'-methylvinyl]-23,25-dimethoxy-13,19,21,27-tetramethyl-11, 28- dioxa-4-azatricyclo[22.3.1.0$^{4,9}$]octacos-18-ene-2,3, 10,16-tetraone;

17-ethyl-1,14-dihydroxy-12-[2'-(4"-(2'''-(m-methylphenyl-2'''-hydroxyethyloxy)-3"-hydroxycyclohexyl)-1'-methylvinyl]-23,25-dimethoxy-13,19,21,27-tetramethyl-11, 28- dioxa-4-azatricyclo[22.3.1.0$^{4,9}$]octacos-18-ene-2,3, 10,16-tetraone;

17-ethyl-1,14-dihydroxy-12-[2'-(4"-(2'''-(m-methoxyphenyl-2'''-hydroxyethyloxy)-3"-isopropoxycyclohexyl)-1'-methylvinyl]-23,25-dimethoxy-13,19,21,27-tetramethyl-11,28 -dioxa-4-azatricyclo[22.3.1.0$^{4,9}$]octacos-18-ene-2, 3,10,16-tetraone;

17-ethyl-1,14-dihydroxy-12-[2'-(4"-(2'''-(m-methoxyphenyl-2'''-hydroxyethyloxy)-3"-allyloxycyclohexyl)-1'-methylvinyl]-23,25-dimethoxy-13,19,21,27-tetramethyl-11,28 -dioxa-4-azatricyclo[22.3.1.0$^{4,9}$]octacos-18-ene-2, 3,10,16-tetraone;

17-ethyl-1,14-dihydroxy-12-[2'-(4"-(2'''-(m-methoxyphenyl-2'''-hydroxyethyloxy)-3"-propyloxycyclohexyl)-1'-methylvinyl]-23,25-dimethoxy-13,19,21,27-tetramethyl-11,28 -dioxa-4-azatricyclo[22.3.1.0$^{4,9}$]octacos-18-ene-2, 3,10,16-tetraone;

17-ethyl-1,14-dihydroxy-12-[2'-(4"-(2'''-(m-methoxyphenyl-2'''-hydroxyethyloxy)-3"-hydroxycyclohexyl)-1'-methylvinyl]-23,25-dimethoxy-13,19,21,27-tetramethyl-11,28 -dioxa-4-azatricyclo[22.3.1.0$^{4,9}$]octacos-18-ene-2, 3,10,16-tetraone;

17-ethyl-1-hydroxy-12-[2'-(4"-(2'''-phenyl-2'''-hydroxyethyloxy)-3"-isopropoxycyclohexyl)-1'-methylvinyl]-23, 25-dimethoxy-13,19,21,27-tetramethyl-11,28-dioxa-4-azatricyclo[22.3.1.0$^{4,9}$]octacos-18-ene-2,3,10,16-tetraone;

17-ethyl-1-hydroxy-12-[2'-(4"-(2'''-phenyl-2'''-hydroxyethyloxy)-3"-allyloxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone;

17-ethyl-1-hydroxy-12-[2'-(4"-(2'''-phenyl-2'''-hydroxyethyloxy)-3"-propyloxycyclohexyl)-1'-methylvinyl]-23, 25-dimethoxy-13,19,21,27-tetramethyl-11,28-dioxa-4-azatricyclo[22.3.1.0$^{4,9}$]octacos-18-ene-2,3,10,16-tetraone;

17-ethyl-1-hydroxy-12-[2'-(4"-(2'''-phenyl-2'''-hydroxyethyloxy)-3"-hydroxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone;

17-ethyl-1-hydroxy-12-[2'-(4"-(2'''-(m-fluorophenyl-2'''-hydroxyethyloxy)-3"-isopropoxycyclohexyl)-1'-methylvinyl]-23,25-dimethoxy-13,19,21,27-tetramethyl-11,28 -dioxa-4-azatricyclo[22.3.1.0$^{4,9}$]octacos-18-ene-2,3,10,16-tetraone;

17-ethyl-1-hydroxy-12-[2'-(4"-(2'''-(m-fluorophenyl-2'''-hydroxyethyloxy)-3"-allyloxycyclohexyl)-I '-methylvinyl]-23,25-dimethoxy-13,19,21,27-tetramethyl-11,28 -dioxa-4-azatricyclo[22.3.1.0$^{4,9}$]octacos-18-ene-2,3,10,16-tetraone;

17-ethyl-1-hydroxy-12-[2'-(4"-(2'''-(m-fluorophenyl-2'''-hydroxyethyloxy)-3"-propyloxycyclohexyl)-1'-methylvinyl]-23,25-dimethoxy-13,19,21,27-tetramethyl-11,28 -dioxa-4-azatricyclo[22.3.1.0$^{4,9}$]octacos-18-ene-2,3,10,16-tetraone;

17-ethyl-1-hydroxy-12-[2'-(4"-(2'''-(m-fluorophenyl-2'''-hydroxyethyloxy)-3"-hydroxycyclohexyl)-1'-methylvinyl]-23,25-dimethoxy-13,19,21,27-tetramethyl-11,28 -dioxa-4-azatricyclo[22.3.1.0$^{4,9}$]octacos-18-ene-2,3,10,16-tetraone;

17-ethyl-1-hydroxy-12-[2'-(4"-(2'''-(m-methylphenyl-2'''-hydroxyethyloxy)-3"-isopropoxycyclohexyl)-1'-methylvinyl]-23,25-dimethoxy-13,19,21,27-tetramethyl-11, 28- dioxa-4-azatricyclo[22.3.1.0$^{4,9}$]octacos-18-ene-2,3, 10,16-tetraone;

17-ethyl-1-hydroxy-12-[2'-(4"-(2'''-(m-methylphenyl-2'''-hydroxyethyloxy)-3"-allyloxycyclohexyl)-1'-methylvinyl]-23,25-dimethoxy-13,19,21,27-tetramethyl-11,28 -dioxa-4-azatricyclo[22.3.1.0$^{4,9}$]octacos-18-ene-2,3,10,16-tetraone;

17-ethyl-1-hydroxy-12-[2'-(4"-(2"'-(m-methylphenyl-2"'-hydroxyethyloxy)-3"-propyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1-hydroxy-12-[2'-(4"-(2"'-(m-methylphenyl-2"'-hydroxyethyloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1-hydroxy-12-[2'-(4"-(2"'-(m-methoxyphenyl-2"'-hydroxyethyloxy)-3"-isopropoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1-hydroxy-12-[2'-(4"-(2"'-(m-methoxyphenyl-2"'-hydroxyethyloxy)-3"-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1-hydroxy-12-[2'-(4"-(2"'-(m-methoxyphenyl-2"'-hydroxyethyloxy)-3"-propyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1-hydroxy-12-[2'-(4"-(2"'-(m-methoxyphenyl-2"'-hydroxyethyloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2"'-m,m-dichlorophenyl-2"'-oxoethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2"'-m,m-dichlorophenyl-2"'-hydroxyethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2"'-m,m-bistrifluoromethoxyphenyl-2"'-oxoethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2"'-m,m-bistrifluoromethoxyphenyl-2"'-hydroxyethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2"'-m,m-bistrifluoromethylphenyl-2"'-oxoethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2"'-m,m-bistrifluoromethylphenyl-2"'-hydroxyethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2"'-m,m-dihydroxyphenyl-2"'oxoethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2"'-m,m-dihydroxyphenyl-2"'-hydroxyethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2"'-(3"",4"",5""-trimethyl)phenyl-2"'-oxoethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2"'-(3"",4"",5""-trimethyl)phenyl-2"'-hydroxyethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2"'-(3"",5""-dimethyl-4""-methoxy)phenyl-2"'-oxoethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3-tetraone;

17-ethyl-1,14-dihydroxy-12-[2'-(4"-(2"'-(3"",5""-dimethyl-4""-methoxy)phenyl-2"'-hydroxyethyloxy)-3"-methoxycyclohexyl)-1'methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2"'-(3"",5""-dimethoxy-4""-methyl)phenyl-2"'-oxoethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2"'-(3"",5""-dimethoxy-4""-methyl)phenyl-2"'-hydroxyethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2"'-(3"",5""-difluoro-4""-methyl)phenyl-2"'-oxoethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2"'-(3"",5""-difluoro-4""-methyl)phenyl-2"'-hydroxyethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2"'-(3"",5""-dimethyl-4""-fluoro)phenyl-2"'-oxoethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2"'-(3"",5""-dimethyl-4""-fluoro)phenyl-2"'-hydroxyethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2"'-(3"",5""-dichloro-4""-methyl)phenyl-2"'-oxoethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2"'-(3"",5""-dichloro-4""-methyl)phenyl-2"'-hydroxyethyloxy)-3"-methoxycyclohexyl)-1'methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2"'-(3"",5""-dimethyl-4""-chloro)phenyl-2"'-oxoethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2"'-(3"",5""-dimethyl-4""-chloro)phenyl-2"'-hydroxyethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2"'-(3"",5""-bistrifluoromethoxy-4""-methyl)phenyl-2"'-oxoethyloxy)-3"-methoxycyclohexyl)-1'methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2"'-(3"",5""-bistrifluoromethoxy-4""-methyl)phenyl-2"'-hydroxyethyloxy)-3"-methoxycyclohexyl)-1'methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2"'-(3"",5""-dimethyl-4""-trifluoromethoxy)phenyl-2"'-oxoethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2"'-(3"",5""-dimethyl-4""-trifluoromethoxy)phenyl-2"'-hydroxyethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2"'-(3"",5""-dimethyl-4""-hydroxy)phenyl-2"'-oxoethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2"'-(3"",5""-dimethyl-4""-hydroxy)phenyl-2"'-hydroxyethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2"'-(3"",5""-dihydroxy-4""-methyl)phenyl-2"'-oxoethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2"'-(3"",5""-dihydroxy-4""-methyl)phenyl-2"'-hydroxyethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-m-thiomethylphenyl-2"'-oxoethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2"'-m-thiomethylphenyl-2"'-hydroxyethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2"'-m,m-bis(thiomethyl)phenyl-2"'-oxoethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2"'-m,m-bis(thiomethyl)phenyl-2"'-hydroxyethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2"'-(3"",5""-bis(thiomethyl)-4""-methyl)phenyl-2"'-oxoethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2"'-(3"",5""-bis(thiomethyl)-4""-methyl)phenyl-2"'-hydroxyethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2"'-(3""-chloro-5""-methyl)phenyl-2"'-oxoethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone;

17-ethyl-1,14-dihydroxy-12-[2'-(4"-(2"'-(3""-chloro-5""-methyl)phenyl-2"'-hydroxyethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2"'-(3""-chloro-5""-fluoro)phenyl-2"'-oxoethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2"'-(3""-chloro-5""-fluoro)phenyl-2"'-hydroxyethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2"'-(3""-chloro-5""-methoxy)phenyl-2"'-oxoethyloxy)-3"-methoxycyclohexyl)-1'methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2"'-(3""-chloro-5""-methoxy)phenyl-2"'-hydroxyethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2"'-(3""-chloro-5""-trifluoromethyl)phenyl-2"'-oxoethyloxy)-3"-methoxycyclohexyl)-1'methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2"'-(3""-chloro-5""-trifluoromethyl)phenyl-2"'-hydroxyethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2"'-(3""-chloro-5""-trifluoromethoxy)phenyl-2"'-oxoethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2"'-(3""-chloro-5""-trifluoromethoxy)phenyl-2"'-hydroxyethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2"'-(3""-fluoro-5""-methyl)phenyl-2"'-oxoethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2"'-(3""-fluoro-5""-methyl)phenyl-2"'-hydroxyethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2"'-(3""-fluoro-5""-methoxy)phenyl-2"'-oxoethyloxy)-3"-methoxycyclohexyl)-1'methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4"-(2"'-(3""-fluoro-5""-methoxy)phenyl-2"'-hydroxyethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-(2'''-(3''''-fluoro-5''''-trifluoromethyl)phenyl-2'''-oxoethyloxy)-3''-methoxycyclohexyl)-1'-methylvinyl]-23,25 -dimethoxy-13,19,21,27-tetramethyl-11,28-dioxa-4-azatricyclo[22.3.1.0$^{4,9}$] octacos-18-ene-2,3,10,16 -tetraone;

17-ethyl-1,14-dihydroxy-12-[2'-(4''-(2'''-(3''''-fluoro-5''''-trifluoromethyl)phenyl-2'''-hydroxyethyloxy)-3''-methoxycyclohexyl)-1'-methylvinyl]-23,25 -dimethoxy-13,19,21, 27-tetramethyl-11,28-dioxa-4-azatricyclo[22.3.1.0$^{4,9}$octacos-18-ene-2,3,10,16 -tetraone;

17-ethyl-1,14-dihydroxy-12-[2'-(4''-(2'''-(3''''-fluoro-5''''-trifluoromethoxy)phenyl-2'''-oxoethyloxy)-3''-methoxycyclohexyl)-1'-methylvinyl]-23,25 -dimethoxy-13,19,21, 27-tetramethyl-11,28-dioxa-4-azatricyclo[22.3.1.0$^{4,9}$] octacos-18-ene-2,3,10,16 -tetraone;

17-ethyl-1,14-dihydroxy-12-[2'-(4''-(2'''-(3''''-fluoro-5''''-trifluoromethoxy)phenyl-2'''-hydroxyethyloxy)-3''-methoxycyclohexyl)-1'-methylvinyl]-23,25 -dimethoxy-13,19, 21,27-tetramethyl-11,28-dioxa-4-azatricyclo[22.3.1.0$^{4,9}$] octacos-18-ene-2,3,10,16 -tetraone;

17-ethyl-1,14-dihydroxy-12-[2'-(4''-(2'''-(3''''-methyl-5''''-methoxy)phenyl-2'''-oxoethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone;

17-ethyl-1,14-dihydroxy-12-[2'-(4''-(2'''-(3''''-methyl-5''''-methoxy)phenyl-2'''-hydroxyethyloxy)-3''-methoxycyclohexyl)-1'methylvinyl]-23,25 -dimethoxy-13,19,21,27-tetramethyl-11,28-dioxa-4-azatricyclo[22.3.1.0$^{4,9}$] octacos-18-ene-2,3,10,16 -tetraone;

17-ethyl-1,14-dihydroxy-12-[2'-(4''-(2'''-(3''''-methyl-5''''-trifluoromethyl)phenyl-2'''-oxoethyloxy)-3''-methoxycyclohexyl)-1'-methylvinyl]-23,25 -dimethoxy-13,19,21, 27-tetramethyl-11,28-dioxa-4-azatricyclo[22.3.1.0$^{4,9}$] octacos-18-ene-2,3,10,16 -tetraone;

17-ethyl-1,14-dihydroxy-12-[2'-(4''-(2'''-(3''''-methyl-5''''-trifluoromethyl)phenyl-2'''-hydroxyethyloxy)-3''-methoxycyclohexyl)-1'methylvinyl]-23,25 -dimethoxy-13,19, 21,27-tetramethyl-11,28-dioxa-4-azatricyclo[22.3.1.0$^{4,9}$] octacos-18-ene-2,3,10,16 -tetraone;

17-ethyl-1,14-dihydroxy-12-[2'-(3'',4''-di-(2'''-phenyl-2'''-oxoethyloxy)-cyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone;

17-ethyl-1,14-dihydroxy-12-[2'-(3'',4''-di-(2'''-phenyl-2'''-hydroxyethyloxy)-cyclohexyl)-1'-methylvinyl]-23,25-dimethoxy-13,19,21,27-tetramethyl-11,28-dioxa-4 -azatricyclo[22.3.1.0$^{4,9}$]octacos18-ene-2,3,10,16-tetraone;

or a pharmaceutically acceptable salt thereof.

B. Preparation of Compounds Within the Scope of the Present Invention

The starting materials for the preparation of the compounds of this invention are represented by Formula II:

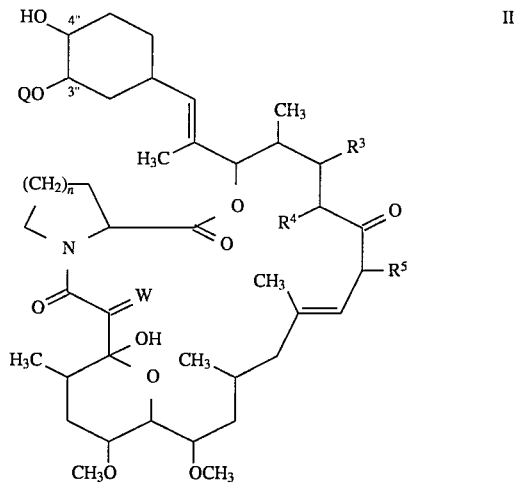

wherein:

Q is hydrogen or methyl;

W is O or (H, OH);

$R^3$ is hydrogen, hydroxy, or $C_1$–$C_6$ alkoxy;

$R^4$ is hydrogen, or $R^3$ and $R^4$ taken together form a double bond;

$R^5$ is methyl, ethyl, propyl or allyl; and n is 1 or 2.

The production and characterization of compounds of Formula II is well known in the literature (see U.S. Pat. No. 4,894,366 issued Jan. 16, 1990; U.S. Pat. No. 4,929,611 issued May 29, 1990; U.S. Pat. No. 3,244,592 issued Apr. 15, 1966; EPO Publication No. 0,323,042; EPO Publication No. 0,356,399; *PBJ Disclosure* 63-17884; *J. Am. Chem. Soc.*, 1987, 109, 5031; and *J. Antibiotics*, 1987, 40, 1249). Both biological fermentation and synthetic processes may be found. A synthetic route to compounds of Formula II can involve modifications of a route described in *J. Am. Chem. Soc.*, 1989, 111, 1157.

Biological fermentation followed by synthetic modification is presently favored in the an as the method to produce compounds of Formula II. Organisms belonging to the genus Streptomyces such as *Streptomyces tsukubaensis*, No. 9993 and *Streptomyces hygroscopicus*, No. 7238 placed in an aqueous nutrient medium will produce desired compounds in isolable amounts. The nutrient medium contains sources of assimilable carbon and nitrogen, preferably under aerobic conditions. Produced in fermentation are four compounds of Formula II, (A) where Q is methyl, W is O, $R^3$ is hydroxyl, $R^4$ is hydrogen, $R^5$ is allyl and n is 2; (B) where Q is methyl, W is O, $R^3$ is hydroxyl, $R^4$ is hydrogen, $R^5$ is ethyl and n is 2; (C) where Q is methyl, W is O, $R^3$ is hydroxyl, $R^4$ is hydrogen, $R^5$ is methyl and n is 2; and (D) where Q is methyl W is O, $R^3$ is hydroxyl, $R^4$ is hydrogen, $R^5$ is allyl and n is 1.

A lyophilized sample of the isolated *Streptomyces tsukubaensis*, No. 9993 was deposited with the Fermentation Research Institute, Agency of Industrial Science and Technology (No. 1–3, Higashi 1-chome, Yatabemachi Tsukubagun, Ibaraki Prefecture, Japan) under the deposit number of FERM P-7886 (deposit date: Oct. 5th, 1984), and then convened to Budapest Treaty route of the same depository on Oct. 19, 1985 under the new deposit number of FERM BP-927.

Using the four compounds produced in fermentation above, the remaining compounds of Formula II may be easily produced. The allyl of $R^5$ may be conveniently reduced to propyl by well known methods, for example as described in U.S. Pat. No. 4,894,366. The hydroxy of $R^3$ may be protected by well known methods, for example as disclosed in EPO Publication No. 0,323,042. Likewise, the hydroxy at C-4" may also be protected. In addition, the hydroxy of $R^3$ may be reduced to a hydrogen or eliminated to form a double bond with $R^4$ (by methods disclosed in U.S. Pat. No. 4,894,366 or EPO Publication No. 0,323,042 or EPO Publication No. 0,413,532). The carbonyl of W may be reduced to the alcohol by methods disclosed in EPO Publication No. 0,323,042 or by methods disclosed in U.S. Pat. No. 5,064,835 or in EPO Publication No. 0,445,975.

The methyl of Q as produced may be replaced with hydrogen or demethylated and subsequently protected as desired, if necessary. This demethylation of compounds wherein Q is methyl may be carried out in a fermentation reaction using the compounds of Formula II as a feedstock. For instance, compound A named under Formula II above may be demethylated at Q above by using the microorganism Actinomycetales ATCC No. 53771 (described in U.S. Pat. No. 4,981,792, issued Jan. 1, 1991) or by using the microorganism *Streptomyces tsukubaensis*, No. 9993 (described in EPO Publication No. 0,353,678). Similarly, compound B named under Formula II above may be demethylated at Q above using the microorganism Actinoplanacete sp. ATCC No. 53771 (described in EPO Publication No. 0,349,061). In addition the compound of Formula II wherein Q is H, W is O, $R^3$ is hydroxy, $R^4$ is hydrogen, $R^5$ is ethyl and n is 2 may be produced directly by fermentation using the mutant microorganism *Streptomyces hygroscopicus* sup. *ascomyceticus*, No. 53855 (being a blocked mutant of *Streptomyces hygroscopicus* sup. *ascomyceticus*, No. 14891) (as described in EPO Publication 0,388,152) Similarly, the compound of Formula II wherein Q is hydrogen, W is O, $R^3$ is hydroxy, $R^4$ is hydrogen, $R^5$ is methyl and n is 2 may be produced directly by fermentation using the mutant microorganism *Streptomyces hygroscopicus* sup. *ascomyceticus, No.* 53855 (being a blocked mutant of *Streptomyces hygroscopicus* sup. *ascomyceticus*, No. 14891) (as described in EPO Publication 0,388,153). Also, the compound of Formula II wherein Q is hydrogen, $R^3$ is hydroxy, $R^4$ is hydrogen, $R^5$ is allyl, W is 0 and n is 2 and the compound of Formula II wherein the C-3" position is oxo (keto), $R^3$ is hydroxy, $R^4$ is hydrogen, $R^5$ is allyl, W is 0 and n is 2 may be produced directly by fermentation using the microorganism *Streptomyces tsukubaensis*, No. 9993 (described in EPO Publication No. 0,353,678). The hydroxy of C-3" may be protected by methods similar to those known for the protection of the hydroxyl groups of $R^3$ and/or C-4", for example as disclosed in U.S. Pat. No. 4,894,366.

Suitable protecting groups for hydroxyl include those groups well known in the art such as:

1-(lower alkylthio)(lower)alkyl, wherein "lower alkyl" indicates a straight, cyclic or branched chain of one to six carbon atoms, such as lower alkylthiomethyl (e.g. methylthiomethyl, ethylthiomethyl, propylthiomethyl, isopropylthiomethyl, butylthiomethyl, isobutylthiomethyl, hexylthiomethyl, etc.), and the like, in which the preferred one may be $C_1$–$C_4$ alkylthiomethyl and the most preferred one may be methylthiomethyl; trisubstituted silyl such as tri(lower)alkylsilyl (e.g. trimethylsilyl, triethylsilyl, tributysilyl, tri-i-propylsilyl, t-butyldimethylsilyl, tri-t-butylsilyl, etc.), lower alkyldiarylsilyl (e.g. methyl-diphenylsilyl, ethyl-diphenylsilyl, propyl-diphenylsilyl, t-butyldiphenylsilyl, etc.), and the like, in which the preferred one may be tri($C_1$–$C_4$)alkylsilyl and $C_1$–$C_4$ alkyl-diphenylsilyl, and the most preferred one may be tert-butyl-dimethylsilyl, tri-i-propylsilyl and tert-butyldiphenylsilyl; acyl such as aliphatic acyl, aromatic acyl and aliphatic acyl substituted with aromatic group, which are derived from carboxylic acids; and the like.

Compounds A, B, C and D of Formula II, organisms to produce the same, conditions of fermentation, separation techniques, and chemical modification of the products are fully described in U.S. Pat. No. 4,894,366, issued Jan. 16, 1990 and U.S. Pat. No. 4,929,611, issued May 29, 1990.

The 5α-reductase inhibitor may be an inhibitor of 5α-reductase isozyme 1 and/or 5α-reductase isozyme 2. A preferred 5α-reductase inhibitor is finasteride. It is also preferred that the 5α-reductase inhibitor be selective for the scalp-associated enzyme 5α-reductase isozyme 1.

4-Aza steriod compounds are known in the art as 5α-reductase inhibitors. For example, See U.S. Pat. Nos. 2,227,876, 3,239,417, 3,264,301 and 3,285,918; French Patent No. 1,465,544; Doorenbos and Solomons, *J. Pharm. Sci.* 62, 4, pp. 638–640 (1973); Doorenbos and Brown, *J. Pharm. Sci.*, 60, 8, pp. 1234–1235 (1971); and Doorenbos and Kim, *J. Pharm. Sci.* 63, 4, pp. 620–622 (1974).

In addition, U.S. Pat. Nos. 4,377,584, 4,220,775, 4,859,681, 4,760,071 and the articles *J. Med. Chem.* 27, p. 1690–1701 (1984) and *J. Med. Chem.* 29, 2998–2315 (1986) of Rasmusson, et al., U.S. Pat. No. 4,845,104 to Carlin, et al., and U.S. Pat. No. 4,732,897 to Cainelli, et al. described 4-aza 17β-substituted-5α-androstan-3-ones useful in the treatment of DHT-related hyperandrogenic conditions.

Cyclosporin may be prepared essentially as described in U.S. Pat. No. 4,117,118 or by R. Wenger, *Transplant. Proc.*, 15 (4), Suppl. 1, 2230 (1983) and is available from Sandoz Pharmaceuticals, East Hanover, N.J.

The potassium channel opener may be minoxidil, cromakalim, pinacidil, a triazine compound, a thiane-1-oxide, or other compounds.

Chemically minoxidil is 6-amino-1,2-dihydro-hydroxy-2-imino-4-piperidinopyrimidine and analogs thereof. The preparation of these compounds are described in U.S. Pat. Nos. 3,382,247, 3,461,461 and 3,644,364 and J. M. McCall, et al., *J. Org. Chem.*, 40, 3304 (1975). Related compounds are sulfoxypyrimidinium, -pyridinium, and -triazinium which are described in U.S. Pat. No. 4,287,338. The term "minoxidil" includes any of the various forms of 6-amino-1,2-dihydro-hydroxy-2-imino-4-piperidinopyrimidine, derivatives and analogs thereof. Minoxidil is distributed by The Upjohn Company, Kalamazoo, Mich.

Chemically cromakalim is (3S-trans) 3,4-dihydro-3-hydroxy-2,2-dimethyl-4-(2-oxo-1 -pyrrolidinyl)-2H-1-benxopyran-6-carbonitrile. Cromakalim is distributed by SmithKline Consumer Products, Philadelphia, Pa.

Pinacidil is chemically, N-cyano-N'-4-pyridinyl-N"-(1,2, 2-trimethylpropyl)-guanidine monohydrate. The preparation of pinacidil is described in U.S. Pat. No. 4,057,636 and is distributed by Eli Lilly and Company, Indianapolis, Ind.

S-Triazine compounds or 2,6-diamino-4-substituted-s-triazine-1-oxides are described in U.S. Pat. No. 3,270,014 assigned to The Upjohn Company, Kalamazoo, Mich.

Thiane-1-oxide compounds are described in U.S. Pat. No. 4,568,682 assigned to Rhone-Poulenc Sante, Courbevoie, France. Other derivatives include those disclosed in patent applications EP 0,321,274 A, EP 0,321,273 A, and EP 0,326,297 A.

Other potassium channel openers include pyranopyridine derivatives described in patent applications GB 2,204,868 A and benzopyran derivatives described in patent publications GB 2,204,868 A, EP 0,314,446 A2, EP 0,339,562 A, EP 0,340,718 A, EP 0,337,179, AU A 18556/88, JA 1,294,677 A, EP 0,359,537 A, and U.S. Pat. No. 4,900,752.

The phospholipids used herein may be obtained from commercial sources. The phospholipids may also be isolated from natural sources (for example, egg yolk, soybean or other oily seed including safflower, sunflower and olive, and brain tissue) or may be produced synthetically. In either case, known techniques can be used for purification of the phospholipids (see, for example, *J. of American Oil Chemists Soc.* 42:53–56 (1965)).

The novel processes for preparing the novel compounds of the present invention are illustrated as follows, wherein $R^1$, $R^2$, $R^3$, $R^5$, Q, W and n are as defined above unless otherwise indicated. It will be readily apparent to one of ordinary skill in the art reviewing the synthetic route depicted below that other compounds within Formula I can be synthesized by substitution of appropriate reactants and agents in the synthesis shown below.

REACTION SCHEME A

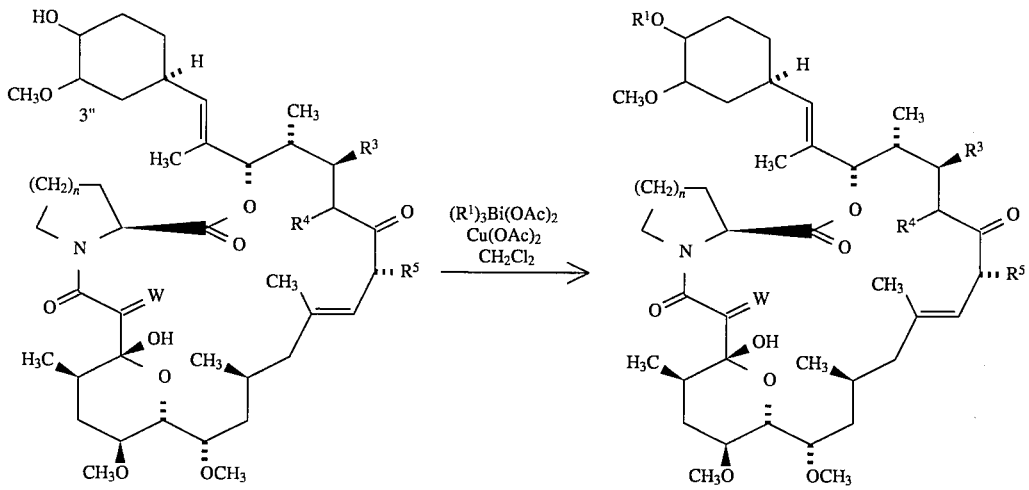

REACTION SCHEME B

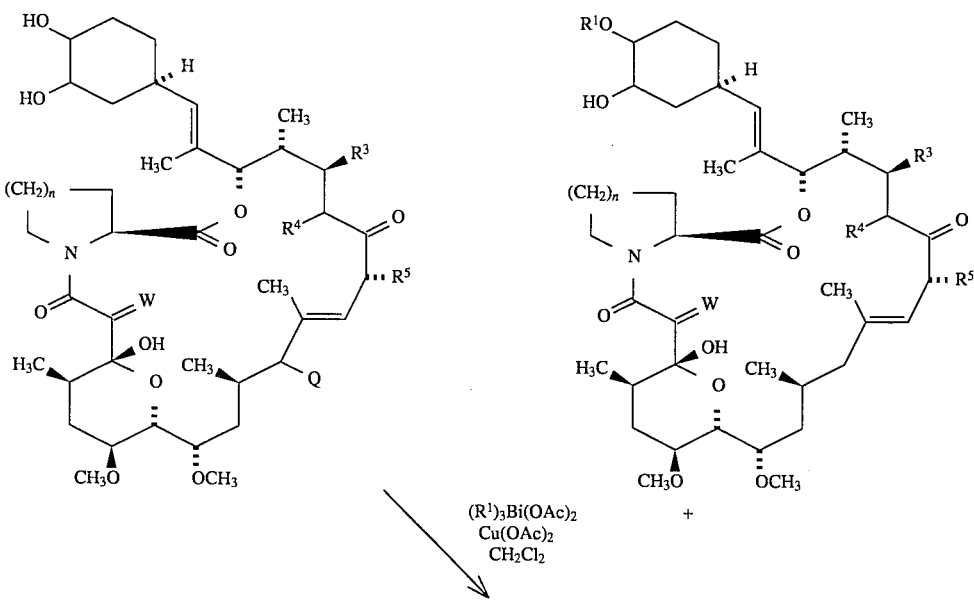

-continued
REACTION SCHEME B
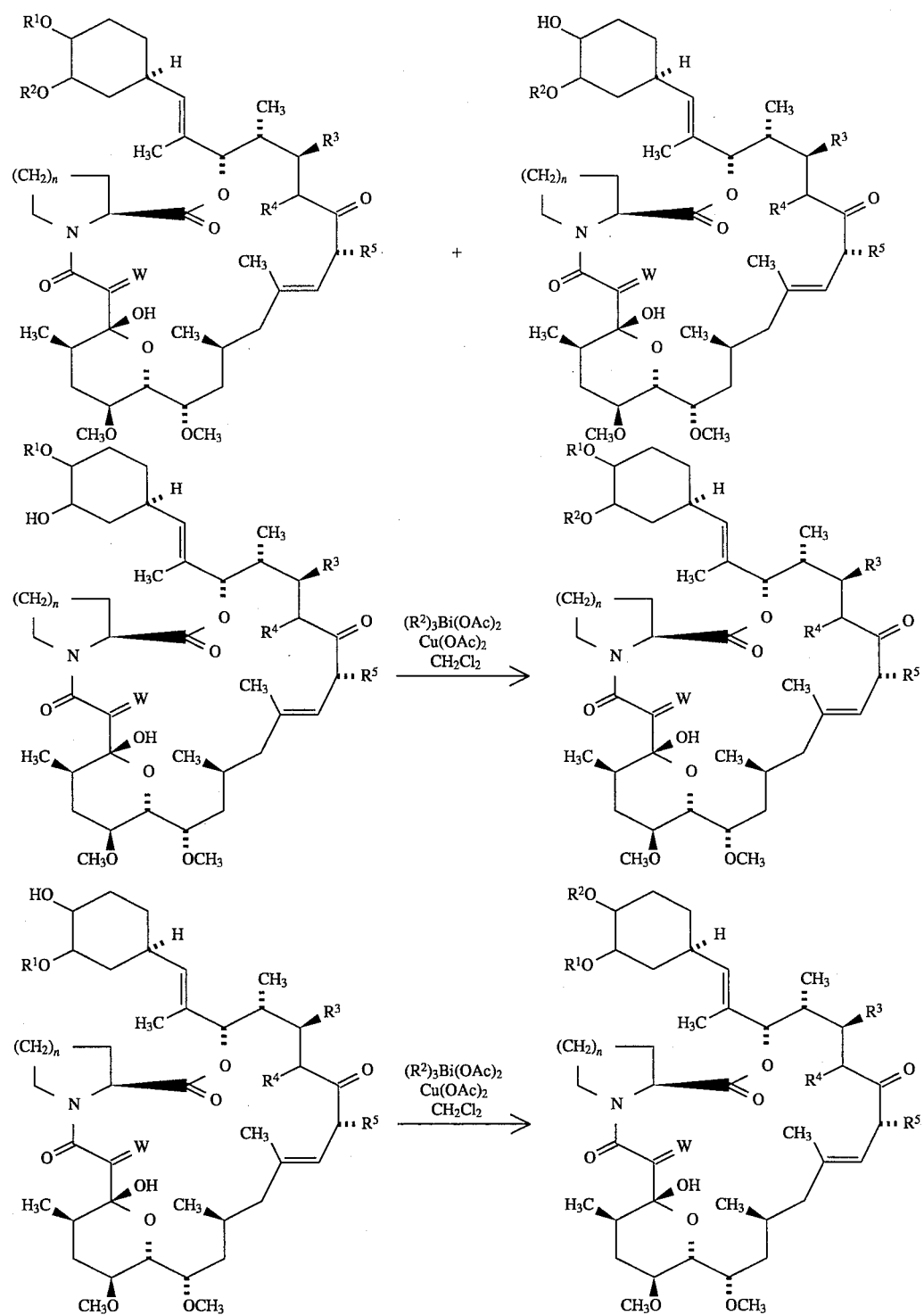

REACTION SCHEME C
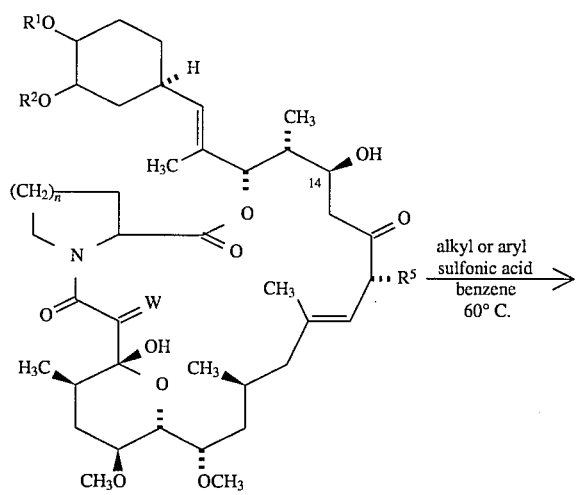
REACTION SCHEME D
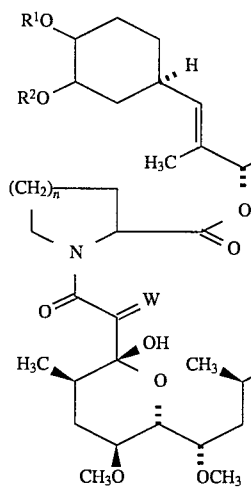
REACTION SCHEME D
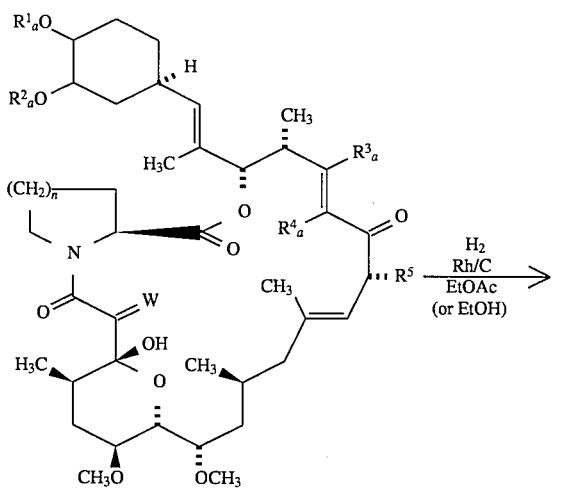
REACTION SCHEME D -continued
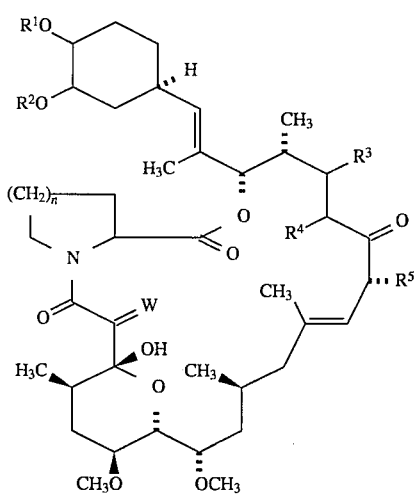
REACTION SCHEME E
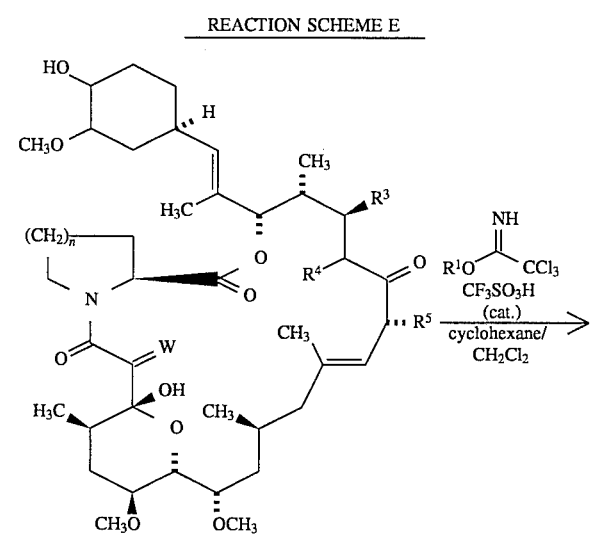

-continued
REACTION SCHEME E
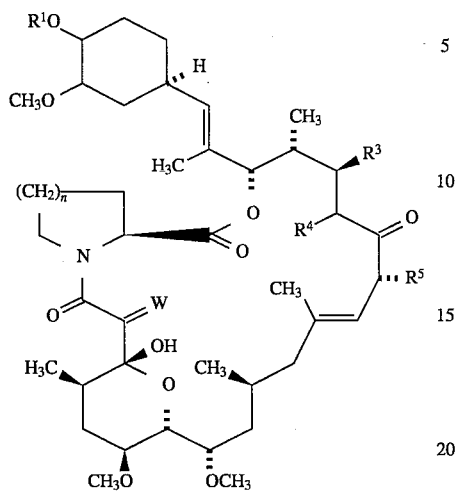
REACTION SCHEME F
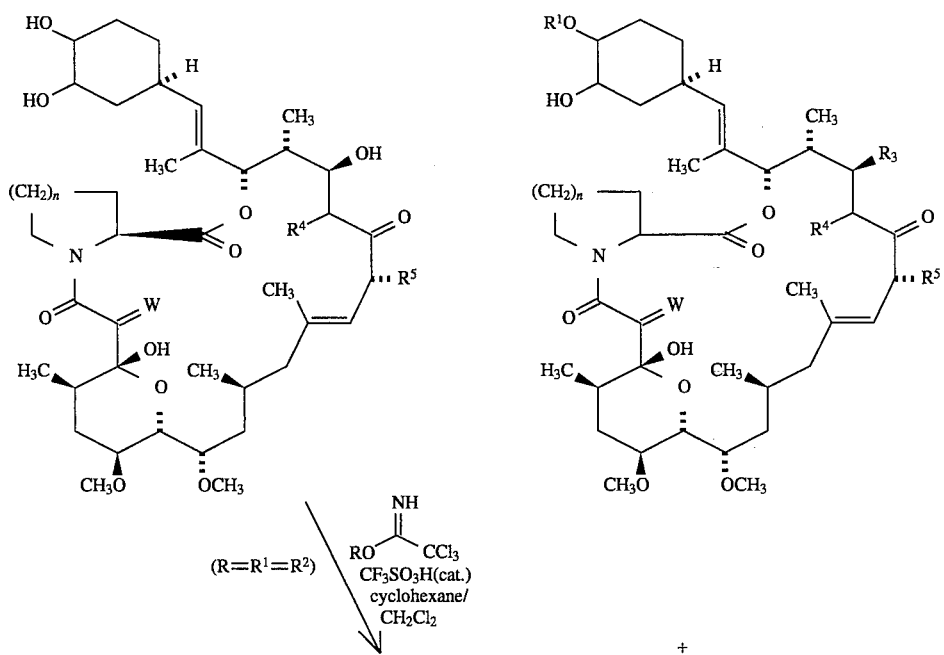

-continued
REACTION SCHEME F
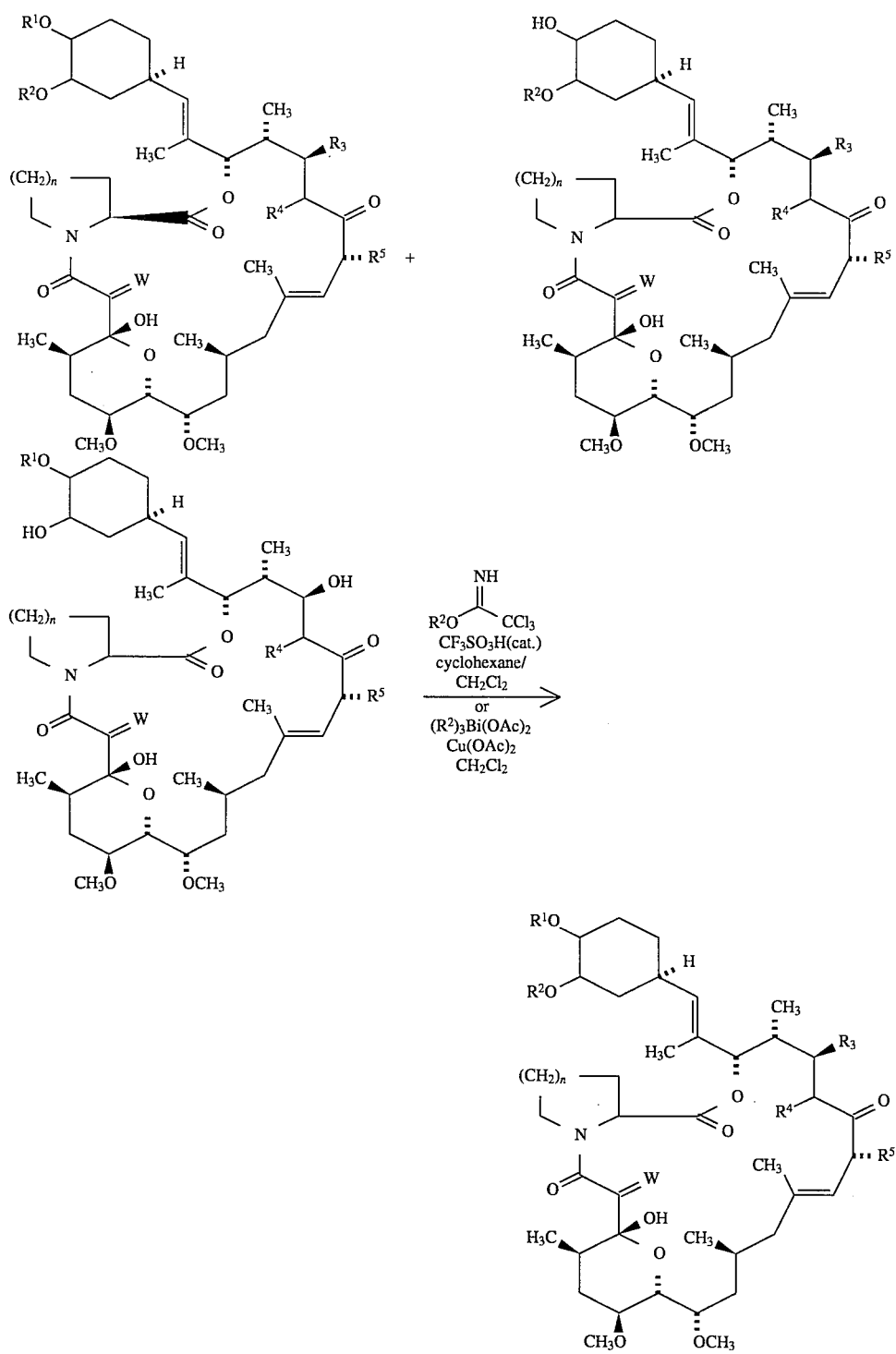

-continued
REACTION SCHEME F
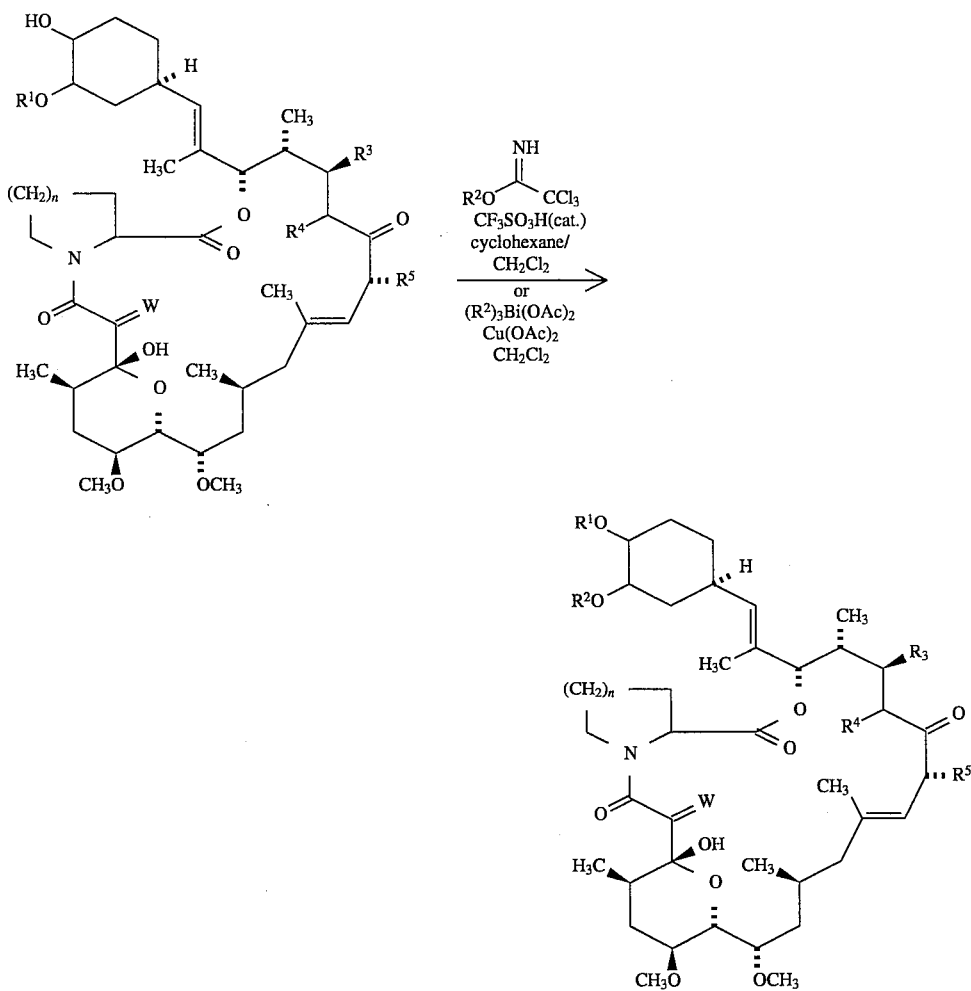
REACTION SCHEME G
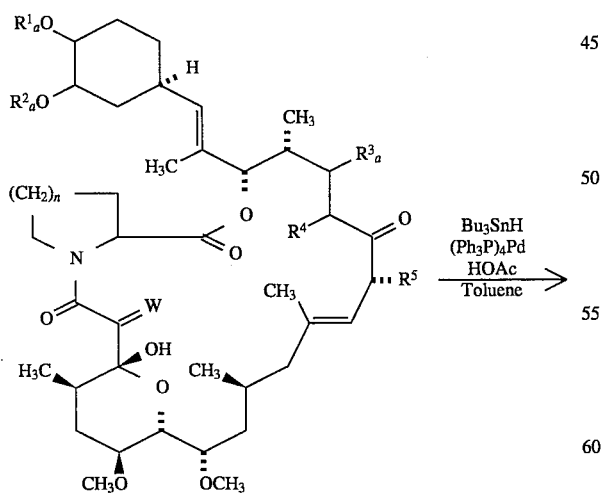
-continued
REACTION SCHEME G
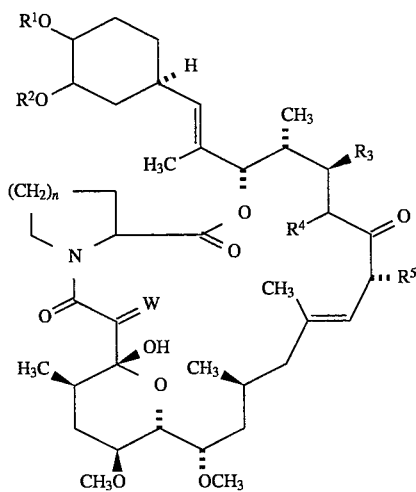

REACTION SCHEME H
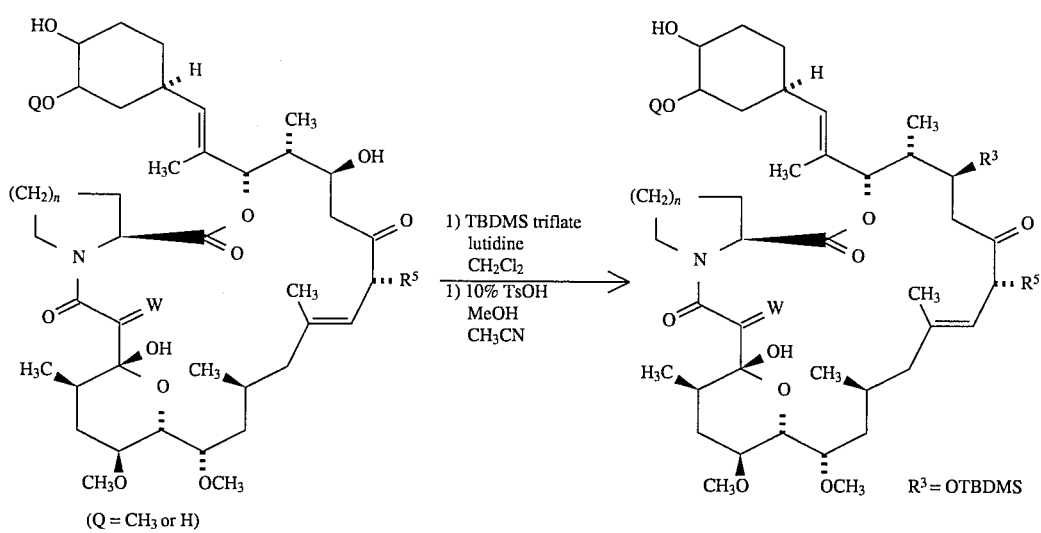
REACTION SCHEME I
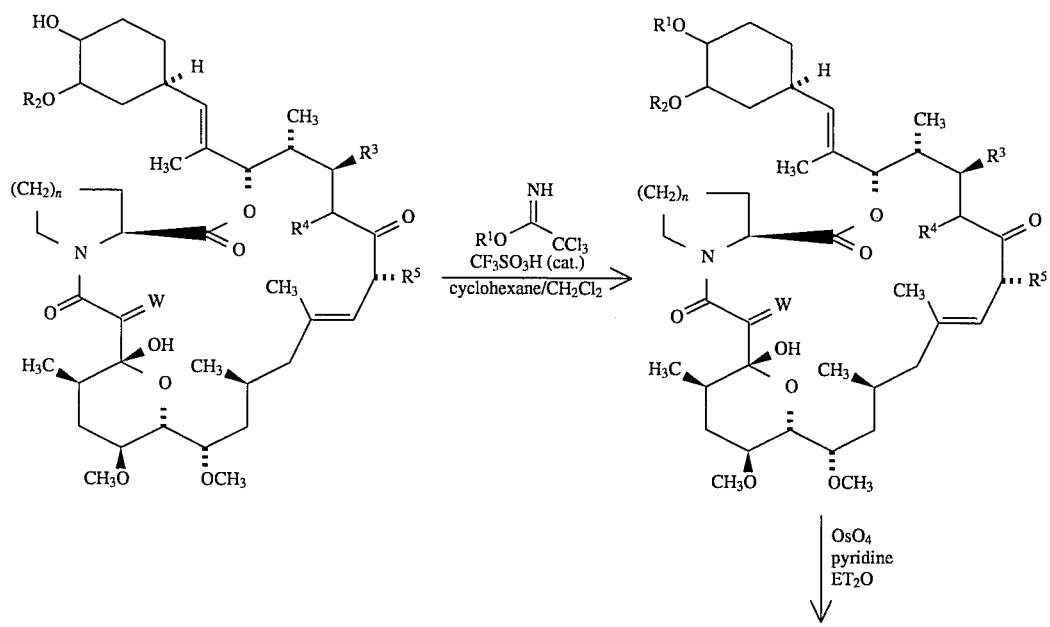

-continued
REACTION SCHEME I
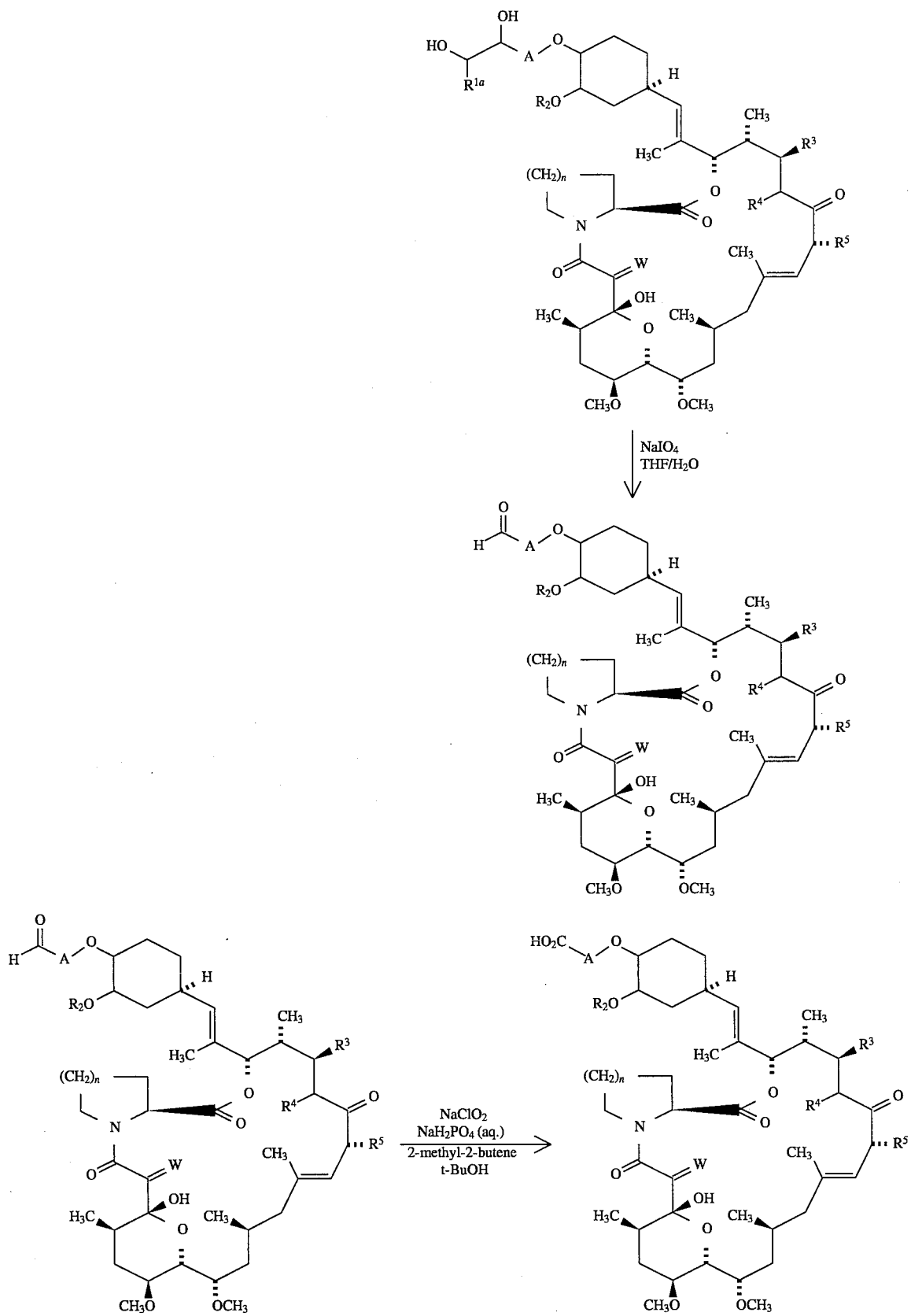

REACTION SCHEME J
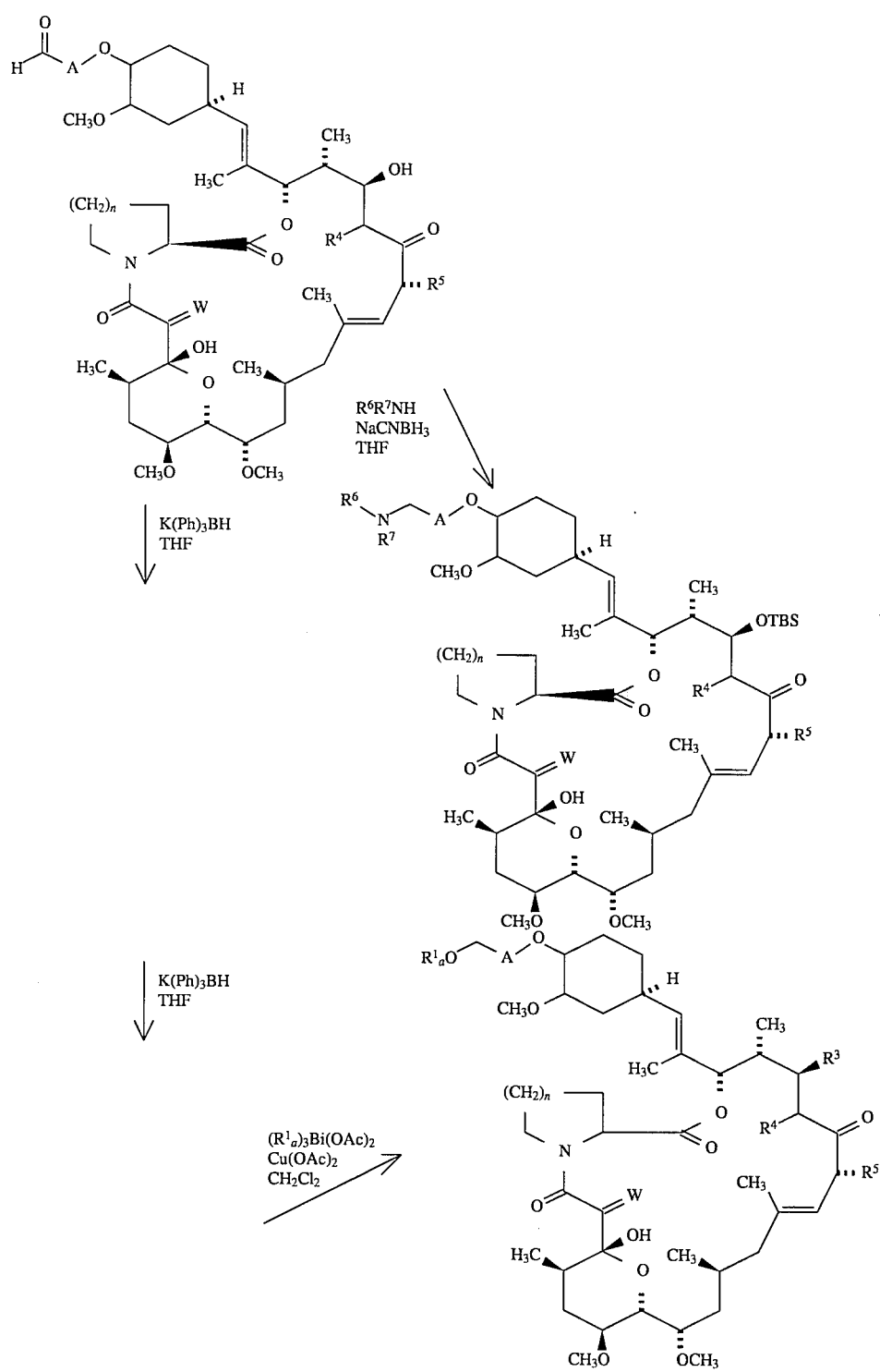

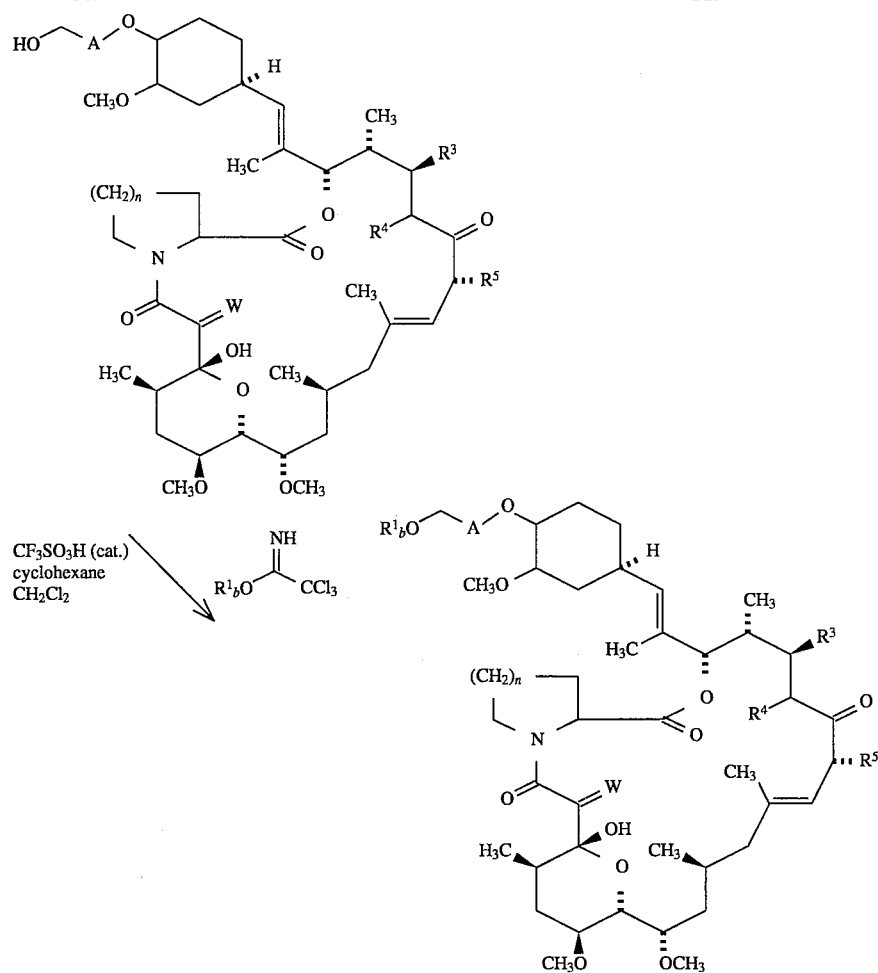
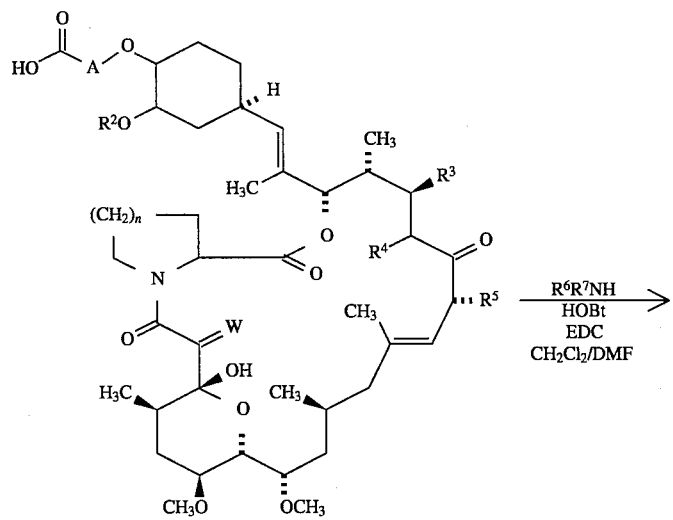
REACTION SCHEME K

-continued
REACTION SCHEME K
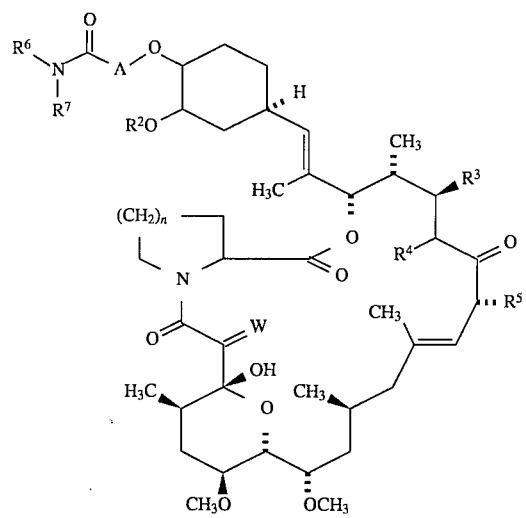
REACTION SCHEME L
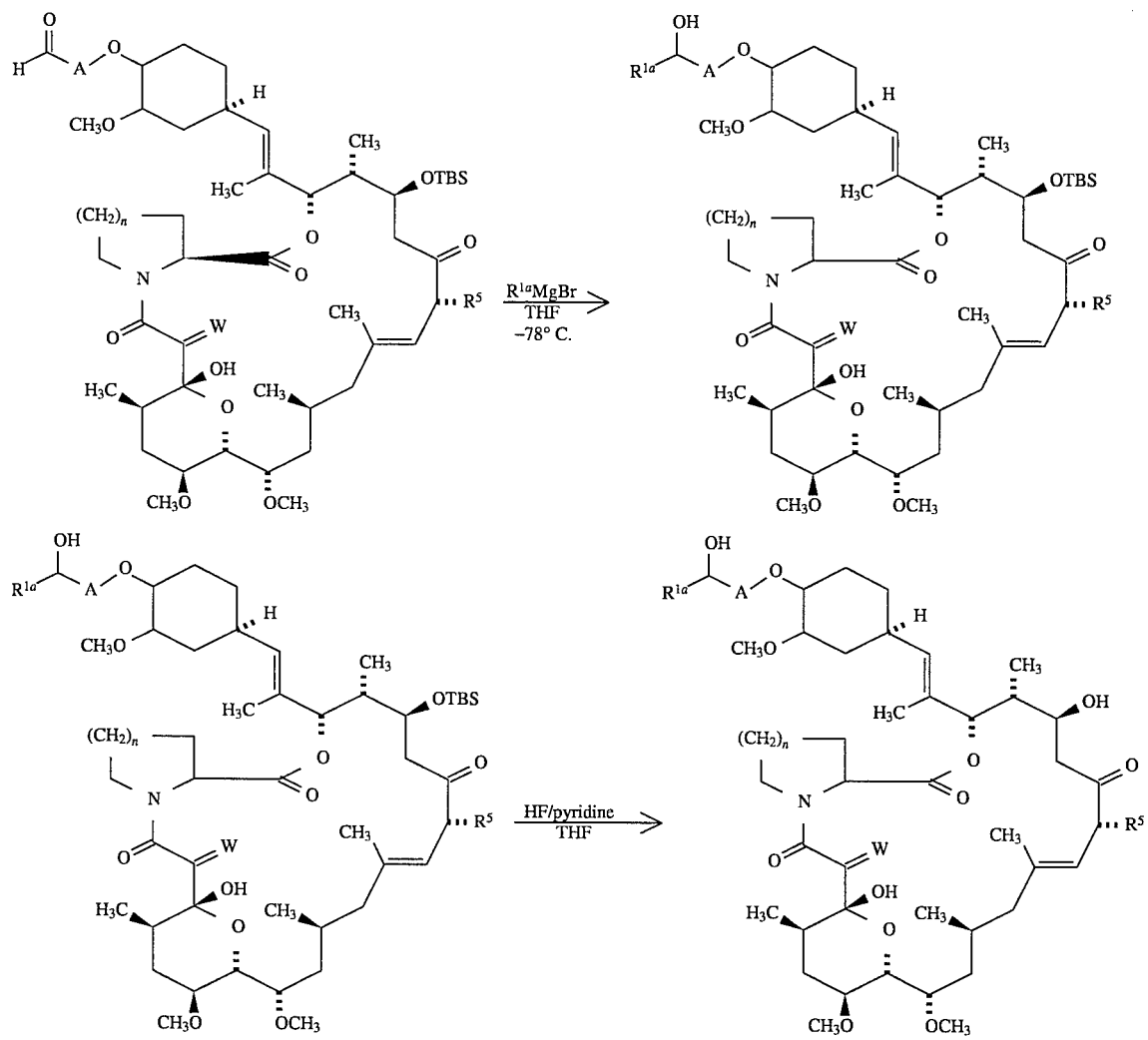

-continued
REACTION SCHEME L
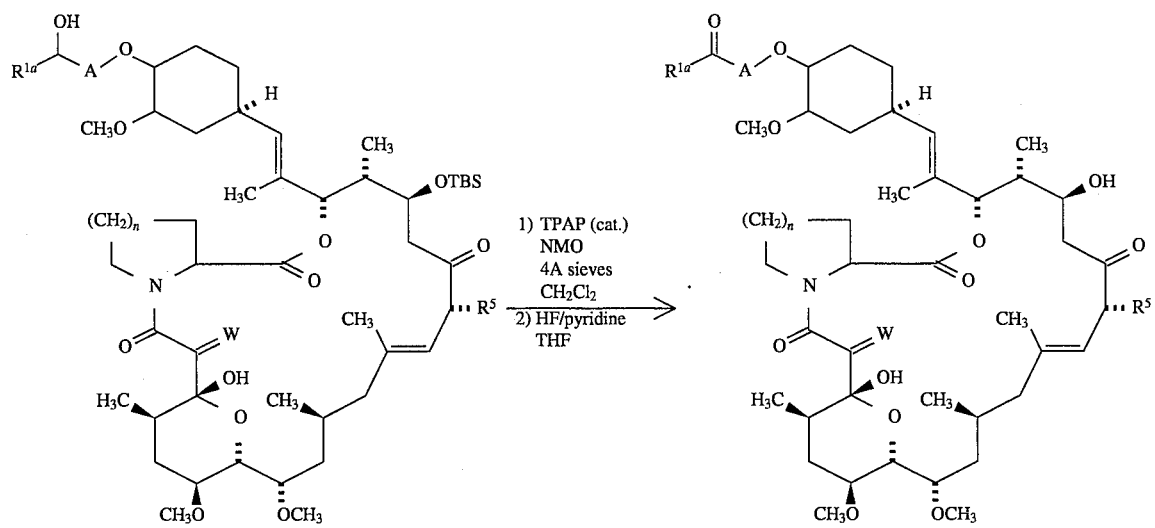
REACTION SCHEME M
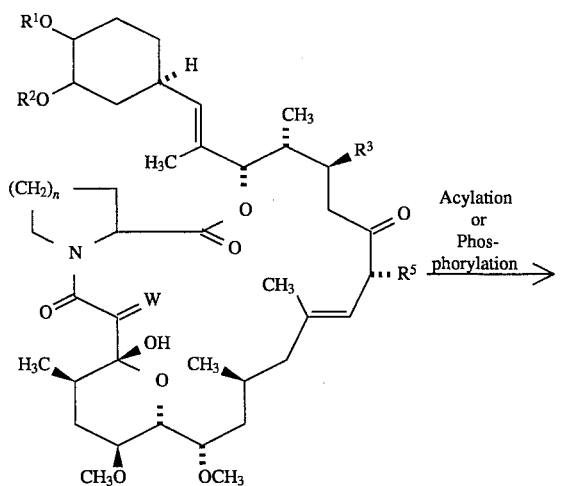
-continued
REACTION SCHEME M
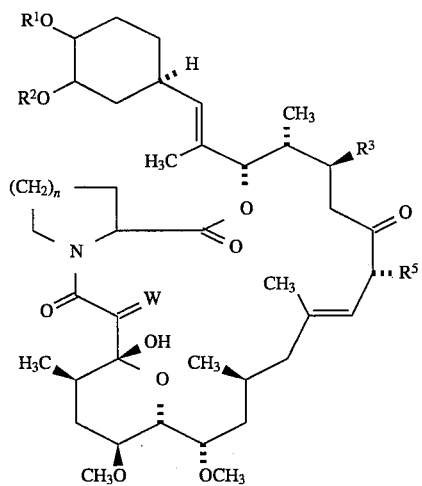

REACTION SCHEME N
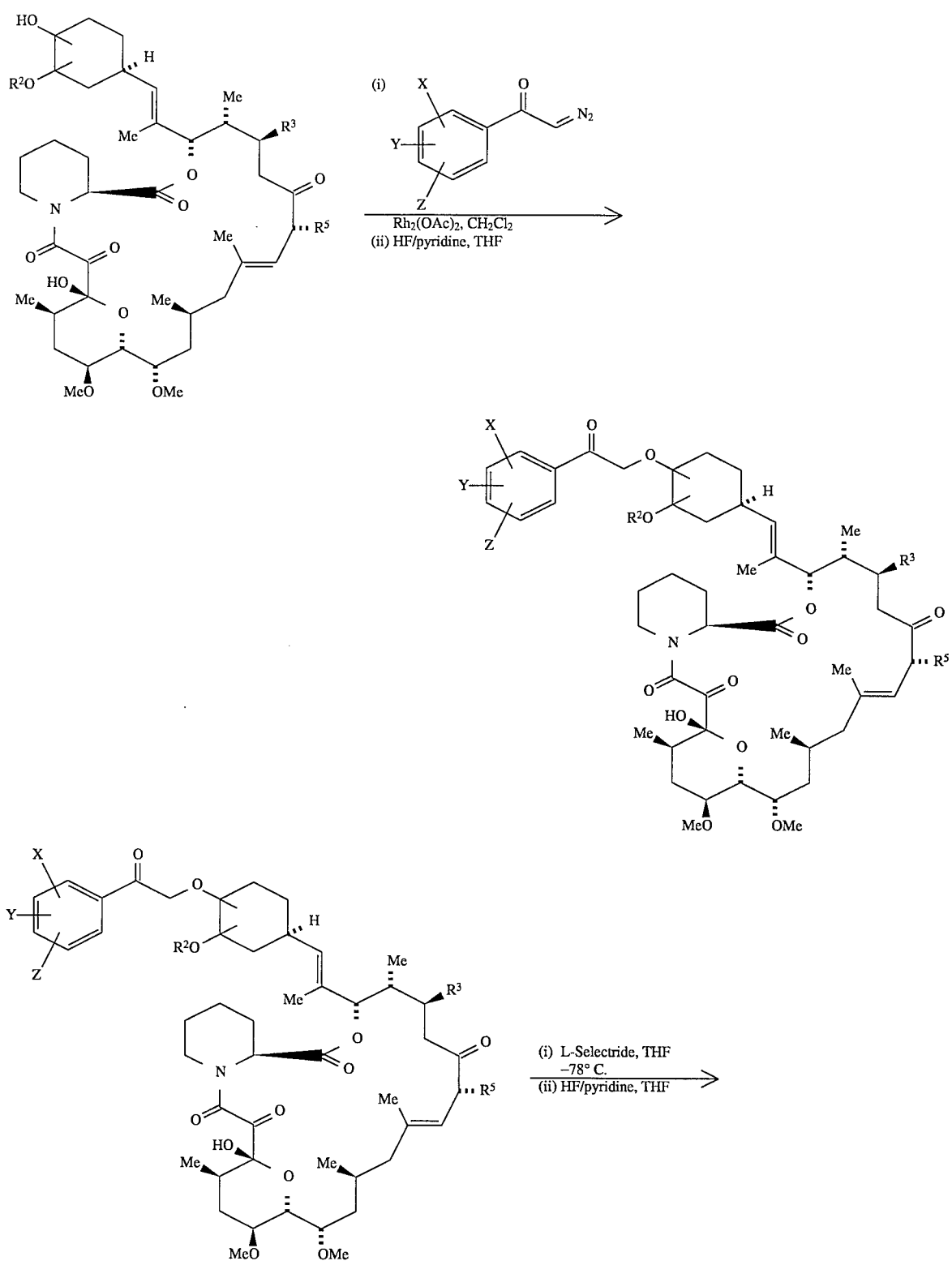

-continued
REACTION SCHEME N
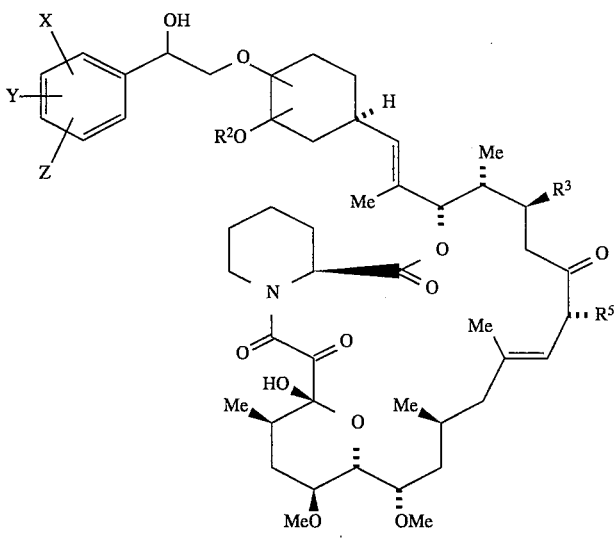
REACTION SCHEME O
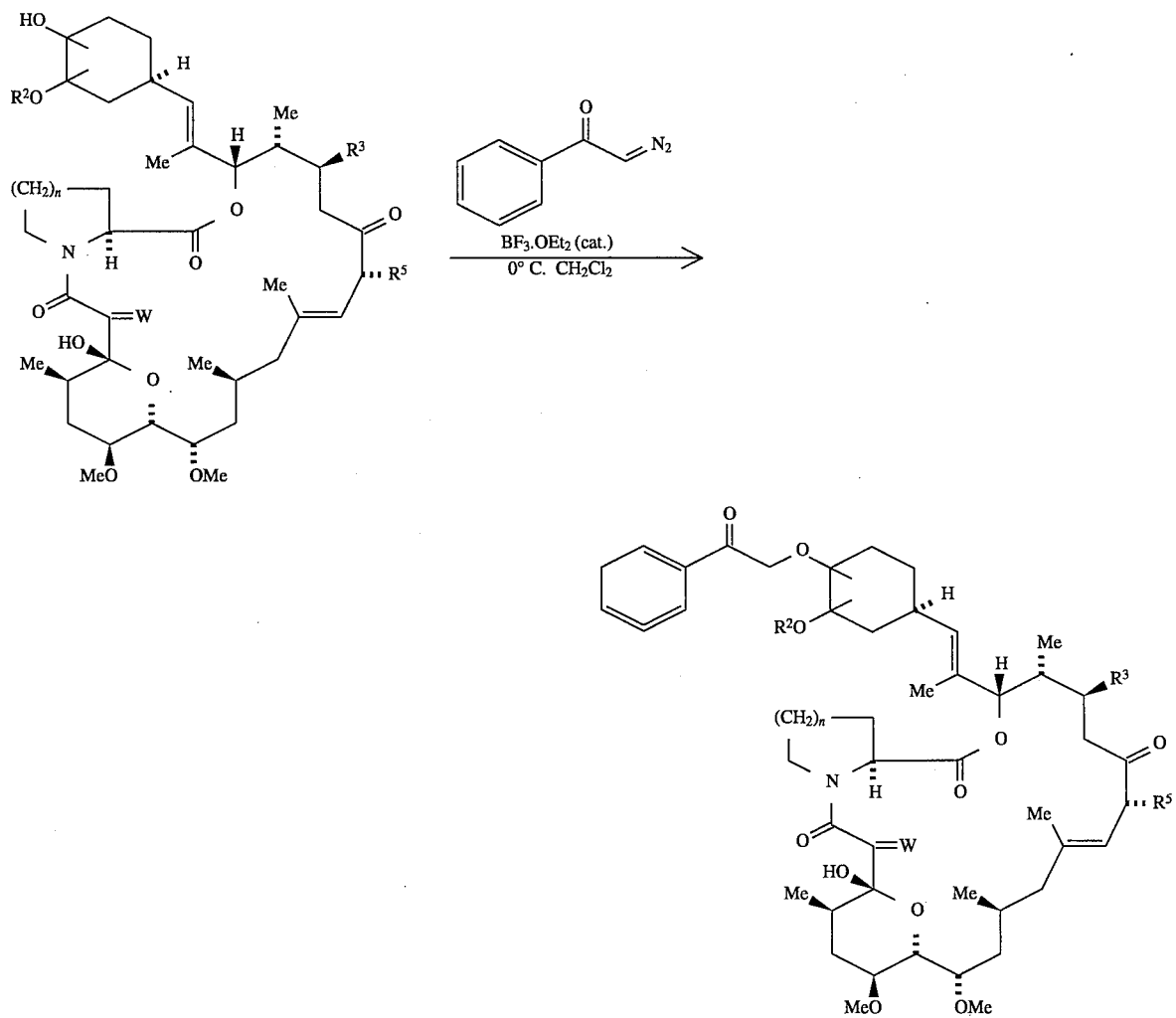

Reaction Scheme A

As shown in Reaction Scheme A, a solution of a 4"-hydroxy-3"-methoxy macrolide in an inert organic solvent such as methylene chloride, benzene, toluene, chloroform, or the like or mixtures thereof is treated with a triarylbismuth diacetate reagent (wherein $R^1$ is aryl) (prepared immediately prior to use by the addition of acetic acid to a suspension of a triarylbismuth carbonate in an inert organic solvent such as methylene chloride, chloroform or the like or mixtures thereof) in the presence of a catalytic amount of copper(II) acetate at a temperature of 20°–50° C., preferably room temperature, for a period of one hour to seven days, preferably one day, to give the 4"-O-aryl-3"-methoxy macrolide. Alternatively, the triarylbismuth(V) reagent can be prepared by treatment of a triarylbismuthine with a suitable oxidant such as peracetic acid, iodobenzene diacetate, bis(trifluoroacetoxy)iodobenzene and the like in an inert solvent such as methylene chloride, chloroform, benzene, toluene and the like. The triarylbismuth(V) reagent can be used without purification or can be purified by silica gel chromatography. Triarylbismuthines may be prepared by the reaction of an appropriate aryl Grignard reagent with bismuth trichloride in an inert organic solvent such as tetrahydrofuran, diethyl ether, or 1,4-dioxane, or mixtures thereof, at or near room temperature for a period of 1 to 48 hours. General procedures for the preparation and use of triaryl bismuth reagents may be found in Barton, D. H. E., et al., *J. Chem. Soc. Chem. Commun.*, 1986, 65 and references cited therein.

Reaction Scheme B

Similarly, as shown in Reaction Scheme B, a solution of the 3",4"-dihydroxy macrolide is treated with a triarylbismuth diacetate reagent as described in Reaction Scheme A, to give a mixture of the 3"-hydroxy-4"-O-aryl macrolide, the 3"-O-aryl-4"-hydroxy macrolide, and the 3",4"-di-O-aryl macrolide. At this stage, a solution of 3"-hydroxy-4"-O-aryl macrolide, or 3"-O-aryl-4"-hydroxy macrolide can be treated with a different triarylbismuth diacetate reagent (prepared immediately prior to use by procedures analogous to those disclosed above), to give 3"-O-aryl-4"-O-aryl macrolides.

Reaction Scheme C

As shown in Reaction Scheme C the 14-hydroxy group of a macrolide (wherein $R^1$, $R^2$, $R^5$, W and n are as defined above) may be eliminated by treatment with p-toluenesulfonic acid, benzenesulfonic acid, methanesulfonic acid, p-nitrobenzenesulfonic acid, p-bromobenzenesulfonic acid, p-chlorobenzenesulfonic acid, or p-methoxybenzenesulfonic acid, or mixtures thereof, in an inert organic solvent such as benzene, or toluene or the like at a temperature of 40° C. to solvent reflux temperature, preferably 60° C., for about 0.5 to 6 hours, or a sufficient period of time to eliminate the 14-hydroxy group. Neutralization with an aqueous solution of a weak base such as aqueous saturated sodium bicarbonate gives the 14,15-dehydro macrolide. The 14-hydroxy group may also be eliminated by activation followed by basic elimination, as described in U.S. Pat. No. 4,894,366.

Reaction Scheme D

As shown in Reaction Scheme D the macrolide (wherein $R^{1a}$ and/or $R^{2a}$ is alkenyl, substituted alkenyl, alkynyl or substituted alkynyl and wherein $R^{3a}$ is hydroxy or $C_{1-6}$ alkoxy, $R^{4a}$ is hydrogen, or $R^{3a}$ and $R^{4a}$ taken together form a double bond) is reduced under an atmosphere of hydrogen in the presence of a noble metal catalyst, such as rhodium on carbon catalyst or rhodium on alumina catalyst, at a pressure of atmospheric pressure to 40 psig, at or near room temperature in an organic solvent such as ethyl acetate or ethanol for about 1 to 24 hours, or until the requisite amount of hydrogen is absorbed to reduce the olefin and give the reduced macrolide.

By changing the sequence of synthetic steps, all possible variations of substitution can be achieved. For example, the C-14 hydroxy group may be eliminated and the resultant double bond reduced prior to the introduction of alkenyl or alkynyl substituents at C-3" and/or C-4".

Reaction Scheme E

As shown in Reaction Scheme E, a solution of the 4"-hydroxy 3"-methoxy macrolide in an inert organic solvent such as methylene chloride, chloroform, pentane, hexane, cyclohexane, heptane or the like or mixtures thereof is treated with an alkyl, alkenyl or alkynyl trichloroacetimidate reagent (prepared by the reaction of an appropriate sodium alkoxide with trichloroacetonitrile, such as described by Wessel, H. P., Iversen, T., Bundle, D. R., *J. Chem. Soc., Perkin Trans. I*, 1985, 2247) in the presence of a mild acid catalyst such as trifluoromethanesulfonic acid, p-toluenesulfonic acid, methanesulfonic acid, benzenesulfonic acid, p-nitrobenzenesulfonic acid, p-bromobenzenesulfonic acid, p-chlorobenzenesulfonic acid, or p-methoxybenzenesulfonic acid, or mixtures thereof at a temperature of 20°–50° C., preferably room temperature, for a period of one hour to seven days, preferably one day, to give the 4"-O-alkyl, -alkenyl or -alkynyl 3"-methoxy macrolide.

Reaction Scheme F

Similarly, as shown in Reaction Scheme F, (wherein $R=R^1=R^2$) a solution of the 3",4"-dihydroxy macrolide in an inert organic solvent such as methylene chloride, chloroform, pentane, hexane, cyclohexane, heptane or the like or mixtures thereof is treated with an alkyl, alkenyl, or alkynyl trichloroacetimidate (prepared by the reaction of an appropriate sodium alkoxide with trichloroacetonitrile, such as described by Wessel, H. P., Iversen, T., Bundle, D. R., *J. Chem. Soc., Perkin Trans. I*, 1985, 2247) in the presence of a mild acid catalyst such as trifluoromethanesulfonic acid, p-toluenesulfonic acid, methanesulfonic acid, benzenesulfonic acid, p-nitrobenzenesulfonic acid, p-bromobenzenesulfonic acid, p-chlorobenzenesulfonic acid, or p-methoxybenzenesulfonic acid, or mixtures thereof of at a temperature of 20°–50° C., preferably 40° C., for a period of one hour to seven days, preferably 6 hours, to give a mixture of the 3"-O-alkyl, -alkenyl or -alkynyl 4"-hydroxy macrolide, the 3"-hydroxy 4"-O-alkyl, -alkenyl or -alkynyl macrolide and the 3",4"-di-O-alkyl, -alkenyl or -alkynyl macrolide.

Reaction Scheme G

The procedures described in Reaction Schemes C and D may optionally be conducted following the procedures of Reaction Scheme E or F. Alternatively, the procedures described in Reaction Scheme G may be performed. In Reaction Scheme G the macrolide (wherein $R^{1a}$ and/or $R^{2a}$ is alkenyl, substituted alkenyl, alkynyl or substituted alkynyl and wherein $R^{3a}$ is hydroxy or $C_{1-6}$ alkoxy, $R^{4a}$ is hydrogen, or $R^{3a}$ and $R^{4a}$ taken together form a double bond) is reduced with tri-n-butyltin hydride in the presence of tetrakis(triphenylphosphine)palladium(O) catalyst and acetic acid in an organic solvent such as toluene or tetrahydrofuran at or near room temperature for about 2 to 10 hours to give the reduced macrolide.

The procedures described in Reaction Scheme F may be conducted on the mono-substituted products of Reaction Scheme B (and visa versa) to obtain the mixed disubstituted compounds. In fact, within Reaction Schemes B and F, treatment of the mono-substituted product with a different reagent will afford the mixed disubstituted compounds.

Reaction Scheme H

Protection of the C-3", C-4" and/or the C-14 hydroxy group may be accomplished by methods known in the prior art for compounds of Formula II such as by treatment with: 2,6-lutidine and triisopropylsilyl trifluoromethanesulfonate in a solution of methylene chloride; 2,6-lutidine and t-butyldimethylsilyl trifluoromethanesulfonate in a solution of methylene chloride; pyridine and acetic anhydride in a solution of methylene chloride; pyridine and benzoyl chloride in a solution of methylene chloride; pyridine and p-nitrobenzoyl chloride in a solution of methylene chloride; imidazole and t-butyldiphenylsilyl chloride in a solution of methylene chloride; and the like. For example, as shown in Reaction Scheme H, the C-4",14-dihydroxy C-3"-methoxy macrolide (or the C-3",4", 14-trihydroxy macrolide) may be protected at C-14 as the t-butyldimethylsilyl ether by treatment with t-butyldimethylsilyl trifluoromethanesulfonate in methylene chloride to give the C-4",3"-di-O-TBDMS macrolide (or the C-3",4", 14-tri-O-TBDMS macrolide). Treatment with toluenesulfonic acid in methanol results in selective removal of the C-4" silyl ether (and C-3" silyl ether, if present) to give the C-14-O-TBDMS macrolide.

Reaction Scheme I

As shown in Reaction Scheme I, the 4"-hydroxy-3"-$R^2O$-macrolide or alternatively the 3"-hydroxy-4"-$R^1O$-macrolide (not depicted) (wherein $R^3$ is protected hydroxy or hydrogen) may be reacted with an alkenyl trichloroacetimidate (wherein $R^1$ is $C_{3-10}$ alkenyl) under conditions described in Reaction Scheme F to give the C-4"-O-alkenyl macrolide. Treatment with a stochiometric amount of osmium tetraoxide in an inert organic solvent, such as diethyl ether or tetrahydrofuran, in the presence of an amine base, such as pyridine or 4-methylmorpholine N-oxide, at or near room temperature gives the corresponding glycol (wherein A is $C_{1-8}$ alkyl). Treatment of the glycol with sodium metaperiodate in a solution of tetrahydrofuran/water gives the aldehyde. Alternatively, the alkenyl macrolide may be treated with sodium metaperiodate in the presence of a catalytic amount of osmium tetraoxide in an organic solvent to give the aldehyde directly. The aldehyde can be further oxidized to the carboxylic acid by treatment with sodium chlorite in buffered, aqueous tert-butanol.

Reaction Scheme J

A variety of compounds may be prepared from the corresponding aldehyde as illustrated in Reaction Scheme J. The aldehyde may be reacted with a primary or secondary amine (wherein $R^6$ and $R^7$ are as defined above) in an organic solvent such as tetrahydrofuran to give an imine which is reduced in situ with a hydride reducing agent, such as potassium triphenyl borohydride or sodium cyanoborohydride, to give the macrolide beating an amino alkoxy functionality at C-4". The aldehyde may also be reduced to the corresponding alcohol by treatment with a hydride reducing agent, such as potassium triphenyl borohydride or sodium cyanoborohydride in an organic solvent such as tetrahydrofuran. The alcohol may be further modified by utilizing the methods of Reaction Scheme B (wherein $R^1_a$ is unsubstituted or substituted phenyl, naphthyl or biphenyl) or Reaction Scheme F (wherein $R^1_b$ is unsubstituted or substituted alkyl, alkenyl or alkynyl). The procedures described in Reaction Scheme J are readily applicable to the preparation of compounds beating analogous functionality at C-3".

Reaction Scheme K

Amide derivatives may be prepared from the carboxylic acid as illustrated in Reaction Scheme K. The carboxylic acid may be coupled with a primary or secondary amine, $HNR^6R^7$ (wherein $R^6$ and/or $R^7$ are as defined) by any of the peptide coupling methods commonly used in the art, such as with BOP reagent, DCC/HOBT, or EDC/HOBT.

Reaction Scheme L

Hydroxy and keto derivatives may be prepared from the corresponding aldehyde as illustrated in Reaction Scheme L. The aldehyde is reacted with a nucleophilic organometallic reagent such as a Grignard reagent, an organolithium reagent, or an organocerium reagent in an organic solvent such as methylene chloride or tetrahydrofuran to give the substituted hydroxy compound. Removal of hydroxy protecting groups at other positions of the macrolide (if necessary) gives the macrolide beating a substituted hydroxy alkoxy functionality at C-4". The alcohol may also be oxidized to the corresponding ketone by well known methods, such as with 4-methylmorpholine-N-oxide in the presence of tetrapropylammonium perruthenate catalyst under dehydrative conditions. Removal of hydroxy protecting groups (if necessary) gives the macrolide bearing a substituted keto alkoxy functionality at C-4". The procedures described in Reaction Scheme L are readily applicable to the preparation of compounds bearing analogous functionality at C-3".

Reaction Scheme M

Hydroxy macrolides (wherein $R^1$, $R^2$, and/or $R^3$ bear a hydroxy group) may be further derivatized by alkylation, acylation or phosphorylation to give ether, ester or phosphate derivatives (wherein $R^1$, $R^2$ and/or $R^3$ bear an —$OR^{11}$ as defined above) by procedures well known to the practitioner of the art.

Reaction Scheme N

As illustrated in Scheme N, the hydroxy macrolide may be derivatized by treatment with a substituted alpha-diazoketone in an inert organic solvent such as methylene chloride in the presence of a catalyst such as rhodium acetate to provide the corresponding ether adduct. The ketone functionality of the appended ether may be selectively reduced in an inert organic solvent such as diethyl ether or tetrahydrofuran at −78° C. by treatment with a reducing agent, such as L-Selectride, potassium triphenlyborohydride, diisobutyl aluminum hydride or lithium triethylborohydride.

Reaction Scheme O

Alternatively, as shown in Scheme O, treatment of the hydroxy macrolide with a substituted 2-diazoacetophenone in an inert organic solvent such as methylene chloride with a Lewis acid catalyst such as boron trifluoride etherate provides the corresponding ether adduct.

The object compounds of Formula I obtained according to the reactions as explained above can be isolated and purified in a conventional manner, for example, extraction, precipitation, fractional crystallization, recrystallization, chromatography, and the like.

It is to be noted that in the aforementioned reactions and the post-treatment of the reaction mixture therein, the stereoisomer(s) of starting and object compounds due to asymmetric carbon atom(s) or double bond(s) of the object compounds of Formula I may occasionally be transformed into the other stereoisomer(s), and such cases are also included within the scope of the present invention.

In the present invention, compounds with asymmetric centers may occur as racemates, as diastereomeric mixtures and as individual diastereomers, with all isomeric forms of the compounds being included in the present invention. These may be prepared by methods such as those disclosed in publications which describe synthetic routes to fragments of the macrolide FR-900506 and the total synthesis of the macrolide FR-900506 itself (See for example, *J. Am. Chem. Soc.* 1989, 111, 1157; *J. Am. Chem. Soc.* 1990, 112, 2998; *J. Org. Chem.* 1990, 55, 2786; *J. Am. Chem. Soc.* 1990, 112, 5583. *Tetrahedron Lett.* 1988, 29, 277; *Tetrahedron Lett.* 1988, 29, 281; *Tetrahedron Lett.* 1988, 29, 3895; *J. Org. Chem.* 1988, 53, 4643; *Tetrahedron Lett.* 1988, 29, 4245; *Tetrahedron Lett.* 1988, 29, 4481; *J. Org. Chem.* 1989, 54, 9; *J. Org. Chem.* 1989, 54, 11; *J. Org. Chem.* 1989, 54, 12; *J. Org. Chem.* 1989, 54, 15; *J. Org. Chem.* 1989, 54, 17; *Tetrahedron Lett.* 1989, 30, 919; *Tetrahedron Lett.* 1989, 30, 1037; *J. Org. Chem.* 1989, 54, 2785; *J. Org. Chem.* 1989, 54, 4267; *Tetrahedron Lett.* 1989, 30, 5235; *Tetrahedron Lett.* 1989, 30, 6611; *Tetrahedron Lett.* 1989, 30, 6963; *Synlett* 1990, 38; *J. Org. Chem.* 1990, 55, 2284; *J. Org. Chem.* 1990, 55, 2771; *J. Org. Chem.* 1990, 55, 2776; *Tetrahedron Lett.* 1990, 31, 1439; *Tetrahedron Lett.* 1990, 31, 1443; *Tetrahedron Lett.* 1990, 31, 3007; *Tetrahedron Lett.* 1990, 31, 3283, 3287).

The compounds of the present invention are capable of forming salts with various inorganic and organic acids and bases and such salts are also within the scope of this invention. Examples of such acid addition salts (which are negative counterions defined herein as $M^-$) include acetate, adipate, benzoate, benzenesulfonate, bisulfate, butyrate, citrate, camphorate, camphorsulfonate, ethanesulfonate, fumarate, hemisulfate, heptanoate, hexanoate, hydrochloride, hydrobromide, hydroiodide, methanesulfonate, lactate, maleate, methanesulfonate, 2-naphthalenesulfonate, oxalate, pamoate, persulfate, picrate, pivalate, propionate, succinate, tartrate, tosylate, and undecanoate. Base salts (which are positive counterions defined herein as $M^+$) include ammonium salts, alkali metal salts such as sodium, lithium and potassium salts, alkaline earth metal salts such as calcium and magnesium salts, salts with organic bases such as dicyclohexylamine salts, N-methyl-D-glucamine, and salts with amino acids such as arginine, lysine and so forth. Also, the basic nitrogen-containing groups may be quaternized with such agents as: lower alkyl halides, such as methyl, ethyl, propyl, and butyl chloride, bromides and iodides; dialkyl sulfates like dimethyl, diethyl, dibutyl; diamyl sulfates; long chain halides such as decyl, lauryl, myristyl and stearyl chlorides, bromides and iodides; aralkyl halides like benzyl bromide and others. The non-toxic physiologically acceptable salts are preferred, although other salts are also useful, such as in isolating or purifying the product.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

C. Utility of the Compounds within the Scope of the Invention

The compounds of Formula I may be employed as immunosuppressants or antimicrobial compounds by methods and in dosages known in the prior art for compounds of Formula II. These compounds possess pharmacological activity such as immunosuppressive activity, antimicrobial activity, and the like, and therefore are useful for the treatment and prevention of the resistance to transplantation or transplantation rejection of organs or tissues (such as heart, kidney, liver, lung, bone marrow, cornea, pancreas, intestinum tenue, limb, muscle, nervus, medulla ossium, duodenum, small-bowel, medulla ossium, skin, pancreatic islet-cell, etc. including xeno transplantation), graft-versus-host diseases by medulla ossium transplantation, autoimmune diseases such as rheumatoid arthritis, systemic lupus erythematosis, nephrotic syndrome lupus, Hashimoto's thyroiditis, multiple sclerosis, myasthenia gravis, type I diabetes mellitus, type II adult onset diabetes, uveitis, nephrotic syndrome, steroid-dependent and steroid-resistant nephrosis, Palmo-planter pustulosis, allergic encephalomyelitis, glomerulonephritis, etc., and infectious diseases caused by pathogenic microorganisms.

The compounds of Formula I are also useful for treating inflammatory, proliferative and hyperproliferative skin diseases and cutaneous manifestations of immunologically-mediated illnesses such as: psoriasis, psoriatic arthritis, atopical dermatitis, contact dermatitis and further eczematous dermatitises, seborrhoeic dermatitis, Lichen planus, Pemphigus, bullous Pemphigoid, Epidermolysis bullosa, urticaria, angioedemas, vasculitides, erythemas, cutaneous eosinophilias, acne Alopecia areata, eosinophilic fasciitis, and atherosclerosis. More particularly, the compounds of Formula I are useful in hair revitalizing, such as in the treatment of male or female pattern alopecia or alopecia senilis, by providing epilation prevention, hair germination, and/or a promotion of hair generation and hair growth.

The compounds of Formula I are further useful in the treatment of respiratory diseases, for example sarcoidosis, fibroid lung, idiopathic interstitial pneumonia, and reversible obstructive airways disease, including conditions such as asthma, including bronchial asthma, allergic asthma, intrinsic asthma, extrinsic asthma and dust asthma, particularly chronic or inveterate asthma (for example late asthma and airway hyperreponsiveness), bronchitis and the like. The compounds of Formula I may also be useful for treating hepatic injury associated with ischemia.

The compounds of the invention are also indicated in certain eye diseases such as keratoconjunctivitis, vernal conjunctivitis, uveitis associated with Behcet's disease, keratitis, herpetic keratitis, conical cornea, dystorphia epithelialis corneae, corneal leukoma, ocular pemphigus, Mooren's ulcer, Scleritis, Graves' ophthalmopathy, severe intraocular intimation, and the like.

The compounds of Formula I are also useful for treating multidrug resistance of tumor cells, (i.e. enhancing the activity and/or sensitivity of chemotherapeutic agents), preventing or treating inflammation of mucosa or blood vessels (such as leukotriene $B_4$-mediated diseases, gastric ulcers, vascular damage caused by ischemic diseases and thrombosis, ischemic bowel disease, inflammatory bowel disease (e.g., Crohn's disease and ulcerative colitis) necrotizing enterocolitis), or intestinal lesions associated with thermal burns, cytomegalovirus infection, particularly HCMV infection.

Further, the compounds of Formula I are also useful for treating or preventing renal diseases including interstitial nephritis, Goodpasture's syndrome, hemolytic-uremic syndrome and diabetic nephropathy; nervous diseases selected from multiple myositis, Guillain-Barre syndrome, Meniere's disease and radiculopathy; endocrine diseases including hyperthyroidism and Basedow's disease; hematic diseases including pure red cell aplasia, aplastic anemia, hypoplastic anemia, idiopathic thrombocytopenic purpura, autoimmune hemolytic anemia, agranulocytosis and anerythroplasia; bone diseases including osteoporosis; respiratory diseases including sarcoidosis, fibroid lung and idiopathic interstitial pneumonia; skin diseases including dermatomyositis, leukoderma vulgaris, ichthyosis vulgaris, photoallergic sensitivity and cutaneous T cell lymphoma; circulatory diseases including arteriosclerosis, aortitis syndrome, polyarteritis nodosa and myocardosis; collagen including scleroderma, Wegener's granuloma and Sjogren's syndrome; adiposis; eosinophilic fasciitis; periodontal disease; nephrotic syndrome; hemolytic-uremic syndrome; and muscular dystrophy.

Further, the compounds of the invention are indicated in the treatment of diseases including intestinal inflammations/allergies such as Coeliac disease, proctitis, eosinophilic gastroenteritis, mastocytosis, Crohn's disease and ulcerative colitis; and food related allergic diseases which have symptomatic manifestation remote from the gastrointestinal tract, for example migraine, rhinitis and eczema.

The compounds of the invention also have liver regenerating activity and/or activity in stimulating hypertrophy and hyperplasia of hepatocytes. Therefore, they are useful for the treatment and prevention of hepatic diseases such as immunogenic diseases (e.g. chronic autoimmune liver diseases including autoimmune hepatitis, primary biliary cirrhosis and sclerosing cholangitis), partial liver resection, acute liver necrosis (e.g. necrosis caused by toxins, viral hepatitis, shock or anoxia), B-virus hepatitis, non-A/non-B hepatitis and cirrhosis.

The compounds of the invention are also indicated for use as antimicrobial agents, and thus may be used in the treatment of diseases caused by pathogenic microorganisms and the like.

The compounds of Formula I may also be useful in the prevention or treatment of immunodepression (such as AIDS, HIV infection, cancer, senile dementia, trauma (including wound healing, surgery and shock), chronic bacterial infection and certain central nervous system disorders), overdosages or toxicity of such immunosuppressive compounds, and as an adjunct to the administration of an antigen in vaccination.

The pharmaceutical compositions of this invention can be used in the form of a pharmaceutical preparation, for example, in solid, semisolid or liquid form, which contains one or more of the compounds of the present invention, as an active ingredient, in admixture with an organic or inorganic carrier or excipient suitable for external, enteral or parenteral applications. The active ingredient may be compounded, for example, with the usual non- toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesia trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. For example, the compounds of Formula I may be utilized with hydroxypropyl methylcellulose essentially as described in U.S. Pat. No. 4,916,138, issued Apr. 10, 1990, or with a surfactant essentially as described in EPO Publication 0,428, 169. Oral dosage forms may be prepared essentially as described by T. Hondo, et al., *Transplantation Proceedings,* 1987, XIX, Supp. 6, 17–22. Dosage forms for external application may be prepared essentially as described in EPO Publication 0,423,714. The active object compound is included in the pharmaceutical composition in an amount sufficient to produce the desired effect upon the process or condition of diseases.

For the treatment of these conditions and diseases caused by immmunoirregularity a compound of Formula I may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

For the treatment of reversible obstructive airways disease, it is preferable that the compound of Formula I be administered by inhalation to the lung, especially in the form of a powder.

For modifying the activity and/or toxicity of FK-506-type immunosuppressants, a compound of Formula I may be administered prior to, in conjuction with or subsequent to the administration of an FK-506-type of a compound.

The compounds of Formula I may optionally be employed in co-therapy with anti-proliferative agents. Particularly preferred is co-therapy with an antiproliferative agent selected from the group consisting of azathioprine (AZA), brequinar sodium, deoxyspergualin (DSG), mizaribine, mycophenolic acid morpholino ester (RS-61443), cyclosporin and rapamycin.

The compounds of Formula I may also be employed in conjunction with (or in a pharmaceutical composition additionally comprising):

(1) a 5α-reductase inhibitor, (2) a cyclosporin, (3) a potassium channel opener (such as minoxidil), or (4) a phospholipid.

Such co-therapy is particularly useful in hair revitalizing, such as in the treatment of male pattern alopecia, female pattern alopecia, alopecia senilis or alopecia areata, by providing epilation prevention, hair germination, and/or a promotion of hair generation and hair growth.

Such co-therapy is further useful in treating the hyperandrogenic conditions of androgenic alopecia, acne vulgaris, seborrhea, and female hirsutism.

For co-therapy of these conditions and diseases a compound of Formula I may be administered in combination with prior to, concurrent to, or subsequent to the administration of other agent(s).

For hair revitalizing the compound of Formula I may be administered topically or orally. Cyclosporin may be administered topically or orally. Although the 5α-reductase inhibitor or the potassium channel opener may be administered topically or orally, it is preferable that it be administered topically to the scalp. For unitary formulation, however, the preferred mode of administration is topically. It is especially preferred that the hair revitalizing composition of the present invention is administered by a percutaneous administration or by spraying onto the skin.

Dosage levels of the compounds of the present invention are of the order from about 0.005 mg to about 50 mg per kilogram of body weight per day, preferably from about 0.1 mg to about 10 mg per kilogram of body weight per day, are useful in the treatment of the above-indicated conditions (from about 0.7 mg to about 3.5 mg per patient per day, assuming a 70 kg patient). In addition, the compounds of the present invention may be administered on an intermittent basis; i.e. at daily, semiweekly, weekly, semi-monthly or monthly intervals.

The amount of active ingredient that may be combined with the carrier materials to produce a single dosage form will vary depending upon the host treated and the particular mode of administration. For example, a formulation intended for the oral administration of humans may contain from 0.5 mg to 5 gm of active agent compounded with an appropriate and convenient amount of carrier material which may vary from about 5 to about 95 percent of the total composition. Dosage unit forms will generally comprise from about 0.01 mg to about 500 mg, and preferably about 0.5 mg to about 100 mg of active ingredient. For external administration the compound of Formula I may be formulated within the range of, for example, 0.0001% to 60% by weight, preferably 0.001 to 10% by weight, and most preferably from about 0.005 to 0.8% by weight.

It will be understood, however, that the specific dose level for any particular patient will depend on a variety of factors including the activity of the specific compound employed, the age, body weight, general health, sex, diet, time of administration, route of administration, rate of excretion, drug combination and the severity of the particular disease undergoing therapy.

The following examples are given for the purpose of illustrating the present invention and shall not be construed as being limitations on the scope or spirit of the instant invention.

EXAMPLE 1

17-Ethyl-1,14-dihydroxy-12-[2'-(4"-phenyloxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred solution of 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone (100 mg, 0.126 mmol, 1 eq) and Cu(OAc)$_2$ (2.8 mg, 0.014 mmol, 0.11 eq) in CH$_2$Cl$_2$ (1 ml) in a 16 mL screw-cap vial equipped with a magnetic stir-bar was added triphenyl bismuth diacetate [prepared immediately prior to use by addition of acetic acid (0.030 mL, 0.504 mmol, 4 eq) to a suspension of triphenyl bismuth carbonate (127 mg, 0.253 mmol, 2 eq) in CH$_2$Cl$_2$ (1 ml)]. The reaction vessel was capped and the mixture stirred for five days. The reaction mixture was diluted with several milliliters of saturated aqueous NaHCO$_3$ and extracted 4 times with CH$_2$Cl$_2$. The organic extracts were combined, dried over anhydrous Na$_2$SO$_4$, filtered and concentrated in vacuo. The product was isolated by preparative TLC on silica gel (eluted with 3:4 EtOAc/hexanes to afford 46 mg of 17-ethyl-1,14-dihydroxy 12-[2'-(4"-phenyloxy-3"-methoxycyclohexyl)-1'-methylvinyl]-23,25 -dimethoxy-13,19,21,27-tetramethyl-11,28-dioxa-4-azatricyclo[22.3.1.0$^{4,9}$]octacos-18-ene-2,3,10,16 -tetraone. ($^1$H NMR, $^{13}$C NMR and mass spectral analysis were consistent with the desired structure.)

EXAMPLE 2

A.
17-Ethyl-1,14-dihydroxy-12-[2'-(3"-phenyloxy-4"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone and B.
17-Ethyl-1,14-dihydroxy-12-[2'-(4"-phenyloxy-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred solution of 17-ethyl-1,14-dihydroxy-12-[2'-(3",4"-dihydroxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone (500 mg, 0.644 mmol, 1 eq) and Cu(OAc)$_2$ (12 mg, 0.064 mmol, 0.1 eq) in CH$_2$Cl$_2$ (10 ml) in a 25 ml recovery flask equipped with a magnetic stir-bar was added triphenyl bismuth diacetate [prepared immediately prior to use by addition of acetic acid (0.220 ml, 3.860 mmol, 6 eq) to a suspension of triphenyl bismuth carbonate (483 mg, 0.965 mmol, 1.5 eq) in CH$_2$Cl$_2$ (10 ml)]. The reaction flask was capped and the mixture stirred at room temperature for 6 hours. The flask was then fitted with a condenser and the mixture was warmed to 40° C. After 40 hours the reaction mixture was cooled, diluted with saturated aqueous NaHCO$_3$ and extracted 4 times with CH$_2$Cl$_2$. The organic extracts were combined, dried over anhydrous Na$_2$SO$_4$, filtered and concentrated in vacuo. The products were separated and purified by flash column chromatography on silica gel [eluted with 4:1 hexanes/acetone followed by preparative TLC on silica gel (eluted with 2:1 hexanes/acetone] to yield 94 mg of 17-ethyl-1,14-dihydroxy-12-[2'-(4"-phenyloxy-3"-hydroxycyclohexyl)-1'-methylvinyl]-23,25-dimethoxy-13,19,21,27 -tetramethyl-11,28-dioxa-4-azatricyclo[22.3.1.0$^{4,9}$]octacos-18-ene-2,3,10,16-tetraone and 110 mg of 17-ethyl-1,14-dihydroxy-12-[2'-(3"-phenyloxy-4"-hydroxycyclohexyl)-1'-methylvinyl]-23,25-dimethoxy-13, 19, 21, 27-tetramethyl-11,28-dioxa-4-azatricyclo[22.3.1.0$^{4,9}$]octacos-18-ene-2,3, 10,16-tetraone. ($^1$H NMR, $^{13}$C NMR and mass spectral analysis were consistent with the desired structure).

EXAMPLE 3

17-Ethyl-1,14-dihydroxy-12-[2'-(4"-(4'''-fluorophenyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred mixture of 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone (100 mg, 0.126 mmol, 1 eq) and Cu(OAc)$_2$ (3 mg, 0.0165 mmol, 0.13 eq) in CH$_2$Cl$_2$ (1 ml) in a 4 mL screw-cap vial equipped with a magnetic stir-bar was added tri(4-fluorophenyl)bismuth diacetate [prepared immediately prior to use by addition of acetic acid (0.030 mL, 0.504 mmol, 4 eq) to a suspension of tri(4-fluorophenyl)bismuth carbonate (100 mg, 0.181 mmol, 1.4 eq) in CH$_2$Cl$_2$ (1 mL)]. The reaction vessel was capped and the mixture stirred for two days. The reaction mixture was diluted with several milliliters of saturated aqueous NaHCO$_3$ and extracted 2 times with CH$_2$Cl$_2$. The organic extracts were combined, dried over anhydrous Na$_2$SO$_4$, filtered and concentrated in vacuo. The product was isolated by preparative TLC on silica gel (eluted with 3:1 hexanes/EtOAc) to afford 39 mg of 17-ethyl-1,14-dihydroxy-12-[2'-(4"-(4"'-fluorophenyloxy)-3"-methoxycyclohexyl)-1'-methyl-vinyl]-23,25-dimethoxy-13,19,21,27-tetramethyl-11,28-dioxa-4-azatricyclo-[22.3.1.0$^{4,9}$]octacos-18-ene-2,3,10,16-tetraone. ($^1$H NMR, $^{13}$C NMR and mass spectral analysis were consistent with the desired structure).

EXAMPLE 4

17-Ethyl-1,14-dihydroxy-12-[2'-(4"-(4"'-chlorophenyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred mixture of 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (150 mg, 0.189 mmol, 1 eq) and Cu(OAc)$_2$ (6.1 mg, 0.033 mmol, 0.17 eq) in CH$_2$Cl$_2$ (2.5 ml) in a round bottom flask equipped with a magnetic stir-bar was added tri(4-chlorophenyl)bismuth diacetate [prepared immediately prior to use by addition of acetic acid (0.075 ml, 1.3 mmol, 6.9 eq) to a suspension of tri(4-chlorophenyl)bismuth carbonate (200 mg, 0.331 mmol, 1.75 eq) in CH$_2$Cl$_2$ (2.5 ml)]. The reaction flask was then fitted with a reflux condenser and the mixture warmed to 40° C. After 20 hours the reaction mixture was cooled, diluted with saturated aqueous NaHCO$_3$ (10 mL) and extracted 4 times with CH$_2$Cl$_2$. The organic extracts were dried over anhydrous Na$_2$SO$_4$, filtered and concentrated in vacuo. The product was separated and purified two times by preparative TLC on silica gel (eluted with 2:1 hexanes/acetone) to give 40 mg 17-ethyl-1,14-dihydroxy-12-[2'-(4"-(4"'-chlorophenyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone. ($^1$H NMR, $^{13}$C NMR, and mass spectral analysis were consistent with the desired structure).

EXAMPLE 5

17-Ethyl-1,14-dihydroxy-12-[2'-(4"-(4"'-methylphenyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred mixture of 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (100 mg, 0.126 mmol, 1 eq) and Cu(OAc)$_2$ (3 mg, 0.0165 mmol, 0.13 eq) in CH$_2$Cl$_2$ (1 ml) in a 4 mL screw cap vial equipped with a magnetic stir-bar was added tri(4-tolyl)bismuth diacetate [prepared immediately prior to use by addition of acetic acid (0.030 ml, 0.525 mmol, 4.2 eq) to a suspension of tri(4-tolyl)bismuth carbonate (130 mg, 0.234 mmol, 1.86 eq) in CH$_2$Cl$_2$ (1 ml)]. The reaction vessel was capped and the mixture stirred for 20 hours at which time TLC analysis showed the reaction to be incomplete. The mixture was treated with additional tri(4-tolyl) bismuth diacetate(0.234 mmol) and stirred for 24 hours then poured into saturated aqueous NaHCO$_3$ and extracted 2 times with CH$_2$Cl$_2$. The organic extracts were combined, dried over anhydrous Na$_2$SO$_4$, filtered and concentrated in vacuo. The product was isolated by preparative TLC on silica gel (eluted with 2:1 hexanes/EtOAc) to give 47 mg 17-ethyl-1,14-dihydroxy-12-[2'-(4"-(4"'-methylphenyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone. ($^1$H NMR, $^{13}$C NMR, and mass spectral analysis were consistent with the desired structure.)

EXAMPLE 6

A.

17-Ethyl-1,14-dihydroxy-12-[2'-(3"-(4"'-methylphenyloxy)-4"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone and

B.

17-Ethyl-1,14-dihydroxy-12-[2'-(4"-(4"'-methylphenyloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred mixture of 17-ethyl-1,14-dihydroxy-12-[2'-(3",4"-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (200 mg, 0.257 mmol, 1 eq) and Cu(OAc)$_2$ (10 mg, 0.055 mmol, 0.2 eq) in CH$_2$Cl$_2$ (2 ml) in a round bottom flask equipped with a magnetic stir-bar was added tri(4-tolyl)bismuth diacetate [prepared immediately prior to use by addition of acetic acid (0.075 ml, 1.31 mmol, 5.1 eq) to a suspension of tri(4-tolyl) bismuth carbonate (300 mg, 0.553 mmol, 2.1 eq) in CH$_2$Cl$_2$ (2 ml)]. The reaction flask was fitted with a reflux condenser and the mixture warmed to 40° C. for 5 hours then stirred without heating. After 18 hours the reaction mixture was diluted with saturated aqueous NaHCO$_3$ and extracted 2 times with CH$_2$Cl$_2$. The organic extracts were combined, dried over anhydrous Na$_2$SO$_4$, filtered and concentrated in vacuo. The products were separated and purified by preparative TLC on silica gel (eluted with 2:1 hexanes/acetone) to afford 31 mg of 17-ethyl-1,14-dihydroxy-12-[2'-(3"-(4"'-methylphenyloxy)-4"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone and 42 mg of 17-ethyl-1,14-dihydroxy-12-[2'-(4"-(4"'-methylphenyloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone. ($^1$H NMR and $^{13}$C NMR analysis were consistent with the desired structures).

EXAMPLE 7

17-Ethyl-1,14-dihydroxy-12-[2'-(4"-(4"'-phenoxyphenyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone A stirred mixture of 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone (150 mg, 0.19 mmol, 1 eq) and Cu(OAc)$_2$ (6.0 mg, 0.033 mmol, 0.17 eq) in CH$_2$Cl$_2$ (2.5 ml) in a round bottom flask equipped with a magnetic stir-bar and a reflux condenser was heated to 40° C. then treated with tri(4-phenoxyphenyl)bismuth diacetate [prepared immediately prior to use by addition of acetic acid (0.075 mL, 1.31 mmol, 6.9 eq) to a suspension of tri(4-phenoxyphenyl)bismuth carbonate (225 mg, 0.29 mmol, 1.5 eq) in CH$_2$Cl$_2$ (2.5 ml)]. After 18 hours TLC analysis showed the reaction to be incomplete and additional tri(4-phenoxyphenyl) bismuth diacetate (0.10 mmol) was added. The reaction mixture was stirred with heating for 5 hours then cooled, diluted with saturated aqueous NaHCO$_3$, and extracted 2 times with CH$_2$Cl$_2$. The extracts were combined, dried over Na$_2$SO$_4$, filtered, and concentrated in vacuo. The product was isolated and purified by preparative TLC on silica gel (2:1 hexanes/acetone) to give 66 mg of 17-ethyl-1,14-dihydroxy-12-[2'-(4"-(4"'-phenoxyphenyloxy)-3"-methoxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone. ($^1$H NMR, $^{13}$C NMR, and mass spectral analysis were consistent with the desired structure).

EXAMPLE 8

A.
17-Ethyl-1,14-dihydroxy-12-[2'-(4"-(4"'-phenoxyphenyloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone and

B.
17-Ethyl-1,14-dihydroxy-12-[2'-(3"-(4"'-phenoxyphenyloxy)-4"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred mixture of 17-ethyl-1,14-dihydroxy-12-[2'-(3",4"-dihydroxycyclohexyl)-1'-methyl-vinyl]-23,25-dimethoxy-13,19,21,27-tetramethyl-11,28-dioxa-4-azatricyclo[22.3.1.0$^{4,9}$]octacos-18-ene-2,3,10,16-tetraone (150 mg, 0.19 mmol, 1 eq) and Cu(OAc)$_2$ (7 mg, 0.039 mmol, 0.21 eq) in CH$_2$Cl$_2$ (2 mL) in a round bottom flask equipped with a magnetic stir-bar was added tri(4-phenoxyphenyl)bismuth diacetate [prepared immediately prior to use by addition of acetic acid (0.070 ml, 1.22 mmol, 6.4 eq) to a suspension of tri(4-phenoxyphenyl)bismuth carbonate (230 mg, 0.30 mmol, 1.58 eq) in CH$_2$Cl$_2$ (2 mL)]. The reaction flask was fitted with a reflux condenser and the mixture warmed to 40° C. After 4 hours the mixture was cooled, diluted with saturated aqueous NaHCO$_3$, and extracted 2 times with CH$_2$Cl$_2$. The extracts were combined, dried over Na$_2$SO$_4$, filtered, and concentrated in vacuo. The products were separated and purified 3× by preparative TLC on silica gel (3:2 hexanes/acetone) to afford 35 mg of 17-ethyl-1,14-dihydroxy-12-[2'-(4"-(4"'-phenoxyphenyloxy)-3"-hydroxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone and 42 mg of 17-ethyl-1,14-dihydroxy-12-[2'-(3"-(4"'-phenoxyphenyloxy)-4"-hydroxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone. ($^1$H NMR, $^{13}$C NMR, and mass spectral analysis were consistent with the desired structures).

EXAMPLE 9

17-Ethyl-1,14-dihydroxy-12-[2'-(4"-(naphth-1-yloxy)-3"-methoxycyclohexyl)-1'-methylvinyl]-23,25-dimethoxy-13,19,21,27 -tetramethyl-11,28-dioxa-4-azatricyclo-[22.3.1.0$^{4,9}$]octacos-18-ene-2,3,10,16-tetraone To a stirred mixture of 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone (150 mg, 0.19 mmol, 1 eq) and Cu(OAc)$_2$ (6 mg, 0.033 mmol, 0.17 eq) in CH$_2$Cl$_2$ (2 ml) in a round bottom flask equipped with a magnetic stir-bar was added tri(1-naphthyl)bismuth diacetate [prepared immediately prior to use by addition of acetic acid (0.070 ml, 1.22 mmol, 6.4 eq) to a suspension of tri(1-naphthyl)bismuth carbonate (150 mg, 0.23 mmol, 1.2 eq)in CH$_2$Cl$_2$ (2 ml)]. The reaction flask was then fitted with a reflux condenser a 2nd the mixture was warmed to 40° C. for 4 hours. After stirring an additional 16 hours at room temperature TLC analysis showed the reaction to be incomplete. The reaction mixture was further treated with tri(1-naphthyl)bismuth diacetate (0.15 mmol) and heated to 40° C. for 4 hours. The mixture was cooled, diluted with saturated aqueous NaHCO$_3$, and extracted 2 times with CH$_2$Cl$_2$. The extracts were combined, dried over anhydrous Na$_2$SO$_4$, filtered, and concentrated in vacuo. The product was isolated and purified 2 times by preparative TLC on silica gel (3:1 hexanes/acetone) to give 38 mg of 17-ethyl-1,14-dihydroxy-12-[2'-(4"-(naphth-1 -yloxy)-3"-methoxycyclohexyl)-1'-methylvinyl]-23,25-dimethoxy-13,19,21,27-tetramethyl-11,28 -dioxa-4-azatricyclo[22.3.1.0$^{4,9}$]-octacos-18-ene-2,3,10,16-tetraone. ($^1$H NMR analysis was consistent with the desired structure).

EXAMPLE 10

A.
17-Ethyl-1,14-dihydroxy-12-[2'-(3"-(naphth-1-yloxy)-4"hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone and

B. 17-Ethyl-1,14-dihydroxy-12-[2'-(4"-(naphth-1-yloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred mixture of 17-ethyl-1,14-dihydroxy-12-[2'(3",4"-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (250 mg, 0.32 mmol, 1 eq) and Cu(OAc)$_2$ (15 mg, 0.08 mmol, 0.25 eq) in $CH_2Cl_2$ (5 ml) in a round bottom flask equipped with a magnetic stir-bar was added tri(1-naphthyl) bismuth diacetate [prepared immediately prior to use by addition of acetic acid (0.100 ml, 1.75 mmol, 5.46 eq) to a suspension of tri(1-naphthyl) bismuth carbonate (350 mg, 0.54 mmol, 1.69 eq) in $CH_2Cl_2$ (5 ml)]. The reaction flask was fitted with a reflux condenser and the mixture warmed to 40° C. for 5 hours then stirred at room temperature. After 16 hours the mixture was diluted with saturated aqueous $NaHCO_3$ and extracted 2 times with $CH_2Cl_2$. The extracts were combined, dried over anhydrous $Na_2SO_4$, filtered, and concentrated in vacuo. The products were separated and purified by preparative TLC on silica gel (eluted with 3:1 hexanes/acetone) to yield 49 mg of 17-ethyl-1,14-dihydroxy-12-[2'-(3"-(naphth-1-yloxy)-4"-hydroxycyclohexyl)-1'-methylvinyl]-23,25-dimethoxy-13,19,21,27 -tetramethyl-11,28-dioxa-4-aza-tricyclo[22.3.1.0$^{4,9}$]octacos-18-ene-2,3,10,16-tetraone and 39 mg of 17-ethyl-1,14-dihydroxy-12-[2'-(4"-(napth-1-yloxy)-3"-hydroxycyclohexyl)-1'-methylvinyl]-23,25-dimethoxy-13,19,21,27-tetramethyl-1,28-dioxa-4 -azatricyclo[22.3.1.0$^{4,9}$]-octacos-18-ene-2,3,10,16-tetraone. ($^1$H NMR analysis was consistent with the desired structure).

EXAMPLE 11

17-Ethyl-1,14-dihydroxy-12-[2'-(4"-(naphth-2-yloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred mixture of 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone (150 mg, 0.189 mmol, 1 eq) and Cu(OAc)$_2$ (6 mg, 0.033 mmol, 0.17 eq) in $CH_2Cl_2$ (2.5 mL) in a round bottom flask equipped with a magnetic stir-bar was added tri(2-naphthyl)bismuth diacetate [prepared immediately prior to use by addition of acetic acid (0.075 ml, 1.31 mmol, 6.9 eq) to a suspension of tri(2-naphthyl)bismuth carbonate in $CH_2Cl_2$ (2.5 ml)]. The reaction flask was fitted with a reflux condenser and the mixture warmed to 40° C. After 4 hours the heating was discontinued and the mixture stirred at room temperature for 16 hours. The mixture was then diluted with saturated aqueous $NaHCO_3$ and extracted 2 times with $CH_2Cl_2$. The extracts were combined, dried over anhydrous $Na_2SO_4$, filtered, and concentrated in vacuo. The product was isolated and purified by preparative TLC on silica gel (3:1 hexanes/acetone) to afford 32 mg of 17-ethyl-1,14-dihydroxy-12-[2'-(4"-(napth-2-yloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone. ($^1$H NMR, $^{13}$C NMR, and mass spectral analysis were consistent with the desired structure).

EXAMPLE 12

A.
17-Ethyl-1,14-dihydroxy-12-[2'-(4"-(naphth-2-yloxy)-3"-hydroxycyclohexyl)-1'-methylvinyl]-23,25-dimethoxy-13,19,21,27-tetramethyl-11,28-dioxa-4-azatricyclo [22.3.1.0$^{4,9}$]octacos-18-ene-2,3,10,16-tetraone and B.
17-Ethyl-1,14-dihydroxy-12-[2'-(3"-(napth-2-yloxy)-4"-hydroxycyclohexyl)-1'-methylvinyl]-23,25-dimethoxy-13,19,21,27-tetramethyl-11,28-dioxa-4-azatricyclo [22.3.1.0$^{4,9}$]octacos-18-ene-2,3,10,16-tetraone To a stirred mixture of 17-ethyl-1,14-dihydroxy-12-[2'-(3",4"-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,-10,16-tetraone (250 mg, 0.32 mmol, 1 eq) and Cu(OAc)$_2$ (10 mg, 0.055 mmol, 0.17 eq) in $CH_2Cl_2$ (5.5 ml) in a round bottom flask equipped with a magnetic stir-bar was added tri(2-naphthyl)bismuth diacetate [prepared immediately prior to use by addition of acetic acid (0.100 mL, 1.75 mmol, 5.46 eq) to a suspension of tri(2-naphthyl)bismuth carbonate (350 mg, 0.538 mmol, 1.7 eq) in $CH_2Cl_2$ (5.5 ml)]. The reaction flask was fitted with a reflux condenser and the mixture warmed to 40° C. for 4 hours then stirred at room temperature. After 3 days the reaction mixture was diluted with saturated aqueous $NaHCO_3$ and extracted 3 times with $CH_2Cl_2$. The extracts were combined, dried over anhydrous $Na_2SO_4$, filtered, and concentrated in vacuo. The products were separated and purified by preparative TLC on silica gel (eluted with 3:1 hexanes/acetone) to give 63 mg of 17-ethyl-1,14-dihydroxy-12-[2'-(3"-(napth-2-yloxy)-4"-hydroxy-cyclohexyl)-1'-methylvinyl]-23,25-dimethoxy-13,19,21,27 -tetramethyl-11,28-dioxa-4-azatricyclo-[22.3.1.0$^{4,9}$]octacos-18-ene-2,3,10,16-tetraone and 49 mg of 17-ethyl-1,14-dihydroxy-12-[2'-(4"-(naphth-2-yloxy)-3"-hydroxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone. ($^1$H NMR was consistent with the desired structure).

EXAMPLE 13

17-Ethyl-1-hydroxy-12-[2'-(4"-(naphth-2-yloxy)-3"-methoxycyclohexyl)-1'-methylvinyl]-23,25-dimethoxy-13,19,21,27-tetramethyl-11.28-dioxa-4-azatricyclo[22.3.1.0$^{4,9}$]octacos-18-ene-2,3,10,16-tetraone To a stirred mixture of 17-ethyl-1-hydroxy-12-[2'-(4"-hydroxy-3"-methoxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone (300 mg, 0.39 mmol, 1 eq) and Cu(OAc)$_2$ (15 mg, 0.083 mmol, 0.21 eq) in $CH_2Cl_2$ (5 ml) in a round bottom flask equipped with a magnetic stir-bar was added tri(2-naphthyl)bismuth diacetate [prepared immediately prior to use by addition of acetic acid to a suspension of tri(2-naphthyl)bismuth carbonate (300 mg, 0.461 mmol, 1.2 eq) in $CH_2Cl_2$ (5 ml)]. The reaction flask was fitted with a reflux condenser and the mixture warmed to 40° C. After 6 hours the mixture was allowed to cool to room temperature and stirred an additional 16 hours. The reaction mixture was diluted with saturated aqueous $NaHCO_3$ and extracted 2 times with CH²Cl₂. The extracts were combined, dried over anhydrous Na₂SO₄, filtered, and concentrated in vacuo. The product was isolated and purified by preparative TLC (3:1 hexanes/acetone) to give 109 mg of 17-ethyl-1-hydroxy-12-[2'-(4''-(naphth-2-yloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone. ($^1$H NMR and $^{13}$C NMR analysis were consistent with the desired structure).

EXAMPLE 14

17-Ethyl-1,14-dihydroxy-12-[2'-(4''-(6'''-methoxy-naphth-2-yloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of tri-(6-methoxy-2-naphthyl)-bismuth diacetate (52 mg, 0.069 mmol, 1.1 eq) in methylene chloride (2 ml) in a 10 ml round bottom flask equipped with a stir bar was added 17-ethyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (50 mg, 0.063 mmol, 1 eq). To the reaction mixture was added a catalytic amount of Cu(OAc)₂ (approximately 20 mg). The reaction flask was fitted with a reflux condenser and the mixture was warmed to 40° C. After 1 hour the mixture was cooled, diluted with saturated aqueous NaHCO₃ and extracted 4 times with CH₂Cl₂. The organic extracts were combined, dried over anhydrous Na₂SO₄, filtered and concentrated in vacuo. The product was isolated by two preparative thin layer chromatographys on silica gel (first chromatography eluted with 2:1 hexanes/acetone, isolated band at $R_f$=0.26 second chromatography eluted with 3.5% methanol/CH₂Cl₂, isolated band at $R_f$=0.62) to give 20 mg of 17-ethyl-1,14-dihydroxy-12-[2'-(4''-(6'''-methoxy-naphth-2-yloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone. ($^1$H NMR and mass spectral analysis were consistent with the desired structure).

EXAMPLE 14A

General Procedure for the Preparation of Triarylbismuthines

To a stirred suspension of magnesium (486 mg, 20 mmol) in dry tetrahydrofuran (10 mL) is added slowly a solution of aryl halide (20 mmol) in dry tetrahydrofuran (10 mL). If necessary the mixture is warmed gently to effect Grignard formation. To the stirred solution of the Grignard reagent is added a solution of bismuth trichloride (1.9 g, 6 mmol) dissolved in dry tetrahydrofuran (20 mL). The resulting mixture is stirred for 24 hours. The reaction mixture is poured into a separatory funnel containing brine and extracted 4× with CH₂Cl₂. The organic extracts were combined and dried over anhydrous Na₂SO₄. The mixture was filtered and concentrated in vacuo. The triarylbismuthine is isolated and purified by flash column chromatography on silica gel.

EXAMPLE 14B

Tri(6-Methoxy-2-naphthyl)bismuth Diacetate

To a stirred solution of tris(6-methoxynaphth-2-yl)bismuthine (100 mg, 0.158 mmol) in CH₂Cl₂ (8 mL) was added iodobenzene diacetate (200 mg, 0.621 mmol). The CH₂Cl₂ was removed in vacuo and the residue was dissolved in several milliliters of 4:1 hexanes/acetone plus small amount of CH₂Cl₂. The solution was passed through a silica gel plug and eluted with 4:1 hexanes/acetone. The filtrate was concentrated in vacuo. The residue was dissolved in 4:1 hexanes/acetone plus small amount of CH₂Cl₂ and passed through a second silica gel plug and eluted with 4:1 hexanes/acetone. The filtrate was concentrated in vacuo leaving 52 mg yellow residue that was used without further purification.

EXAMPLE 15

A.

17-Ethyl-1,14-dihydroxy-12-[2'-(3''-(6'''-methoxy-naphth-2-yloxy)-4''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone and

B.

17-Ethyl-1,14-dihydroxy-12-[2'-(4''-(6'''-methoxy-naphth-2-yloxy)-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,1 0,16-tetraone To a solution of tri-(6-methoxy-2-naphthyl) bismuth diacetate (22 mg, 0.028 mmol, 1 eq) in methylene chloride (2 ml) in a 10 mL round bottom flask equipped with a stir bar was added 17-ethyl-1,14-dihydroxy-12-[2'-(3'',4''-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (22 mg, 0.028 mmol, 1 eq). To the reaction mixture was added a catalytic amount of Cu(OAc)₂ (approximately 20 mg). The reaction flask was fitted with a reflux condenser and the mixture was warmed to 40° C. After 1 hour the mixture was cooled, diluted with saturated aqueous NaHCO₃ and extracted 4 times with CH₂Cl₂. The organic extracts were combined, dried over anhydrous Na₂SO₄, filtered and concentrated in vacuo. The product was isolated by preparative thin layer chromatography on silica gel (eluted with 2:1 hexanes/acetone) to give 7.1 mg of 17-ethyl-1,14-dihydroxy-12-[2'-(4''-(6'''-methoxynaphth-2-yloxy)-3''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone ($R_f$=0.35) and 9 mg of 17-ethyl-1,14-dihydroxy-12-[2'-(3''-(6'''-methoxy-naphth-2-yloxy)-4''-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone ($R_f$=0.28). ($^1$H NMR and mass spectral analysis were consistent with the desired structures).

EXAMPLE 16

17-Ethyl-1,14-dihydroxy-12-[2'-(4''-(4'''-methoxyphenyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred solution of tris(4-methoxyphenyl)bismuthine (200 mg, 0.377 mmol) in CH₂Cl₂ (4 mL) was added bis(trifluoroacetoxy)iodobenzene (162 mg, 0.377 mmol). The mixture was stirred 5 minutes, then passed through a silica gel plug and eluted with EtOAc. The eluant was concentrated in vacuo. The residue was dissolved in CH$_2$Cl$_2$ (4 mL) in a 50 mL round bottom flask equipped with a magnetic stir bar. To this stirred mixture was added 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (132 mg, 0.167 mmol) and Cu(OAc)$_2$ (10 mg 0.055 mmol). The flask was capped and the mixture stirred 48 hours. The reaction was quenched by addition of saturated aqueous NaHCO$_3$ and extracted 4× with CH$_2$Cl$_2$. The organic extracts were combined and dried over anhydrous Na$_2$SO$_4$. The mixture was filtered and concentrated in vacuo. The products were isolated by preparative TLC on silica gel (2:1 hexanes/acetone) to afford 26.8 mg of 17-ethyl-1,14-dihydroxy-12-[2'-(4"-(4'''-methoxyphenyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (R$_f$=0.35). ($^1$H NMR and mass spectral analysis were consistent with the desired structure).

EXAMPLE 17

17-Ethyl-1,14-dihydroxy-12-[2'-(4"-(3'''-methoxyphenyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred solution of tris(3-methoxyphenyl)bismuthine (200 mg, 0.377 mmol) in CH$_2$Cl$_2$ (3 mL) was added bis(trifluoroacetoxy)iodobenzene (162 mg, 0.377 mmol). The mixture was stirred 5 minutes, then passed through a silica gel plug and eluted with EtOAc. The eluant was concentrated in vacuo. The residue was dissolved in CH$_2$Cl$_2$ (4 mL) in a 50 mL round bottom flask equipped with a magnetic stir bar. To this stirred mixture was added 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (112 mg 0.141 mmol) and Cu(OAc)$_2$ (10 mg, 0.055 mmol). The flask was capped and the mixture stirred 48 hours. The reaction was quenched by addition of saturated aqueous NaHCO$_3$ and extracted 4× with CH$_2$Cl$_2$. The organic extracts were combined and dried over anhydrous Na$_2$SO$_4$. The mixture was filtered and concentrated in vacuo. The products were isolated by radial chromatography on silica gel (2 mm plate eluted with 3:1 hexanes/acetone) and then by preparative TLC on silica gel (eluted with 2:1 hexanes/acetone) to afford 78.4 mg of 17-ethyl-1,14-dihydroxy-12-[2'-(4"-(3'''-methoxyphenyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (R$_f$=0.40). ($^1$H NMR and mass spectral analysis were consistent with the desired structure).

EXAMPLE 18

17-Ethyl-1,14-dihydroxy-12-[2'-(4"-(6'''-tert-butyldimethylsilyloxynaphth-2-yloxy)-3"-methoxycyclohexyl)-1'-methyl-vinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred solution of tris(6-tert-butyldimethylsilyloxynaphth-2-yl)bismuthine (100 mg, 0.215 mmol) in CH$_2$Cl$_2$ (4 mL) was added peracetic acid (0.05 mL, 0.238 mmol, 32 wt % in dilute acetic acid). To this stirred solution was added THF (1 mL), 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (100 mg, 0.126 mmol) and Cu(OAc)$_2$ (catalytic amount). The flask was fitted with a reflux condenser and the mixture was heated to 40° C. for 2 hours. The mixture was allowed to cool and was stirred 72 hours. The reaction was quenched with saturated aqueous NaHCO$_3$ and extracted 4× with CH$_2$Cl$_2$. The organic extracts were combined and dried over anhydrous Na$_2$SO$_4$. The mixture was filtered and concentrated in vacuo. The products were isolated by preparative TLC on silica gel (eluted with 2:1 hexanes/acetone) to afford 47 mg of 17-ethyl-1,14-dihydroxy-12-[2'-(4"-(6'''-tert-butyldimethylsilyloxynaphth-2-yloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (R$_f$=0.56). ($^1$H NMR and mass spectral analysis were consistent with the desired structure).

EXAMPLE 19

17-Ethyl-1,14-dihydroxy-12-[2'-(4"-(6'''-hydroxynaphth-2-yloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred solution of 17-ethyl-1,14-dihydroxy-12-[2'-(4"-(6'''-tert-butyldimethylsilyloxynaphth-2-yloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (73 mg, 0.07 mmol) in CH$_2$Cl$_2$ (2 mL) was added a solution of p-toluenesulfonic acid in methanol (2 mL, 10% solution). The flask was capped and the mixture stirred 4 hours. The reaction was quenched with saturated aqueous NaHCO$_3$ and extracted 4× with CH$_2$Cl$_2$. The organic extracts were combined and dried over anhydrous Na$_2$SO$_4$. The mixture was filtered and concentrated in vacuo. The product was isolated by preparative TLC on silica gel (eluted with 2:1 hexanes/acetone) to afford 44.2 mg of 17-ethyl-1,14-dihydroxy-12-[2'-(4"-(6'''-hydroxynaphth-2-yloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (R$_f$=0.23). ($^1$H NMR and mass spectral analysis were consistent with the desired structure).

EXAMPLE 20

17-Ethyl-1,14-dihydroxy-12-[2'-(4"-(4'''-tert-butyldimethylsilyloxyphenyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred solution of tris(4-tert-butyldimethylsilyloxyphenyl)bismuthine (187 mg, 0.252 mmol) in CH$_2$Cl$_2$ (4 mL) was added peracetic acid (0.053 mL, 0.252 mmol, 32 wt % solution in dilute acetic acid). To this stirred solution was added 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (100 mg, 0.126 mmol), Cu(OAc)$_2$ (8.5 mg, 0.046 mmol), and tetrahydrofuran (0.5 mL.). After stirring 48 hours the reaction mixture was quenched with saturated aqueous NaHCO$_3$ and extracted 4× with CH$_2$Cl$_2$. The organic extracts were combined and dried over anhydrous $Na_2SO_4$. The mixture was filtered and concentrated in vacuo. The products were isolated by preparative TLC on silica gel (eluted with 2:1 hexanes/acetone) to afford 81 mg of 17-ethyl-1,14-dihydroxy-12-[2'-(4"-(4'''-tertbuytl-dimethylsilyloxyphenyloxy)-3"-methoxycyclohexyl)-1'-methylvinyl]-23,25 -dimethoxy-13,19,21,27'-tetramethyl-11,28-dioxa-4-azatricyclo[22.3.1.0$^{4,9}$]-octacos-18-ne-2,3,10,16-tetraone ($R_f$=0.49). ($^1$H NMR and mass spectral analysis were consistent with the desired structure).

EXAMPLE 21

17-Ethyl-1,14-dihydroxy-12-[2'-(4"-(4'''-hydroxyphenyloxy)-3"-methoxycyclohexyl)-1'-methylvinyl]-23,25-dimethoxy-13,19,21,27-tetramethyl-11,28-dioxa-4- azatricyclo[22.3.1.0$^{4,9}$]octacos-18-ene-2,3,10,16-tetraone To a stirred solution of 17-ethyl-1,14-dihydroxy-12-[2'-(4"-(4'''-tert-buytldimethylsilyloxyphenyloxy)-3"-methoxycyclohexyl)-1'-methylvinyl]-23,25 -dimethoxy-13,19,21, 27-tetramethyl-11,28-dioxa-4-azatricyclo[22.3.1.0$^{4,9}$] octacos-18-ene-2,3,10,16 -tetraone (74.8 mg, 0.075 mmol) in $CH_2Cl_2$ was added a solution of p-toluenesulfonic acid in methanol (2 mL, 10% p-TsOH on methanol). The mixture was stirred 4 hours. The reaction mixture was quenched with saturated aqueous $NaHCO_3$ and extracted 4× with $CH_2Cl_2$. The organic extracts were combined and dried over anhydrous $Na_2SO_4$. The mixture was filtered and concentrated in vacuo. The products were isolated by preparative TLC on silica gel (eluted with 2:1 hexanes/acetone) to afford 52 mg of 17-ethyl-1,14-dihydroxy-12-[2'-(4"-(4'''-hydroxyphenyloxy)-3"-methoxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone ($R_f$=0.25). ($^1$H NMR and mass spectral analysis were consistent with the desired structure).

EXAMPLE 22

17-Ethyl-1,14-dihydroxy-12-[2'-(4"-(4'''-methylthiophenyloxy)-3"-methoxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-22.3.10.16-tetraone To a stirred solution of tris(4-methylthiophenyl)bismuthine (146 mg, 0.252 mmol) in $CH_2Cl_2$ was added peracetic acid (0.106 mL, 0.504 mmol). To this solution was added 17-ethyl-1,14-dihydroxy-12-[2'-(4"-hydroxy-3" -methoxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone (100 mg, 0.126 mmol), $Cu(OAc)_2$ (1 mg, 0.061 mmol), and tetrahydrofuran (0.5 mL). The mixture was stirred for 96 hours. The reaction mixture was quenched with saturated aqueous $NaHCO_3$ and extracted 4× with $CH_2Cl_2$. The organic extracts were combined and dried over anhydrous $Na_2SO_4$. The mixture was filtered and concentrated in vacuo. The products were isolated by preparative TLC on silica gel (eluted with 2:1 hexanes/acetone) to afford 15.5 mg of 17-ethyl-1,14-dihydroxy-12-[2'-(4"-(4'''-methylthiophenyloxy)-3"-methoxycyclohexyl)-1'-methylvinyl]-23,25-dimethoxy-13,19,21,27 -tetramethyl-11,28-dioxa-4-azatricyclo[22.3.1.0$^{4,9}$]octacos-18-ene-2,3,10, 16-tetraone ($R_f$=0.47). ($^1$H NMR and mass spectral were analysis consistent with the desired structure).

EXAMPLE 23

17-Ethyl-1,14-dihydroxy-12-[2'-(4"-(2'''-methylphenyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred solution of tris(2-methylphenyl)bismuthine (50 mg, 0.104 mmol) in $CH_2Cl_2$ (2 mL) was added bis(trifluoroacetoxy)iodobenzene (45 mg, 0.104 mmol). To this stirred solution was added 17-ethyl-1,14-dihydroxy-12-[2'-(4"-hydroxy-3"-methoxycyclohexyl)-1'-methylvinyl]-23, 25-dimethoxy-13,19,21,27-tetramethyl-11,28-dioxa-4-azatricyclo[22.3.1.0$^{4,9}$]octacos-18 -ene-2,3,10,16-tetraone (82 mg, 0.104 mmol), $Cu(OAc)_2$ (catalytic), and acetic acid (0.060 mL, 0.104 mmol). The flask was fitted with a reflux condenser and the mixture warmed to 40° C. and stirred overnight. The reaction mixture was cooled and diluted with $CH_2Cl_2$. The reaction mixture was quenched with saturated aqueous $NaHCO_3$ and extracted 4× with $CH_2Cl_2$. The organic extracts were combined and dried over anhydrous $Na_2SO_4$. The mixture was filtered and concentrated in vacuo. The products were isolated by preparative TLC on silica gel (eluted with 2:1 hexanes/acetone) to afford 23.8 mg of 17-ethyl-1,14-dihydroxy-12-[2'-(4"-(2'''-methylphenyloxy)-3"-methoxycyclohexyl)-1'-methylvinyl]-23,25-dimethoxy-13,19,21,27-tetramethyl-11,28 -dioxa-4-azatricyclo[22.3.1.0$^{4,9}$]octacos-18-ene-2,3,10,16-tetraone ($R_f$=0.46). ($^1$H NMR and mass spectral analysis were consistent with the desired structure).

EXAMPLE 24

17-Ethyl-1,14-dihydroxy-12-[2'-(4"-(3'''-methylphenyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred solution of tris(3-methylphenyl)bismuthine (189 mg, 0.392 mmol) in $CH_2Cl_2$ (3 mL) was added bis(trifluoroacetoxy)iodobenzene (168 mg, 0.392 mmol). To this stirred solution was added 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene2,3,10,16-tetraone (150 mg, 0.189 mmol) and $Cu(OAc)_2$ (catalytic). The flask was capped and the mixture stirred overnight. The reaction mixture was quenched with saturated aqueous $NaHCO_3$ and extracted 4× with $CH_2Cl_2$. The organic extracts were combined and dried over anhydrous $Na_2SO_4$. The mixture was filtered and concentrated in vacuo. The products were isolated by radial chromatography on silica gel (eluted with 3:1 hexanes/ethyl acetate) to afford 70.9 mg of 17-ethyl-1,14-dihydroxy-12-[2'-(4"-(3'''-methylphenyloxy)-3"-methoxycyclohexyl)-1'-methyl-vinyl]-23,25-dimethoxy-13,19,21, 27-tetramethyl-11,28-dioxa-4 -azatricyclo[22.3.1.0$^{4,9}$] octacos-18-ene-2,3,10,16-tetraone. ($^1$H NMR and mass spectral analysis were consistent with the desired structure).

EXAMPLE 25

17-Ethyl-1,14-dihydroxy-12-[2'-(4"-(3''',4'''-dimethylphenyloxy)-3"-methoxycyclohexyl)-1'-methylvinyl]-23,25-dimethoxy-13,19,21,27-tetramethyl-11,28-dioxa-4- azatricyclo[22.3.1.0$^{4,9}$]octacos-18-ene-2,3,10,16-tetraone To a stirred solution of tris(3,4-dimethylphenyl)bismuthine (200 mg, 0.381 mmol) in $CH_2Cl_2$ (3 mL.) was added bis(trifluoroacetoxy)iodobenzene (165 mg, 0.383 mmol). One mL of this solution was transferred to a 10 mL flask. To this solution was added 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28 -dioxa-4-azatricyclo[22.3.1.0$^{4,9}$]octacos-18-ene-2,3,10,16-tetraone (100 mg, 0.128 mmol) and Cu(OAc)$_2$ (catalytic). The mixture was stirred overnight. The reaction mixture was quenched with saturated aqueous NaHCO$_3$ and extracted 4× with CH$_2$Cl$_2$. The organic extracts were combined and dried over anhydrous Na$_2$SO$_4$. The mixture was filtered and concentrated in vacuo. The products were isolated by radial chromatography on silica gel (eluted with 3.5% methanol/CH$_2$Cl$_2$) and then purified by preparative TLC on silica gel (eluted with 3:1 hexanes/acetone) to afford 24.3 mg of 17-ethyl-1,14-dihydroxy-12-[2'-(4"-(3"',4"'-dimethylphenyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16 -tetraone. ($^1$H NMR and mass spectral analysis were consistent with the desired structure).

EXAMPLE 26

A.
17-Ethyl-1,14-dihydroxy-12-[2'-(3"-(4"'-methoxyphenyloxy)-4"-hydroxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone and

B.
17-Ethyl-1,14-dihydroxy-12-[2'-(4"-(4"'-methoxyphenyloxy)-3"-hydroxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone To a stirred solution of tri(4-methoxyphenyl)bismuthine (136 mg., 0.257 mmol., 2 eq.) in methylene chloride (4 mL.) was added peracetic acid (0.054 mL., 0.257 mmol., 2 eq., 32% solution in dilute acetic acid). To this stirred solution was added 17-ethyl-1,14-dihydroxy-12-[2'-(3",4"-dihydroxycyclohexyl)-1'-methylvinyl]-23,25-dimethoxy-13,19, 21,27-tetramethyl-11,28-dioxa-4 -azatricyclo[22.3.1.0$^{4,9}$] octacos-18-ene-2,3,10,16-tetraone (100 mg., 0.126 mmol., 1 eq.), THF (0.5 mL.), and copper (II) acetate (7 mg., 0.038 mmol., 0.3 eq.). The mixture was allowed to stir for 7 days. The reaction was quenched with saturated aqueous NaCl plus 2 drops 2N HCl and extracted 4× with methylene chloride. The organic extracts were combined, dried over anhydrous Na$_2$SO$_4$, filtered, and concentrated in vacuo. The products were separated by preparative TLC on silica gel (2:1 hexanes/acetone). Each compound was repurified 2× by preparative TLC on silica gel (3:1 hexanes/acetone then 3.5% MeOH/CH$_2$Cl$_2$) affording 23.4 mg of 17-ethyl-1,14-dihydroxy-12-[2'-(4"-(4"'-methoxyphenyloxy)-3"-hydroxycyclohexyl)-1'-methylvinyl]-23,25-dimethoxy-13,19,21,27 -tetramethyl-11,28-dioxa-4-azatricyclo-22.3.1.0$^{4,9}$]octacos-18-ene-2,3,10,16-tetraone and 28.4 mg of 17-ethyl-1,14-dihydroxy-12-[2'-(3"-(4"'-methoxyphenyloxy)-4"-hydroxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone. ($^1$H NMR and mass spectral analysis were consistent with the desired structures).

EXAMPLE 27

A.
17-Ethyl-1,14-dihydroxy-12-[2'-(3"-(3"'-methoxyphenyloxy)-4"-hydroxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone and

B.
17-Ethyl-1,14-dihydroxy-12-[2'-(4"-(3"'-methoxyphenyloxy)-3"-hydroxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone To a stirred solution of tri(3-methoxyphenyl)bismuthine (136 mg., 0.257 mmol., 2 eq.) in methylene chloride (4 mL.) was added peracetic acid (0.054 mL., 0.257 mmol., 2 eq., 32% solution in dilute acetic acid). To this stirred solution was added 17-ethyl-1,14-dihydroxy-12-[2'-(3",4"-dihydroxycyclohexyl)-1'-methylvinyl]-23,25-dimethoxy-13,19, 21,27-tetramethyl-11,28-dioxa-4 -azatricyclo[22.3.1.0$^{4,9}$] octacos-1 8-ene-2,3,10,16-tetraone (100 mg., 0.126 mmol., 1 eq.), THF (0.5 mL.), and copper (II) acetate (7 mg., 0.038 mmol., 0.3 eq.). The mixture was allowed to stir for 7 days. The reaction was quenched with saturated aqueous NaCl plus 2 drops 2N HCl and extracted 4× with methylene chloride. The organic extracts were combined, dried over anhydrous Na$_2$SO$_4$, filtered, and concentrated in vacuo. The products were separated by preparative TLC on silica gel (2:1 hexanes/acetone). Each compound was repurified 2× by preparative TLC on silica gel (2:1 hexanes/acetone then 3.5% MeOH/CH$_2$Cl$_2$) affording 27 mg of 17-ethyl-1,14-dihydroxy-12-[2'-(4"-(3"'-methoxyphenyloxy)-3"-hydroxycyclohexyl)-1'-methylvinyl]-23,25-dimethoxy-13,19,21,27-tetramethyl-11,28 -dioxa-4-azatricyclo[22.3.1.0$^{4,9}$]octacos-18-ene-2,3,10,16-tetraone and 35 mg of 17-ethyl-1,14-dihydroxy-12-[2'-(3"-(3"'-methoxyphenyloxy)-4"-hydroxycyclohexyl)-1'-methylvinyl]-23,25-dimethoxy-13, 19,21,27-tetramethyl-11,28-dioxa-4 -azatricyclo[22.3.1.0$^{4,9}$]octacos-18-ene-2,3,10,16-tetraone. ($^1$H NMR and mass spectral analysis were consistent with the desired structures).

EXAMPLE 28

A.
17-Ethyl-1,14-dihydroxy-12-[2'-(3"-(4"'-tert-butyldimethylsilyloxyphenyloxy)-4"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone and

B.
17-Ethyl-1,14-dihydroxy-12-[2'-(4"-(4"'-tert-butyldimethylsilyloxyphenyloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred solution of tri(4-tert-butyldimethylsilyloxyphenyl)bismuthine (213 mg., 0.257 mmol., 2 eq.) in methylene chloride (4 mL.) was added peracetic acid (0.054 mL., 0.257 mmol., 2 eq., 32% solution in dilute acetic acid). To this stirred solution was added 17-ethyl-1,14-dihydroxy-12-

[2'-(3",4"-dihydroxycyclohexyl)-1'-methylvinyl]-23,25-dimethoxy-13,19,21,27-tetramethyl-11,28 -dioxa-4-azatricyclo[22.3.1.0$^{4,9}$]octacos-18-ene-2,3,10,16-tetraone (100 mg., 0.126 mmol., 1 eq.), THF (0.5 mL.), and copper (II) acetate (7 mg., 0.038 mmol., 0.3 eq.). The mixture was allowed to stir for 7 days. The reaction was quenched with saturated aqueous NaCl plus 2 drops 2N HCl and extracted 4× with methylene chloride. The organic extracts were combined, dried over anhydrous Na$_2$SO$_4$, filtered, and concentrated in vacuo. The products were separated by preparative TLC on silica gel (2:1 hexanes/acetone) affording 41.9 mg. of 17-ethyl-1,14-dihydroxy-12-[2'-(4"-(4"'-tert-butyldimethylsilyloxyphenyloxy)-3"-hydroxycyclohexyl)-1'-methylvinyl]-23,25 -dimethoxy-13,19,21,27-tetramethyl-11,28-dioxa-4-azatricyclo[22.3.1.0$^{4,9}$]octacos-18-ene-2,3, 10,16 -tetraone and 42.5 mg. of 17-ethyl-1,14-dihydroxy-12-[2'-(3"-(4"'-tert-butyldimethylsilyloxyphenyloxy)-4"-hydroxycyclo-hexyl)-1 '-methylvinyl]-23,25-dimethoxy-13,19,21,27 -tetramethyl-11,28-dioxa-4-azatricyclo[22.3.1.0$^{4,9}$]octacos-18-ene-2,3,10,16-tetraone. ($^1$H NMR and mass spectral analysis were consistent with the desired structures).

EXAMPLE 29

17-Ethyl-1,14-dihydroxy-12-[2'-(3"-(4"'-hydroxyphenyloxy)-4"-hydroxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone To a stirred solution of 17-ethyl-1,14-dihydroxy-12-[2'-(3"-(4"'-tert-butyldimethylsilyloxyphenyloxy)-4"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (42.5 mg) in CH$_2$Cl$_2$ (1.5 mL.) at 0° C. was added a solution of p-toluenesulfonic acid in methanol (1.5 mL. of a 10% w/v solution). The mixture was stirred 3H at 0° C. and then 3H at room temperature. The reaction mixture was quenched with saturated aqueous NaHCO$_3$ and extracted 4× with CH$_2$Cl$_2$. The organic extracts were combined and dried over anhydrous Na$_2$SO$_4$. The mixture was filtered and concentrated in vacuo. The product was isolated by preparative TLC on silica gel (eluted with 2:1 hexanes/acetone) affording 25.7 mg of 17-ethyl-1, 14-dihydroxy-12-[2'-(3"-(4"'-hydroxyphenyloxy)-4"-hydroxycyclohexyl)-1'-methylvinyl]23,25-dimethoxy-13,19, 21,27 -tetramethyl-11,28-dioxa-4-azatricyclo[22.3.1.0$^{4,9}$] octacos-18-ene-2,3,10,16-tetraone. ($^1$H NMR and mass spectral analysis were consistent with the desired structure).

EXAMPLE 30

17-Ethyl-1,14-dihydroxy-12-[2'-(4"-(4"'-hydroxyphenyloxy)-3"-hydroxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone To a stirred solution of 17-ethyl-1,14-dihydroxy-12-[2'-(4"-(4"'-tert-butyldimethylsilyloxyphenyloxy)-3"-hydroxycyclohexyl)-1'-methylvinyl]-23,25-dimethoxy-13,19,21,27 -tetramethyl-11,28-dioxa-4-azatricyclo[22.3.1.0$^{4,9}$]octacos-18-ene-2,3,10,16-tetraone (41.9 mg) in CH$_2$Cl$_2$ (1.5 mL.) at 0° C. was added a solution of p-toluenesulfonic acid in methanol (1.5 mL. of a 10% w/v solution). The mixture was stirred 3H at 0° C. and then 3H at room temperature. The reaction mixture was quenched with saturated aqueous NaHCO$_3$ and extracted 4× with CH$_2$Cl$_2$. The organic extracts were combined and dried over anhydrous Na$_2$SO$_4$. The mixture was filtered and concentrated in vacuo. The product was isolated by preparative TLC on silica gel (eluted with 2:1 hexanes/acetone) affording 23.9 mg of 17-ethyl-1, 14-dihydroxy-12-[2'-(4"-(4"'-hydroxyphenyloxy)-3"-hydroxycyclohexyl)-1'-methylvinyl]-23,25-dimethoxy-13,19, 21,27 -tetramethyl-11,28-dioxa-4-azatricyclo[22.3.1.0$^{4,9}$] octacos-18-ene-2,3,10,16-tetraone. ($^1$H NMR and mass spectral analysis are consistent with the desired structure).

EXAMPLE 31

A.

17-ethyl-1,14-dihydroxy-12-[2'-(3"'-(6"'-tert-butyldimethylsilyloxynaphth-2-yloxy)-4"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone and

B.

17-Ethyl-1,14-dihydroxy-12-[2'-(4"-(6"'-tert-butyldimethylsilyloxynaphth-2 -yloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred solution of tri(6-tert-butyldimethylsilyloxynaphth-2-yl)bismuthine (252 mg., 0.257 mmol., 2 eq.) in methylene chloride (4 mL.) was added peracetic acid (0.054 mL., 0.257 mmol., 2 eq., 32% solution in dilute acetic acid). To this stirred solution was added 17-ethyl-1,14-dihydroxy-12-[2'-(3",4"-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18 -ene-2,3,10,16-tetraone (100 mg., 0.126 mmol., 1 eq.), THF (0.5 mL.), and copper (II) acetate (7 mg., 0.038 mmol., 0.3 eq.). The mixture was allowed to stir for 7 days. The reaction was quenched with saturated aqueous NaCl plus 2 drops 2N HCl and extracted 4× with methylene chloride. The organic extracts were combined, dried over anhydrous Na$_2$SO$_4$, filtered, and concentrated in vacuo. The products were separated by preparative TLC on silica gel (2:1 hexanes/acetone) affording 39.8 mg. of 17-ethyl-1,14-dihydroxy-12-[2'-(4"-(6"'-tert-butyldimethylsilyloxynaphth-2-yloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18 -ene-2,3,10,16-tetraone and 41.6 mg. of 17-ethyl-1,14-dihydroxy-12-[2'-(3"-(6"'-tert-butyldimethylsilyloxynaphth-2-yl-oxy)-4"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16 -tetraone. ($^1$H NMR and mass spectral analysis were consistent with the desired structures).

EXAMPLE 32

17-Ethyl-1,14-dihydroxy-12-[2'-(4"-(6"'-hydroxynaphth-2-yloxy)-3"-hydroxycyclohexyl)-1'-methylvinyl]-23,25-dimethoxy-13,19,21,27-tetramethyl-11,28-dioxa-4- azatricyclo[22.3.1.0$^{4,9}$]octacos-18-ene-2,3,10,16-tetraone To a stirred solution of 17-ethyl-1,14-dihydroxy-12-[2'-(4"-(6"'-tert-butyldimethylsilyloxynaphth-2-yloxy)-3"-hydroxycyclohexyl)-1'-methylvinyl]-23,25 -dimethoxy-13,19, 21,27-tetramethyl-11,28-dioxa-4-azatricyclo[22.3.1.0$^{4,9}$] octacos-18-ene-2,3,10,16 -tetraone (39.8 mg) in CH$_2$Cl$_2$ (1.5 mL.) at 0° C. was added a solution of p-toluenesulfonic acid in methanol (1.5 mL. of a 10% w/v solution). The mixture was stirred 1.25 h at 0° C. and then 1.75 h at room temperature. The reaction mixture was quenched with saturated aqueous NaHCO$_3$ and extracted 4× with CH$_2$Cl$_2$. The organic extracts were combined and dried over anhydrous Na$_2$SO$_4$. The mixture was filtered and concentrated in vacuo. The product was isolated by preparative TLC on silica gel (eluted 2× with 2:1 hexanes/acetone) affording 17 mg of 17-ethyl-1,14-dihydroxy-12-[2'-(4"-(6'''-hydroxynaphth-2-yloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone. ($^1$H NMR and mass spectral analysis were consistent with the desired structure).

EXAMPLE 33

17-Ethyl-1,14-dihydroxy-12-[2'-(3"-(6'''-hydroxynaphth-2-yloxy)-4"-hydroxycyclohexyl)-1'-methylvinyl]-23,25-dimethoxy-13,19,21,27-tetramethyl-11,28-dioxa-4- azatricyclo[22.3.1.0$^{4,9}$]octacos-18-ene-2,3,10,16-tetraone To a stirred solution of 17-ethyl-1,14-dihydroxy-12-[2'-(3"-(6'''-tert-butyldimethylsilyloxynaphth-2-yloxy)-4"-hydroxycyclohexyl)-1'-methylvinyl]-23,25 -dimethoxy-13,19, 21,27-tetramethyl-11,28-dioxa-4-azatricyclo[22.3.1.0$^{4,9}$] octacos-18-ene-2,3,10,16 -tetraone (41.6 mg) in CH$_2$Cl$_2$ (1.5 mL.) at 0° C. was added a solution of p-toluenesulfonic acid in methanol (1.5 mL. of a 10% w/v solution). The mixture was stirred 1.25 h at 0° C. and then 1.75 h at room temperature. The reaction mixture was quenched with saturated aqueous NaHCO$_3$ and extracted 4× with CH$_2$Cl$_2$. The organic extracts were combined and dried over anhydrous Na$_2$SO$_4$. The mixture was filtered and concentrated in vacuo. The product was isolated by preparative TLC on silica gel (eluted 2× with 2:1 hexanes/acetone) affording 20.8 mg of 17-ethyl-1,14-dihydroxy-12-[2'-(3"-(6'''-hydroxynaphth-2-yloxy)-4"-hydroxycyclohexyl)-1'-methylvinyl] 23,25-dimethoxy-13,19,21,27-tetramethyl-11,28-dioxa-4-azatricyclo[22.3.1.0$^{4,9}$]octacos-18-ene-2,3,10,16-tetraone. ($^1$H NMR and mass spectral analysis were consistent with the desired structure).

EXAMPLE 34

17-Ethyl-1,14-dihydroxy-12-[2'-(4"-(ethoxycarbomethoxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a stirred solution of 17-ethyl-1,14-dihydroxy-12-[2'-(4"-hydroxy-3"-methoxycyclohexyl)-1'-methylvinyl]-23, 25-dimethoxy-13,19,21,27-tetramethyl-11,28-dioxa-4 -azatricyclo[22.3.1.0$^{4,9}$]octacos-18-ene-2,3,10,16-tetraone (200 mg., 0.253 mmol., 1 eq.) in diethyl ether (6 mL.) was added boron trifluoride etherate (0.009 mL., 0.073 mmol., 0.3 eq.) and ethyl diazoacetate (0.080 mL., 0.760 mmol., 3 eq.). The reaction mixture was stirred 12 h. The reaction mixture was quenched with saturated aqueous NaHCO$_3$ and extracted 4× with CH$_2$Cl$_2$. The organic extracts were combined and dried over anhydrous Na$_2$SO$_4$. The mixture was filtered and concentrated in vacuo. The products were isolated by preparative TLC on silica gel (3:2 EtOAc/hexanes) and a second preparative TLC (eluted 2× with 3:1 hexanes/acetone) affording 24.7 mg of 17-ethyl-1,14-dihydroxy-12-[2'-(4"-(ethoxycarbomethoxy)-3"-methoxycyclohexyl)-1'-methylvinyl]-23,25-dimethoxy-13,19,21,27 -tetramethyl-11, 28-dioxa-4-azatricyclo[22.3.1.0$^{4,9}$]octacos-18-ene-2,3,10, 16-tetraone. ($^1$H NMR, $^{13}$C NMR and mass spectral analysis were consistent with the desired structure).

EXAMPLE 35

17-Ethyl-1,14-dihydroxy-12-[2'-(4"-(3''',4'''-dichlorophenyloxy)-3"-methoxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone To a stirred solution of tri(3,4-dichlorophenyl)bismuthine (163 mg.,0.25 mmol.) in CH$_2$Cl$_2$ (2 mL.) was added bis-(trifluoroacetoxy)iodobenzene (107 mg., 0.25 mmol.). The mixture was stirred for 15 minutes then treated with Cu(OAc)$_2$ followed by a solution of 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18 -ene-2,3,10,16-tetraone (100 mg., 0.126 mmol.) in CH$_2$Cl$_2$ (2 mL.). After stirring an additional 2 hours the reaction mixture was quenched by addition of saturated aqueous NaHCO$_3$ and extracted 2× with CH$_2$Cl$_2$. The organic extracts were combined, dried over anhydrous Na$_2$SO$_4$, filtered, and concentrated in vacuo. The product was separated and purified by preparative TLC on silica (eluted with 3:1 Hexane/Acetone) to give 51 mg 17-ethyl-1,14-dihydroxy-12-[2'-(4"-(3''',4'''-dichlorophenyloxy)-3"-methoxycyclohexyl)-1'-methylvinyl]-23,25 -dimethoxy-13,19,21,27-tetramethyl-11,28-dioxa-4-azatricyclo[22.3.1.0$^{4,9}$]octacos-18-ene-2,3,10,16-tetraone ($^1$H NMR, $^{13}$H NMR, and mass spectral analysis are consistent with the desired structure).

EXAMPLE 36

17-Ethyl-1,14-dihydroxy-12-[2'-(4"-(phenanthr-9-yl)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-18-ene-2,3,10,16-tetraone To a stirred solution of tri(9-phenanthryl)bismuthine (150 mg., 0.20 mmol) in CH$_2$Cl$_2$ (3 mL) was added peracetic acid (0.050 mL, 0.22 mmol, 32 wt % solution in dilute acetic acid). After 15 minutes the solution was treated with 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone (100 mg, 0.126 mmol) and Cu(OAc)$_2$ (10 mg, 0.055 mmol) and stirred for 18 hours. The reaction mixture was quenched with saturated aqueous NaHCO$_3$ and extracted 3× with CH$_2$Cl$_2$. The extracts were combined, dried with Na$_2$SO$_4$, filtered and concentrated in vacuo. The product was isolated and purified by preparative TLC on silica gel (eluted with 2:1 hexane/acetone to give 12 mg of 17-ethyl-1,14-dihydroxy-12-[2'-(4"-(phenanthr-9-yl)-3"-methoxycyclohexyl)-1'-methylvinyl ]-23,25-dimethoxy-13,19,21,27-tetramethyl-11,28 -dioxa-4-azatricyclo[22.3.1.0$^{4,9}$]octacos-18-ene-2,3,10,16-tetraone ($^1$H NMR was consistent with the desired structure).

EXAMPLE 37

17-Ethyl-1,14-dihydroxy-12-[2'-(4"-(3''',4'''-methylenedioxyphenyloxy)-3"-methoxycyclohexyl)-1'-methylvinyl]-23,25-dimethoxy-13,19,21,27-tetramethyl-11,28-dioxa-4- azatricyclo[22.3.1.0$^{4,9}$]octacos-18-ene-2,3,10,16-tetraone To a stirred solution of tri(3,4-methylenedioxyphenyl)bismuthine (150 mg., 0.26 mmol) in $CH_2Cl_2$ (2 mL) was added peracetic acid (0.060 mL, 0.26 mmol, 32 wt % solution in dilute acetic acid). After approximately 10 minutes the solution was treated with $Cu(OAc)_2$ (25 mg, 0.138 mmol) and 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28 -dioxa-4-azatricyclo[22.3.1.0$^{4,9}$] octacos-18-ene-2,3,10,16-tetraone (100 mg, 0.126 mmol) and stirred for 18 hours. The reaction mixture was quenched with saturated aqueous $NaHCO_3$ and extracted 2× with $CH_2Cl_2$. The extracts were combined, dried with anhydrous $Na_2SO_4$, filtered, and concentrated in vacuo. The product was isolated and purified by preparative TLC on silica gel (eluted with 2:1 Hexane/Acetone) to give 37 mg of 17-ethyl-1,14-dihydroxy-12-[2'-(4"-(3''',4'''-methylenedioxyphenyloxy)-3"-methoxycyclohexyl)-1'-methylvinyl]-23,25 -dimethoxy-13,19,21,27-tetramethyl-11,28-dioxa-4-azatricyclo[22.3.1.0$^{4,9}$]octacos-18-ene-2,3,10,16 -tetraone ($^1$H NMR and mass spectral analysis were consistent with the desired structure).

EXAMPLE 38

17-Ethyl-1,14-dihydroxy-12-[2'-(4"-(2''',3'''-dihydrobenzofuran-5- yl)-3"-methoxycyclohexyl)-1'-methylvinyl]-23,25-dimethoxy-13,19,21,27-tetramethyl-11,28-dioxa-4- azatricyclo[22.3.1.0$^{4,9}$]octacos-18-ene-2,3,10,16-tetraone To a stirred solution of tri(2,3-dihydrobenzofuran-5yl)bismuthine (32 mg, 0.056 mmol) in $CH_2Cl_2$ (1 mL) was added peracetic acid (0.020 mL, 0.09 mmol, 32 wt % solution in dilute acetic acid). After approximately 15 minutes the solution was treated with $Cu(OAc)_2$ (20 mg, 0.11 mmol) and 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28 -dioxa-4-azatricyclo[22.3.1.0$^{4,9}$]octacos-18-ene-2,3,10,16-tetraone (50 mg, 0.06 mmol) and stirred for three days. The reaction mixture was quenched with saturated aqueous $NaHCO_3$ and extracted with $CH_2Cl_2$. The extracts were combined, dried with anhydrous $Na_2SO_4$, filtered and concentrated in vacuo. The product was purified by preparative TLC on silica gel (eluted with 2:1 Hexane/ Acetone) to give 14 mg of 17-ethyl-1,14-dihydroxy-12-[2'-(4"-(2''',3'''-dihydrobenzofuran-5-yl)-3"-methoxycyclohexyl)-1'-methylvinyl-]-23,25-dimethoxy-13,19,21,27 -tetramethyl-11,28-dioxa-4-azatricyclo[22.3.1.0$^{4,9}$]octacos-18-ene-2,3,10,16-tetraone characterized by ($^1$H NMR and mass spectral analysis were consistent with the desired structure).

EXAMPLE 39

17-Allyl-1,14-dihydroxy-12-[2'-(4"-(naphth-2-yl)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone A mixture of 17-allyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (400 mg, 0.5 mmol) and $Cu(OAc)_2$ (35 mg, 0.19 mmol) in $CH_2Cl_2$ (6 mL) was warmed to 40° C. for 15 minutes then treated with tri(2-naphthyl)bismuth diacetate [prepared immediately prior to use by addition of acetic acid (0.18 mL, 3 mmol) to a suspension of tri(2-naphthyl)bismuth carbonate (600 mg, 0.92 mmol) in $CH_2Cl_2$ (6 mL)]. Heating was maintained for 4 hours after which time the mixture was stirred at room temperature for 18 hours. The reaction mixture was quenched with saturated aqueous $NaHCO_3$ and extracted with $CH_2Cl_2$. The extracts were combined, dried with $Na_2SO_4$, filtered and concentrated in vacuo. The product was isolated and purified by preparative TLC on silica gel (eluted with 3:1 Hexane/Acetone) to give 234 mg of 17-allyl-1,14-dihydroxy-12-[2'-(4"-(naphth-2 -yl)-3"-methoxycyclohexyl)-1'-methylvinyl]-23,25-dimethoxy-13,19,21,27-tetramethyl-11,28-dioxa-4 -azatricyclo[22.3.1.0$^{4,9}$] octacos-18-ene-2,3,10,16-tetraone ($^1$H NMR and mass spectral analysis were consistent with the desired structure).

EXAMPLE 40

17-Ethyl-1,14-dihydroxy-12-[2'-(4'-(1''',4'''-benzodioxane-6- yl)-3"-methoxycyclohexyl)-1'-methylvinyl]-23,25-dimethoxy-13,19,21,27-tetramethyl-11,28-dioxa-4- azatricyclo[22.3.1.0$^{4,9}$]octacos-18-ene-2,3,10,16-tetraone To a stirred solution of tris(1,4-benzodioxan-6-yl)bismuthine (90 mg, 0.146 mmol) in $CH_2Cl_2$ (1 mL) was added peracetic acid (0.030 mL, 0.13 mmol, 32 wt % in dilute acetic acid). After 20 minutes the mixture was treated with 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone (100 mg, 0.126 mmol) followed by $Cu(OAc)_2$ (15 mg, 0.08 mmol) and stirred for 2 days. The reaction mixture was quenched with saturated aqueous $NaHCO_3$ and extracted with $CH_2Cl_2$. The extracts were combined, dried with $Na_2SO_4$, filtered and concentrated in vacuo. The product was purified by preparative TLC on silica gel (eluted with 4% $CH_3OH$ in $CH_2Cl_2$) to give 18 mg of 17-ethyl-1,14-dihydroxy-12-[2'-(4"'-(1''',4'''-benzodioxane-6 -yl)-3"-methoxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone ($^1$H NMR and mass spectral analysis were consistent with the desired structure).

EXAMPLE 40B

17-Ethyl-1-hydroxy-12-[2'-(4"-(4'''-dimethylamino)-phenyloxy-3"-hydroxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone (A)

and

17-Ethyl-1-hydroxy-12-[2'-(4"-hydroxy-3"-(4'''-dimethylamino)phenyloxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone (B)

Peracetic acid (850ml) was added to a solution of tri(4-dimethylaminophenyl)bismuthine (1.27 g) in 30 ml tetrahydrofuran. After 10 minutes 17-ethyl-1-hydroxy-12-[2'-(3", 4"-dihydroxycyclohexyl)-1'-methylvinyl]-23,25- dimethoxy-13,19,21,27-tetramethyl-5 11,28-dioxa-4-azatricyclo[22.3.1.0$^{4,9}$]-octacos-18-ene-2,3,10,16-tetraone (100mg) was added followed by copper acetate (280mg) and the mixture heated to 60° C. for 48 hours. The mixture was then cooled and quenched by pouring into saturated sodium bicarbonate, extracting with ether (3×25 ml). The combined organic washes were dried with magnesium sulphate and concentrated. The crude residue was purified by column chromatography on silica gel eluting with70% hexane: 30% ethyl acetate to give the title compounds A (93mg) and B (102mg) each as white solids.

EXAMPLE 41

17-Ethyl-1,2,14-trihydroxy-12-[2'-(4"-(naphth-2-yl)-3"-methoxycyclohexyl)-1'-methylvinyl]-23,25-dimethoxy-13,19,21,27-tetramethyl-11,28-dioxa-4-azatricyclo[22.3,1.0$^{4,9}$]octacos-18-ene-3,10,16-trione A solution of 1,2-diiodoethane (42 mg, 0.15 mmol) in dry THF (1 mL) was added dropwise to a stirred mixture of samarium metal (46.5 mg, 0.31 mmol) in dry THF (1 mL) and stirred for 1.5 hours. The reaction mixture was then cooled to −78° C. (dry ice/acetone) and treated with a solution of 17-ethyl-1,14-dihydroxy-12-[2'-(4"-(naphth-2-yl)-3"-methoxycyclohexyl)-1 '-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone (100 mg, 0.109 mmol) in 1:1 THF/CH$_3$OH. The mixture was maintained at −78° C. for 15 minutes then allowed to warm to room temperature. The reaction was quenched with cold saturated aqueous K$_2$CO$_3$ and quickly extracted with CH$_2$Cl$_2$. The extracts were combined, dried with Na$_2$SO$_4$, filtered and concentrated in vacuo. Purified by preparative TLC on silica gel (eluted with 7% CH$_3$OH in CH$_2$Cl$_2$) to give 22 mg of 17-ethyl-1,2,14-trihydroxy-12-[2'-(4"-(naphth-2-yl)-3"-methoxycyclohexyl)-1'-methylvinyl]-23, 25-dimethoxy-13,19,21,27-tetramethyl-11,28 -dioxa-4-azatricyclo[22.3.1.0$^{4,9}$]octacos-18-ene-3,10,16-trione ($^1$H NMR and mass spectral analysis are consistent with the desired structure).

EXAMPLE 42

17-Ethyl-1,14-dihydroxy-12-[2'-(4"-allyloxy-3"-methoxycyclohexyl)-1'-methylvinyl]-23,25-dimethoxy-13,19,21,27-tetramethyl-11,28-dioxa-4-azatricyclo[22,3.1.0$^{4,9}$]octacos-18-ene-2,3,10,16-tetraone To a solution of 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone (200 mg in 3.0 ml 33% methylene chloride in cyclohexane), allyl trichloroacetimidate (88 µl neat) was added and the reagents allowed to mix for 5 minutes. Trifluoromethanesulfonic acid as (4.5 µl neat) was added slowly via syringe and the mixture stirred at room temperature. After 18 hours the reaction was quenched by the addition of saturated sodium bicarbonate and extracted with ethyl acetate (3×5 ml). The combined organics were washed with brine and dried over magnesium sulfate. Purification of the concentrate by flash chromatography on silica gel (ethyl acetate: hexane (1:2)+1% methanol) gave the title compound (156 mg).

MASS: (FAB) 838 (M+Li).

Partial $^1$H NMR δ: 5.82 (m, 1H); 4.85 (m), 4.20 (brs, 1H); 4.59 (brd J=4.5 Hz, 1H); 4.41 (brd J=14 Hz, 1H); 4.03 (dt J=4.0, 1.0 Hz, 2H).

EXAMPLE 43

17-Ethyl-1,14-dihydroxy-12-[2'-(4"-(2-butynyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone (50 mg in 1.5 ml 33% methylene chloride in cyclohexane), 2-butynyl trichloroacetimidate (20 µl neat) was added and the reagents allowed to mix for 5 minutes. Trifluoromethanesulfonic acid (2 µl neat) was added slowly via syringe and the mixture stirred at room temperature. After 16 hours the reaction was quenched by the addition of saturated sodium bicarbonate and extracted with ethyl acetate (3×5 ml). The combined organics were washed with brine and dried over magnesium sulfate. Purification of the concentrate by preparative TLC on silica gel (ethyl acetate: hexane (1:1)+1% methanol) gave the title compound (17 mg).

MASS: (FAB) 843 (M+Na).

Partial $^1$H NMR δ: 5.32(Major amide rotamer), 5.29(minor amide rotamer) (brd J=3.0 Hz, 1H); 4.83 m, 4.21M (brs, 1H); 4.59 (brd J=4.0 Hz, 1H); 4.42 Cord J=14.0 Hz, 1H); 4.26 (m, 2H); 1.83 (t J=2.0 Hz,3H).

EXAMPLE 44

17-Ethyl-1,14-dihydroxy-12-[2'-(4"-cinnamyloxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone (50 mg in 1.5 ml 33% methylene chloride in cyclohexane), cinnamyl trichloroacetimidate (26 µl neat) was added and the reagents allowed to mix for 5 minutes. Trifluoromethanesulfonic acid (2 µl neat) was added slowly via syringe and the mixture stirred at room temperature. After 15 minutes the reaction was quenched by the addition of saturated sodium bicarbonate and extracted with ethyl acetate (3×5 ml). The combined organics were washed with brine and dried over magnesium sulfate. Purification of the concentrate by preparative TLC on silica gel (ethyl acetate: hexane (1:1)+1% methanol) gave the title compound (10 mg).

MASS: (FAB) 907 (M+Na).

Partial $^1$H NMR δ: 6.62 (d J=15 Hz, 1H); 6.30 (dt J=15, 6.0 Hz, 1H); 5.33M, 5.19 m (brd J=3.0 Hz, 1H); 4.83 m, 4.21M (brs, 1H); 4.58 (brd J=4.0 Hz, 1H); 4.41 (brd J=14 Hz, 1H); 4.30 (d J=6.0 Hz, 2H).

EXAMPLE 45

17-Ethyl-1,14-dihydroxy-12-[2'-(3"-methoxy-4"-phenylpropyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4"-cinnamyloxy-3"-methoxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone (37 mg in 2 ml ethanol) was added 4 mg of 5% rhodium on carbon catalyst. The reaction flask was fitted with a hydrogen balloon, evacuated and recharged with hydrogen (3 times) and stirred at room temperature. After 1.5 hours, the mixture was filtered over Celite, concentrated and purified by preparative TLC on silica gel (ethyl acetate: hexane (1:2)+1% methanol) to give the title compound (19.5 mg).

MASS: (FAB) 932 (M+Na); 916 (M+Li).

Partial $^1$H NMR δ: 5.31M, 5.28 m (d J=3.0 Hz, 1H); 4.85 m, 4.21M (brs, 1H); 4.58 (brd J=4.0 Hz, 1H); 4.41 Cord J=14 Hz, 1H); 2.69 (t J=8.0 Hz, 2H).

EXAMPLE 46

A. 7-Ethyl-1,14-dihydroxy-12-[2'-(4"-allyloxy-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone
and B. 17-Ethyl-1,14-dihydroxy-12-[2'-(3"-allyloxy-4"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(3",4"-dihydroxycyclohexyl)-1'-methylvinyl]-23,25-dimethoxy-13,19,21,27-tetramethyl-11,28-dioxa-4-azatricyclo [22.3.1.0$^{4,9}$]octacos-18-ene-2,3,10,16-tetraone (100 mg in 1.5 ml 33% methylene chloride in cyclohexane), allyl trichloroacetimidate (53 μl neat) was added and the reagents allowed to mix for 5 minutes. Trifluoromethanesulfonic acid (2 μl neat) was added slowly via syringe and the mixture stirred at room temperature. After 3 hours the reaction was quenched by the addition of saturated sodium bicarbonate and extracted with ethyl acetate (3×5 ml). The combined organics were washed with brine and dried over magnesium sulfate. Purification of the concentrate by flash chromatography on silica gel (ethyl acetate: hexane (1:1)+1% methanol) gave the title compounds (21 mg 4"-ether; 17 mg 3"-ether).

A. (4"-ether):
Partial $^1$H NMR δ: 5.93 (m, 1H); 4.87 m, 4.19M (brs, 1H); 4.59 (brd J=4.0 Hz, 1H); 4.41 (brd J=14 Hz, 1H); 2.67 Cord J=3.7 Hz, B. (3"-ether):
Partial $^1$H NMR δ: 5.93 (m, 1H); 4.83 m, 4.23M (brs, 1H); 4.59 (brd J=4.0 Hz, 1H); 4.41 (brd J=14 Hz, 1H); 2.63 (brs, 1H).

EXAMPLE 47

A. 17-Ethyl-1,14-dihydroxy-12-[2'-(3"-hydroxy-4"-isopropoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone
and B. 17-Ethyl-1,14-dihydroxy-12-[2'-(4"-hydroxy-3"-isopropoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(3",4"-dihydroxycyclohexyl)-1'-methylvinyl]-23,25-dimethoxy-13,19,21,27-tetramethyl-11,28-dioxa-4-azatricyclo [22.3.1.0$^{4,9}$]octacos-18-ene-2,3,10,16-tetraone (110 mg in 1.5 ml 33% methylene chloride in cyclohexane), isopropyl trichloroacetimidate (52 μl neat) was added and the reagents allowed to mix for 5 minutes. Trifluoromethane-sulfonic acid (2 μl neat) was added slowly via syringe and the mixture stirred at room temperature. After 3 hours the reaction was quenched by the addition of saturated sodium bicarbonate and extracted with ethyl acetate (3×5 ml). The combined organics were washed with brine and dried over magnesium sulfate. Purification of the concentrate by preparative TLC on silica gel (ethyl acetate: hexane (1:1)+1% methanol) gave the title compounds (15 mg 4"-ether; 16 mg 3"-ether).

A. (4"-ether):
MASS: (FAB) 826 (M+Li).
Partial $^1$H NMR δ: 5.31 (d J=3.0 Hz,1H); 4.85 m, 4.18M (brs, 1H); 4.58 (brd J=4.0 Hz, 1H); 4.40 (brd J=14 Hz, 1H); 2.63(brs, B. (3"-ether):
MASS: (FAB) 826 (M+Li).
Partial $^1$H NMR δ: 5.31 (d J=3.0 Hz, 1H); 4.81 m, 4.22M (brs, 1H); 4.58 (brd J =4.0 Hz,1H); 4.40 (brd J=14 Hz, 1H); 2.60(brs, 1H).

EXAMPLE 48

A. 17-Ethyl-1,14-dihydroxy-12-[2'-(4"-sec-butenyloxy-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone
and B. 17-Ethyl-1,14-dihydroxy-12-[2'-(3"-sec-butenyloxy-4"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(3",4"-dihydroxycyclohexyl)-1'-methylvinyl]-23,25-dimethoxy-13,19,21,27-tetramethyl-11,28-dioxa-4-azatricyclo [22.3.1.0$^{4,9}$]octacos-18-ene-2,3,10,16-tetraone (150 mg in 3 ml 33% methylene chloride in cyclohexane), sec-butenyl trichloroacetimidate (62 μl neat) was added and the reagents allowed to mix for 5 minutes. Trifluoromethanesulfonic acid (2 μl neat) was added slowly via syringe and the mixture stirred at room temperature. After 15 minutes the reaction was quenched by the addition of saturated sodium bicarbonate and extracted with ethyl acetate (3×8 ml). The combined organics were washed with brine and dried over magnesium sulfate. Purification of the concentrate by preparative TLC on silica gel (ethyl acetate: hexane (1:1)+1% methanol) gave the title compounds (11 mg 4"-ether; 13 mg 3"-ether).

A. (4"-ether):
MASS: (FAB) 831 (M+Na). Partial $^1$H NMR δ: 5.65 (m, 1H); 5.32 (brd J=3.0 Hz, 1H); 4.87 m, 4.1 8M (brs, 1H); 4.58 (brd J=4.0 Hz, 1H); 4.41 (brd J=14 Hz, 1H).

B. (3"-ether):
MASS: (FAB) 831 (M+Na).
Partial $^1$H NMR δ: 5.65 (m, 1H); 5.31 (brs, 1H); 4.82 m, 4.22M (brs, 1H); 4.58 (brd J=4.0 Hz, 1H); 4.41 (brd J=14 Hz, 1H).

EXAMPLE 49

A. 17-Ethyl-1,14-dihydroxy-12-[2'-(4"-(trans-2'''-butenyloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone and B. 17-Ethyl-1,14-dihydroxy-12-[2'-(3"-(trans-2'''-butenyloxy)-4"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(3",4"-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (115 mg in 3 ml 33% methylene chloride in cyclohexane), trans-2-butenyl trichloroacetimidate (48 µl neat) was added and the reagents allowed to mix for 5 minutes. Trifluoromethanesulfonic acid (2 µl neat) was added slowly via syringe and the mixture stirred at room temperature. After 35 minutes the reaction was quenched by the addition of saturated sodium bicarbonate and extracted with ethyl acetate (3×8 ml). The combined organics were washed with brine and dried over magnesium sulfate. Purification of the concentrate by preparative TLC on silica gel (ethyl acetate: hexane (1:1)+1% methanol) gave the title compounds (14 mg 4"-ether; 12 mg 3"-ether).

A. (4"-ether):
  MASS: (FAB) 831 (M+Na).
  Partial $^1$H NMR δ: 5.65(m, 1H); 5.31 (brd J=3.0 Hz, 1H); 4.86 m, 4.19M (brs, 1H); 4.59 (brd J=4.0 Hz, 1H); 4.41 (brd J=14 Hz, 1H); 2.68 (brs, 1H).

B. (3"-ether):
  MASS: (FAB) 831 (M+Na).
  Partial $^1$H NMR δ: 5.65 (m, 1H); 5.30 (brs, 1H); 4.81 m, 4.22M (brs, 1H); 4.59 (brd J=4.0 Hz, 1H); 4.41 (brd J=14 Hz, 1H); 2.64 (brs, 1H).

EXAMPLE 50

A. 17-Ethyl-1,14-dihydroxy-12-[2'-(3"-hydroxy-4"-(3'''-methyl-2-butenyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone and B. 7-Ethyl-1,14-dihydroxy-12-[2'-(4"-hydroxy-3"-(3'''-methyl-2-butenyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(3",4"-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (100 mg in 2 ml methylene chloride), 3-methyl-2-butenyl trichloroacetimidate (39 µl neat) was added and the reagents allowed to mix for 5 minutes. Camphorsulfonic acid (5 mg) was added and the mixture stirred at room temperature. After 21 hours the reaction was quenched by the addition of saturated sodium bicarbonate and extracted with ethyl acetate (3×8 ml). The combined organics were washed with brine and dried over magnesium sulfate. Purification of the concentrate by preparative TLC on silica gel (ethyl acetate: hexane (1:1)+1% methanol) gave the title compounds (24 mg 4"-ether; 21 mg 3"-ether).

A. (4"-ether):
  MASS: (FAB) 845 (M+Na).
  Partial $^1$H NMR δ: 4.87 m, 4.19M (brs, 1H); 4.58 (brd J=4.0 Hz, 1H); 4.41 (brd J=14 Hz, 1H); 2.70 (brs, 1H); 1.75 (s, 3H); 1.67 (s, 3H).

B. (3"-ether):
  MASS: (FAB) 845 (M+Na).
  Partial $^1$H NMR δ: 4.82 m, 4.23M (brs, 1H); 4.58 (brd J=4.0 Hz, 1H); 4.41 (brd J=14 Hz, 1H); 2.67 (brs, 1H); 1.75 (s,3H); 1.67 (s, 3H).

EXAMPLE 51

A. 17-Ethyl-1,14-dihydroxy-12-[2'-(3"-hydroxy-4"-(2'''-methylpropenyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone and B. 17-Ethyl-1,14-dihydroxy-12-[2'-(4"-hydroxy-3"-(2'''-methylpropenyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(3",4"-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (200 mg in 3 ml 33% methylene chloride in cyclohexane), 2-methylpropenyl trichloroacetimidate (84 µl neat) was added and the reagents allowed to mix for 5 minutes. Trifluoromethanesulfonic acid (2 µl neat) was added slowly via syringe and the mixture stirred at room temperature. After 1 hour the reaction was quenched by the addition of saturated sodium bicarbonate and extracted with ethyl acetate (3×8 ml). The combined organics were washed with brine and dried over magnesium sulfate. Purification of the concentrate by preparative TLC on silica gel (ethyl acetate: hexane (1:1)+1% methanol) gave the title compounds (34 mg 4"-ether; 24 mg 3"-ether).

A. (4"-ether):
  MASS: (FAB) 831 (M+Na).
  Partial $^1$H NMR δ: 5.32 (brs, 1H); 4.87 (brs, 1H); 4.59 (brs, 1H); 4.41 (brd J=14 Hz, 1H); 4.19M (brs, 1H); 2.60 (brs, 1H); 1.74 (s, 3H).

B. (3"-ether):
  MASS: (FAB) 831 (M+Na).
  Partial $^1$H NMR δ: 5.32 (brs, 1H); 4.87 (brs, 1H); 4.81 m, 4.23M (brs, 1H); 2.63 (brs, 1H); 1.74 (s, 3H).

EXAMPLE 52

17-Ethyl-1,14-dihydroxy-12-[2'-(3"-cinnamyloxy-4"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(3",4"-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (100 mg in 3 ml 33% methylene chloride in cyclohexane), cinnamyl trichloroacetimidate (52 μl neat) was added and the reagents allowed to mix for 5 minutes. Trifluoromethanesulfonic acid (2 μl neat) was added slowly via syringe and the mixture stirred at room temperature. After 15 minutes the reaction was quenched by the addition of saturated sodium bicarbonate and extracted with ethyl acetate (3×8 ml). The combined organics were washed with brine and dried over magnesium sulfate. Purification of the concentrate by preparative TLC on silica gel (ethyl acetate: hexane (1:1)+1% methanol) gave the title compound (17 mg).

MASS: (FAB) 893 (M+Na).

Partial $^1$H NMR δ: 6.61 (d J=15 Hz, 1H); 6.28 (dt J=15, 6.0 Hz, 1H); 5.32 m, 5.19M (brd J=3.0 Hz, 1H); 4.82 m, 4.22M (brs,1H); 4.52 (brd J=4.0 Hz, 1H); 4.41 (brd J=14 Hz, 1H); 2.66 (brs,

EXAMPLE 53

17-Ethyl-1-hydroxy-12-[2'-(4"-hydroxy-3"-isopropoxycyclohexyl)-1'-methylvinyl]-23,25-dimethoxy-13,19,21,27-tetramethyl-11,28-dioxa-4-azatricyclo[22.3.1.0$^{4,9}$]-octacos-18- ene-2,3,10,16-tetraone To a solution of 17-ethyl-1-hydroxy-12-[2'-(3",4"-dihydroxycyclohexyl)-1'-methylvinyl]-23,25-dimethoxy-13,19, 21,27-tetramethyl-11,28-dioxa-4-azatricyclo[22.3.1.0$^{4,9}$]octacos-18 -ene-2,3,10,16-tetraone (69 mg in 3 ml 33% methylene chloride in cyclohexane), isopropyl trichloroacetimidate (22 μl neat) was added and the reagents allowed to mix for 5 minutes. Trifluoromethanesulfonic acid (2 μl neat) was added slowly via syringe and the mixture stirred at room temperature. After 24 hours the reaction was quenched by the addition of saturated sodium bicarbonate and extracted with ethyl acetate (3×8 ml). The combined organics were washed with brine and dried over magnesium sulfate. Purification of the concentrate by preparative TLC on silica gel (ethyl acetate:hexane (1:1)+1% methanol) gave the title compound (12 mg).

MASS: (FAB) 803 (M+Li).

Partial $^1$H NMR δ: 4.87 (brd J=10 Hz, 1H); 4.56 (d J=4.0 Hz, 1H); 4.42 m, 4.33M (brs, 1H); 2.61 (brs, 1H); 1.16 (d J=7.0 Hz, 6H).

EXAMPLE 54

A.
17-Ethyl-1,14-dihydroxy-12-[2'-(4"-sec-butenyloxy-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone
and B.
7-Ethyl-1,14-dihydroxy-12-[2'-(3"-sec-butenyloxy-4"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(3",4"-dihydroxycyclohexyl)-1'-methylvinyl]-23,25-dimethoxy-13,19,21,27-tetramethyl-11,28-dioxa-4-azatricyclo [22.3.1.0$^{4,9}$]octacos-18-ene-2,3,10,16-tetraone (150 mg in 3 ml 33% methylene chloride in cyclohexane), sec-butenyl trichloroacetimidate (62 ml neat) was added and the reagents allowed to mix for 5 minutes. Trifluoromethanesulfonic acid (2 μl neat) was added slowly via syringe and the mixture stirred at room temperature. After 15 minutes the reaction was quenched by the addition of saturated sodium bicarbonate and extracted with ethyl acetate (3×8 ml). The combined organics were washed with brine and dried over magnesium sulfate. Purification of the concentrate by preparative TLC on silica gel (ethyl acetate: hexane (1:1)+1% methanol) gave the title compounds (11 mg 4"-ether; 13 mg 3"-ether).

A. (4"-ether):
MASS: (FAB) 831 (M+Na). Partial $^1$H NMR δ: 5.65 (m, 1H); 5.32 (brd J=3.0 Hz, 1H); 4.87 m, 4.18M (brs, 1H); 4.58 (brd J=4.0 Hz, 1H); 4.41 (brd J=14 Hz, 1H).

B. (3"-ether):
MASS: (FAB) 831 (M+Na). Partial $^1$H NMR δ: 5.65 (m, 1H); 5.31 (brs, 1H); 4.82 m, 4.22M (brs, 1H); 4.58 (brd J=4.0 Hz, 1H); 4.41 (brd J=14 Hz, 1H).

EXAMPLE 55

17-Ethyl-1-hydroxy-12-[2'-(4"-cinnamyloxy-3"-methoxycyclohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone To a solution of 17-ethyl-1-hydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo [22.3.1.0$^{4,9}$]octacos-18-ene-2,3,10,16-tetraone (100 mg in 3 ml 33% methylene chloride in cyclohexane), cinnamyl trichloroacetimidate (54 μl neat) was added and the reagents allowed to mix for 5 minutes. Trifluoromethanesulfonic acid (2 μl neat) was added slowly via syringe and the mixture stirred at room temperature. After 30 minutes the reaction was quenched by the addition of saturated sodium bicarbonate and extracted with ethyl acetate (3×8 ml). The combined organics were washed with brine and dried over magnesium sulfate. Purification of the concentrate by preparative TLC on silica gel (ethyl acetate: hexane (1:2)+1% methanol) gave the title compound (45 mg).

MASS: (FAB) 891 (M+Li). Partial $^1$H NMR δ: 6.62 (d J=15 Hz, 1H); 6.31 (dt J=15, 6.0 Hz, 1H); 4.56 (brd J=4.0 Hz, 1H); 4.31 (d J=6.0 Hz, 2H).

EXAMPLE 56

17-Ethyl-1-hydroxy-12-[2'-(3"-methoxy-4"-phenylpropyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-[2'-(4"-cinnamyloxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (16 mg in 2 ml ethanol) was added 2 mg of 5% rhodium on carbon catalyst. The reaction flask was fitted with a hydrogen balloon, evacuated and recharged with hydrogen (3 times) and stirred at room temperature. After 30 minutes, the mixture was filtered over diatomacous earth, concentrated and purified by preparative TLC on silica gel (ethyl acetate: hexane (1:2)+1% methanol) to give the title compound (5.5 mg).

MASS: (FAB) 916 (M+Na). Partial $^1$H NMR δ: 4.58 Cord J=4.0 Hz, 1H); 4.42 m, 4.32M (brs, 1H); 4.40 (brd J=14 Hz, 1H); 2.69 (t J=8.0 Hz, 2H).

EXAMPLE 57

17-Ethyl-1,14-dihydroxy-12-[2'-(4"-sec-phenethyloxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone (75 mg in 3 ml 33% methylene chloride in cyclohexane), sec-phenethyl trichloroacetimidate (38 μl neat) was added and the reagents allowed to mix for 5 minutes. Trifluoromethanesulfonic acid (3 μl neat) was added slowly via syringe and the mixture stirred at room temperature. After 30 minutes the reaction was quenched by the addition of saturated sodium bicarbonate and extracted with ethyl acetate (3×10 ml). The combined organics were washed with brine and dried over magnesium sulfate. Purification of the concentrate by flash chromatography on silica gel (ethyl acetate: hexane (1:2)+1% methanol) gave the title compound (13 mg).

MASS: (FAB) 918 (M+Na) 902 (M+Li). Partial $^1$H NMR δ: 5.28 (m, 1H); 4.56 (m, 1H); 4.41 (brd J=14 Hz, 1H); 4.86 m, 4.20M (brs, 1H).

EXAMPLE 58

17-Ethyl-1,14-dihydroxy-12-[2'-(4"-(2'''-methyl-cinnamyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone (50 mg in 1.5 ml 33% methylene chloride in cyclohexane), 2-methylcinnamyl trichloroacetimidate (28 μl neat) was added and the reagents allowed to mix for 5 minutes. Trifluoromethanesulfonic acid (3 μl neat) was added slowly via syringe and the mixture stirred at room temperature. After 20 minutes the reaction was quenched by the addition of saturated sodium bicarbonate and extracted with ethyl acetate (3×10 ml). The combined organics were washed with brine and dried over magnesium sulfate. Purification of the concentrate by flash chromatography on silica gel (ethyl acetate: hexane (1:2)+1% methanol) gave the title compound (9 mg).

MASS: (FAB) 944 (M+Na). Partial $^1$H NMR δ: 6.53 (brs, 1H); 5.32 (brd, J=3 Hz, 1H); 4.85 m, 4.21M (brs, 1H); 4.59 (brd J=4 Hz, 1H); 4.41 (brd J=14 Hz, 1H); 4.16 (brs, 2H); 1.90 (brs, 3H).

EXAMPLE 59

17-Ethyl-1,14-dihydroxy-12-[2'-(4"-(4'''-methyl-2''',4'''-hexadienyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone (200 mg in 6 ml 33% methylene chloride in cyclohexane), 4-methyl-2,4-hexadienyl trichloroacetimidate (97 μl neat) was added and the reagents allowed to mix for 5 minutes. Trifluoromethanesulfonic acid (5 μl neat) was added slowly via syringe and the mixture stirred at room temperature. After 4 hours the reaction was quenched by the addition of saturated sodium bicarbonate and extracted with ethyl acetate (3×20 ml). The combined organics were washed with brine and dried over magnesium sulfate. Purification of the concentrate by flash chromatography on silica gel (ethyl acetate: hexane (1:2)+1% methanol) gave the title compound (8 mg).

MASS: (FAB) 892 (M+Li). Partial $^1$H NMR δ: 6.25 (d J=15 Hz, 1H); 5.64 (dt J=15,7 Hz, 1H); 5.31 (brd J=3 Hz, 1H); 4.83 m, 4.21M (brs, 1H); 4.59 (brd J=4 Hz, 1H); 4.41 (brd J=14 Hz, 1H); 4.18 (brd J=7 Hz, 2H).

EXAMPLE 60

17-Ethyl-1,14-dihydroxy-12-[2'-(4"-(p-methoxycinnamyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone (200 mg in 6 ml 33% methylene chloride in cyclohexane), p-methoxycinnamyl trichloroacetimidate (117 μl neat) was added and the reagents allowed to mix for 5 minutes. Trifluoromethanesulfonic acid (3 μl neat) was added slowly via syringe and the mixture stirred at room temperature. After 20 minutes the reaction was quenched by the addition of saturated sodium bicarbonate and extracted with ethyl acetate (3×20 ml). The combined organics were washed with brine and dried over magnesium sulfate. Purification of the concentrate by flash chromatography on silica gel (ethyl acetate: hexane (1:2)+1% methanol) gave the title compound (16 mg).

MASS: (FAB) 960 (M+Na) 944 (M+Li). Partial $^1$H NMR δ: 7.29 (brd J=9 Hz, 2H); 6.85 (brd J=9 Hz, 2H); 5.32M, 5.19 m (brd J=3 Hz, 1H); 4.84 m, 4.21M (brs, 1H); 4.61 (brd J=5 Hz, 2H); 4.41 (brd J=14 Hz, 1H).

EXAMPLE 61

17-Ethyl-1,14-dihydroxy-12-[2'-(4"-(3''',4'''-methylenedioxycinnamyloxy)-3"-methoxycyclohexyl)-1'-methylvinyl]-23,25-dimethoxy-13,19,21,27- tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone (200 mg in 6 ml 33% methylene chloride in cyclohexane), 3',4'-methylenedioxycinnamyl trichloroacetimidate (122 μl neat) was added and the reagents allowed to mix for 5 minutes. Trifluoromethanesulfonic acid (3 μl neat) was added slowly via syringe and the mixture stirred at room temperature. After 30 minutes the reaction was quenched by the addition of saturated sodium bicarbonate and extracted with ethyl acetate (3×20 ml). The combined organics were washed with brine and dried over magnesium sulfate. Purification of the concentrate by flash chromatography on silica gel (ethyl acetate: hexane (1:2)+1% methanol) gave the title compound (10 mg).

MASS: (FAB) 974 (M+Na). Partial $^1$H NMR δ: 6.54 (d J=16 Hz, 1H); 6.14 (dt J-16,6 Hz, 1H); 5.95 (s, 2H) 5.33M, 5.19 m (brd J=3 Hz, 1H); 4.59 (brd J=4 Hz, 1H); 4.41 (brd J=14 Hz, 1H); 4.27 Cord J=6 Hz, 2H).

EXAMPLE 62

17-Ethyl-1,14-dihydroxy-12-[2'-(4"-(4''',4'''-dimethyl-2'''-trans-pentenyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone (200 mg in 6 ml 33% methylene chloride in cyclohexane), 4,4-dimethyl-2-trans-pentenyl trichloroacetimidate (98 μl neat) was added and the reagents allowed to mix for 5 minutes. Trifluoromethanesulfonic acid (10 μl neat) was added slowly via syringe and the mixture stirred at room temperature. After 1.5 hours the reaction was quenched by the addition of saturated sodium bicarbonate and extracted with ethyl acetate (3×20 ml). The combined organics were washed with brine and dried over magnesium sulfate. Purification of the concentrate by flash chromatography on silica gel (ethyl acetate: hexane (1:2)+1% methanol) gave the title compound (17 mg).

MASS: (FAB) 894 (M+Li). Partial $^1$H NMR δ: 5.70 (d J=16 Hz, 1H); 5.48 (dt J=16,7 Hz, 1H); 5.31 (brd J=3 Hz, 1H); 4.84 m, 4.21M (brs, 1H); 4.59 (brd J=4 Hz, 1H); 4.41 (brd J=14 Hz, 1H); 4.18 (brd J=7 Hz, 2H); 1.01 (s, 9H).

EXAMPLE 63

17-Ethyl-1,14-dihydroxy-12-[2'-(4"-(3'''-cyclohexyl-2'''-trans-propenyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone (200 mg in 6 ml 33% methylene chloride in cyclohexane), 3-cyclohexyl-2-trans-propenyl trichloroacetimidate (108 μl neat) was added and the reagents allowed to mix for 5 minutes. Trifluoromethanesulfonic acid (7 μl neat) was added slowly via syringe and the mixture stirred at room temperature. After 1 hour the reaction was quenched by the addition of saturated sodium bicarbonate and extracted with ethyl acetate (3×20 ml). The combined organics were washed with brine and dried over magnesium sulfate. Purification of the concentrate by flash chromatography on silica gel (ethyl acetate: hexane (1:2)+1% methanol) gave the title compound (20 mg).

MASS: (FAB) 936 (M+Na). Partial $^1$H NMR δ: 5.32M, 5.19 m (brd J=3 Hz, 1H); 4.84 m, 4.21M (brs, 1H); 4.59 (brd J=4 Hz, 1H); 4.41 (brd J=14 Hz, 1H); 4.06 (brd J=5 Hz, 2H).

EXAMPLE 64

17-Ethyl-1,14-dihydroxy-12-[2'-(4"-p-fluorocinnamyloxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone (200 mg in 6 ml 33% methylene chloride in cyclohexane), p-fluorocinnamyl trichloroacetimidate (112 μl neat) was added and the reagents allowed to mix for 5 minutes. Trifluoromethanesulfonic acid (7 μl neat) was added slowly via syringe and the mixture stirred at room temperature. After 20 minutes the reaction was quenched by the addition of saturated sodium bicarbonate and extracted with ethyl acetate (3×20 ml). The combined organics were washed with brine and dried over magnesium sulfate. Purification of the concentrate by flash chromatography on silica gel (ethyl acetate: hexane (1:2)+1% methanol) gave the title compound (33 mg).

MASS: (FAB) 932 (M+Li). Partial $^1$H NMR δ: 7.37 (d J=6 Hz, 1H); 7.31 (d J=6 Hz, 1H); 7.01 (d J=9 Hz, 1H); 6.96 (d J=9 Hz, 1H); 6.57 (d J=16 Hz, 1H); 6.21 (dt J=16, 6 Hz, 1H); 5.32M, 5.19 m (brd J=3 Hz, 1H); 4.83 m, 4.21M (brs, 1H); 4.59 (brd J=4 Hz, 1H); 4.41 (brd J=14 Hz, 1H); 4.29 (d J=6 Hz, 2H).

EXAMPLE 65

17-Ethyl-1,14-dihydroxy-12-[2'-(4"-p-chlorocinnamyloxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone (200 mg in 6 ml 33% methylene chloride in cyclohexane), p-chlorocinnamyl trichloroacetimidate (119 μl neat) was added and the reagents allowed to mix for 5 minutes. Trifluoromethanesulfonic acid (7 μl neat) was added slowly via syringe and the mixture stirred at room temperature. After 30 minutes the reaction was quenched by the addition of saturated sodium bicarbonate and extracted with ethyl acetate (3×20 ml). The combined organics were washed with brine and dried over magnesium sulfate. Purification of the concentrate by flash chromatography on silica gel (ethyl acetate:hexane (1:2)+1% methanol) gave the title compound (34 mg).

MASS: (FAB) 948 (M+Li). Partial $^1$H NMR δ: 6.58 (d J=16 Hz, 1H); 6.27 (dt J=16, 6 Hz, 1H); 5.32M, 5.19 m (brd J=3 Hz, 1H); 4.84 m, 4.21M (brs, 1H); 4.59 (brd J=4 Hz, 1H); 4.41 (brd J=14 Hz, 1H); 4.30 (d J=6 Hz,

EXAMPLE 66

17-Ethyl-1,14-dihydroxy-12-[2'-(4"-p-bromocinnamyloxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone (200 mg in 6 ml 33% methylene chloride in cyclohexane), p-bromocinnamyl trichloroacetimidate (135 μl neat) was added and the reagents allowed to mix for 5 minutes. Trifluoromethanesulfonic acid (7 μl neat) was added slowly via syringe and the mixture stirred at room temperature. After 1 hour the reaction was quenched by the addition of saturated sodium bicarbonate and extracted with ethyl acetate (3×20 ml). The combined organics were washed with brine and dried over magnesium sulfate. Purification of the concentrate by flash chromatography on silica gel (ethyl acetate: hexane (1:2)+1% methanol) gave the title compound (19 mg).

MASS: (FAB) 984, 986 (M+). Partial $^1$H NMR δ: 7.42 (d J=9 Hz, 2H); 7.20 (d J=9 Hz, 2H); 6.56 (d J=16 Hz, 1H); 6.29 (dt J=16, 6 Hz, 1H); 5.31M, 5.19 m (brd J=3 Hz, 1H); 4.85 m, 4.21M(brs, 1H); 4.59 (brd J=4 Hz, 1H); 4.41 (brd J=14 Hz, 1H); 4.28 (d J=6 Hz, 2H).

EXAMPLE 67

17-Ethyl-1,14-dihydroxy-12-[2'-(3"-methoxy-4"-p-fluorophenpropyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4"-p-fluorocinnamyloxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (22 mg in 2 ml ethanol) was added 6 mg of 5% rhodium on carbon catalyst. The reaction flask was fitted with a hydrogen balloon, evacuated and recharged with hydrogen (3 times) and stirred at room temperature. After 45 minutes, the mixture was filtered over Celite, concentrated and purified by preparative TLC on silica gel (ethyl acetate: hexane (1:2)+1% methanol) to give the title compound (7.5 mg).

MASS: (FAB) 934 (M+Li). Partial $^1$H NMR δ: 7.16 (d J=6 Hz, 1H); 7.12 (d J=6 Hz, 1H); 6.97 (d J=9 Hz, 1H); 6.92 (d J=9 Hz, 1H); 5.32M, 5.19 m (brd J=3 Hz, 1H); 4.85 m, 4.21M (brs, 1H); 4.59 (brd J=4 Hz, 1H); 4.41 (brd J=14 Hz, 1H); 2.67 (t J=8 Hz, 2H).

EXAMPLE 68

17-Ethyl-1-hydroxy-12-[2'-(3",4"-diallyloxy-cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-[2'-(3",4"-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (20 mg in 0.75 ml 33% methylene chloride in cyclohexane), allyl trichloroacetimidate (16 μL neat) was added and the reagents allowed to mix for 5 minutes. Trifluoromethanesulfonic acid (2.0 μL neat) was added slowly via syringe and the mixture stirred at room temperature. After 5 hours the reaction was quenched by the addition of saturated sodium bicarbonate and extracted with ethyl acetate (3×5 ml). The combined organics were washed with brine and dried over magnesium sulfate. Purification of the concentrate by flash chromatography on silica gel (ethyl acetate:hexane (1:3)+1% methanol) gave the title compound (6.8 mg). ($^1$H NMR was consistent with the desired structure).

EXAMPLE 69

17-Ethyl-1-hydroxy-12-[2'-(3",4"-dipropyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-12-[2'-(3",4"-diallyloxycyclohexyl)-1'-methylvinyl]-23,25-dimethoxy-13,19, 21,27-tetramethyl-11,28-dioxa-4-azatricyclo[22.3.1.0$^{4,9}$]octacos-18-ene-2,3,10,16-tetraone (6.8 mg in 600 μl ethyl acetate) was added 4 mg of 5% rhodium on carbon catalyst. The reaction flask was fitted with a hydrogen balloon, evacuated and recharged with hydrogen (3 times) and stirred at room temperature. After 25 minutes, the mixture was filtered over Celite, concentrated and purified by flash chromatography on silica gel (ethyl acetate: hexane (1:3)+1% methanol) to give the title compound (4.5 mg).

MASS: (FAB) 852 (M+Li). Partial $^1$H NMR δ: 4.59 (brm, 1H); 4.42 m, 4.33M (brs, 1H); 4.41 (brd, J=14 Hz, 1H); 3.54 (m, 4H).

EXAMPLE 70

17-Ethyl-1,14-dihydroxy-12-[2'-(4"-(2'"-benzylamino)-ethoxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone

Step A

17-Ethyl-1-hydroxy-14-(tert-butyldimethylsiloxy)-12-[2'-(4"-(tert-butyldimethylsiloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (2.35 g) in dry methylene chloride (20 ml) was added an excess of 2,6-lutidine (1.04 ml) and the mixture was stirred at room temperature. After 10 minutes, tert-butyldimethylsilyl trifluoromethanesulfonate (1.50 ml) was added via syringe. After 1 hour the reaction mixture was diluted with ethyl acetate, extracted from saturated sodium bicarbonate, washed with brine and the organic phase dried over magnesium sulfate. Removal of the solvent in vacuo and flash chromatography on silica gel (ethyl acetate: hexane (1:3)+1% methanol) gave the title compound (2.91 g). ($^1$H NMR was consistent with the desired structure).

Step B

17-Ethyl-1-hydroxy-14-(tert-butyldimethylsiloxy)-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-14-(tert-butyldimethylsiloxy)-12-[2'-(4"-(tert-butyldimethylsiloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (2.91 g) in acetonitrile (15 ml) was added a solution of 2% hydrogen fluoride in aqueous acetonitrile (2 ml), and the mixture stirred at room temperature. After 4 hours, the solution was diluted with ethyl acetate, extracted with saturated sodium bicarbonate solution and the organic phase dried over magnesium sulfate. Purification of the concentrate by flash chromatography on silica gel (ethyl acetate:hexane (1:1)+1% methanol) gave the title compound (1.51 g). (1 H NMR was consistent with the desired structure).

Step C

17-Ethyl-1-hydroxy-14-(tert-butyldimethylsiloxy)-12-[2'-(4"-allyloxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-14-(tert-butyldimethylsiloxy)-12-[2'-(4"-hydroxy-3"-methoxycyclohexyl)-1'-methylvinyl]-23,25-dimethoxy-13,19,21,27-tetramethyl-11,28 -dioxa-4-azatricyclo[22.3.1.0$^{4,9}$]octacos-18-ene-2,3,10,16-tetraone (820 mg in 9 ml 33% methylene chloride in cyclohexane) allyl trichloroacetimidate (366 µl neat) was added and the reagents allowed to mix for 5 minutes. Trifluoromethanesulfonic acid (16 µl neat) was added slowly via syringe and the mixture stirred at room temperature. After 17 hours the reaction was quenched by the addition of saturated sodium bicarbonate and extracted with ethyl acetate (3×15 ml). The combined organics were washed with brine and dried over magnesium sulfate. Purification of the concentrate by flash chromatography on silica gel (ether:hexane (2:3)) gave the title compound (800 mg). ($^1$H NMR was consistent with the desired structure).

Step D

17-Ethyl-1-hydroxy-14-(tert-butyldimethylsiloxy)-12-[2'-(4"'-(2"',3"'-dihydroxypropyloxy)-3"-methoxycyclohexyl)-1'-methylvinyl]-23,25-dimethoxy-13,19,21,27-tetramethyl-11,28 -dioxa-4-azatricyclo[22.3.1.0$^{4,9}$]octacos-18-ene-2,3,10,16-tetraone To a solution of 17-ethyl-1-hydroxy-14-(tert-butyldimethylsiloxy)-12-[2'-(4"-allyloxy-3"-methoxycyclohexyl)-1'-methylvinyl]-23,25-dimethoxy-13,19,21,27-tetramethyl-11,28 -dioxa-4-azatricyclo[22.3.1.0$^{4,9}$]octacos-18-ene-2,3,10,16-tetraone (344 mg in 3 ml dry diethyl ether) was added 150 µl pyridine followed by 1.6 ml of a 0.25M osmium tetraoxide solution in THF and the mixture stirred at room temperature. After 15 minutes, 10 ml of a 20% sodium bisulfite solution were added and the mixture diluted with 20 ml ethyl acetate. The layers were separated and the organic portion re-extracted with 20% sodium bisulfite (3×20 ml) then washed with a saturated brine solution and dried over sodium sulfate. The concentrate was purified by flash chromatography on silica gel (ethyl acetate:hexane (1:1)+1% methanol, then methylene chloride:hexane:methanol (10:2:1)) to give the title compound (300 mg) ($^1$H NMR was consistent with the desired structure).

Step E

17-Ethyl-1-hydroxy-14-(tert-butyldimethylsiloxy)-12-[2'-(4"-ethanaloxy-3"-methoxycyclohexyl)-1'-methylvinyl]23,25-dimethoxy-13,19,21,27-tetramethyl-11,28-dioxa-4-azaricyclo[22.3.1.0$^{4,9}$]octacos-18-ene-2,3,10,16-tetraone To a solution of 17-ethyl-1-hydroxy-14-(tert-butyldimethylsiloxy)-12-[2'-(4"-(2"',3"'-dihydroxypropyloxy)-3"-methoxycyclohexyl)-1'-methylvinyl]-23,25 -dimethoxy-13,19,21,27-tetramethyl-11,28-dioxa-4-aza-tricyclo[22.3.1.0$^{4,9}$] octacos-18-ene-2,3,10,16 -tetraone (284 mg in 6 ml of in 20% aqueous tetrahydrofuran) was added sodium metaperiodate (72.3 mg) and the mixture stirred vigorously for 2 hours. At this time an additional 50 mg of sodium metaperiodate were added. After 1.5 hours the mixture was diluted with ethyl acetate and extracted from half-saturated sodium bicarbonate. The organic portion was dried over magnesium sulfate and purified by flash chromatography on silica gel (ethyl acetate:hexane (1:1)+1% methanol) to give the title compound (151 mg). ($^1$H NMR was consistent with the desired structure).

Step F

17-Ethyl-1-hydroxy-14-(tert-butyldimethylsiloxy)-12-[2'-(4"-(2"'-benzylamino)-ethoxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-14-(tert-butyldimethylsiloxy)-12-[2'-(4"-ethanaloxy-3"-methoxycyclohexyl)-1'-methylvinyl]-23,25-dimethoxy-13,19,21,27-tetramethyl-11,28 -dioxa-4-azatricyclo[22.3.1.0$^{4,9}$]octacos-1 8-ene-2,3,10,16-tetraone (9.5 mg in 0.25 ml dry terahydrofuran) was added benzylamine (2.5 µl) and the mixture stirred for 10 minutes at room temperature. This was cooled to −78° C. and acetic acid (10 µl) was added followed by potassium triphenylborohydride (25 µl of a 0.5M solution in THF). After 45 minutes, the reaction was quenched by the addition of saturated ammonium chloride and warmed to room temperature. The mixture was extracted with ethyl acetate (3×5 ml) and dried over magnesium sulfate. The concentrate was purified by flash chromatography on silica gel (ethyl acetate:hexane (1:2)+1% methanol, then 2% ammonium hydroxide, 5% methanol in methylene chloride) to give the title compound (3.5 mg).

MASS (FAB) 1039 (M+). ($^1$H NMR was consistent with the desired structure).

Step G

17-Ethyl-1,14-dihydroxy-12-[2'-(4"-(2"'-benzylamino)ethoxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3.,10,16-tetraone To a solution of 17-ethyl-1-hydroxy-14-(tert-butyldimethylsiloxy)-12-[2'-(4"-(2"'-benzylamino)ethoxy-3"-methoxycyclohexyl)-1'-methylvinyl]-23,25-dimethoxy-13,19,21,27-tetramethyl-11,28 -dioxa-4-azatricyclo[22.3.1.0$^{4,9}$]octacos-18-ene-2,3,10,16-tetraone (3.5 mg) in acetonitrile (100 µl) was added a solution of 2% HF in aqueous acetonitrile (100 µl), and the mixture stirred at room temperature. After 2 hours, the solution was diluted with ethyl acetate, extracted with saturated sodium bicarbonate solution and the organic phase dried over magnesium sulfate. Purification of the concentrate by flash chromatography on silica gel (ethyl acetate: hexane (1:1)+1% methanol, then 2% ammonium hydroxide, 5% methanol in methylene chloride) gave the title compound (2 mg).

MASS (FAB) 925 (M+). Partial $^1$H NMR δ: 7.32 (m, 5H); 5.32M, 5.17 m (brd J=3 Hz, 1H); 4.84 m, 4.21M (brs, 1H); 4.59 (brd, J=4 Hz, 1H); 4.41 (brd J=14 Hz, 1H); 3.84 (brs, 2H).

EXAMPLE 71

17-Ethyl-1-hydroxy-12-[2'-(4"-(2'''-benzyl-
amino)ethoxy-3"-methoxycyclohexyl)-1'-methylvinyl]-
23,25-dimethoxy-13,19,21,27-tetramethyl-11,28-
dioxa-4-azatricyclo[22.3.1.0$^{4,9}$]octacos-18-ene-
2,3,10,16-tetraone

Step A

17-Ethyl-1-hydroxy-12-[2'-(4"-allyloxy-3"-methoxy-
cyclohexyl)-1'-methylvinyl]-23,25-dimethoxy-
13,19,21,27-tetramethyl-11,28-dioxa-4-azatri-
cyclo[22.3.1.0$^{4,9}$]octacos-18-ene-2,3,10,16-tetraone To a solution of 17-ethyl-1-hydroxy-12-[2'-(4"-hydroxy-
3"-methoxycyclohexyl)-1'-methylvinyl]-23,25-dimethoxy-
13,19,21,27-tetramethyl-11,28-dioxa-4-azatricyclo
[22.3.1.0$^{4,9}$]octacos-18-ene-2,3,10,16-tetraone (400 mg in 6
ml 33% methylene chloride in cyclohexane), allyl trichlo-
roacetimidate (209 µl neat) was added and the reagents
allowed to mix for 5 minutes. Trifluoromethanesulfonic acid
(9 µl neat) was added slowly via syringe and the mixture
stirred at room temperature. After 6 hours the reaction was
quenched by the addition of saturated sodium bicarbonate
and extracted with ethyl acetate (3×10 ml). The combined
organics were washed with brine and dried over magnesium
sulfate. Purification of the concentrate by flash chromatog-
raphy on silica gel (ethyl acetate: hexane (1:3)+1% metha-
nol) gave the title compound (320 mg). ($^1$H NMR was
consistent with the desired structure).

Step B

17-Ethyl-1-hydroxy-12-[2'-(4"-(2''',3'''-dihydroxypro-
pyloxy)-3"-methoxycyclohexyl)-1'-methyl-vinyl]-
23,25-dimethoxy-13,19,21,27-tetramethyl-11,28-
dioxa-4-azatricyclo[22.3.1.0$^{4,9}$]octacos-18-
ene-2,3,10,16-tetraone To a solution of 17-ethyl-1-hydroxy-12-[2'-(4"-allyloxy-
3"-methoxycyclohexyl)-1'-methylvinyl]-23,25-dimethoxy-
13,19,21,27-tetramethyl-11,28-dioxa-4-azatricyclo
[22.3.1.0$^{4,9}$]octacos-18-ene-2,3,10,16-tetraone (310 mg in
3.5 ml dry ether) was added 350 pyridine followed by 1.5 ml
of a 0.25M osmium tetraoxide solution in THF and the
mixture stirred at room temperature. After 15 minutes, 10 ml
of a 20% sodium bisulfite solution were added and the
mixture diluted with 20 ml ethyl acetate. The layers were
separated and the organic portion re-extracted with 20%
sodium bisulfite (3×20 ml) then washed with a saturated
brine solution and dried over sodium sulfate. The concen-
trate was purified by flash chromatography on silica gel
(ethyl acetate:hexane (1:1)+1% methanol, then methylene
chloride: hexane:methanol (10:2:1)) to give the title com-
pound (232 mg). ($^1$H NMR was consistent with the desired
structure).

Step C

17-Ethyl-1-hydroxy-12-[2'-(4"-ethanaloxy-3"-
methoxycyclohexyl)-1'-methylvinyl]-23,25-dimeth-
oxy-13,19,21,27-tetramethyl-11,28-dioxa-4-azatri-
cyclo[22.3.1.0$^{4,9}$]octacos-18-ene-2,3,10,16-tetraone To a solution of 17-ethyl-1-hydroxy-12-[2'-(4"-(2''',3'''-
dihydroxypropyloxy)-3"-methoxycyclohexyl)-1'-methylvi-
nyl]-23,25-dimethoxy-13,19,21,27-tetramethyl-11,28 -di-
oxa-4-azatricyclo[22.3.1.0$^{4,9}$]octacos-18-ene-2,3,10,16-
tetraone (232 mg in 25% aqueous tetrahydrofuran) was
added sodium metaperiodate (70.2 mg) and the mixture
stirred vigorously. After 4 hours the mixture was diluted
with ethyl acetate and extracted from half-saturated sodium
bicarbonate. The organic portion was dried over magnesium
sulfate and purified by flash chromatography on silica gel
(ethyl acetate:hexane (1:1)+1% methanol) to give the title
compound (112 mg). ($^1$H NMR was consistent with the
desired structure).

Step D

17-Ethyl-1-hydroxy-12-[2'-(4"-(2'''-benzylamino)-
ethoxy-3"-methoxycyclohexyl)-1'-methylvinyl]-23,25-
dimethoxy-13,19,21,27-tetramethyl-11,28-dioxa-4-
azatricyclo[22.3.1.0$^{4,9}$]octacos-18-ene-2,3,10,16-
tetraone To a solution of 17-ethyl-1-hydroxy-12-[2'-(4"-etha-
naloxy-3"-methoxycyclohexyl)-1'-methylvinyl]-23,25-
dimethoxy-13,19,21,27-tetramethyl-11,28-dioxa-4-azatri-
cyclo[22.3.1.0$^{4,9}$]octacos-18-ene-2,3,10,16-tetraone (4 mg
in 0.30 ml dry terahydrofuran) was added benzylamine (2.0
µl) and the mixture stirred for 10 minutes at room tempera-
ture. This was cooled to −78° C. and acetic acid (7 µl) was
added followed by potassium triphenylborohydride (16 µl of
a 0.5M solution in THF). After 35 minutes, the reaction was
quenched by the addition of saturated ammonium chloride
and warmed to room temperature. The mixture was
extracted with ethyl acetate (3×5 ml) and dried over mag-
nesium sulfate. The concentrate was purified by flash chro-
matography on silica gel (ethyl acetate:hexane (1:2)+1%
methanol, then 2% ammonium hydroxide, 5% methanol in
methylene chloride) to give the title compound (2.1 mg).

Partial $^1$H NMR δ: 7.32 (m, 5H); 4.56 (brd, J=4 Hz, 1H);
4.41 (brd J=14 Hz, 1H); 3.82 (brs, 2H).

EXAMPLE 72

17-Ethyl-1,14-dihydroxy-12-[2'-(4"-(2'''-benzyloxy-
ethoxy)-3"-methoxycyclohexyl)-1'-methylvinyl]-23,25-
dimethoxy-13,19,21,27-tetramethyl-11,28-dioxa-4-
azatricyclo[22.3.1.0$^{4,9}$]octacos-18-ene-2,3,10,16-
tetraone

Step A

17-Ethyl-1-hydroxy-14-(tert-butyldimethylsiloxy)-
12-[2'-(4"-(2-hydroxyethoxy)-3"-methoxycyclohexyl)-1-
'methylvinyl]-23,25-dimethoxy-13,19,21,27-tetra-
methyl-11,28-dioxa-4-azatricyclo[22.3.1.0$^{4,9}$]octacos-
18-ene-2,3,10,16-tetraone To a solution of 17-ethyl-1-hydroxy-14-(tert-butyldimeth-
ylsiloxy)-12-[2'-(4"-ethanaloxy-3"-methoxycyclohexyl)-1'-
methylvinyl]-23,25-dimethoxy-13,19,21,27-tetramethyl-
11,28 -dioxa-4-azatricyclo[22.3.1.0$^{4,9}$]octacos-18-ene-2,3,
10,16-tetraone (126 mg in 1.3 ml dry terahydrofuran) at
−78° C. was added potassium triphenylborohydride (320 µl
of a 0.5M solution in THF). After 45 minutes, the reaction
was quenched by the addition of saturated ammonium
chloride and warmed to room temperature. The mixture was
extracted with ethyl acetate (3×15 ml) and dried over
magnesium sulfate. The concentrate was purified by flash
chromatography on silica gel (ethyl acetate:hexane (2:1+1%
methanol) to give the title compound (80.2 mg). ($^1$H NMR
was consistent with the desired structure).

Step B

17-Ethyl-1-hydroxy-14-(tert-butyldimethylsiloxy)-12-[2'-(4"-(2-benzyloxyethoxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-14-(tert-butyldimethylsiloxy)-12-[2'-(4"-(2-hydroxyethoxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (41.7 mg in 0.6 ml 33% methylene chloride in cyclohexane), benzyl trichloroacetimidate (15.8 μl neat) was added and the reagents allowed to mix for 5 minutes. Trifluoromethanesulfonic acid (2 μl neat) was added slowly via syringe and the mixture stirred at room temperature. After 7 hours the reaction was quenched by the addition of saturated sodium bicarbonate and extracted with ethyl acetate (3×5 ml). The combined organics were washed with brine and dried over magnesium sulfate. Purification of the concentrate by flash chromatography on silica gel (ethyl acetate: hexane (1:3)+1% methanol) gave the title compound (24 mg). ($^1$H NMR was consistent with the desired structure).

Step C

17-Ethyl-1,14-dihydroxy-12-[2'-(4"-(2'''-benzyloxyethoxy)-3"-methoxycyclohexyl)-1'-methyl-vinyl]-23,25-dimethoxy-13,19,21,27-tetra-methyl-11,28-dioxa-4-azatricyclo[22.3.1.0$^{4,9}$]octacos-18-ene-2,3,10,16-tetraone To a solution of 17-ethyl-1-hydroxy-14-(tert-butyldimethylsiloxy)-12-[2'-(4"-(2'''-benzyloxyethoxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone(10 mg) in acetonitrile (500 μl) was added a solution of 2% HF in aqueous acetonitrile (200 μl), and the mixture stirred at room temperature. After 2.5 hours, the solution was diluted with ethyl acetate, extracted with saturated sodium bicarbonate solution and the organic phase dried over magnesium sulfate. Purification of the concentrate by flash chromatography on silica gel (ethyl acetate: hexane (1:2)+1% methanol) gave the title compound (4 mg).

MASS (FAB) 932 (M+Li). Partial $^1$H NMR δ: 7.33(m, 5H); 5.32M, 5.19 m (brd J=3 Hz, 1H); 4.85 m, 4.21M (brs, 1H); 4.58 (s 2H); 4.41 (brd J=14 Hz, 1H).

EXAMPLE 73

17-Ethyl-1,14-dihydroxy-12-[2'-(4"-benzyloxymethoxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone (150 mg in 2 ml methylene chloride) was added disopropylethylamine (99.4 μl) followed by benzyl chloromethyl ether (34.2 μl neat) and the mixture stirred at room temperature. After 4 hours, the reaction was quenched by the addition of saturated sodium bicarbonate and extracted with ethyl acetate (3×20 ml). The combined organics were washed with brine and dried over magnesium sulfate. Purification of the concentrate by flash chromatography on silica gel (ethyl acetate:hexane (1:2)+1% methanol) gave the title compound (92 mg).

MASS: (FAB) 918 (M+Li). Partial $^1$H NMR δ: 7.33 (m, 5H); 5.32M, 5.19 m (brd J=3 Hz, 1H); 4.87 (s, 2H); 4.63 (s, 2H); 4.59 (brd J=4 Hz, 1H); 4.41 (brd J=14 Hz, 1H).

EXAMPLE 74

17-Ethyl-1,14-dihydroxy-12-[2'-(4"-(napth-2-yloxy)-3"-allyloxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4"-(napth-2-yloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone in 33% methylene chloride/cyclohexane is added 1.5 equivalents of allyl trichloroacetimidate, and the reagents are allowed to mix for 5 minutes. A catalytic amount of trifluoromethanesulfonic acid is then added slowly via syringe and the mixture is stirred at room temperature. After 3 hours the reaction is quenched by the addition of saturated sodium bicarbonate and extracted with ethyl acetate. The combined organics are washed with brine and dried over magnesium sulfate. Purification of the concentrate by flash chromatography on silica gel gives the title compound.

EXAMPLE 75

17-Ethyl-1,14-dihydroxy-12-[2'-(4"-(4'''-t-butyldimethylsiloxycinnamyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone (700 mg in 12 ml methylene chloride)4-t-butyldimethylsiloxycinnamyl trichloroacetimidate (550 μl neat) was added and the reagents allowed to mix for 5 minutes. Camphorsulfonic acid (35 mg) was added and the mixture stirred at room temperature. After 5 hours the reaction was quenched by the addition of saturated sodium bicarbonate and extracted with ethyl acetate (3×15 ml). The combined organics were washed with brine and dried over magnesium sulfate. Purification oof the concentrate by flash chromatography on silica gel (ethyl acetate:hexane (1:2)+1% methanol) gave the title compound (190 mg).

$^1$H NMR spectrum was consistent with the desired structure.

EXAMPLE 76

17-Ethyl-1,14-dihydroxy-12-[2'-(4"-(4'''-hydroxycinnamyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4"-(4'''-t-butyldimethylsiloxycinnamyloxy)-3"-methoxycyclohexyl)-1'-methylvinyl]-23,25-dimethoxy-13,19,21,27 -tetramethyl-11,28-dioxa-4-azatricyclo[22.3.1.0$^{4,9}$]octacos-18- ene-2,3,10,16-tetraone (190 mg in 2 ml tetrahydrofuran contained in a polypropylene vial) was added 500 μl of a solution of hydrogen fluoride-pyridine complex (40% in (2:1) tetrahydrofuran:pyridine) and the mixture stirred at room temperature. After 2 hours, the reaction was quenched by the careful addition of saturated sodium bicarbonate and extracted with ethyl acetate. The combined organics were dried over magnesium sulfate, concentrated in vacuo and purified by flash chromatography on silica gel (ethyl acetate-:hexane (2:1) to give the title compound (50 mg).

MS(FAB) 930 (M+Li). $^1$H NMR spectrum was consistent with the desired structure.

EXAMPLE 77

17-Ethyl-1,14,dihydroxy-12-[2'-(4"-(2"'-phenyl-2"'-oxo-ethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone

Step A

17-Ethyl-1-hydroxy-14-(tert-butyldimethylsiloxy)-12-[2'-4"-(2"'-phenyl-2"'-hydroxyethyloxy)-3"-methoxycyclohexyl)-1'-methylivinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-14-(tert-butyldimethylsiloxy)-12-[2'-(4"-ethanaloxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (41 mg in 0.5 ml methylene chloride) at −78° C. was added phenylmagnesium bromide (15 μL of a 3M solution in diethyl ether) and the mixture stirred a low temperature. After 30 minutes the reaction was quenched by addition of saturated ammonium chloride and extracted with ethyl acetate. The organics were dried by passage through a magnesium sulfate plug and the concentrate purified by flash chromatography on silica gel (ethyl acetate:hexane (1:2)+1% methanol then (1:1+1% methanol) to give the title compound (13 mg).

($^1$H NMR consistent with the desired structure)

Step B

17-Ethyl-1-hydroxy-14-(tert-butyldimethylsiloxy)-12-[2'-(4"-(2"'-phenyl-2"'-oxoethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To solution of 17 ethyl-1-hydroxy-14-(tert-butyldimethylsiloxy)-12-[2'-(4"-(2"'-phenyl-2"hydroxyethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (13 mg in 0.3 mL methylene chloride) was added powdered 4A molecular sieves (10 mg), 4-methylmorpholine N-oxide (6.0 mg), tetrapropylammonium perruthenate (1.0 mg) and the reaction stirred at room temperature. After 30 minutes the mixture was filtered through a small diatomaceous earth/silica gel plug and the filtrate concentrated in vacuo. Purification by flash chromatography on silica gel (ethyl acetate-:hexane (1:2)+1% methanol) gave the title compound (10 mg).

($^1$H NMR consistent with the desired structure)

Step C

17-Ethyl-1,14-dihydroxy-12-[2'-(4"-(2"'-phenyl-2"'-oxo-ethyloxy)-3"-methoxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone To a solution of 17-ethyl-1-hydroxy-14-(tert-butyldimethylsiloxy)-12-[2'-(4"-(2"'-phenyl-2"'-oxo-ethyloxy)-3"-methoxycyclohexyl)-1'-methylvinyl]-23,25-dimethoxy-13,19, 21,27 -tetramethyl-11,28-dioxa-4-azatricyclo[22.3.1.0$^{4,9}$] octacos-18-ene-2,3,10,16-tetraone (10 mg in 0.4 mL tetrahydrofuran contained in a polypropylene vial) was added 20 μL of a solution of hydrogen fluoride-pyridine complex (40% in (2:1) tetrahydrofuran:pyridine) and the mixture stirred at room temperature. After 96 hours, the reaction was quenched by the careful addition of saturated sodium bicarbonate and extracted with ethyl acetate. The combined organics were dried by passage through a magnesium sulfate plug, concentrated in vacuo and purified by flash chromatography (ethyl acetate:hexane (1:1)+1% methanol) to give the title compound (5.2 mg).

MASS: (FAB) 917(M+Li). Partial $^1$H NMR δ: 7.92 (d J=7 Hz, 2H); 7.47 (m, 3H); 5.31M, 5.17 m (brd J=3 Hz, 1H); 4.81 m, 4.20M (brs, 1H); 4.41 (brd J=14 Hz, 1H); 3.06 (d J=4 Hz, 1H).

EXAMPLE 77B

17-Ethyl-1,14-dihydroxy-12-[2'-(4"-(2"'-phenyl-2"'-oxo-ethyloxy)-3"-methoxycyclohexyl)-1'-methylvinyl]-23,25-dimethoxy-13,19-21,27-tetramethyl-11,28-dioxa-4-azatricyclo[22.3.1.0$^{4,9}$]octacos-18-ene-2,3,10,16-tetraone

Step A

17-Ethyl-1-hydroxy-14-(tert-butyldimethylsiloxy)-12-[2'-(4"-(2"'-phenyl-2"'-oxo-ethyloxy)-3"-methoxycyclohexyl)-1'-methylvinyl]-23,25-dimethoxy-13,19,21,27'-tetramethyl-11,28-dioxa-4-azatricyclo[22.3.1.0$^{4,9}$]octacos-18-ene-2,3,10,16-tetraone To a solution of 17-ethyl-1-hydroxy-14-(tert-butyldimethylsiloxy)-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3, 10,16-tetraone (400 mg in 3.0 mL N,N-dimethylformamide) was added 2-bromoacetophenone (263 mg) followed by potassium fluoride (25.6 mg) and the mixture heated to 70° C. After 48 hours, the mixture was cooled to room temperature, filtered over diatomaceous earth, diluted with ethyl acetate and washed with saturated sodium bicarbonate, water, and brine. The combined organics were dried over magnesium sulfate and concentrated in vacuo. Purification by flash chromatography on silica gel (ethyl acetate:hexane (1:2)+1% methanol) gave the desired product (145 mg).

($^1$H NMR consistent with the desired structure)

Step B

17-Ethyl-1,14-dihydroxy-12-[2'-(4"-(2'''-phenyl-2'''-oxo-ethyloxy)-3"-methoxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone Conducted essentially as described in Example 77 Step C to give the desired product (86 mg).
($^1$H NMR consistent with the desired structure).

EXAMPLE 78

17-Ethyl-1,14-dihydroxy-12-[2'-(4"-2'''-(3''''-methyoxyphenyl)-2'''-oxo-ethyloxy)-3"-methoxycyclohexyl)-1'-methylvinyl]-23,25-dimethoxy-13,19-21,27-tetramethyl-11,28-dioxa-4-azatricyclo-22,3.1.0$^{4,9}$]octacos-18-ene-2,3,10,16-tetraone The title compound was prepared employing the procedure essentially as described in Example 77, Steps A–C using 3-methoxyphenylmagnesium bromide as the nucleophile in Step A.

MASS: (FAB) 940(M+). Partial $^1$H NMR δ: 7.46 (m, 2H); 7.33 (t J=8 Hz, 1H); 7.09 (dd J=8,2 Hz, 1H); 5.31M, 5.17 m (brd J=3 Hz, 1H); 4.81 m, 4.20M (brs, 1H); 4.41 (brd J=14 Hz, 1H); 3.84 (s, 3H); 3.07 (d J=Hz, 1H).

EXAMPLE 79

17-Ethyl-1,14-dihydroxy-12-[2'-(4"-(2'''-(3''''-methoxyphenyl)-2'''-hydroxyethyloxy)-3"-methoxycyclohexyl)-1'-methylvinyl]-23,25-dimethoxy-13,19,21,27-tetramethyl-11,28-dioxa-4-azatricylo-22.3.1.0$^{4,9}$]octacos-18-ene-2,3,10,16-tetraone To a solution of 17-ethyl-1-hydroxy-14-(tert-butyldimethylsiloxy)-12-[2'-(4"-(2'''-(3''''-methyoxyphenyl)-2'''-hydroxyethyloxy-)3"-methoxycyclohexyl)-1'-methylvinyl]-23,25 -dimethoxy-13,19,21,27-tetramethyl-11,28-dioxa-4-azatricyclo[22.3.1.0$^{4,9}$]octacos-1-8 -ene-2,3,10,16-tetrone (29 mg in 0.6 mL tetrahydrofuran contained in a polypropylene vial) was added 80 μL of a solution of hydrogen fluoride-pyridine complex (40% in (2:1) tetrahydrofuran: pyridine) and the mixture stirred at room temperature. After 48 hours, the reaction was quenched by the careful addition of saturated sodium bicarbonate and extracted wiht ethyl acetate. The combined organics were dried by passage through a magnesium sulfate plug, concentrated in vacuo and purified by flash chromatography (ethyl acetate:hexane (1:1)+1% methanol) to give the title compound (9.5 mg).

MASS (FAB) 942 (M+). Partial $^1$H NMR δ: 7.23 (m, 1H); 6.94 (s, 1H); 6.91 (d J=8 Hz, 1H); 6.79 (d J=8 Hz, 1H); 5.31M, 5.17 m (brd J=3 Hz, 1H); 4.41 (brd J=14 Hz, 1H); 3.78 (s, 3H); 3.07 (d J=4 Hz, 1H).

EXAMPLE 80

17-Ethyl-1,14-dihydroxy-12-[2'-(4"-(2'''-(4''''-methoxyphenyl)-2'''-oxo-ethyloxy)-3"-methoxycyclohexyl)-1'-methylvinyl]-23,25-dimethoxy-13,19,21,27-tetramethyl-11,28 -dioxa-4-azatricylo[22.3.1.0$^{4,9}$]octacos-18-ene-2,3,10,16-tetraone The title compound was prepared employing the procedure essentially as described in Example 77, Steps A–C using 4-methoxyphenylmagnesium bromide as the nucelophile in Step A.

MASS (FAB) 940 (M+). Partial $^1$H NMR δ: 7.92 (d J=9 Hz,2H); 6.91 (d J=9 Hz, 2H); 1H); 5.31M, 5.17 m (brd J=3 Hz, 1H); 4,81 m, 4.20M (brs, 1H); 4.41 (brd J=14 Hz, 1H); 3.84 (s, 3H); 3.07 (d J=4 Hz, 1H).

EXAMPLE 81

17-Ethyl-1,14-dihydroxy-12-[2'-(4"-(m-fluorocinnamyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Example 44 using m-fluorocinnamyl trichloroacetimidate as the electrophile.

MASS (FAB) 948 (M+Na). Partial $^1$H NMR δ: 7.30–6.85 (m, 4H); 6.59 (d J=17 Hz, 1H); 6.30 (dt J=17, 6 Hz, 1H); 5.30M, 5.17 m (brd J=3 Hz, 1H); 4.41 (d J=14 Hz, 1H); 4.31 (d J=5 Hz, 2H).

EXAMPLE 82

17-Ethyl-1,14-dihydroxy-12-[2'-(4"-(3''',5'''-difluorocinnamyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Example 44 using 3,5-difluorocinnamyl trichloroacetimidate as the electrophile.

MASS (FAB) 950 (M+Li). Partial $^1$H NMR δ: 6.92–6.56 (m, 3H); 6.55 (d J=16 Hz, 1H); 6.31 (dt J=16, 6 Hz, 1H); 5.30M, 5.17 m (brd J=3 Hz, 1H); 4.41 (d J=14 Hz, 1H); 4.31 (d J=5 Hz, 2H).

EXAMPLE 83

17-Ethyl-1,14-dihydroxy-12-[2'-(4"-(m-nitrocinnamyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone

Step A

17-Ethyl-1-hydroxy-14-(tert-butyldimethylsiloxy)-12-[2'-(4"-(m-nitrocinnamyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Example 70 (Step C) using m-nitrocinnamyl trichloroacetimidate as the electrophile.

$^1$H NMR consistent with the desired structure.

Step B

17-Ethyl-1,14-dihydroxy-12-[2'-(4"-(m-nitrocinnamyloxy)-3"-methoxycyclohexyl)-1'-methylvinyl]-23,25-dimethoxy-13,19,21,27-tetramethyl-11,28-dioxa-4-azatricyclo[22,3.1.0$^{4,9}$]octacos-18-ene-2,3,10,16-tetraone To a solution of 17-ethyl-1-hydroxy-14-(tert-butyldimethylsiloxy)-12-[2'-(4"-(m-nitrocinnamyloxy)-2'''-hydroxyethyloxy)-3"-methoxycyclohexyl)-1'-methylvinyl]-23,25 -dimethoxy-13,19,21,27-tetramethyl-11,28-dioxa-4-azatricyclo[22.3.1.0$^{4,9}$]octacos-18-ene-2,3,10,16 -tetraone (124 mg in 1.5 mL tetrahydrofuran contained in a polypropylene vial) was added 600 mL of a solution of hydrogen fluoride-pyridine complex (40% in (2:1) tetrahydrofuran:pyridine) and the mixture stirred at room temperature. After 30 hours, the reaction was quenched by the careful addition of saturated sodium bicarbonate and extracted with ethyl acetate. The combined organics were dried by passage through a magnesium sulfate plug, concentrated in vacuo and purified by flash chromatography on silica gel (ethyl acetate:hexane (1:1)+1% methanol) to give the title compound (43 mg).

MASS (FAB) 959 (M+Li). Partial $^1$H NMR δ: 8.22 (s, 1H); 8.06 (brd J=8 Hz, 1H); 7.66 (brd J=8 Hz, 1H); 7.46 (t J=8 Hz, 1H); 6.69 (d J=16 Hz, 1H); 6.44 (dt J=16, 6 Hz, 1H); 5.30M, 5.17 m (brd J=3 Hz, 1H); 4.41 (d J=14 Hz, 1H).

EXAMPLE 84

17-Ethyl-1,14-dihydroxy-12-[2'-(4"-(3'"-phenyl-2-propynyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Example 83 using 3-phenylpropynyl trichloroacetimidate as the electrophile.

MASS (FAB) 912 (M+Li). Partial $^1$H NMR δ: 7.54–7.28 (m, 5H); 5.30M, 5.17 m (brd J=3 Hz, 1H); 4.41 (d J=14 Hz, 1H).

EXAMPLE 85

17-Ethyl-1,14-dihydroxy-12-[2'-(4"-(2'"-phenyl-2'"-propenyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Example 83 using 2-phenyl-2-propenyl trichloroacetimidate as the electrophile.

MASS (FAB) 915 (M+Li). Partial $^1$H NMR δ: 7.47 (d J=8 Hz, 2H); 7.26 (m, 3H); 5.49 (s, 1H); 5.37 (s, 1H); 5.30M, 5.17 m (brd J=3 Hz, 1H); 4.41 (d J=14 Hz, 1H).

EXAMPLE 86

17-Ethyl-1,14-dihydroxy-12-[2'-(4"-(p-hydroxycinnamyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Example 83 using p-(tert-butyldimethylsiloxy)cinnamyl trichloroacetimidate as the electrophile.

MASS (FAB) 930 (M+Li). Partial $^1$H NMR δ: 7.22 (d J=10 Hz, 2H); 6.76 (d J=10 Hz, 2H); 6.51 (d J=16 Hz, 1H); 6.11 (dt J=16, 6 Hz, 1H); 5.30M, 5.17 m (brd J=3 Hz, 1H); 4.41 (d J=14 Hz, 1H).

EXAMPLE 87

17-Ethyl-1,14-dihydroxy-12-[2'-(4"-(p-hydroxyphenpropyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Examples 83(Step A), 56, 83(Step B) using p-(tert-butyldimethylsiloxy)cinnamyl trichloroacetimidate as the electrophile.

MASS (FAB) 949 (M+Na). Partial $^1$H NMR δ: 7.04 (d J=9 Hz, 2H); 6.72 (d J=9 Hz, 2H); 5.30M, 5.17 m (brd J=3 Hz, 1H); 4.41 (d J=14 Hz, 1H).

EXAMPLE 88

17-Ethyl-1,14-dihydroxy-12-[2'-(4"-(m-hydroxycinnamyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Example 83 using m-(tert-butyldimethylsiloxy)cinnamyl trichloroacetimidate as the electrophile.

MASS (FAB) 930 (M+Li). Partial $^1$H NMR δ: 7.17–6.63 (m, 5H); 6.52 (d J=16 Hz, 1H); 6.23 (dt J=16, 6 Hz, 1H); 5.69 (s, 1H); 5.30M, 5.17 m (brd J=3 Hz, 1H); 4.41 (d J=14 Hz, 1H).

EXAMPLE 89

17-Ethyl-1,14-dihydroxy-12-[2'-(4"-(m-hydroxymethylbenzyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone

Step A

17-Ethyl-1-hydroxy-14-(tert-butyldimethylsiloxy)-12-[2'-(4"-(m-hydroxymethylbenzyloxy)-3"-methoxycyclo-hexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone Prepared essentially as described in Example 70 (Step C) using m-(tert-butyldimethylsiloxymethyl)-benzyl trichloroacetimidate as the electrophile.

$^1$H NMR consistent with the desired structure.

Step B

17-Ethyl-1,14-dihydroxy-12-[2'-(4"-(m-hydroxymethyl)-benzyloxy)-3"-methoxycyclohexyl)-1'-methylvinyl]-23,25-dimethoxy-13,1. 9,21,27-tetramethyl-11,28-dioxa-4-azatricyclo[22.3.1.0$^{4,9}$]octacos-18-ene-2,3,10,16-tetraone To a solution of 17-ethyl-1-hydroxy-14-(tert-butyldimethylsiloxy)-12-[2'-(4"-(m-tert-butyldimethylsiloxymethyl)-benzyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16 -tetraone (19.7 mg) in acetonitrile (0.5 ml) was added a solution of 2% HF in aqueous acetonitrile (40 ml), and the mixture stirred at room temperature. After 3.5 hours, the solution was diluted with ethyl acetate, extracted with saturated sodium bicarbonate solution and the organic phase dried over magnesium sulfate. Purification of the concentrate by flash chromatography on silica gel (ethyl acetate: hexane (1:1)+1% methanol) gave the title compound (6 mg).

MASS (FAB) 934 (M+Na). Partial $^1$H NMR δ: 7.41–7.22 (m, 4H); 5.30M, 5.17 m (brd J=3 Hz, 1H); 4.41(d J=14 Hz, 1H).

EXAMPLE 90

17-Ethyl-1,14-dihydroxy-12-[2'-(4"-(m-hydroxy-cinnamyloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone

Step A

17-Ethyl-1-hydroxy-14-(tert-butyldimethylsiloxy)-12-[2'-(3",4"-di(tert-butyldimethylsiloxy)-cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(3",4"-dihydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (8.0 g) in dry methylene chloride (150 mL) was added an excess of 2,6-lutidine (4.8 mL) and the mixture was stirred at room temperature. After 10 minutes, tert-butyldimethylsilyl trifluoromethanesulfonate (7.57 mL) was added via syringe. After 1 hour the reaction mixture was diluted with ethyl acetate, extracted from 1N hydrochloric acid, washed with water, saturated sodium bicarbonate, brine, and the organic phase dried over magnesium sulfate. Removal of the solvent in vacuo gave the title compound (crude 12.5 g).

$^1$H NMR consistent with the desired structure.

Step B

17-Ethyl-1-hydroxy-14-(tert-butyldimethylsiloxy)-12-[2'-(3",4"-hydroxycylohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-14-(tert-butyldimethylsiloxy)-12-[2'-(3",4"-di(tert-butyldimethylsiloxy)cyclohexyl)-1 '-methylvinyl]-23,25-dimethoxy-13,19,21,27-tetramethyl-11,28 -dioxa-4-azatri-cyclo[22.3.1.0$^{4,9}$]octacos-18-ene-2,3,10,16-tetraone (11.6 g) in methylene chloride (100 mL) was added a methanolic solution of p-toluenesulfonic acid (100 mL of a 10% solution w/v) and the mixture stirred at room temperature. After 30 minutes, the reaction was cooled to 0° C. and quenched by the careful addition of saturated sodium bicarbonate solution. The mixture was extracted with ethyl acetate and the organic portion washed with brine, dried over magnesium sulfate, and the concentrate purified by flash chromatography on silica gel (ethyl acetate:hexane (3:2) to give the title compound (8.4 g)

$^1$H NMR consistent with the desired structure.

Step C

17-Ethyl-1-hydroxy-14-(tert-butyldimethylsiloxy)-12-[2'-(4"-hydroxy-3"-(tert-butyldimethylsiloxy)-cylohexyl)-1'-methylvinyl]-23,25-dimethoxy-13,19,21,27-tetramethyl-11,28-dioxa-4-azatricyclo[22.3.1.0$^{4,9}$]-octacos-18-ene-2,3,10,16-tetraone
and
17-Ethyl-1-hydroxy-14-(tert-butyldimethylsiloxy)-12-[2'-(4"-(tert-butyldimethylsiloxy)-3"-hydroxycylohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-14-(tert-butyldimethylsiloxy)-12-[2'-(3",4"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (8.17 g) in dry methylene chloride (92 mL) was added an excess of 2,6-lutidine (1.6 mL) and the mixture was stirred at 0° C. on an ice bath. After 10 minutes, tert-butyldimethylsilyl trifluoromethanesulfonate (2.1 mL) was added via syringe and the mixture allowed to warm slowly to room temperature. After 1 hour the reaction mixture was diluted with ethyl acetate, extracted from 1N hydrochloric acid, washed with water, saturated sodium bicarbonate, brine, and the organic phase dried over magnesium sulfate. Purification of the concentrate by flash chromatography on silica gel (10% acetone in hexane) gave the title compounds (3" ether: 1.81 g, 4" ether: 1.20 g).

$^1$H NMR consistent with the desired structure.

Step D

17-Ethyl-1,14-dihydroxy-12-[2'-(4"-(m-hydroxy-cinnamyloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Example 83 using m-(tert-butyldimethylsiloxy)cinnamyl trichloroacetimidate as the electrophile.

MASS (FAB) 916 (M+Li). Partial $^1$H NMR δ: 7.22–6.67 (m, 5H); 6.52 (d J=16 Hz, 1H); 6.23 (dt J=16, 6 Hz, 1H); 5.30M, 5.17 m (brd J=3 Hz, 1H); 4.41 (d J=1 4 Hz, 1H).

EXAMPLE 91

17-Ethyl-1,14-dihydroxy-12-[2'-(4"-(3''',5'''-difluoro-cinnamyloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Example 90 using 3,5difluorocinnamyl trichloroacetimidate as the electrophile.

MASS (FAB) 936 (M+Li). Partial $^1$H NMR δ: 6.90–6.58 (m, 3H); 6.51(d J=16 Hz, 1H); 6.38 (dt J=16, 6 Hz, 1H); 5.30M, 5.17 m (brd J=3 Hz, 1H); 4.41 (d J=14 Hz, 1H).

EXAMPLE 92

17-Ethyl-1,14-dihydroxy-12-[2'-(4"-(p-carboxybenzyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone

Step A

17-Ethyl-1-hydroxy-14-(tert-butyldimethylsiloxy)-12-[2'-(4"-(p-(tert-butyldimethylsiloxymethyl)-benzyloxy)-3"-methoxycyclohexyl)-1'-methylvinyl]-23,25-dimethoxy-13,19,21,27-tetramethyl-11,28-dioxa-4-azatricyclo-22.3.1.0$^{4,9}$]octacos-18-ene-2,3,10,16-tetraone Prepared essentially as described in Example 44 using p-(tert-butyldimethylsiloxymethyl)-benzyl trichloroacetimidate as the electrophile.

$^1$H NMR consistent with the desired structure.

Step B

17-Ethyl-1-hydroxy-14-(tert-butyldimethylsiloxy)-12-[2'-(4"-(p-hydroxymethyl)-benzyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-14-(tert-butyldimethylsiloxy)-12-[2'-(4"-(p-(tert-butyldimethylsiloxymethyl)-benzyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16 -tetraone (420 mg) in methylene chloride (10 mL) was added a methanolic solution of p-toluenesulfonic acid (10 mL of a 10% solution w/v) and the mixture stirred a t room temperature. After 5 minutes, the reaction was cooled to 0° C. and quenched by the careful addition of saturated sodium bicarbonate solution. The mixture was extracted with ethyl acetate and the organic portion washed with brine, dried over magnesium sulfate, and the concentrate purified by flash chromatography on silica gel (ethyl acetate:hexane (1:1+1% methanol) to give the title compound (316 mg).

$^1$H NMR consistent with the desired structure.

Step C

17-Ethyl-1-hydroxy-14-(tert-butyldimethylsiloxy)-12-[2'-(4"-(p-formylbenzyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-14-(tert-butyldimethylsiloxy)-12-[2'-(4"-(p-hydroxymethyl)-benzyloxy)-3"-methoxycyclohexyl)-1'-methylvinyl]-23,25-dimethoxy-13, 19,21,27 -tetramethyl-11,28-dioxa-4-azatricyclo[22.3.1.0$^{4,9}$]octacos-18-ene-2,3,10,16-tetraone (316 mg) in methylene chloride (6.0 mL) was added powdered 4 Å molecular sieves (20 mg) followed by 4-methylmorpholine-N-oxide (84.5 mg) and tetra-n-propylammonium perruthenate (5.5 mg), and the mixture stirred at room temperature. After 15 minutes, the mixture was filtered through a small silica gel column, washed with ethyl acetate, and the concentrated organics purified by flash chromatography on silica gel (ethyl acetate:hexane (1:1)+1% methanol) to give the title compound (282 mg).

$^1$H NMR consistent with the desired structure.

Step D

17-Ethyl-1-hydroxy-14-(tert-butyldimethylsiloxy)-12-[2'-(4"-(p-carboxybenzyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-14-(tert-butyldimethylsiloxy)-12-[2'-(4"-(p-formylbenzyloxy)-3"-methoxycyclohexyl)-1'-methylvinyl]-23,25-dimethoxy-13,19,21,27 -tetramethyl-11,28-dioxa-4-azatricyclo[22.3.1.0$^{4,9}$]octacos-18-ene-2,3,10,16-tetraone (50 mg) in tert-butanol (1.0 mL) was added 2-methyl-2-butene (250 mL) followed by 0.5 mL of an aqueous solution of sodium chlorite (41 mg) and sodium dihydrogen phosphate (48 mg), and the mixture stirred at room temperature. After 1.5 hours, the mixture was concentrated and redissolved in ethyl acetate:hexane (1:1) and washed with water. The organic portion was dried over sodium sulfate, and the concentrate purified by flash chromatography on silica gel (ethyl acetate:hexane (4:1)+1% methanol+0.5% acetic acid) to give the title compound (43 mg).

$^1$H NMR consistent with the desired structure.

Step E

17-Ethyl-1,14-dihydroxy-12-[2'-(4"-(p-carboxybenzyloxy)-3"-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone Prepared essentially as described in Example 89 (Step B)

MASS (FAB) 933 (M+Li). Partial $^1$H NMR δ: 8.04 (d J=8 Hz, 2H); 7.44 (d J=8 Hz, 2H); 5.30M, 5.17 m (brd J=3 Hz, 1H); 4.41 (d J=14 Hz, 1H); 4.73 (s, 2H).

EXAMPLE 93

17-Ethyl-1,14-dihydroxy-12-[2'-(4"-(m-carboxybenzyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Example 92 using m-(tert-butyldimethylsiloxy)cinnamyl trichloroacetimidate as the electrophile.

MASS (FAB) 949 (M+Na). Partial $^1$H NMR δ: 8.07 (s, 1H); 7.97 (d J=8 Hz, 1H); 7.60 (d J=8 Hz, 1H); 7.41 (t J=8 Hz, 1H); 5.30M, 5.17 m (brd J=3 Hz, 1H); 4.41 (d J=14 Hz, 1H).

EXAMPLE 94

17-Ethyl-1,14-dihydroxy-12-[2'-(4"-(m-carbomethoxybenzyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4"-(m-carboxybenzyloxy)-3"-methoxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone (7 mg) in methylene chloride: methanol (2:1, 0.75 mL) at 0° C. was added a methylene chloride solution of trimethylsilyldiazomethane (10% by weight) until a yellow colored persisted. The mixture was then warmed to room temperature, concentrated in vacuo, and purified by flash chromatography on silica gel (acetone:hexane (1:2)) to give the title compound (5.5 mg).

MASS (FAB) 963 (M+Na). Partial $^1$H NMR δ: 8.03 (d J=8 Hz, 2H); 7.46 (d J=8 Hz, 2H); 5.30M, 5.17 m (brd J=3 Hz, 1H); 4.41 (d J=14 Hz, 1H); 3.92(s, 3H).

EXAMPLE 95

17-Ethyl-1,14-dihydroxy-12-[2'-(4"-(m-isopropylcarboxamidobenzyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone

Step A

17-Ethyl-1-hydroxy-14-(tert-butyldimethylsiloxy)-(12-[2'-(4"-(m-isopropylcarboxamidobenzyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-14-(tert-butyldimethylsiloxy)-12-[2'-(4"-(m-carboxybenzyloxy)-3"-methoxycyclohexyl)-1'-methylvinyl]-23,25-dimethoxy-13,19,21,27 -tetramethyl-11,28-dioxa-4-azatricyclo[22.3.1.0$^{4,9}$]octacos-18-ene-2,3,10,16-tetraone (50 mg) in methylene chloride (1.0 mL) was added 4-benzotriazol-1-yloxy-tris(dimethylamino)phosphonium hexafluoro-phosphate (BOP, 32 mg) followed by triethylamine (14 µL) and the mixture stirred at room temperature. After 10 minutes, isopropylamine (8.0 µL) was added, and the reaction stirred at room temperature for 12 hours. At this time the mixture was concentrated and purified by flash chromatography on silica gel (ethyl acetate-:hexane (1:1)+1% methanol) to give the title compound (43 mg).

$^1$H NMR consistent with the desired structure.

Step B

17-Ethyl-1,14-dihydroxy-12-[2'-(4"-(m-isopropylcarboxamidobenzyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Example 89 (Step B).
MASS (FAB) 974 (M+Li). Partial $^1$H NMR δ: 7.81 (s, 1H); 7.69 (d J=7 Hz, 1H); 7.44 (m, 2H); 6.00 (d J=8 Hz, 1H); 4.75 (s, 2H); 5.30M, 5.17 m (brd J=3 Hz, 1H); 4.41 (d J=14 Hz, 1H).

EXAMPLE 96

17-Ethyl-1,14-dihydroxy-12-[2'-(4"-(m-butylcarboxamidobenzyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Examples 95 (Step A), (Step B) using n-butyl amine as the nucleophile.
MASS (FAB) 988 (M+Li). Partial $^1$H NMR δ: 7.82 (s, 1H); 7.70 (d J=7 Hz, 1H); 7.44 (m, 2H); 6.18 (t J=5 Hz, 1H); 5.30M, 5.17 m (brd J=3 Hz, 1H); 4.41 (d J=14 Hz, 1H).

EXAMPLE 97

17-Ethyl-1,14-dihydroxy-12-[2'-(4"-acetamidoxy-3"-methoxycyclohexyl)-1'-methylvinyl]-23,25-dimethoxy 13,19,21,27-tetramethyl-11,28-dioxa-4-azatricyclo-22.3.1.0$^{4,9}$]octacos-18-ene-2,3,10,16-tetraone Step A 17-Ethyl-1-hydroxy-14-(tert-butyldimethylsiloxy)-12-[2'-(4"-carboxymethoxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-14-(tert-butyldimethylsiloxy)-12-[2'-(4"-ethanaloxy-3"-methoxycyclohexyl)-1'-methylvinyl]-23,25-dimethoxy-13,19,21,-27-tetramethyl-11,28 -dioxa-4-azatricyclo[22.3.1.0$^{4,9}$]-octacos-18-ene-2,3, 10,16-tetraone (311 mg) in tert-butanol (6.6 ml) and 2-methyl-2-butene (1.65 ml) was added sodium chlorite (273 mg) and sodium dihydrogen phosphate (272 mg) in water (2.7 ml) slowly. After 2 hours, the solvent was removed in vacuo, and the resulting residue was dissolved in water and acidified to pH 3 with 1N HCl. The aqueous layer was extracted with ethyl acetate (3×10 ml), and the combined organic portions washed with brine, dried over magenesium sulfate and purified by flash chromatography on silica gel (2% methanol in methylene chloride followed by 2% methanol in methylene chloride+0.5% acetic acid) to give the title compound (255 mg).

$^1$H NMR consistent with the desired structure.

Step B

17-Ethyl-1-hydroxy-14-(tert-butyldimethylsiloxy)-12-[2'-(4"-acetamidoxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-14-(tert-butyldimethylsiloxy)-12-[2'-(4"-carboxymethoxy-3"-methoxycyclohexyl)-1'-methylvinyl]-23,25-dimethoxy-13,19,21,27-tetramethyl-11,28 -dioxa-4-azatricyclo[22.3.1.0$^{4,9}$]octacos-18-ene-2,3,10,16-tetraone (24.3 mg) in methylene chloride:N, N-dimethylformamide (4:1, 0.5 mL) was added an admixture of 1-hydroxybenzotriazole hydrate (4.0 mg) and 1-(3-dimethylaminopropyl)-3-ethylcarbodiimide hydrochloride (6.7 mg) and the mixture stirred at room temperature. After 30 minutes, ammonium hydroxide (4.0 µL of a 25% aqueous solution) was added and the mixture stirred for an additional 4 hours. At this time, the solution was filtered over diatomaceous earth, diluted with ethyl acetate, and extracted with sodium bicarbonate. The organic portion was dried over magnesium sulfate, concentrated in vacuo, and purified by flash chromatography on silica gel (ethyl acetate-:hexane (1:1)+1% methanol, then (2:1)+1% methanol) to give the title compound (14 mg).

$^1$H NMR consistent with the desired structure.

Step C

17-Ethyl-1,14-dihydroxy-12-[2'-(4"-acetamidoxy-3"-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone Prepared essentially as described in Example 83 (Step B).
MASS (FAB) 872 (M+Na). Partial $^1$H NMR δ: 7.79 (s, 2H); 5.30M, 5.17 m (brd J=3 Hz, 1H); 4.41 (d J=14 Hz, 1H).

EXAMPLE 98

17-Ethyl-1,14-dihydroxy-12-[2'-(4"-carboxymethoxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Example 89 (Step B).
MASS (FAB) 863 (M+2Li). Partial $^1$H NMR δ: 5.24 (m, 2H); 5.02 (brd J=9 Hz, 1H); 4.94 (m, 1H); 4.44 (m, 2H).

EXAMPLE 99

17-Ethyl-1,14-dihydroxy-12-[2'-(4"-(N-phenylacetamidoxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Example 95 (Step A) from 17-ethyl-1,14-dihydroxy-12-[2'-(4"-carboxymethoxy-3"-methoxycyclohexyl)-1'-methylvinyl]23,25-dimethoxy- 13,19,21,27-tetramethyl-11,28-dioxa-4-azatricyclo [22.3.1.0$^{4,9}$]octacos-18-ene-2,3,10,16-tetraone using aniline as the nucleophile.

MASS (FAB) 932 (M+Li). Partial $^1$H NMR δ: 9.57 (brs, 1H); 7.61–7.05 (m, 5H); 5.26 (m, 2H); 4.42 (m, 2H).

EXAMPLE 100

17-Ethyl-1,14-dihydroxy-12-[2'-(4"-(N-benzylacetamidoxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Example 97 (Step B) from 17-ethyl-1,14-dihydroxy-12-[2'-(4"-carboxymethoxy-3"-methoxycyclohexyl)-1'-methylvinyl]23,25-dimethoxy-13,19,21,27-tetramethyl-11,28-dioxa-4-azatricyclo [22.3.1.0$^{4,9}$]octacos-18-ene-2,3,10,16-tetraone using benzylamine as the nucleophile.

MASS (FAB) 946 (M+Li). partial $^1$H NMR δ: 8.14 (brs, 1H); 7.30 (m, 5H); 5.21 (m, 2H); 3.04 (s, 2H).

EXAMPLE 101

17-Ethyl-1-hydroxy-12-[2'-(4"-carboxymethoxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Example 97 (Step A) from 17-ethyl-1-hydroxy-12-[2'-(4"-ethanaloxy-3"-methoxycyclohexyl)-1'-methylvinyl]-23,-25-dimethoxy-13,19, 21,27-tetramethyl-11,28-dioxa-4-azatricyclo[22.3.1.0$^{4,9}$]octacos-18 -ene-2,3,10,16-tetraone.

$^1$H NMR consistent with the desired structure.

EXAMPLE 102

17-Ethyl-1-hydroxy-12-[2'-(4"-(N-benzylamidoxymethoxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Example 95 (Step A) using benzylamine as the nucleophile.

MASS (FAB) 930 (M+Li). Partial $^1$H NMR δ: 8.19 (brs, 1H); 7.29 (m, 5H); 4.85 (brd J=8 Hz, 1H); 4.55 (m, 2H).

EXAMPLE 103

17-Ethyl-1-hydroxy-12-[2'-(4"-(N-methyltyrosine)amidoxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Example 95 (Step A) using tyrosine methyl ester hydrochloride as the nucleophile.

MASS (FAB) 1018 (M+Li). Partial $^1$H NMR δ: 6.98 (m, 2H); 6.73 (m, 2H); 4.02 (m, 2H); 3.69 (s, 3H).

EXAMPLE 104

17-Ethyl-1,14-dihydroxy-12-[2'-(4"-(2"'-(m-methylphenyl)-2"'-oxoethyloxy)-3"-methoxycyclohexyl)-1'-methylvinyl]-23,25-dimethoxy-13,19,21,27-tetramethyl-11,28 -dioxa-4-azatricyclo[22.3.1.0$^{4,9}$]octacos-18-ene-2,3,10,16-tetraone Prepared essentially as described in Example 77 using m-methylphenyl magnesium bromide as the nucleophile.

MASS (FAB) 931 (M+Li). Partial $^1$H NMR δ: 7.70 (m, 2H); 7.32 (m, 2H); 5.30M, 5.17 m (brd J=3 Hz, 1H); 4.41 (d J=14 Hz, 1H); 2.39 (s, 3H).

EXAMPLE 105

17-Ethyl-1,14-dihydroxy-12-[2'-(4"-(2"'-(p-methylphenyl)-2"'-oxoethyloxy)-3"-methoxycyclohexyl)-1'-methylvinyl]-23,25-dimethoxy-13,19,21,27-tetramethyl-11,28 -dioxa-4-azatricyclo[22.3.1.0$^{4,9}$]octacos-18-ene-2,3,10,16-tetraone Prepared essentially as described in Example 77 using p-methylphenyl magnesium bromide as the nucleophile.

Partial $^1$H NMR δ: 7.82 (d J=8 Hz, 2H); 7.23 (d J=8 Hz, 2H); 5.30M, 5.17 m (brd J=3 Hz, 1H); 4.41 (d J=14 Hz, 1H); 2.33 (s, 3H).

EXAMPLE 106

17-Ethyl-1,14-dihydroxy-12-[2'-(4"-(2"'-phenyl-2"'-hydroxyethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Example 77 (Steps A,C) using phenyl magnesium bromide as the nucleophile.

MASS (FAB) 919 (M+Li). Partial $^1$H NMR δ: 7.32 (m, 5H); 5.30M, 5.17 m (brd J=3 Hz, 1H); 4.41 (d J=14 Hz, 1H); 3.08 (d J=3 Hz, 1H).

EXAMPLE 107

17-Ethyl-1,14-dihydroxy-12-[2'-(4"-(2"'-(m-methylphenyl)-2"'-hydroxyethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2.3.10.16-tetraone Prepared essentially as described in Example 77 (Steps A,C) using m-methylphenyl magnesium bromide as the nucleophile.

MASS (FAB) 933 (M+Li). Partial $^1$H NMR δ: 7.25–7.03 (m, 4H); 5.30M, 5.17 m (brd J=3 Hz, 1H); 4.41 (d J=14 Hz, 1H); 2.32 (s, 3H).

EXAMPLE 108

17-Ethyl-1,14-dihydroxy-12-[2'-(4"-(2"'-(m-ethylphenyl)-2"'-oxoethyloxy)-3"-methoxycyclohexyl)-1'-methylvinyl]-23,25-dimethoxy-13,19,21,27-tetramethyl-11,28 -dioxa-4-azatricyclo[22.3.1.0$^{4,9}$]octacos-18-ene-2,3,10,16-tetraone Prepared essentially as described in Examples 77 (Step A), 56, 77 (Steps B,C) using m-vinylphenyl magnesium bromide as the nucleophile.

MASS (FAB) 945 (M+Li). Partial $^1$H NMR δ: 7.75 (s, 1H); 7.71 (d J=6 Hz, 1H); 7.37 (m, 2H); 5.30M, 5.17 m (brd J=3 Hz, 1H); 4.41 (d J=14 Hz, 1H); 2.68 (q J=8 Hz, 2H); 1.22 (t J=8 Hz, 3H).

EXAMPLE 109

17-Ethyl-1,14-dihydroxy-12-[2'-(4"-(2"'-phenylethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone

Step A

17-Ethyl-1-hydroxy-14-(tert-butyldimethylsiloxy)-12-[2'-(4"-(2"'-phenyl-2"-trifluoroacetoxyethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-14-(tert-butyldimethylsiloxy)-12-[2'-(4"-(2"'-phenyl-2"-hydroxyethyloxy)-3"-methoxycyclohexyl)-1'-methylvinyl]-23,25 -dimethoxy-13, 19,21,27-tetramethyl-11,28-dioxa-4-azatricyclo[22.3.1.0$^{4,9}$]octacos-18-ene-2,3,10,16 -tetraone (23.3 mg) in methylene chloride (0.6 mL) was added triethylamine (12 μL) followed by trifluoroacetic anhydride (6.4 μL) and N,N-dimethylaminopyridine (3 mg) and the mixture stirred at room temperature. After 15 minutes, the reaction was quenched by the addition of saturated sodium bicarbonate solution, extracted with ethyl acetate, and the organics dried over magnesium sulfate. Purification of the concentrate by flash chromatography on silica gel (ethyl acetate:hexane (1:3)+1% methanol) gave the title compound (5 mg).

$^1$H NMR consistent with the desired structure.

Step B

17-Ethyl-1,14-dihydroxy-12-[2'-(4"-(2"'-phenylethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Examples 56 and 83 (Step B).

MASS (FAB) 919 (M+Na). Partial $^1$H NMR δ: 7.30–7.22 (m, 5H); 5.30M, 5.17 m (brd J=3 Hz, 1H); 4.41 (d J=14 Hz, 1H).

EXAMPLE 110

17-Ethyl-1,14-dihydroxy-12-[2'-(4"-(2"'-phenyl-2"'-acetoxyethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Examples 104 (Step A) and 83 (Step B) using acetic anhydride as the electrophile.

Partial $^1$H NMR δ: 7.33 (m, 5H); 6.03 (m, 1H); 5.30M, 5.17 m (brd J=3 Hz, 1H); 4.41 (d J=14 Hz, 1H); 2.09 (s, 3H).

EXAMPLE 111

17-Ethyl-1,14-dihydroxy-12-[2'-(4"-(2"'-morpholinoethyloxy)-3"-methoxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone

Step A

17-Ethyl-1-hydroxy-14-(tert-butyldimethylsiloxy)-12-[2'-(4"-(2"'-methanesulfonyloxyethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16 -tetraone To a solution of 17-ethyl-1-hydroxy-14-(tert-butyldimethylsiloxy)-12-[2'-(4"-(2"'-hydroxyethyloxy)-3"-methoxycyclohexyl)-1'-methylvinyl]-23,25-dimethoxy-13,19,21,27-tetramethyl-11,28 -dioxa-4-azatricyclo[22.3.1.0$^{4,9}$]octacos-18-ene-2,3,10,16-tetraone (80.8 mg) in methylene chloride (1.0 mL) was added triethylamine (23 μL) followed by methanesulfonyl chloride (7.2 μL) and the mixture stirred at room temperature. After 10 minutes, the reaction was quenched by the addition of saturated sodium bicarbonate solution, extracted with ethyl acetate, and the organic portion dried over magnesium sulfate. Purification of the concentrate by flash chromatography on silica gel (ethyl acetate:hexane (2:1)+1% methanol) gave the title compound (74 mg).

$^1$H NMR consistent with the desired structure.

Step B

17-Ethyl-1-hydroxy-14-(tert-butyldimethylsiloxy)-12-[2'-(4"-(2"'-morpholinoethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-14-(tert-butyldimethylsiloxy)-12-[2'-(4"-(2"'-methanesulfonyloxyethyloxy)-3"-methoxycyclohexyl)-1'-methylvinyl]-23,25-dimethoxy-13, 19,21,27 -tetramethyl-11,28-dioxa-4-azatricyclo[22.3.1.0$^{4,9}$]octacos-18-ene-2,3,10,16-tetraone (26.5 mg) in dry tetrahydofuran (0.3 mL) was added 200 μL of a sodium morpholine solution (prepared by addition of 10 μL morpholine to a suspension of 2.3 mg sodium hydride in 0.5 mL of tetrahydrofuran) and the mixture heated to 70° C. After 6 hours, the mixture is cooled to room temperature and quenched by the addition of saturated ammonium chloride solution, extracted with ethyl acetate, and the organic portion dried over magnesium sulfate. Purification of the concentrate by flash chromatography on silica gel (ethyl acetate:hexane (2:1)+1% methanol, then 2% ammonium hydroxide, 5% methanol, in methylene chloride) gave the title compound (10 mg).

$^1$H NMR consistent with the desired structure.

Step C

17-Ethyl-1,14-dihydroxy-12-[2'-(4"-(2"'-morpholinoethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Example 83 (Step B).

MASS (FAB) 911 (M+Li). Partial ¹H NMR δ: 5.30M, 5.17 m (brd J=3 Hz, 1H); 4.41 (d J=14 Hz, 1H); 3.71 (m, 4H); 2.56 (m, 4H).

EXAMPLE 112

17-Ethyl-1,14-dihydroxy-12-[2'-(4"-(naphth-2-ylmethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Example 44 using naphth-2-ylmethyl trichloroacetimidate as the electrophile and diethyl ether as the solvent.

MASS (FAB) 938 (M+Li). ¹H NMR consistent with the desired structure.

EXAMPLE 113

17-Ethyl-1,14-dihydroxy-12-[2'-(4"-(4''',5'''-methylenedioxybenzyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Example 44 using 4,5-methylenedioxybenzyl trichloroacetimidate as the electrophile.

MASS (FAB) 932 (M+Li). Partial ¹H NMR δ: 6.88 (s, 1H); 6.78 (d J=7 Hz, 1H); 6.74 (d J=7 Hz, 1H); 5.92 (s, 2H); 4.59 (d J=8 Hz, 1H); 4.52 (d J=8 Hz, 1H).

EXAMPLE 114

17-Ethyl-1,14-dihydroxy-12-[2'-(4"-(4'''-N,N,-dimethylaminophenyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Example 1 using tri-(p-N,N-dimethylphenyl) bismuth diacetate as the arylating agent.

MASS (FAB) 917 (M+Li). Partial ¹H NMR δ: 6.87 (d J=10 Hz, 2H); 6.68 (d J=10 Hz, 2H); 2.83 (s, 6H).

EXAMPLE 115

17-Ethyl-1,14-dihydroxy-12-[2'-(4"-(3'''-fluorophenyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Example 1 using tri-(m-fluorophenyl) bismuth diacetate as the arylating agent.

MASS (FAB) 892 (M+Li). ¹H NMR consistent with the desired structure.

EXAMPLE 116

17-Ethyl-1,14-dihydroxy-12-[2'-(4"-(3'''-(2''''-dioxolanylphenyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Example 1 using tris(3-(2'-dioxolanyl)phenyl) bismuth diacetate as the arylating agent.

MASS (FAB) 946 (M+Li). Partial ¹H NMR δ: 7.3–6.9 (m, 4H); 5.78 (s, 1H); 4.13-3.97 (m, 4H).

EXAMPLE 117

17-Ethyl-1,14-dihydroxy-12-[2'-(4"-(3'''-formylphenyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Example 90 (Step B) from 17-Ethyl-1,14-dihydroxy-12-[2'-(4"-(3'''-(2''''-dioxolanylphenyloxy)-3"-methoxycyclohexyl)-1'-methylvinyl]-23,25-dimethoxy-13,19,21,27 -tetramethyl-11,28-dioxa-4-azatricyclo [22.3.1.0$^{4,9}$]octacos-18-ene-2,3,10,16-tetraone.

MASS (FAB) 902 (M+Li). ¹H NMR consistent with the desired structure.

EXAMPLE 118

17-Ethyl-1,14-dihydroxy-12-[2'-(4"-(3'''-carboxyphenyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Example 92 (Step D) from 17-ethyl-1,14-dihydroxy-12-[2'-(4"-(3'''-formylphenyloxy)-3" methoxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone.

¹H NMR consistent with the desired structure.

EXAMPLE 119

17-Ethyl-1,14-dihydroxy-12-[2'-(4"-(3''',4'''-dimethoxyphenyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Example 1 using tris(3,4-dimethoxyphenyl) bismuth acetate as the alkylating agent.

MASS (FAB) 934 (M+Li). Partial ¹H NMR δ: 6.72 (d J=8 Hz., 1H); 6.56 (d J=2.5 Hz, 1H); 6.47 (dd J=8, 2.5 Hz, 1H); 4.57 (brd J=8 Hz, 1H); 4.39 (brd J=1 4.5 Hz, 1H); 3.79 (s, 3H); 3.77 (s, 3H).

EXAMPLE 120

17-Ethyl-1,14-dihydroxy-12-[2'-(4"-(4'"-trifluoromethylphenyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Example 1 using tris(4-trifluoromethylphenyl) bismuth acetate as the alkylating agent.

MASS (FAB) 942 (M+Li). Partial $^1$H NMR δ: 7.48 (d J=9.5 Hz, 2H); 6.98 (d J=9.5 Hz, 2H); 4.59 (brd J=5 Hz, 1H); 4.41 (brd, J=14.5 Hz,1H).

EXAMPLE 121

17-Ethyl-1,14-dihydroxy-12-[2'-(4"-(3'",5'"-bis(trifluoromethyl)phenyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Example 1 using tris(3,5-bis(trifluoromethyl)phenyl) bismuth acetate as the alkylating agent.

MASS (FAB) 1010 (M+Li). Partial $^1$H NMR δ: 7.39 (s, 1H); 7.34 (s, 2H); 4.59 (brd J=5 Hz, 1H); 14.4(brd J=14.5 Hz, 1H).

EXAMPLE 122

A. 17-Ethyl-1-hydroxy-12-[2'-(4"-(4'"-methylphenyloxy)-3"-hydroxycyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone and B. 17-Ethyl-1-hydroxy-12-[2'-(4"-hydroxy-3"-(4'"-methylphenyloxy)cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Example 2 from 17-ethyl-1-hydroxy-12-[2'-(3",4"-dihydroxycyclohexyl)-1'-methylvinyl]-23,25-dimethoxy-13,19,21,27-tetramethyl-11,28-dioxa-4 -azatricyclo-22.3.1.0$^{4,9}$]octacos-18-ene-2,3,10,16-tetraone using tri-(p-methylphenyl) bismuth diacetate as the alkylating agent.

A. (4"-ether):
Partial $^1$H NMR δ: 7.07 (d J=8.4 Hz, 2H); 6.83 (d J=8.4 Hz, 2H); 5.2–4.8 (m, 3H); 4.75(s, 1H).

B. (3"-ether):
MASS (FAB) 859 (M+Li). Partial $^1$H NMR δ: 7.07 (d J=8.4 Hz, 2H); 6.82 (d J=8.4 Hz, 2H); 5.15–4.8 (m, 3H)

EXAMPLE 123

A. 17-Ethyl-1-hydroxy-12-[2'-(4"-(4'"-hydroxyphenyloxy)-3"-hydroxycyclohexyl)-1'-methylvinyl]-23,25-dimethoxy-13,19,21,27-tetramethyl-11,28'dioxa-4-azatricyclo[22.3.1.0$^{4,9}$]-octacos-18-ene-2,3,10,16-tetraone and B. 17-Ethyl-1-hydroxy-12-[2'-(4"-hydroxy-3"-(4'"-hydroxyphenyloxy)cyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone Prepared essentially as described in Examples 122 and 90 (Step B) using tris-(p-(tert-butyldimethylsiloxy)phenyl) bismuth diacetate as the alkylating agent.

A. (4"-ether):
MASS (FAB) 862 (M+Li). Partial $^1$H NMR δ: 6.80 (d J=9 Hz, 2H); 6.72 (d J=9 Hz, 2H); 5.24 (brs, 1H); 5.1–4.8(m, 3H).

B. (3"-ether): MASS (FAB) 862 (M+Li). Partial $^1$H NMR δ: 6.80 (d J=9 Hz, 2H); 6.72 (d J=9 Hz, 2H); 5.37 (brs, 1H); 5.1–4.9 (m, 3H).

EXAMPLE 124

A. 17-Ethyl-1-hydroxy-12-[2'-(4"-(4'"-hydroxymethylphenyloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone and B. 17-Ethyl-1-hydroxy-12-[2'-(4"-hydroxy-3"-(4'"-hydroxymethylphenyloxy)cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Examples 122 and 90 (Step B) using tris-(p-(tert-butyldimethylsiloxymethyl)phenyl) bismuth diacetate as the alkylating agent.

A. (4"-ether):
MASS (FAB) 875 (M+Li). Partial $^1$H NMR δ: 7.26 (d J=10.2 Hz, 2H); 6.90 (d J=10.2 Hz, 2H); 5.1–4.8 (m, 3H); 4.59(s, 2H).

B. (3"-ether):
MASS (FAB) 875 (M+Li). Partial $^1$H NMR δ: 7.26 (d J=9.75 Hz, 2H); 6.91 (d J=9.75 Hz, 2H); 5.1–4.8 (m, 3H); 4.59(brs, 2H).

EXAMPLE 125

17-Ethyl-1-hydroxy-12-[2'-(4"-hydroxy-3"-(4'"-formylphenyloxy)cyclohexyl)-1'-methylvinyl]-23,25-dimethoxy-13,19,21,27'tetramethyl-11,28-dioxa-4-azatricyclo[22.3.1.0$^{4,9}$]octacos-18-ene-2,3,10,16-tetraone Prepared essentially as described in Example 92 (Step C) from 17-ethyl-1-hydroxy-12-[2'-(4"-hydroxy-3"-(4'"-hydroxymethylphenyloxy)cyclohexyl)-1'-methylvinyl]-23,25-dimethoxy-13,19,21,27-tetramethyl-11,28-dioxa-4 -azatricyclo[22.3.1.0$^{4,9}$]octacos-18-ene-2,3,10,16-tetraone.

Partial $^1$H NMR δ: 9.80 (s, 1H); 7.83 (d J=8.5 Hz, 2H); 7.01 (d J=8.5 Hz, 2H); 5.20–4.95 (m, 2H); 4.87 (d J=9.4 Hz, 1H).

EXAMPLE 126

A. 17-Ethyl-1-hydroxy-12-[2'-(4"-(4'"-N,N-dimethylaminophenyloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone and B. 17-Ethyl-1-hydroxy-12-[2'-(4"-hydroxy-3"-(4'"-N,N-dimethylaminophenyloxy)cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Example 122 using tri-(p-N,N-dimethylaminophenyl) bismuth diacetate as the alkylating agent.

A. (4"-ether):
Partial $^1$H NMR δ: 6.86 (d J=9.06 Hz, 2H); 6.68 (d J=9.06 Hz, 2H); 5.15–4.80(m, 3 H).
B. (3"-ether):
Partial $^1$H NMR δ: 6.87 (d J=7.3 Hz, 2H); 6.68 (d J=7.3 Hz, 2H); 5.1–4.80 (m, 3H).

EXAMPLE 127

A. 17-Ethyl-1-hydroxy-12-[2'-(4"-phenyloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone and B. 17-Ethyl-1-hydroxy-12-[2'-(4"-hydroxy-3"-phenyl-oxy)cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Example 122 using tris-(phenyl) bismuth diacetate as the alkylating agent.
A. (4"-ether):
MASS (FAB) 860 (M+Na). Partial $^1$H NMR δ: 7.25 (m, 2H); 6.92 (m, 3H); 5.10M, 4.85 m (t J=9 Hz, 2H); 5.00 (m, 2H).
B. (3"-ether):
MASS (FAB) 860 (M+Na). Partial $^1$H NMR δ: 7.25 (m, 2H); 6.93 (m, 3H); 5.07 (t J=9 Hz, 2H); 4.97 (m, 2H); 4.82 (m, 2H); 4.52 (d J=5 Hz, 2H).

EXAMPLE 128

A. 17-Ethyl-1-hydroxy-12-[2'-(4"-(4'''-methoxyphenyloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone and B. 17-Ethyl-1-hydroxy-12-[2'-(4"-hydroxy-3"-(4'''-methoxyphenyloxy)cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Example 122 using tris-(p-methoxyphenyl) bismuth diacetate as the alkylating agent.
A. (4"-ether):
MASS (FAB) 875 (M+Li)
B. (3"-ether):
MASS (FAB) 875 (M+Li). Partial $^1$H NMR δ: 6.87 (m, 2H); 6.78 (m, 2H); 5.05 (t J=9 Hz, 2H); 3.72 (s, 3H).

EXAMPLE 129

A. 17-Ethyl-1-hydroxy-12-[2'-(4"-(3'''-methoxyphenyloxy)-3"-hydroxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone and B. 17-Ethyl-1-hydroxy-12-[2'-(4"-hydroxy-3"-(3'''-methoxyphenyloxy)cyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Prepared essentially as described in Example 122 using tris-(m-methoxyphenyl) bismuth diacetate as the alkylating agent.
A. (4"-ether):
MASS (FAB) 875 (M+Li). Partial $^1$H NMR δ: 7.13 (t J=10 Hz, 1H); 6.51 (m, 3H); 5.00 (m, 4H); 3.72 (s, 3H).
B. (3"-ether):
MASS (FAB) 875 (M+Li). Partial $^1$H NMR δ: 7.14 (t J=10 Hz, 1H); 6.49 (t J=10 Hz, 3H); 4.52 (d J=5 Hz, 1H); 4.38 m,4.32M (s, 1H); 3.75 (s, 3H).

EXAMPLE 130

17-Ethyl-1,14-dihydroxy-12-[2'-(4"-(2'''-phenyl-2'''-oxoethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone

Step A:

17-Ethyl-1-hydroxy-14-(tert-butyldimethylsiloxy)-12-[2'-(4"-(2'''-phenyl-2'''-oxoethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-14-(tert-butyldimethylsiloxy)-12-[2'-(4"-hydroxy-3"-methoxycyclohexyl)-1'-methylvinyl]-23,25-dimethoxy-13,19,21,27-tetramethyl-11,28 -dioxa-4-azatricyclo[22.3.1.0$^{4,9}$]octacos-18-ene-2,3,10,16-tetraone (500 mg) and rhodium acetate (5 mg, 2 mol %) in dichloromethane (4 ml) was added α-diazoacetophenone (159 mg, 2 eq.) in dichloromethane (2 ml) dropwise. The reaction mixture was stirred for 15 minutes after the addition and then filtered through a silica gel pad washing with ethyl acetate. The filtrate was concentrated and purified by column chromatography on silica gel eluting with 60% hexane:40% ethyl acetate to give the desired product (188 mg).

Step B:

17-Ethyl-1,14-dihydroxy-12-[2'-(4"-(2'''-phenyl-2'''-oxoethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of the product from Step A (188 mg) in THF (2.8 ml) was added hydrogen fluoride/pyridine and the reaction mixture stirred at room temperature for 24 hours. The reaction was then quenched by the addition of saturated aqueous sodium bicarbonate and extracted into ethyl acetate. The organic phase was dried with magnesium sulphate and concentrated. The crude material was purified by column chromatography on silica gel eluting with 50% hexane:50% ethyl acetate to give the title compound (102 mg).

Partial $^1$H NMR (400 MHz, CDCl$_3$) δ: 7.91 (2H, d, J=7.2 Hz), 7.53 (1H, t, J=7.2 Hz), 7.43 (1H, t, J=7.2 Hz), 5.3 (1H major, d, J=2 Hz), 5.17 (1H minor, d, J=2 Hz), 4.98 (4H, m), 4.82 (1H minor, s), 4.59 (1H, d, J=4.8 Hz), 4.4 (1H, d, J=14 Hz), 4.21 (1H major, s).

EXAMPLE 131

17-Ethyl-1,14-dihydroxy-12-[2'-(4"-(2'''-p-t-butylphenyl-2'''-oxoethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The title compound was prepared essentially as described in Example 130 using p-t-butylbenzoyl diazomethane as the reagent in Step A.

MS(FAB) 973 (M+Li). Partial $^1$H NMR (400 MHz, CDCl$_3$) δ: 7.87 (2H, d, J=8.3 Hz), 7.43 (2H, d, J=8.3 Hz), 5.3 (1H major, d, J=2 Hz), 5.17 (1H minor, d, J=2 Hz), 4.98 (4H, m), 4.82 (1H minor, s), 4.59 (1H, d, J=4.8 Hz), 4.4 (1H, d, J=14 Hz), 4.21 (1H major, s).

EXAMPLE 132

17-Ethyl-1,14-dihydroxy-12-[2'-(4''-(2'''-m-nitrophenyl-2'''-oxoethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The title compound was prepared essentially as described in Example 130 using m-nitrobenzoyl diazomethane as the reagent in Step A.

MS (FAB) 961 (M+Li). Partial $^1$H NMR (400 MHz, CDCl$_3$) δ: 8.8 (1H, s), 8.4 (1H, dd, J=8 Hz), 8.3 (1H, d, J=8 Hz), 7.66 (1H, t, J=8 Hz), 5.3 (1H major, s), 5.18 (1H minor, s), 5.92 (4H, m), 4.82 (1H minor, s), 4.59 (1H, d, J=4.8 Hz), 4.4 (1H, d, J=14 Hz), 4.21 (1H major, s).

EXAMPLE 133

17-Ethyl-1,14-dihydroxy-12-[2'-(4''-(2'''-m-isopropoxyphenyl-2'''-oxoethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The title compound was prepared essentially as described in Example 130 using m-isopropoxybenzoyl diazomethane as the reagent in Step A.

MS(FAB) 974 (M+Li). Partial $^1$H NMR (400 MHz, CDCl$_3$) δ: 7.43 (2H, m), 7.31 (1H, t, J=7.1 Hz), 7.06 (1H, d, J=7.1 Hz), 5.3 (1H major, d, J=2 Hz), 5.17 (1H minor, d, J=2 Hz), 4.98 (4H, m), 4.82 (1H minor, s), 4.59 (2H, m), 4.4 (1H, d, J=14 Hz), 4.21 (1H major, s).

EXAMPLE 134

17-Ethyl-1,14-dihydroxy-12-[2'-(4''-(2'''-m-bromophenyl-2'''-oxoethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The title compound was prepared essentially as described in Example 130 using m-bromobenzoyl diazomethane as the reagent in Step A.

Partial $^1$H NMR (400 MHz, CDCl$_3$) δ: 8.08 (1H, s), 7.86 (1H, d, J=7.5 Hz), 7.69 (1H, d, J=7.5 Hz), 5.3 (1H major, d, J=2 Hz), 5.17 (1H minor, d, J=2 Hz), 4.92 (5H, m), 4.59 (2H, m), 4.4 (1H, d, J=13.6 Hz), 4.21 (1H major, s).

EXAMPLE 135

17-Ethyl-1,14-dihydroxy-12-[2'-(4''-(2'''-m-fluorophenyl-2'''-oxoethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The title compound was prepared essentially as described in Example 130 using m-fluorobenzoyl diazomethane as the reagent in Step A.

MS(FAB) 934 (M+Li). Partial $^1$H NMR (400 MHz, CDCl$_3$) δ: 7.7 (1H, d, J=7.7 Hz), 7.64 (1H, d, J=9.5 Hz), 7.41 (1H, q, J=5.5 Hz), 7.23 (1H, m), 5.3 (1H major, s), 5.18 (1H minor, s), 4.9 (4H, m), 4.82 (1H minor, s), 4.59 (1H, d, J=4.8 Hz), 4.4 (1H, d, J=14 Hz), 4.21 (1H major, s).

EXAMPLE 136

17-Ethyl-1,14-dihydroxy-12-[2'-(4''-(2'''-m-chloromethylphenyl-2'''-oxoethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The title compound was prepared essentially as described in Example 130 using m-chloromethylbenzoyl diazomethane as the reagent in Step A.

MS(FAB) 964 (M+Li). Partial $^1$H NMR (400 MHz, CDCl$_3$) δ: 7.93 (1H, s), 7.87 (1H, d, J=7 Hz), 7.58 (1H, d, J=7 Hz), 7.43 (1H, t, J=7 Hz), 5.3 (1H major, s), 5.18 (1H minor, s), 4.9 (4H, m), 4.82 (1H minor, s), 4.60 (2H, s), 4.58 (1H, d, J=4.8 Hz), 4.40 (1H, d, J=14 Hz), 4.21 (1H major, s).

EXAMPLE 137

17-Ethyl-1,14-dihydroxy-12-[2'-(4''-(2'''-m-cyanophenyl-2'''-oxoethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The title compound was prepared essentially as described in Example 130 using m-cyanobenzoyl diazomethane as the reagent in Step A.

MS(FAB) 941 (M+Li). Partial $^1$H NMR (400 MHz, CDCl$_3$) δ: 8.35 (1H, s), 8.22 (1H, d, J=3 Hz), 7.85 (1H, d, J=3 Hz), 7.62 (1H, t, J=3 Hz), 5.34 (1H major, s), 5.21 (1H minor, s), 5.04 (2H, m), 4.90 (2H, m), 4.61 (1H, d, J=6 Hz), 4.44 (1H, d, J=13 Hz), 4.25 (1H, s).

EXAMPLE 138

17-Ethyl-1,14-dihydroxy-12-[2'-(4''-(2'''-m,m-difluorophenyl-2'''-oxoethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The title compound was prepared essentially as described in Example 130 using m,m-difluorobenzoyl diazomethane as the reagent in Step A.

MS(FAB) 952 (M+Li). Partial $^1$H NMR (400 MHz, CDCl$_3$) δ: 7.54 (2H, d, J=3 Hz), 7.1 (1H, m), 5.33 (1H major, s), 5.20 (1H minor, s), 5.60 (1H major, d, J=9 Hz), 5.02 (1H, m), 4.86 (2H, m), 4.60 (1H, d, J=5 Hz), 4.24 (1H, s).

EXAMPLE 139

17-Ethyl-1,14-dihydroxy-12-[2'-(4''-(2'''-m,m-dimethylphenyl-2'''-oxoethyloxy)-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The title compound was prepared essentially as described in Example 130 using m,m-dimethylbenzoyl diazomethane as the reagent in Step A.

MS(FAB) 939 (M+1). Partial $^1$H NMR (400 MHz, CDCl$_3$) δ: 7.50 (2H, s), 7.18 (1H, s), 5.30 (1H major, d, J=1.8 Hz), 5.16 (1H minor, d, J=1.4 Hz), 4.98 (4H, m), 4.80 (1H minor, s), 4.57 (1H, d, J=5.0 Hz), 4.40 (1H, d, J=12.5 Hz), 4.21 (1H major, s).

EXAMPLE 140

17-Ethyl-1,14-dihydroxy-12-[2'-(4"-(2'''-m-chlorophenyl-2'''-oxoethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The title compound was prepared essentially as described in Example 130 using m-chlorobenzoyl diazomethane as the reagent in Step A.

MS(FAB) 950 (M+Li). Partial $^1$H NMR (400 MHz, CDCl$_3$) δ: 7.91 (1H, s), 7.8 (1H, d, J=6.9 Hz), 7.52 (1H, m), 7.38 (1H, t, J=7.5 Hz), 5.3 (1H major, s), 5.18 (1H minor, s), 4.9 (4H, m), 4.82 (1H minor, s), 4.59 (1H, d, J=4.8 Hz), 4.4 (1H, d, J=14 Hz), 4.21 (1H major, s).

EXAMPLE 141

17-Ethyl-1,14-dihydroxy-12-[2'-(4"-(2'''-m-triflouromethylphenyl-2'''-oxoethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The title compound was prepared essentially as described in Example 130 using m-trifloromethylbenzoyl diazomethane as the reagent in Step A.

MS(FAB) 984.1 (M+Li). Partial $^1$H NMR (400 MHz, CDCl$_3$) δ: 8.21 (1H, s), 8.13 (1H, d, J=7.7 Hz), 7.80 (1H, J=7.7 Hz), 7.59 (1H, t, J=7.7 Hz), 5.30 (1H major, d, J=2.0 Hz), 5.17 (1H minor, d, J=1.8 Hz), 4.97 (4H, m), 4.81 (1H minor, s), 4.57 (1H, d, J=4.4 Hz), 4.40 (1H, d, J=12.4 Hz), 4.22 (1H major, s).

EXAMPLE 142

17-Ethyl-1,14-dihydroxy-12-[2'-(4"-(2'''-(2-naphthyl)-2'''-oxoethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The title compound was prepared essentially as described in Example 130 using 2-naphthoyl diazomethane as the reagent in Step A ($^1$H NMR was consistent with the desired structure).

EXAMPLE 143

17-Ethyl-1,14-dihydroxy-12-[2'-(4"-(2'''-phenyl-2'''-hydroxyethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone

Step A

17-Ethyl-1-hydroxy-14-(tert-butyldimethylsiloxy)-12-[2'-(4"-(2'''-phenyl-2'''-hydroxyethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-14-(tert-butyldimethylsiloxy)-12-[2'-(4"-(2'''-phenyl-2'''-oxoethyloxy)-3"-methoxycyclohexyl)-1'-methylvinyl]-23,25-dimethoxy-13,19,21,27 -tetramethyl-11,28-dioxa-4-azatricyclo[22.3.1.0$^{4,9}$]octacos-18-ene-2,3,10,16-tetraone (350 mg) in THF (6.2 ml) at −78° C. was added L-Selectride (342 µl, 1 eq.) dropwise over 30 minutes. The reaction was stirred for a further 15 minutes after addition and then quenched by pouring into saturated aqueous ammonium chloride solution and extracted into ethyl acetate. The organic phase was dried with magnesium sulphate and concentrated. The crude material was purified by column chromatography on silica gel eluting with 60% hexane:40% ethyl acetate to give the desired product (216 mg).

Step B

17-Ethyl-1,14-dihydroxy-12-[2'-(4"-(2'''-phenyl-2'''-hydroxyethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of the product from Step A (29 mg) in THF (400 µl) was added hydrogen fluoride/pyridine and the reaction mixture stirred at room temperature for 24 hours. The reaction was then quenched by the addition of saturated aqueous sodium bicarbonate and extracted into ethyl acetate. The organic phase was dried with magnesium sulphate and concentrated. The crude material was purified by column chromatography on silica gel eluting with 70% hexane:30% ethyl acetate to give the title compound (11 mg).

MS(FAB) 934 (M+Na). partial $^1$H NMR (400 MHz, CDCl$_3$) δ: 7.32 (5H, m), 5.30 (1H major, s), 5.18 (1H minor, s), 5.0 (3H, m), 4.87 (2H, m), 4.65 (1H, m), 4.59 (1H, d, J=5.5 Hz), 4.4 (1H, d, J=14 Hz), 4.21 (1H major, s).

EXAMPLE 144

17-Ethyl-1,14-dihydroxy-12-[2'-(4"-(2'''-m-methylphenyl-2'''-hydroxyethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The title compound was prepared essentially as described in Example 143.

partial ¹H NMR (400 MHz, CDCl₃) δ: 7.15 (4H, m), 5.3 (1H major, s), 5.18 (1H minor, s), 5.0 (3H, m), 4.82 (2H, m), 4.59 (1H, d, J=5.5 Hz), 4.4 (1H, d, J=14 Hz), 4.21 (1H major, s).

EXAMPLE 145

17-Ethyl-1,14-dihydroxy-12-[2'-(4"-(2"'-m-fluorophenyl-2"'-hydroxyethyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone The title compound was prepared essentially as described in Example 143.

MS(FAB) 936 (M+Li). partial ¹H NMR (400 MHz, CDCl₃) δ: 7.26 (1H, m), 7.1 (2H, m), 6.92 (1H, m), 5.3 (1H major, s), 5.18 (1H minor, s), 5.0 (3H, m), 4.85 (2H, m), 4.78 (1H minor, br.s.), 4.59 (1H, d, J=5.5 Hz), 4.4 (1H, d, J=14 Hz), 4.21 (1H major, s).

EXAMPLE 146

17-Ethyl-1,14-dihydroxy-12-[2'-(4"-(2"'-m-chloromethylphenyl-2"'-hydroxyethyloxy)-3"-methoxycyclohexyl)-1'-methylvinyl]-23,25-dimethoxy-13,19,21,27-tetramethyl-11,28-dioxa-4-azatricyclo22.3.1.0⁴,⁹]octacos-18-ene-2,3,10,16-tetraone The title compound was prepared essentially as described in Example 143.

MS(FAB) 966 (M+Li). partial ¹H NMR (400 MHz, CDCl₃) δ: 7.40 (1H, s), 7.29 (3H, m), 5.3 (1H major, d, J=2 Hz), 5.17 (1H minor, d, J=2 Hz), 5.01 (2H, m), 4.88 (1H, m), 4.58 (1H, s), 4.41 (1H, d, J=13.5 Hz).

EXAMPLE 147

17-Ethyl-1,14-dihydroxy-12-[2'-(4"-(2"'-m,m-difluorophenyl-2"'-hydroxyethyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone The title compound was prepared essentially as described in Example 143.

MS(FAB) 948 (M+1). partial ¹H NMR (400 MHz, CDCl₃) δ: 6.88 (2H, d, J=6.5 Hz), 6.67 (1H, t, J=6.5 Hz), 5.30 (1H major, d, J=1.8 Hz), 5.17 (1H minor, d, J=1.8 Hz), 5.0 (3H, m), 4.82 (2H, m), 4.57 (1H, d, J=5.3 Hz), 4.4 (1H, d, J=14 Hz)4.21 (1H, s).

EXAMPLE 148

17-Ethyl-1,14-dihydroxy-12-[2'-(4"-(2"'-m,m-dimethylphenyl-2"'-hydroxyethyloxy)-3"-methoxycyclohexyl)-1'-methylvinyl]-23,25-dimethoxy-13,19,21,27-tetramethyl-11,28-dioxa-4-azatricyclo22.3.1.0⁴,⁹]octacos-18-ene-2,3,10,16-tetraone The compound was prepared essentially as described in Example 143.

MS (FAB) 941 (M+1). partial ¹H NMR (400 MHz, CDCl₃) δ: 6.96 (2H, s), 6.88 (1H, s), 5.30 (1H major, d, J=1.8 Hz), 5.17 (1H minor, d, J=1.6 Hz), 5.02 (2H, m), 4.86 (1H minor, s), 4.79 (1H, d, J=9.9 Hz), 4.58 (1H, d, J=5.2 Hz), 4.41 (1H, d, J=14.1 Hz), 4.22 (1H major, s).

EXAMPLE 149

17-Ethyl-1,14-dihydroxy-12-[2'-(4"-(2"'-m-chlorophenyl-2"'-hydroxyethyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone The title compound was prepared essentially as described in Example 143.

MS(FAB) 946 (M+H). partial ¹H NMR (400 MHz, CDCl₃) δ: 7.38 (1H, s), 5.3 (1H major, s), 5.18 (1H minor, s), 5.0 (3H, m), 4.73 (2H, m), 4.58 (1H, d, J=5.2 Hz), 4.4 (1H, d, J=14 Hz), 4.22 (1H major, s).

EXAMPLE 150

17-Ethyl-1,14-dihydroxy-12-[2'-(4"-(2"'-m-trifluoromethylphenyl-2"'-hydroxyethyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹]octacos-18-ene-2,3,10,16-tetraone The title compound was prepared essentially as described in Example 143.

MS(FAB) 986.1 (M+Li). partial ¹H NMR (400 MHz, CDCl₃) δ: 7.70 (1H, s), 7.55 (2H, d, J=7.8 Hz), 7.47 (1H, d, J=7.8 Hz), 5.35 (1H major, d, J=2.3 Hz), 5.22 (1H minor, d, J=0.9 Hz), 5.05 (2H, m), 4.95 (1H, d, J=9.9 Hz), 4.88 (1H minor, s), 4.62 (1H, d, J=4.5 Hz), 4.45 (1H, d, J=12.5 Hz), 4.26 (1H major, s).

EXAMPLE 151

17-Ethyl-1,14-dihydroxy-12-[2'-(4"-(2"'-(2-naphthyl)-2"'-hydroxyethyloxy)-3"-methoxycyclohexyl)-1'-methylvinyl]-23,25-dimethoxy-13,19,21,27-tetramethyl-11,28-dioxa-4-azatricyclo22.3.1.0⁴,⁹]octacos-18-ene-2,3,10,16-tetraone

Step A

17-Ethyl-1-hydroxy-14-(tert-butyldimethylsiloxy)-12-[2'-(4"-(2"'-(2-naphthyl)-2"'-hydroxyethyloxy)-3"-methoxycyclohexyl)-1'-methylvinyl]-23,25-dimethoxy-13,19,21,27-tetramethyl-11,28-dioxa-4-azatricyclo[22.3.1.0⁴,⁹] octacos-18-ene-2,3,10,16-tetraone To a stirred solution of 17-ethyl-1-hydroxy-14-(t-butyldimethylsilyloxy)-12-[2'-(4"-ethanaloxy-3"'-methoxycyclohexyl)-1'-methylvinyl]-23,25-dimethoxy-13,19,21,27-tetramethyl-11,28 -dioxa-4-azatricyclo[22.3.1.0⁴,⁹]octacos-18-ene-2,3,10,16-tetraone (1.0 g) in THF (10 mL) at −50° C. was added a solution of 2-naphthyl magnesium bromide (0.5M in THF). The solution was stirred for 0.5 hr. then quenched by addition of aqueous NH₄Cl solution and the product extracted 2× with CH₂Cl₂. The extracts were combined, dried with Na$_2$SO$_4$, filtered and concentrated in vacuo. Purification of the residue by column chromatography followed by preparative TLC afforded 332 mg of the title compound as a colorless solid.

Step B

17-Ethyl-1,14-dihydroxy-12-[2'-(4"-(2'''-(2-naphthyl)-2'''-hydroxyethyloxy)-3"-methoxycyclohexyl)-1'-methylvinyl]-23,25-dimethoxy-13,19,21,27-tetramethyl-11,28-dioxa-4-azatricyclo-22.3.1.0$^{4,9}$]octacos-18-ene-2,3,10,16-tetraone The product from Step A was deprotected with HF/pyridine as described in Step B from above to afford 190 mg of the title compound as a colorless solid (1H NMR was consistent with the desired structure).

EXAMPLE 154

17-Ethyl-1,14-dihydroxy-12-[2'-(4"-(2'''-phenyl-2'''-benzyloxyethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Step A 17-Ethyl-1-hydroxy-14-(tert-butyldimethylsiloxy)-12-[2'-(4"-(2'''-phenyl-2'''-benzyloxyethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-14-(tert-butyldimethylsiloxy)-12-[2'-(4"-(2'''-phenyl-2'''-hydroxyethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (40 mg) in cyclohexane (0.8 ml) and dichloromethane (0.4 ml) was added 2,2,2-benzyltrichloroacetimidate at 0° C. followed by triflic acid. The reaction was allowed to warm to room temperature and stir for 1.5 hours after which time it was poured into saturated aqueous sodium bicarbonate solution and extracted into ethyl acetate. The organic extracts were dried (MgSO$_4$) and concentrated and the crude material was purified by column chromatography on silica gel eluting with 65% hexane:35% ethyl acetate to give the desired product (22 mg).

Step B

17-Ethyl-1,14-dihydroxy-12-[2'-(4"-(2'''-phenyl-2'''-benzyloxyethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of the product from Step A (22 mg) in THF (100 μl) was added hydrogen fluoride/pyridine and the reaction stirred at room temperature for 6 hours. The reaction was then quenched by the addition of saturated aqueous sodium bicarbonate and extracted into ethyl acetate. The organic phase was dried with magnesium sulphate and concentrated. The crude material was purified by column chromatography on silica gel eluting with 50% hexane:50% ethyl acetate to give the title compound (15 mg).

MS(FAB) 1002 (M+H). partial $^1$H NMR (400 MHz, CDCl$_3$) δ: 7.30 (10H, m), 5.30 (1H major, s), 5.16 (1H minor, s), 5.0 (2H, m), 4.85 (1H minor, s), 4.53 (3H, m), 4.38 (2H, m), 4.21 (1H major, s).

EXAMPLE 155

17-Ethyl-1,14-dihydroxy-12-[2'-(4"-(2'''-phenyl-2'''-allyloxyethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The title compound was prepared essentially as described in Example 154 using allyltrichloroacetimidate as the reagent in Step A.

MS(FAB) 951 (M$^+$). partial $^1$H NMR (400 MHz, CDCl$_3$) δ: 7.30 (5H, m), 5.88 (1H, ddd, J=28, 10 and 5.3 Hz), 5.30 (1H major, s), 5.22 (1H, d, J=18 Hz), 5.16 (1H minor, s), 5.1 (1H, d, J=8.6 Hz), 5.0 (2H, m), 4.83 (1H minor, s), 4.56 (1H, s), 4.48 (1H, dd, J=7 and 4.6 Hz), 4.40 (1H, d, J=14 Hz), 4.20 (1H major, s).

EXAMPLE 156

17-Ethyl-1,14-dihydroxy-12-[2'-(4"-(2'''-phenyl-2'''-methoxyethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone Step A 17-Ethyl-1-hydroxy-14-(tert-butyldimethylsiloxy)-12-[2'-(4"-(2'''-phenyl-2'''-methoxyethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-14-(tert-butyldimethylsiloxy)-12-[2'-(4"-(2'''-phenyl-2'''-hydroxyethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (27 mg) in methyl iodide (0.5 ml) under nitrogen atmosphere was added silver oxide and the reaction was stirred at room temperature for 48 hours. The reaction was then diluted with ethyl acetate and filtered through a silica gel pad. The filtrate was concentrated and purified by column chromatography on silica gel eluting with 60% hexane:40% ethyl acetate to give the desired compound (12.6 mg).

Step B

17-Ethyl-1,14-dihydroxy-12-[2'-(4"-(2'''-phenyl-2'''-methoxyethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone The title compound was prepared essentially as described in Example 154, Step B to yield 5 mg.

MS(FAB) 932 (M+Li). partial $^1$H NMR (400 MHz, CDCl$_3$) δ: 7.30 (5H, m), 5.88 (1H, ddd, J=28, 10 and 5.3 Hz), 5.30 (1H major, s), 5.22 (1H, d, J=18 Hz), 5.16 (1H minor, s), 5.1 (1H, d, J=8.6 Hz), 5.0 (2H, m), 4.83 (1H minor, s), 4.56 (1H, s), 4.48 (1H, dd, J=7 and 4.6 Hz), 4.40 (1H, d, J=14 Hz), 4.20 (1H major, s).

EXAMPLE 157

17-Ethyl-1,14-dihydroxy-12-[2'-(4"-(2'''-phenyl-2'''-aminoethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone

Step A

17-Ethyl-1-hydroxy-14-(tert-butyldimethylsiloxy)-12-[2'-(4"-(2'''-phenyl-2'''-azidoethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1-hydroxy-14-(tert-butyldimethylsiloxy)-12-[2'-(4"-(2'''-phenyl-2'''-hydroxyethyloxy)-3"-methoxycyclohexyl)-1'-methylvinyl]-23,25-dimethoxy-13, 19,21,27 -tetramethyl-11,28-dioxa-4-azatricyclo[22.3.1.0$^{4,9}$]octacos-18-ene-2,3,10,16-tetraone (35 mg) in dichloromethane (1 ml) at −10° C. was added triethylamine (14 μl) followed by methane sulphonyl chloride (8 μl) and the reation stirred for 30 minutes. The reaction was concentrated and the residue was dissolved in DMF (1 ml). Sodium azide (22 mg) was added and the reaction was heated to 60° C. for 45 minutes before being poured into brine and extacted with ethyl acetate. The organic extracts were dried (MgSO$_4$), concentrated and purified by column chromatography on silica gel eluting with 60% hexane:40% ethyl acetate to give the desired compound (27 mg).

Step B

17-Ethyl-1,14-dihydroxy-12-[2'-(4"-(2'''-phenyl-2'''-aminoethyloxy)-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of the product from Step A (27 mg) in wet benzene (0.5 ml) was added triphenyl phosphine (15 mg) and the reaction heated to 60° C. for 2 hours. The reaction mixture was concentrated, dissolved in THF (200 μl) and treated with hydrogen fluoride/pyridine for 24 hours at room temperature. The reaction was quenched with saturated aqueous sodium bicarbonate solution and extacted into ethyl acetate. The crude material was purified by preparative plate chromatography (20cm×20cm, 500 microns) eluting with 90% dichloromethane:10% methanol+1% ammonium hydroxide to give the title compound (9 mg).

MS(FAB) 910 (M$^+$). partial $^1$H NMR (400 MHz, CDCl$_3$) δ: 7.30 (5H, m), 5.30 (1H major, s), 5.18 (1H minor, s), 5.0 (3H, m), 4.59 (1H, d, J=5.5 Hz), 4.4 (1H, d, J=14 Hz), 4.21 (1H major, s).

EXAMPLE 158

17-Ethyl-1,14-dihydroxy-12-[2'-(4"-(2'''-phenyl-2'''-oxoethloxy)-3"-isopropoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone To a solution of 17-ethyl-1,14-dihydroxy-12-[2'-(4"-hydroxy-3"-isopropoxycyclohexyl)-1'-methylvinyl]-23,25-dimethoxy-13,19-21,27-tetramethyl-11,28-dioxa-4 -azatricyclo[22.3.1.0$^{4,9}$]octacos-18-ene-2,3,10,16-tetraone (88.4 mg in 1.1 mL methylene chloride) at 0° C. was added α-diazoacetophenone (31.6 mg) followed by boron trifluoride etherat (2.7 μL). After 20 minutes, additional boron trifluoride etherate (3 μL) was added and the mixture warmed slowly to room temperature. The reaction was quenched after 1.5 hours by the addition of saturated sodium bicarbonate solution. The mixture was extracted with ethyl acetate, washed with saturated sodium chloride solution, and the organic portion dried over magnesium sulfate. Purification by flash chromatography on silica gel (ethyl acetate-:hexane (1:2)+1% methanol) followed by silica gel preparative tlc (acetone:hexane 2:8) gave the title compound (2.8 mg).

MS: (FAB) 960 (M+Na). partial $^1$H NMR δ: 7.90 (d, J=7 Hz, 2H); 7.55 (t, J=7 Hz, 1H); 7.43 (t, J=7 Hz, 2H); 5.30M, 5.16 m (brs, 1H); 4.41 (brd, J=14 Hz, 1H); 3.10 (d, J=2.5 Hz, 1H); 1.14 (d, J=6 Hz, 3H); 1.11 (d, J=6 Hz, 3H).

EXAMPLES 158–196

Utilizing the general procedures described in Examples 1 to 157, the following compounds of Formula I (wherein R$^4$ is hydrogen, R$^5$ is methyl, ethyl, propyl or allyl and n is 2) are prepared from the appropriately substituted starting materials and reagents.

| EXAMPLE NO. | R$^1$ | R$^2$ | R$^3$ | R$^5$ |
|---|---|---|---|---|
| 158 | HO-C$_6$H$_4$- | CH$_3$ | H | CH$_3$CH$_2$ |
| 159 | HO-C$_6$H$_4$- | CH$_2$=CHCH$_2$— | OH | CH$_3$CH$_2$ |

-continued

| EXAMPLE NO. | R$^1$ | R$^2$ | R$^3$ | R$^5$ |
|---|---|---|---|---|
| 160 | 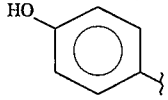 4-HO-C$_6$H$_4$- | CH$_3$ | OH | CH$_2$=CHCH$_2$- |
| 161 | 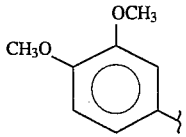 3,4-(CH$_3$O)$_2$-C$_6$H$_3$- | CH$_3$ | OH | CH$_3$CH$_2$CH$_2$ |
| 162 | 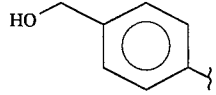 4-HOCH$_2$-C$_6$H$_4$- | CH$_3$ | OH | CH$_3$CH$_2$ |
| 163 | 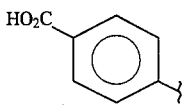 4-HO$_2$C-C$_6$H$_4$- | CH$_3$ | OH | CH$_3$CH$_2$ |
| 164 | 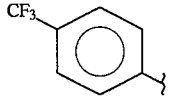 4-CF$_3$-C$_6$H$_4$- | CH$_3$ | OH | CH$_3$CH$_2$CH$_2$ |
| 165 | 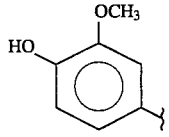 3-CH$_3$O-4-HO-C$_6$H$_3$- | CH$_3$ | H | CH$_2$=CHCH$_2$- |
| 166 | 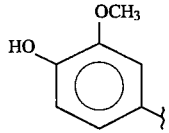 3-CH$_3$O-4-HO-C$_6$H$_3$- | CH$_2$=CHCH$_2$- | OH | CH$_3$CH$_2$ |
| 167 | 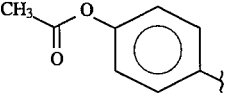 4-CH$_3$C(O)O-C$_6$H$_4$- | CH$_3$ | OH | CH$_3$CH$_2$ |
| 168 | 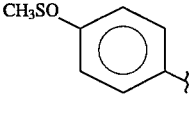 4-CH$_3$SO-C$_6$H$_4$- | CH$_3$ | OH | CH$_3$CH$_2$ |
| 169 | 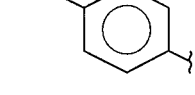 4-CH$_3$SO$_2$-C$_6$H$_4$- | CH$_3$ | OH | CH$_3$CH$_2$ |
| 170 | 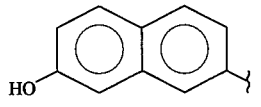 6-HO-2-naphthyl | CH$_3$ | OH | CH$_3$CH$_2$ |
| 171 | 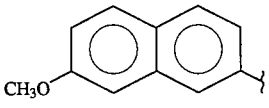 6-CH$_3$O-2-naphthyl | CH$_3$ | OH | CH$_3$CH$_2$ |
| 172 | 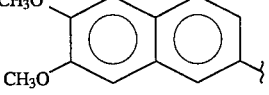 6,7-(CH$_3$O)$_2$-2-naphthyl | CH$_3$ | H | CH$_2$=CHCH$_2$- |

-continued
| EXAMPLE NO. | R¹ | R² | R³ | R⁵ |
|---|---|---|---|---|
| 173 | 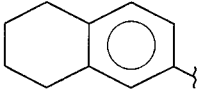 | CH₃ | OH | CH₃CH₂ |
| 174 | 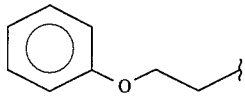 | CH₃ | OH | CH₃CH₂ |
| 175 | 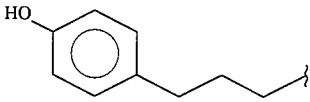 | CH₃ | OH | CH₃CH₂ |
| 176 | 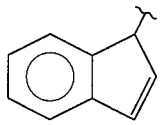 | CH₃ | OH | CH₃ |
| 177 | 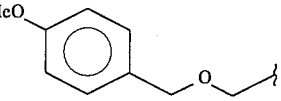 | CH₃ | OH | CH₃CH₂ |
| 178 | 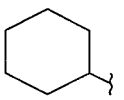 | CH₃ | OH | CH₃CH₂ |
| 179 | 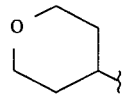 | CH₃ | OH | CH₃CH₂ |
| 180 | 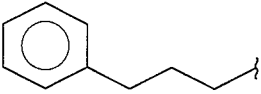 | CH₃ | H | CH₃CH₂ |
| 181 | 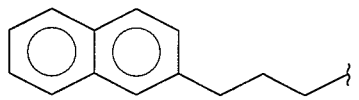 | CH₃ | H | CH₃CH₂ |
| 182 |  | CH₃CH₂ | OH | CH₃CH₂ |
| 183 |  | (CH₃)₂CH | OH | CH₃CH₂ |
| 184 | 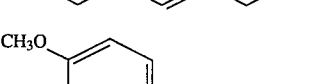 | (CH₃)₂CH | OH | CH₃CH₂ |
| 185 | 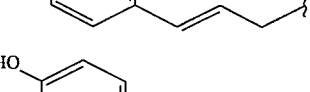 | CH₃CH₂ | OH | CH₃CH₂ |
| 186 | 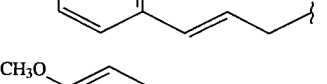 | CH₃CH₂CH₂ | OH | CH₃CH₂ |

-continued

| EXAMPLE NO. | R¹ | R² | R³ | R⁵ |
|---|---|---|---|---|
| 187 | HO-C₆H₄-CH=CH-CH₂- | $CH_3CH_2CH_2$ | OH | $CH_3CH_2$ |
| 188 | HO-C₆H₄-CH=CH-CH₂- | $CH_3CH_2CH_2$ | OH | $CH_3CH_2$ |
| 189 | CH₃O-C₆H₄-CH=CH-CH₂- | $(CH_3)_2CH$ | OH | $CH_3CH_2$ |
| 190 | HO-C₆H₄-CH=CH-CH₂- | $(CH_3)_2CH$ | OH | $CH_3CH_2$ |
| 191 | $H_2NCH_2CH_2-$ | $CH_3$ | OH | $CH_3CH_2$ |
| 192 | $H_2NCH_2CH_2-$ | $CH_3$ | H | $CH_3CH_2$ |
| 193 | $(CH_3)_2NCH_2CH_2-$ | $CH_3$ | OH | $CH_3CH_2$ |
| 194 | $(CH_3)_2NCH_2CH_2-$ | $CH_3$ | H | $CH_3CH_2$ |
| 195 | $CH_3NHCH_2CH_2-$ | $CH_3$ | OH | $CH_3CH_2$ |
| 196 | $CH_3NHCH_2CH_2-$ | $CH_3$ | H | $CH_3CH_2$ |

EXAMPLE 197

T-Cell Proliferation Assay

1. Sample Preparation

The compounds to be assayed were dissolved in absolute ethanol at 1 mg/ml.

2. Assay

Spleens from C57B1/6 mice were taken under sterile conditions and gently dissociated in ice-cold RPMI 1640 culture medium (GIBC), Grand Island, N.Y.) supplemented with 10% heat-inactivated fetal calf serum (GIBO)). Cells were pelleted by centrifugation at 1500 rpm for 8 minutes. Contaminating red cells were removed by treating the pellet with ammonium chloride lysing buffer (GIBO)) for 2 minutes at 4° C. Cold medium was added and cells were again centrifuged at 1500 rpm for 8 minutes. T lymphocytes were then isolated by separation of the cell suspension on nylon wool columns as follows: Nylon wool columns were prepared by packing approximately 4 grams of washed and dried nylon wool into 20 ml plastic syringes. The columns were sterilized by autoclaving at 25° F. for 30 minutes. Nylon wool columns were wetted with warm (37° C.) culture medium and rinsed with the same medium. Washed spleen cells resuspended in warm medium were slowly applied to the nylon wool. The columns were then incubated in an upright position at 37° C. for 1 hour. Non-adherent T lymphocytes were eluted from the columns with warm culture medium and the cell suspensions were spun as above.

Purified T lymphocytes were resuspended at $2.5\times10^5$ cells/ml in complete culture medium composed of RPMI 1640 medium with 10% heat-inactivated fetal calf serum, 100 mM glutamine, 1 mM sodium pyruvate, $2\times10^{-5}$M 2-mercaptoethanol and 50 µg/ml gentamycin. Ionomycin was added at 250 ng/ml and PMA at 10 ng/ml. The cell suspension was immediately distributed into 96 well flat-bottom microculture plates (Costar) at 200 µl/well. The various dilutions of the compound to be tested were then added in triplicate wells at 20 µl/well. The compound 17-allyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone was used as a standard. The culture plates were then incubated at 37° C. in a humidified atmosphere of 5% $CO_2$-95% air for 44 hours. The proliferation of T lymphocytes was assessed by measurement of tritiated thymidine incorporation. After 44 hours of culturing, the cells were pulse-labelled with 2 µCi/well of tritiated thymidine (NEN, Cambridge, Mass.). After another 4 hours of incubation, cultures were harvested on glass fiber filters using a multiple sample harvester. Radioactivity of filter discs corresponding to individual wells was measured by standard liquid scintillation counting methods (Beta-counter). Mean counts per minute of replicate wells were calculated and the results expressed as concentration of compound required to inhibit tritiated thymidine uptake of T-cells by 50%.

A selection of compounds were tested according to the previous procedure. The title compounds of the following Examples had activity in inhibiting the proliferation of T-cells in the aforementioned assay:

1, 2A, 2B, 3, 4, 5, 6A, 6B, 7, 8A, 8B, 9, 10A, 10B, 11, 12A, 12B, 13, 14, 15A, 15B, 16, 17, 18, 19, 20, 21, 22, 23, 24, 25, 26, 43, 44, 45, 46A, 46B, 47B, 48A, 49A, 49B, 50A, 50B, 51A, 51B, 52, 53, 54A, 54B, 55, 56, 57, 58, 59, 60, 61, 64, 70, 73, 76, 77, 77B, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122A, 122B, 123A, 123B, 124A, 124B, 125, 126A, 126B, 127A, 127B, 128A, 128B, 129A, 129B, 130, 131, 132, 133, 134, 135, 136, 137, 138, 139, 140, 141, 142, 143, 144, 145, 146, 147, 148, 149, 150, 151, 152, 153, 154, 155, 156, & 157.

The results of this assay are representative of the intrinsic immunosuppressive activity of the compounds of the present invention.

While the foregoing specification teaches the principles of the present invention, with examples provided for the purpose of illustration, it will be understood that the practice of the invention encompasses all of the casual variations, adaptations, modifications, deletions, or additions of procedures and protocols described herein, as come within the scope of the following claims and its equivalents.

What is claimed is:

1. A compound of Formula XI, XII, XIII or XIV:

XI

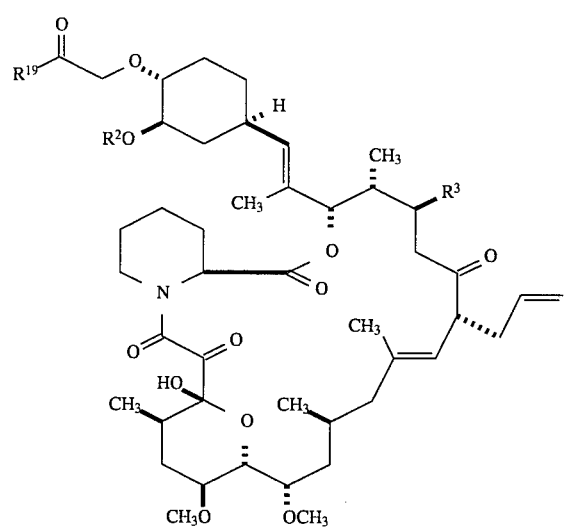

XII

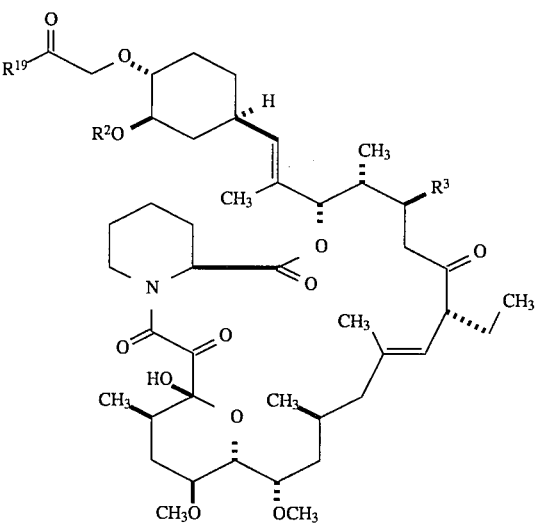

XIII

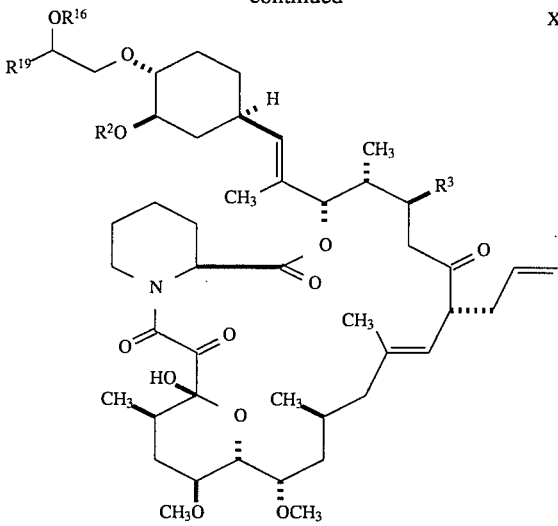

XIV

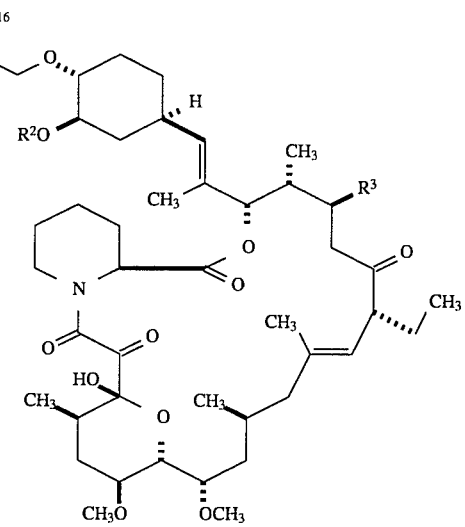

wherein:

$R^2$ is selected from the group consisting of H, methyl, ethyl, allyl, n-propyl, hydroxyethyl and isopropyl;

$R^3$ is OH or H;

$R^{16}$ is H, methyl, ethyl, allyl or benzyl; and $R^{19}$ is selected from the following group of substituents:

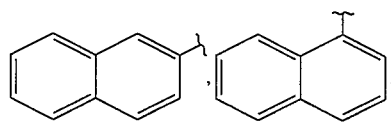

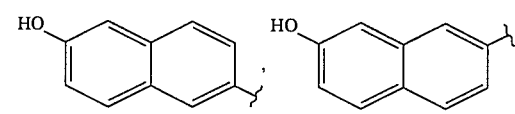

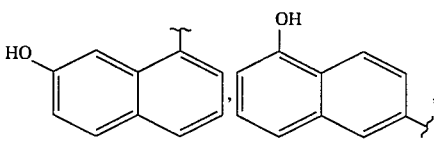

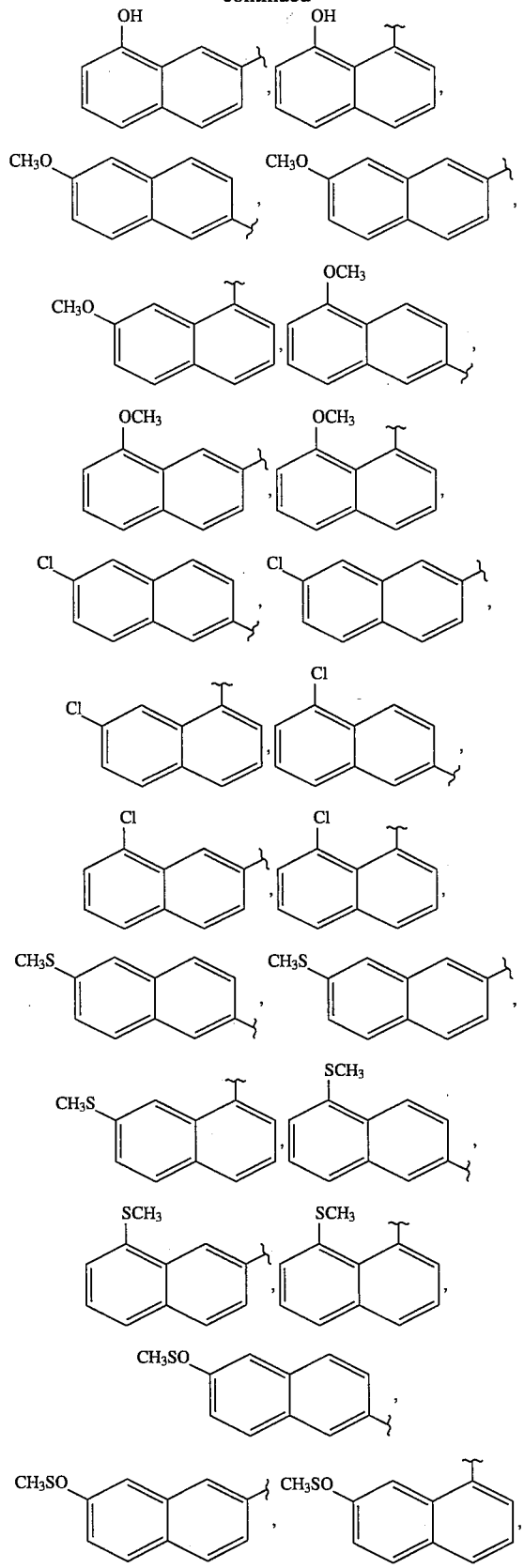
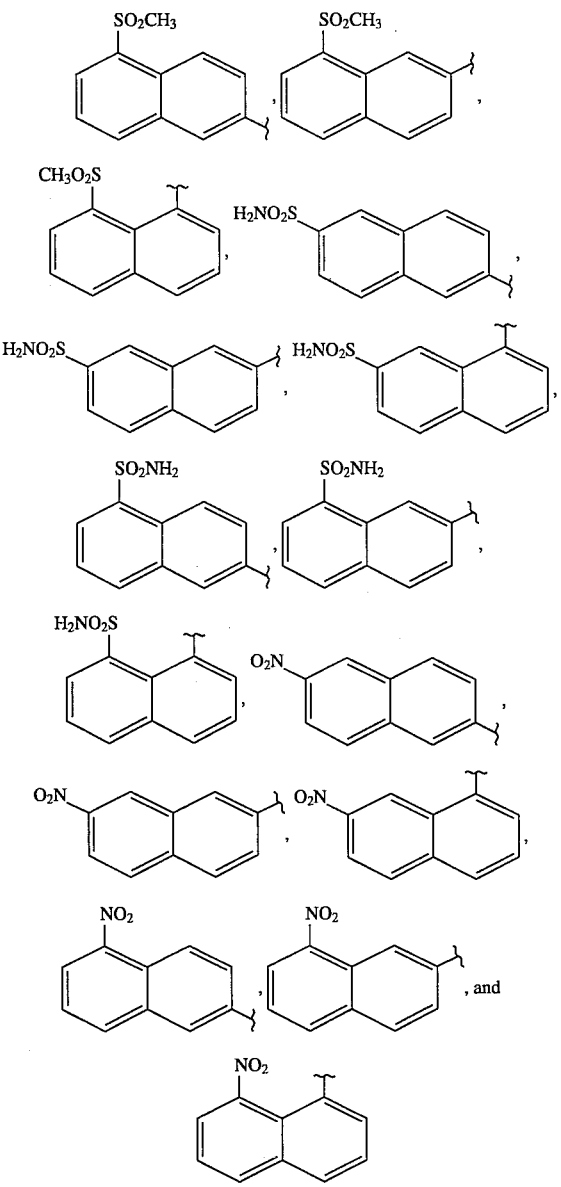

or a pharmaceutically acceptable salt thereof.

2. A compound which is selected from the group consisting of:

17-ethyl-1,14-dihydroxy-12-[2'-(4''-(2'''-(2-naphthyl)-2'''-oxoethyl-oxy)-3''-methoxycyclohexyl)-1'-methylvinyl]-23,25-dimethoxy-13,19,21,27-tetramethyl-11,28 -dioxa-4-azatricyclo[22.3.1.0$^{4,9}$]octacos-18-ene-2,3,10,16-tetraone; and 17-ethyl-1,14-dihydroxy-12-[2'-(4''-(2'''-(2-naphthyl)-2'''-hydroxyethyloxy)-3''-methoxycyclohexyl)-1'-methylvinyl]-23,25-dimethoxy-13,19,21,27-tetramethyl-11,28 -dioxa-4-azatricyclo-[22.3.1.0$^{4,9}$]octacos-18-ene-2,3,10,16-tetraone;

or a pharmaceutically acceptable salt thereof.

* * * * *